(12) United States Patent
Novotny et al.

(10) Patent No.: US 11,124,483 B2
(45) Date of Patent: Sep. 21, 2021

(54) HER3 LIGANDS AND USES THEREOF

(71) Applicant: THE REGENTS OF THE UNIVERSITY OF CALIFORNIA, Oakland, CA (US)

(72) Inventors: Christopher Novotny, San Francisco, CA (US); Kevan Shokat, San Francisco, CA (US); Natalia Jura, San Francisco, CA (US)

(73) Assignee: The Regents of the University of California, Oakland, CA (US)

( * ) Notice: Subject to any disclaimer, the term of this patent is extended or adjusted under 35 U.S.C. 154(b) by 234 days.

(21) Appl. No.: 15/756,543

(22) PCT Filed: Sep. 2, 2016

(86) PCT No.: PCT/US2016/050177
§ 371 (c)(1),
(2) Date: Feb. 28, 2018

(87) PCT Pub. No.: WO2017/040982
PCT Pub. Date: Mar. 9, 2017

(65) Prior Publication Data
US 2020/0223799 A1  Jul. 16, 2020

Related U.S. Application Data

(60) Provisional application No. 62/213,455, filed on Sep. 2, 2015.

(51) Int. Cl.
| | | |
|---|---|---|
| *C07D 215/54* | (2006.01) | |
| *A61K 45/06* | (2006.01) | |
| *A61K 31/4706* | (2006.01) | |
| *C07D 239/94* | (2006.01) | |
| *A61K 31/517* | (2006.01) | |
| *C07D 401/12* | (2006.01) | |
| *A61K 31/4709* | (2006.01) | |
| *C07D 401/14* | (2006.01) | |

(52) U.S. Cl.
CPC ........ *C07D 215/54* (2013.01); *A61K 31/4706* (2013.01); *A61K 31/4709* (2013.01); *A61K 31/517* (2013.01); *A61K 45/06* (2013.01); *C07D 239/94* (2013.01); *C07D 401/12* (2013.01); *C07D 401/14* (2013.01)

(58) Field of Classification Search
CPC .. C07D 215/54; C07D 239/94; C07D 401/12; C07D 401/14; A61K 31/4706; A61K 31/4709; A61K 31/517; A61K 45/06; A61P 35/00
See application file for complete search history.

(56) References Cited

U.S. PATENT DOCUMENTS

| | | |
|---|---|---|
| 2004/0242604 A1 | 12/2004 | Bhattacharya et al. |
| 2007/0004627 A1 | 1/2007 | Seely et al. |
| 2007/0015775 A1 | 1/2007 | Carter et al. |
| 2011/0245245 A1 | 10/2011 | Mortensen et al. |
| 2015/0216972 A1 | 8/2015 | Lin et al. |

FOREIGN PATENT DOCUMENTS

| | | | | |
|---|---|---|---|---|
| WO | WO-0068201 A1 * | 11/2000 | .............. | A61P 43/00 |
| WO | WO-02/36570 A1 | 5/2002 | | |
| WO | WO-2014/029007 A1 | 2/2014 | | |
| WO | WO-2014029007 A1 * | 2/2014 | ........... | C07D 215/22 |

OTHER PUBLICATIONS

Milka Kostic and Lyn H. Jones, Critical Assessment of Targeted Protein Degradation as a Research Tool and Pharmacological Modality, Trends in Pharmacological Sciences, May 2020, vol. 41, No. 5, 305-317, https://doi.org/10.1016/j.tips.2020.02.006 (Year: 2020).*
Laura Garuti, Marinella Roberti, Giovanni Bottegoni, Multi-kinase inhibitors, Curr Med Chem 2015;22(6):695-712. doi: 10.2174/0929867321666141216125528 (Year: 2015).*
Extended European Search Report dated Feb. 11, 2019, for EP Patent Application No. 16843101.3, 11 pages.
Garske, A.L. et al. (Sep. 13, 2011, e-published Aug. 18, 2011). "Chemical genetic strategy for targeting protein kinases based on covalent complementarity," *PNAS USA* 108(37):15046-15052.
International Search Report dated Nov. 17, 2016, for PCT Application No. PCT/US2016/050177, filed Sep. 2, 2016, 3 pages.
Okaniwa, M. et al. (Apr. 12, 2012, e-published Mar. 14, 2012). "Design and synthesis of novel DFG-out RAF/vascular endothelial growth factor receptor 2 (VEGFR2) inhibitors. 1. Exploration of [5,6]-fused bicyclic scaffolds," *J Med Chem* 55(7):3452-3478.
Shi, F. et al. (Apr. 27, 2010, e-published Mar. 29, 2010). "ErbB3/HER3 intracellular domain is competent to bind ATP and catalyze autophosphorylation," *PNAS USA* 107(17):7692-7697.
Wissner, A. et al. (Aug. 2000). "4-Anilino-6,7-dialkoxyquinoline-3-carbonitrile inhibitors of epidermal growth factor receptor kinase and their bioisosteric relationship to the 4-anilino-6,7-dialkoxyquinazoline inhibitors," *J Med Chem* 43(17):3244-3256.

(Continued)

*Primary Examiner* — Sarah Pihonak
*Assistant Examiner* — Jason Deck
(74) *Attorney, Agent, or Firm* — Mintz Levin Cohn Ferris Glovsky and Popeo, P.C.

(57) ABSTRACT

Described herein, inter alia, are compositions of HER3 ligands and methods for treating diseases using the same.

13 Claims, 11 Drawing Sheets
Specification includes a Sequence Listing.

(56) References Cited

OTHER PUBLICATIONS

Wissner, A. et al. (Jan. 2, 2003). "Synthesis and structure-activity relationships of 6,7-disubstituted 4-anilinoquinoline-3-carbonitriles. The design of an orally active, irreversible inhibitor of the tyrosine kinase activity of the epidermal growth factor receptor (EGFR) and the human epidermal growth factor receptor-2 (HER-2)," *J Med Chem* 46(1):49-63.
Written Opinion dated Nov. 17, 2016, for PCT Application No. PCT/US2016/050177, filed Sep. 2, 2016, 8 pages.

\* cited by examiner

50A

179D

74A

75A

73

74B

75B

50A

87

8003

179D

183

SEQUENCE LISTING

<160> NUMBER OF SEQ ID NOS: 6

<210> SEQ ID NO 1
<211> LENGTH: 1342
<212> TYPE: PRT
<213> ORGANISM: Homo sapiens

<400> SEQUENCE: 1

```
Met Arg Ala Asn Asp Ala Leu Gln Val Leu Gly Leu Leu Phe Ser Leu
1               5                   10                  15

Ala Arg Gly Ser Glu Val Gly Asn Ser Gln Ala Val Cys Pro Gly Thr
            20                  25                  30

Leu Asn Gly Leu Ser Val Thr Gly Asp Ala Glu Asn Gln Tyr Gln Thr
            35                  40                  45

Leu Tyr Lys Leu Tyr Glu Arg Cys Glu Val Val Met Gly Asn Leu Glu
50                  55                  60

Ile Val Leu Thr Gly His Asn Ala Asp Leu Ser Phe Leu Gln Trp Ile
65                  70                  75                  80

Arg Glu Val Thr Gly Tyr Val Leu Val Ala Met Asn Glu Phe Ser Thr
            85                  90                  95

Leu Pro Leu Pro Asn Leu Arg Val Val Arg Gly Thr Gln Val Tyr Asp
            100                 105                 110

Gly Lys Phe Ala Ile Phe Val Met Leu Asn Tyr Asn Thr Asn Ser Ser
            115                 120                 125

His Ala Leu Arg Gln Leu Arg Leu Thr Gln Leu Thr Glu Ile Leu Ser
            130                 135                 140

Gly Gly Val Tyr Ile Glu Lys Asn Asp Lys Leu Cys His Met Asp Thr
145                 150                 155                 160

Ile Asp Trp Arg Asp Ile Val Arg Asp Arg Asp Ala Glu Ile Val Val
            165                 170                 175

Lys Asp Asn Gly Arg Ser Cys Pro Pro Cys His Glu Val Cys Lys Gly
            180                 185                 190

Arg Cys Trp Gly Pro Gly Ser Glu Asp Cys Gln Thr Leu Thr Lys Thr
            195                 200                 205

Ile Cys Ala Pro Gln Cys Asn Gly His Cys Phe Gly Pro Asn Pro Asn
            210                 215                 220

Gln Cys Cys His Asp Glu Cys Ala Gly Gly Cys Ser Gly Pro Gln Asp
225                 230                 235                 240

Thr Asp Cys Phe Ala Cys Arg His Phe Asn Asp Ser Gly Ala Cys Val
            245                 250                 255

Pro Arg Cys Pro Gln Pro Leu Val Tyr Asn Lys Leu Thr Phe Gln Leu
            260                 265                 270

Glu Pro Asn Pro His Thr Lys Tyr Gln Tyr Gly Gly Val Cys Val Ala
            275                 280                 285

Ser Cys Pro His Asn Phe Val Val Asp Gln Thr Ser Cys Val Arg Ala
            290                 295                 300

Cys Pro Pro Asp Lys Met Glu Val Asp Lys Asn Gly Leu Lys Met Cys
305                 310                 315                 320

Glu Pro Cys Gly Gly Leu Cys Pro Lys Ala Cys Glu Gly Thr Gly Ser
            325                 330                 335

Gly Ser Arg Phe Gln Thr Val Asp Ser Ser Asn Ile Asp Gly Phe Val
            340                 345                 350

Asn Cys Thr Lys Ile Leu Gly Asn Leu Asp Phe Leu Ile Thr Gly Leu
            355                 360                 365

Asn Gly Asp Pro Trp His Lys Ile Pro Ala Leu Asp Pro Glu Lys Leu
            370                 375                 380

Asn Val Phe Arg Thr Val Arg Glu Ile Thr Gly Tyr Leu Asn Ile Gln
385                 390                 395                 400

Ser Trp Pro Pro His Met His Asn Phe Ser Val Phe Ser Asn Leu Thr
            405                 410                 415

Thr Ile Gly Gly Arg Ser Leu Tyr Asn Arg Gly Phe Ser Leu Leu Ile
```

-continued

```
                420             425             430
Met Lys Asn Leu Asn Val Thr Ser Leu Gly Phe Arg Ser Leu Lys Glu
                435             440             445
Ile Ser Ala Gly Arg Ile Tyr Ile Ser Ala Asn Arg Gln Leu Cys Tyr
                450             455             460
His His Ser Leu Asn Trp Thr Lys Val Leu Arg Gly Pro Thr Glu Glu
465             470             475             480
Arg Leu Asp Ile Lys His Asn Arg Pro Arg Asp Cys Val Ala Glu
                485             490             495
Gly Lys Val Cys Asp Pro Leu Cys Ser Ser Gly Cys Trp Gly Pro
                500             505             510
Gly Pro Gly Gln Cys Leu Ser Cys Arg Asn Tyr Ser Arg Gly Gly Val
                515             520             525
Cys Val Thr His Cys Asn Phe Leu Asn Gly Glu Pro Arg Glu Phe Ala
                530             535             540
His Glu Ala Glu Cys Phe Ser Cys His Pro Glu Cys Gln Pro Met Glu
545             550             555             560
Gly Thr Ala Thr Cys Asn Gly Ser Gly Ser Asp Thr Cys Ala Gln Cys
                565             570             575
Ala His Phe Arg Asp Gly Pro His Cys Val Ser Ser Cys Pro His Gly
                580             585             590
Val Leu Gly Ala Lys Gly Pro Ile Tyr Lys Tyr Pro Asp Val Gln Asn
                595             600             605
Glu Cys Arg Pro Cys His Glu Asn Cys Thr Gln Gly Cys Lys Gly Pro
                610             615             620
Glu Leu Gln Asp Cys Leu Gly Gln Thr Leu Val Leu Ile Gly Lys Thr
625             630             635             640
His Leu Thr Met Ala Leu Thr Val Ile Ala Gly Leu Val Val Ile Phe
                645             650             655
Met Met Leu Gly Gly Thr Phe Leu Tyr Trp Arg Gly Arg Arg Ile Gln
                660             665             670
Asn Lys Arg Ala Met Arg Arg Tyr Leu Glu Arg Gly Glu Ser Ile Glu
                675             680             685
Pro Leu Asp Pro Ser Glu Lys Ala Asn Lys Val Leu Ala Arg Ile Phe
                690             695             700
Lys Glu Thr Glu Leu Arg Lys Leu Lys Val Leu Gly Ser Gly Val Phe
705             710             715             720
Gly Thr Val His Lys Gly Val Trp Ile Pro Glu Gly Glu Ser Ile Lys
                725             730             735
Ile Pro Val Cys Ile Lys Val Ile Glu Asp Lys Ser Gly Arg Gln Ser
                740             745             750
Phe Gln Ala Val Thr Asp His Met Leu Ala Ile Gly Ser Leu Asp His
                755             760             765
Ala His Ile Val Arg Leu Leu Gly Leu Cys Pro Gly Ser Ser Leu Gln
                770             775             780
Leu Val Thr Gln Tyr Leu Pro Leu Gly Ser Leu Leu Asp His Val Arg
785             790             795             800
Gln His Arg Gly Ala Leu Gly Pro Gln Leu Leu Leu Asn Trp Gly Val
                805             810             815
Gln Ile Ala Lys Gly Met Tyr Tyr Leu Glu Glu His Gly Met Val His
                820             825             830
Arg Asn Leu Ala Ala Arg Asn Val Leu Leu Lys Ser Pro Ser Gln Val
                835             840             845
```

```
Gln Val Ala Asp Phe Gly Val Ala Asp Leu Leu Pro Pro Asp Asp Lys
    850                 855                 860

Gln Leu Leu Tyr Ser Glu Ala Lys Thr Pro Ile Lys Trp Met Ala Leu
865                 870                 875                 880

Glu Ser Ile His Phe Gly Lys Tyr Thr His Gln Ser Asp Val Trp Ser
                885                 890                 895

Tyr Gly Val Thr Val Trp Glu Leu Met Thr Phe Gly Ala Glu Pro Tyr
            900                 905                 910

Ala Gly Leu Arg Leu Ala Glu Val Pro Asp Leu Leu Glu Lys Gly Glu
        915                 920                 925

Arg Leu Ala Gln Pro Gln Ile Cys Thr Ile Asp Val Tyr Met Val Met
    930                 935                 940

Val Lys Cys Trp Met Ile Asp Glu Asn Ile Arg Pro Thr Phe Lys Glu
945                 950                 955                 960

Leu Ala Asn Glu Phe Thr Arg Met Ala Arg Asp Pro Pro Arg Tyr Leu
                965                 970                 975

Val Ile Lys Arg Glu Ser Gly Pro Gly Ile Ala Pro Gly Pro Glu Pro
            980                 985                 990

His Gly Leu Thr Asn Lys Lys Leu  Glu Glu Val Glu Leu  Glu Pro Glu
        995                1000                1005

Leu Asp  Leu Asp  Leu Asp  Leu  Glu Ala Glu Glu Asp  Asn Leu Ala
   1010                1015                1020

Thr Thr  Thr Leu Gly Ser Ala  Leu Ser Leu Pro Val  Gly Thr Leu
   1025                1030                1035

Asn Arg  Pro Arg Gly Ser Gln  Ser Leu Leu Ser Pro  Ser Ser Gly
   1040                1045                1050

Tyr Met  Pro Met Asn Gln Gly  Asn Leu Gly Glu Ser  Cys Gln Glu
   1055                1060                1065

Ser Ala  Val Ser Gly Ser Ser  Glu Arg Cys Pro Arg  Pro Val Ser
   1070                1075                1080

Leu His  Pro Met Pro Arg Gly  Cys Leu Ala Ser Glu  Ser Ser Glu
   1085                1090                1095

Gly His  Val Thr Gly Ser Glu  Ala Glu Leu Gln Glu  Lys Val Ser
   1100                1105                1110

Met Cys  Arg Ser Arg Ser Arg  Ser Arg Ser Pro Arg  Pro Arg Gly
   1115                1120                1125

Asp Ser  Ala Tyr His Ser Gln  Arg His Ser Leu Leu  Thr Pro Val
   1130                1135                1140

Thr Pro  Leu Ser Pro Pro Gly  Leu Glu Glu Glu Asp  Val Asn Gly
   1145                1150                1155

Tyr Val  Met Pro Asp Thr His  Leu Lys Gly Thr Pro  Ser Ser Arg
   1160                1165                1170

Glu Gly  Thr Leu Ser Ser Val  Gly Leu Ser Ser Val  Leu Gly Thr
   1175                1180                1185

Glu Glu  Glu Asp Glu Asp Glu  Glu Tyr Glu Tyr Met  Asn Arg Arg
   1190                1195                1200

Arg Arg  His Ser Pro Pro His  Pro Pro Arg Pro Ser  Ser Leu Glu
   1205                1210                1215

Glu Leu  Gly Tyr Glu Tyr Met  Asp Val Gly Ser Asp  Leu Ser Ala
   1220                1225                1230

Ser Leu  Gly Ser Thr Gln Ser  Cys Pro Leu His Pro  Val Pro Ile
   1235                1240                1245
```

-continued

```
Met Pro Thr Ala Gly Thr Thr Pro Asp Glu Asp Tyr Glu Tyr Met
1250                1255                1260

Asn Arg Gln Arg Asp Gly Gly Pro Gly Gly Asp Tyr Ala Ala
1265                1270                1275

Met Gly Ala Cys Pro Ala Ser Glu Gln Gly Tyr Glu Glu Met Arg
1280                1285                1290

Ala Phe Gln Gly Pro Gly His Gln Ala Pro His Val His Tyr Ala
1295                1300                1305

Arg Leu Lys Thr Leu Arg Ser Leu Glu Ala Thr Asp Ser Ala Phe
1310                1315                1320

Asp Asn Pro Asp Tyr Trp His Ser Arg Leu Phe Pro Lys Ala Asn
1325                1330                1335

Ala Gln Arg Thr
1340

<210> SEQ ID NO 2
<211> LENGTH: 1255
<212> TYPE: PRT
<213> ORGANISM: Homo sapiens

<400> SEQUENCE: 2

Met Glu Leu Ala Ala Leu Cys Arg Trp Gly Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
        35                  40                  45

Leu Tyr Gln Gly Cys Gln Val Val Gln Gly Asn Leu Glu Leu Thr Tyr
50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
            100                 105                 110

Ala Leu Ala Val Leu Asp Asn Gly Asp Pro Leu Asn Asn Thr Thr Pro
        115                 120                 125

Val Thr Gly Ala Ser Pro Gly Gly Leu Arg Glu Leu Gln Leu Arg Ser
130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
210                 215                 220

Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
            260                 265                 270
```

-continued

```
Thr Tyr Asn Thr Asp Thr Phe Glu Ser Met Pro Asn Pro Glu Gly Arg
        275                 280                 285
Tyr Thr Phe Gly Ala Ser Cys Val Thr Ala Cys Pro Tyr Asn Tyr Leu
    290                 295                 300
Ser Thr Asp Val Gly Ser Cys Thr Leu Val Cys Pro Leu His Asn Gln
305                 310                 315                 320
Glu Val Thr Ala Glu Asp Gly Thr Gln Arg Cys Glu Lys Cys Ser Lys
                325                 330                 335
Pro Cys Ala Arg Val Cys Tyr Gly Leu Gly Met Glu His Leu Arg Glu
            340                 345                 350
Val Arg Ala Val Thr Ser Ala Asn Ile Gln Glu Phe Ala Gly Cys Lys
        355                 360                 365
Lys Ile Phe Gly Ser Leu Ala Phe Leu Pro Glu Ser Phe Asp Gly Asp
    370                 375                 380
Pro Ala Ser Asn Thr Ala Pro Leu Gln Pro Glu Gln Leu Gln Val Phe
385                 390                 395                 400
Glu Thr Leu Glu Glu Ile Thr Gly Tyr Leu Tyr Ile Ser Ala Trp Pro
                405                 410                 415
Asp Ser Leu Pro Asp Leu Ser Val Phe Gln Asn Leu Gln Val Ile Arg
            420                 425                 430
Gly Arg Ile Leu His Asn Gly Ala Tyr Ser Leu Thr Leu Gln Gly Leu
        435                 440                 445
Gly Ile Ser Trp Leu Gly Leu Arg Ser Leu Arg Glu Leu Gly Ser Gly
    450                 455                 460
Leu Ala Leu Ile His His Asn Thr His Leu Cys Phe Val His Thr Val
465                 470                 475                 480
Pro Trp Asp Gln Leu Phe Arg Asn Pro His Gln Ala Leu Leu His Thr
                485                 490                 495
Ala Asn Arg Pro Glu Asp Glu Cys Val Gly Glu Gly Leu Ala Cys His
            500                 505                 510
Gln Leu Cys Ala Arg Gly His Cys Trp Gly Pro Gly Pro Thr Gln Cys
        515                 520                 525
Val Asn Cys Ser Gln Phe Leu Arg Gly Gln Glu Cys Val Glu Glu Cys
    530                 535                 540
Arg Val Leu Gln Gly Leu Pro Arg Glu Tyr Val Asn Ala Arg His Cys
545                 550                 555                 560
Leu Pro Cys His Pro Glu Cys Gln Pro Gln Asn Gly Ser Val Thr Cys
                565                 570                 575
Phe Gly Pro Glu Ala Asp Gln Cys Val Ala Cys Ala His Tyr Lys Asp
            580                 585                 590
Pro Pro Phe Cys Val Ala Arg Cys Pro Ser Gly Val Lys Pro Asp Leu
        595                 600                 605
Ser Tyr Met Pro Ile Trp Lys Phe Pro Asp Glu Glu Gly Ala Cys Gln
    610                 615                 620
Pro Cys Pro Ile Asn Cys Thr His Ser Cys Val Asp Leu Asp Asp Lys
625                 630                 635                 640
Gly Cys Pro Ala Glu Gln Arg Ala Ser Pro Leu Thr Ser Ile Ile Ser
                645                 650                 655
Ala Val Val Gly Ile Leu Leu Val Val Val Leu Gly Val Val Phe Gly
            660                 665                 670
Ile Leu Ile Lys Arg Arg Gln Gln Lys Ile Arg Lys Tyr Thr Met Arg
        675                 680                 685
```

-continued

```
Arg Leu Leu Gln Glu Thr Glu Leu Val Glu Pro Leu Thr Pro Ser Gly
    690             695                 700

Ala Met Pro Asn Gln Ala Gln Met Arg Ile Leu Lys Glu Thr Glu Leu
705             710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
            740                 745                 750

Lys Val Leu Arg Glu Asn Thr Ser Pro Lys Ala Asn Lys Glu Ile Leu
        755                 760                 765

Asp Glu Ala Tyr Val Met Ala Gly Val Gly Ser Pro Tyr Val Ser Arg
770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
            820                 825                 830

Met Ser Tyr Leu Glu Asp Val Arg Leu Val His Arg Asp Leu Ala Ala
        835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
            900                 905                 910

Trp Glu Leu Met Thr Phe Gly Ala Lys Pro Tyr Asp Gly Ile Pro Ala
        915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
            980                 985                 990

Asp Leu Gly Pro Ala Ser Pro Leu Asp Ser Thr Phe Tyr Arg Ser Leu
        995                 1000                1005

Leu Glu Asp Asp Asp Met Gly Asp Leu Val Asp Ala Glu Glu Tyr
    1010                1015                1020

Leu Val Pro Gln Gln Gly Phe Phe Cys Pro Asp Pro Ala Pro Gly
    1025                1030                1035

Ala Gly Gly Met Val His His Arg His Arg Ser Ser Ser Thr Arg
    1040                1045                1050

Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
```

```
                    1100              1105              1110

Glu Asp Pro Thr Val Pro Leu Pro Ser Glu Thr Asp Gly Tyr Val
    1115              1120              1125

Ala Pro Leu Thr Cys Ser Pro Gln Pro Glu Tyr Val Asn Gln Pro
    1130              1135              1140

Asp Val Arg Pro Gln Pro Ser Pro Arg Glu Gly Pro Leu Pro
    1145              1150              1155

Ala Ala Arg Pro Ala Gly Ala Thr Leu Glu Arg Pro Lys Thr Leu
    1160              1165              1170

Ser Pro Gly Lys Asn Gly Val Val Lys Asp Val Phe Ala Phe Gly
    1175              1180              1185

Gly Ala Val Glu Asn Pro Glu Tyr Leu Thr Pro Gln Gly Gly Ala
    1190              1195              1200

Ala Pro Gln Pro His Pro Pro Ala Phe Ser Pro Ala Phe Asp
    1205              1210              1215

Asn Leu Tyr Tyr Trp Asp Gln Asp Pro Pro Glu Arg Gly Ala Pro
    1220              1225              1230

Pro Ser Thr Phe Lys Gly Thr Pro Thr Ala Glu Asn Pro Glu Tyr
    1235              1240              1245

Leu Gly Leu Asp Val Pro Val
    1250              1255

<210> SEQ ID NO 3
<211> LENGTH: 12
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (5)..(5)
<223> OTHER INFORMATION: PHOSPHORYLATION
<220> FEATURE:
<221> NAME/KEY: MOD_RES
<222> LOCATION: (9)..(9)
<223> OTHER INFORMATION: PHOSPHORYLATION

<400> SEQUENCE: 3

Arg Ala Glu Asp Ser Gly Asn Glu Ser Glu Gly Glu
1               5                   10

<210> SEQ ID NO 4
<211> LENGTH: 22
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(10)
<223> OTHER INFORMATION: Amino acid is Gly, and some or all may be
      absent
<220> FEATURE:
<221> NAME/KEY: MOD_RES
<222> LOCATION: (15)..(15)
<223> OTHER INFORMATION: PHOSPHORYLATION
<220> FEATURE:
<221> NAME/KEY: MOD_RES
<222> LOCATION: (19)..(19)
<223> OTHER INFORMATION: PHOSPHORYLATION

<400> SEQUENCE: 4

Xaa Xaa Xaa Xaa Xaa Xaa Xaa Xaa Xaa Xaa Arg Ala Glu Asp Ser Gly
1               5                   10                  15
```

```
Asn Glu Ser Glu Gly Glu
            20

<210> SEQ ID NO 5
<211> LENGTH: 11
<212> TYPE: PRT
<213> ORGANISM: Artificial Sequence
<220> FEATURE:
<223> OTHER INFORMATION: Synthetic polypeptide
<220> FEATURE:
<221> NAME/KEY: MOD_RES
<222> LOCATION: (6)..(6)
<223> OTHER INFORMATION: PHOSPHORYLATION
<220> FEATURE:
<221> NAME/KEY: MOD_RES
<222> LOCATION: (10)..(10)
<223> OTHER INFORMATION: PHOSPHORYLATION

<400> SEQUENCE: 5

Asp Arg Ile Ile Asp Ser Gly Leu Asp Ser Met
1               5                   10

<210> SEQ ID NO 6
<211> LENGTH: 21
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (1)..(10)
<223> OTHER INFORMATION: Amino acid is Gly, and some or all may be
      absent
<220> FEATURE:
<221> NAME/KEY: MOD_RES
<222> LOCATION: (16)..(16)
<223> OTHER INFORMATION: PHOSPHORYLATION
<220> FEATURE:
<221> NAME/KEY: MOD_RES
<222> LOCATION: (20)..(20)
<223> OTHER INFORMATION: PHOSPHORYLATION

<400> SEQUENCE: 6

Xaa Xaa Xaa Xaa Xaa Xaa Xaa Xaa Xaa Xaa Asp Arg Ile Ile Asp Ser
1               5                   10                  15

Gly Leu Asp Ser Met
            20
```

HER3 LIGANDS AND USES THEREOF

CROSS-REFERENCES TO RELATED APPLICATIONS

This application is the national stage filing under USC 371 of international application PCT/US2016/050177, filed Sep. 2, 2016, which claims the benefit of U.S. Provisional Application No. 62/213,455, filed Sep. 2, 2015, which are incorporated hereby by reference in their entirety for all purposes.

STATEMENT AS TO RIGHTS TO INVENTIONS MADE UNDER FEDERALLY SPONSORED RESEARCH AND DEVELOPMENT

This invention was made with government support under grant no. R01 GM109176, awarded by the National Institutes of Health. The government has certain rights in the invention.

REFERENCE TO A "SEQUENCE LISTING," A TABLE, OR A COMPUTER PROGRAM LISTING APPENDIX SUBMITTED AS AN ASCII FILE

The Sequence Listing written in file 048536-572N01US_ST25.TXT, created Jul. 18, 2018, 24,690 bytes, machine format IBM-PC, MS-Windows operating system, is hereby incorporated by reference in its entirety and for all purposes.

BACKGROUND

Pseudokinases are members of the large protein kinase family which do not exhibit substantial enzymatic activity. However, they do participate in signal transduction through orchestration of protein-protein interactions with other active enzymes. HER3 in particular binds to HER2 which is an active kinase. There is a need in the art for efficient and effective blockers of HER3 function.

Disclosed herein are solutions to these and other problems in the art.

BRIEF SUMMARY

Provided herein, inter alma, are ligands for HER3, and methods of using the same.

In an aspect is provided a compound having the formula:

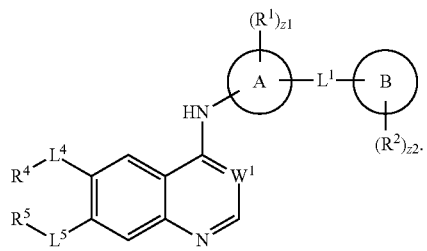

Ring A is aryl or heteroaryl. Ring B is aryl or heteroaryl. $W^1$ is N or $C(R^6)$. $R^1$ is independently a halogen, $-CX^1_3$, $-CHX^1_2$, $-CH_2X^1$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $R^2$ is independently a halogen, $-CX^2_3$, $-CHX^2_2$, $-CH_2X^2$, $-CN$, $-SO_{n2}R^{14}$, $-SO_{v2}NR^{11}R^{12}$, $-NHNH_2$, $-ONR^{11}R^{12}$, $-NHC=(O)NHNR^{11}R^{12}$, $-NHC=(O)NR^{11}R^{12}$, $-N(O)_{m2}$, $-NR^{11}R^{12}$, $-C(O)R^{13}$, $-C(O)-OR^9$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^2_3$, $-OCHX^2_2$, $-OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^4$ is independently a hydrogen, halogen, $-CX^4_3$, $-CHX^4_2$, $-CH_2X^4$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently a hydrogen, halogen, $-CX^5_3$, $-CHX^5_2$, $-CH_2X^5$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^5_3$, $-OCHX^5_2$, $-OCH_2X^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is independently a hydrogen, halogen, $-CX^6_3$, $-CHX^6_2$, $-CH_2X^6$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^6_3$, $-OCHX^6_2$, $-OCH_2X^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^7$, $R^8$, $R^9$, $R^{10}$, $R^{11}$, $R^{12}$, $R^{13}$, and $R^{14}$ are independently hydrogen, halogen, $-CX^A_3$, $-CHX^A_2$, $-CH_2X^A$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^A_3$, $-OCHX^A_2$, $-OCH_2X^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. $L^1$ is a bond, —O—, —NH—, —C(O)—, —C(O)NH—, —NHC(O)—, —C(O)O—, —OC(O)—, —NHC(O)NH—, —S—, substituted or unsubstituted alkylene or substituted or unsubstituted heteroalkylene. $L^4$ is a bond or a divalent linker. $L^5$ is a bond or a divalent linker. z1 and z2 are independently an integer from 0 to 7. m1, m2, v1, and v2 are independently 1 or 2. n1 and n2 are independently an integer from 0 to 4. $X^1$, $X^2$, $X^4$, $X^5$, $X^6$, and $X^A$ are independently —Cl, —Br, —I, or —F.

In an aspect is provided a pharmaceutical composition including a compound described herein or a pharmaceutically acceptable salt thereof, and a pharmaceutically acceptable excipient.

In an aspect is provided a method of treating a disease associated with HER3 activity in a patient in need of such treatment, the method including administering a therapeutically effective amount of a compound described herein, or a pharmaceutically acceptable salt thereof.

In an aspect is provided a method of treating a disease associated with EGFR activity, HER2 activity, HER4 activity, c-MET activity, PI3K activity, MEK activity, MAPK activity, RAF activity, BRAF activity, AKT activity, RAS activity, KRAS activity, heregulin activity, or neuregulin activity in a patient in need of such treatment, the method including administering a therapeutically effective amount of a compound described herein, or a pharmaceutically acceptable salt thereof.

In an aspect is provided a method of treating cancer in a patient in need of such treatment, the method including administering a therapeutically effective amount of a compound described herein, or a pharmaceutically acceptable salt thereof.

In an aspect is provided a method of inhibiting HER3 activity, the method including contacting HER3 with an effective amount of a compound described herein, or a pharmaceutically acceptable salt thereof.

BRIEF DESCRIPTION OF THE DRAWINGS

FIG. 1 depicts ribbon diagrams showing binding of bosutinib to X-ray crystallographic structure of HER3 in two orientations differing by approximately 90°. Structure of bosutinib depicted below ribbon diagrams. See Littlefield et al., Chem. Biol. 20:453 (2014).

FIG. 2 depicts temperature dependence of unfolding (percent unfolding) for DMSO (circles), bosutinib (squares) 179D (triangles tip up), and 183 (triangles tip down). FIG. 2 also depicts structures of bosutinib, TAK-185, Lapatinib, CP-724.714, Neratinib, 179D, and 183.

FIG. 3 depicts a region of ribbon diagram showing 179D binding in the back pocket in a Type 1 manner to EGFR. This depicts that building off of the terminal rings meta or para position may create a type 2 inhibitor.

FIG. 4 demonstrates confirmation of 50A binding to HER3 TKD. Y-axis: percent unfolded protein; x-axis: temperature. Legend: DMSO (circles), 179D (squares), 50A (triangles). Structures of 50A and 179D are provided. Observed is particularly tight binding of 50A to the HER3 TKD.

FIG. 5A: In vitro Src kinase assay (30-min). Legend: bosutinib (circles), 50A (squares). $IC_{50}$ (bosutinib)=3.3 nM. $IC_{50}$ (50A)=3.3 nM. Y-axis: percent (%) activity vs. DMSO (control); x-axis: log [compound]. FIG. 5B: In vitro HER2 kinase assay (15-min). Legend: lapatinib (circles); 50A (triangles). Axes: as in FIG. 5A.

FIG. 6A depicts a cartoon structure of the interaction of HER2 and HER3 at the membrane. FIG. 6B depicts results of treatment for 1-hr in CHL-1 cells for (in order top to bottom): pHER2 (Y1139), HER2, pHER3 (Y1289), HER3, pAkt (T308), Akt, p-ERK, ERK, and COX IV. Assay conditions (left to right) at the indicated concentrations: DMSO, LAP, bosutinib, 179D and 50A. Chemical structures of bosutinib, 179D and 50A are provided below the data. It is observed that Ambit profiling shows that bosutinib binds tightly to MEK1, 2 and 5.

FIG. 7 depicts percent unfolding as a function of temperature in the HER3 TKD Thermofluor assay. Legend: DMSO (small squares), 50A (triangles tip up), 73 (triangles tip down), 74A (diamonds), 74B (circles), 75A (larger squares), 75B (open triangle tip up). Chemical structures of 74A, 75A, 73 74B, 75B and 50A are provided below the graph.

FIG. 8 depicts binding of compound 73 in EGFR. Structure of cmpd 73 is provided below ribbon diagram of expanded region of binding of 73 in EGFR.

DETAILED DESCRIPTION

A. Definitions

Figure 1:
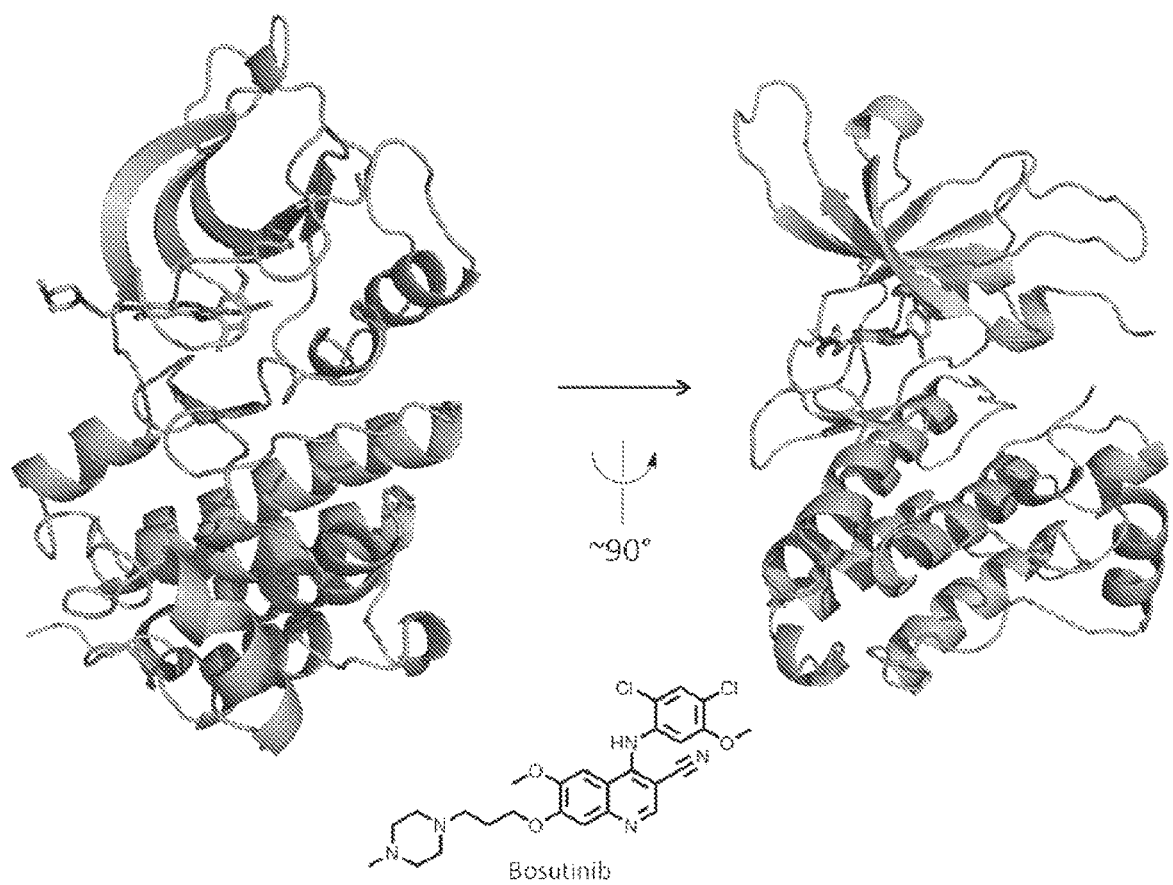
FIG. 1. Bosutinib potently binds to HER3.
Figure 2:
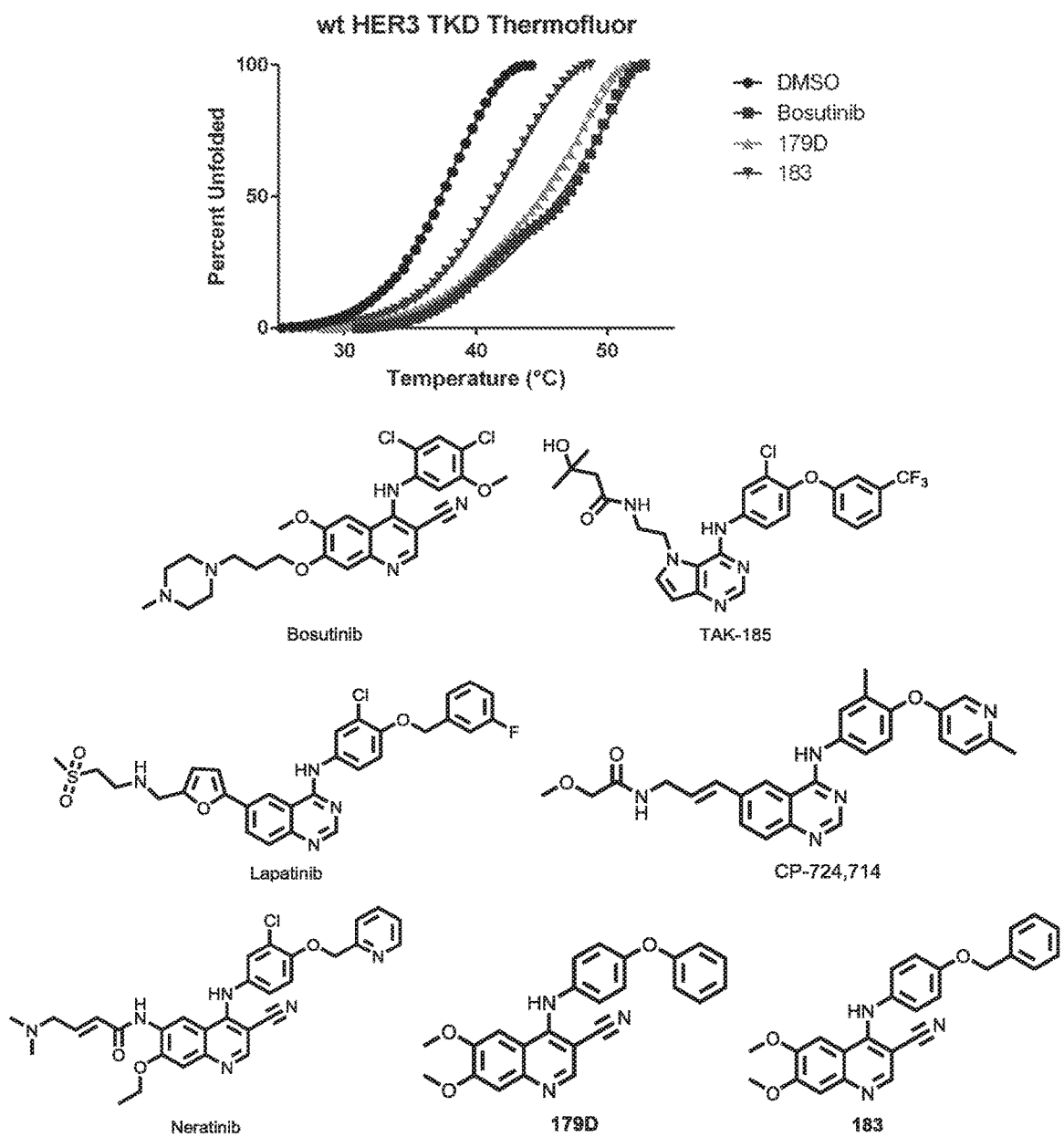
FIG. 2.
Figure 3:
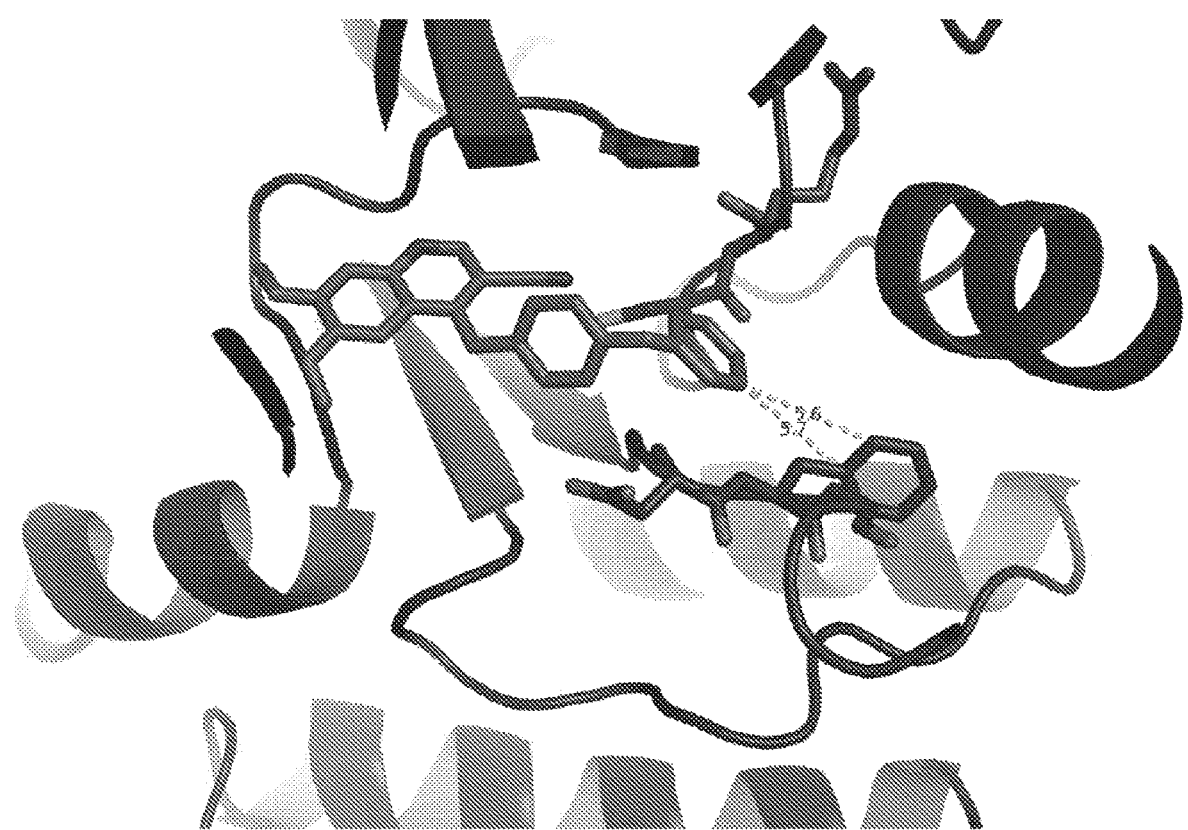
FIG. 3.
Figure 4:
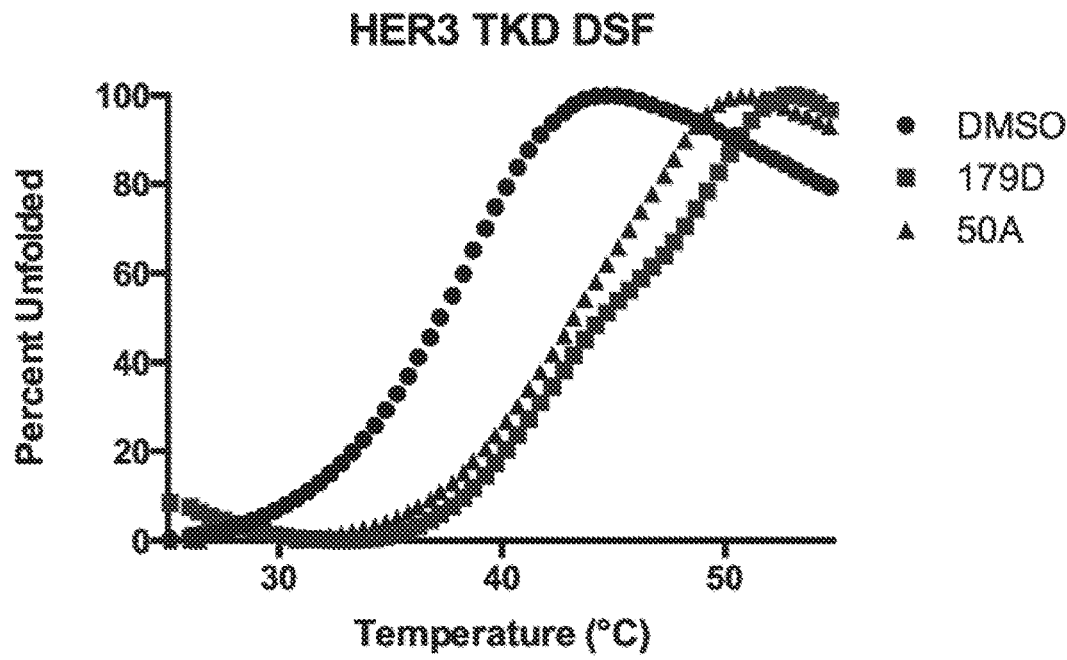
FIG. 4.
Figure 4:
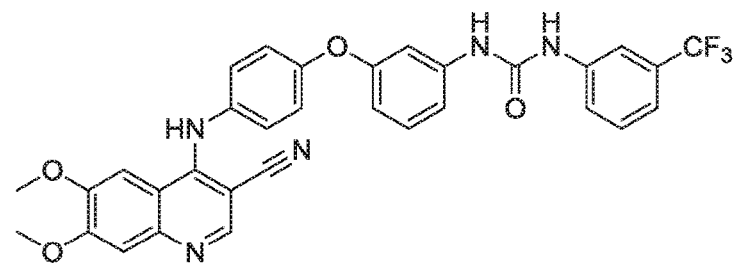
Figure 4:
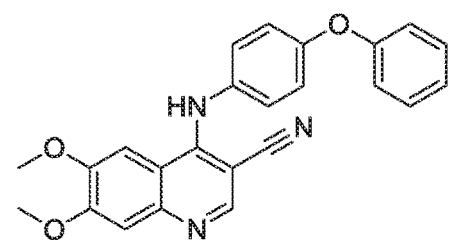
Figure 5A:
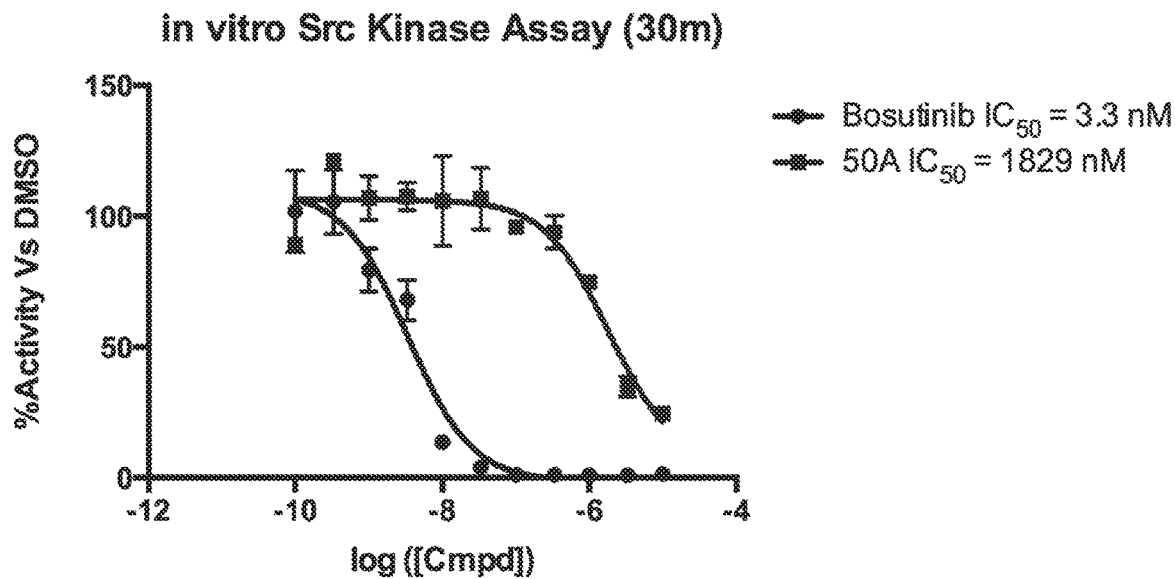
FIGS. 5A-5B. In vitro kinase assays with 50A.
Figure 5B:
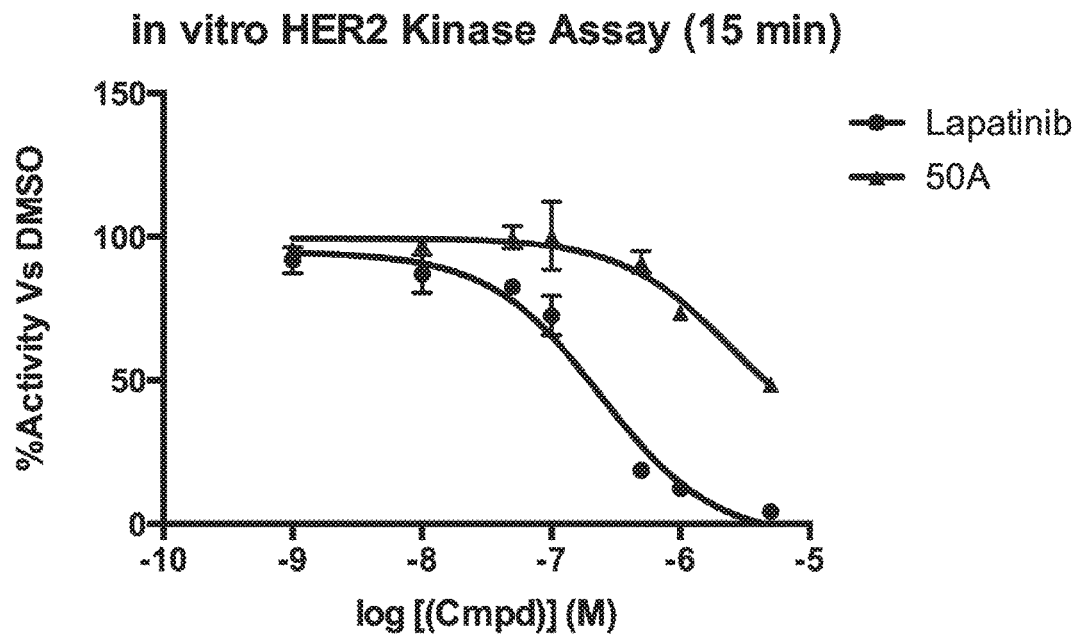
Figure 6A:
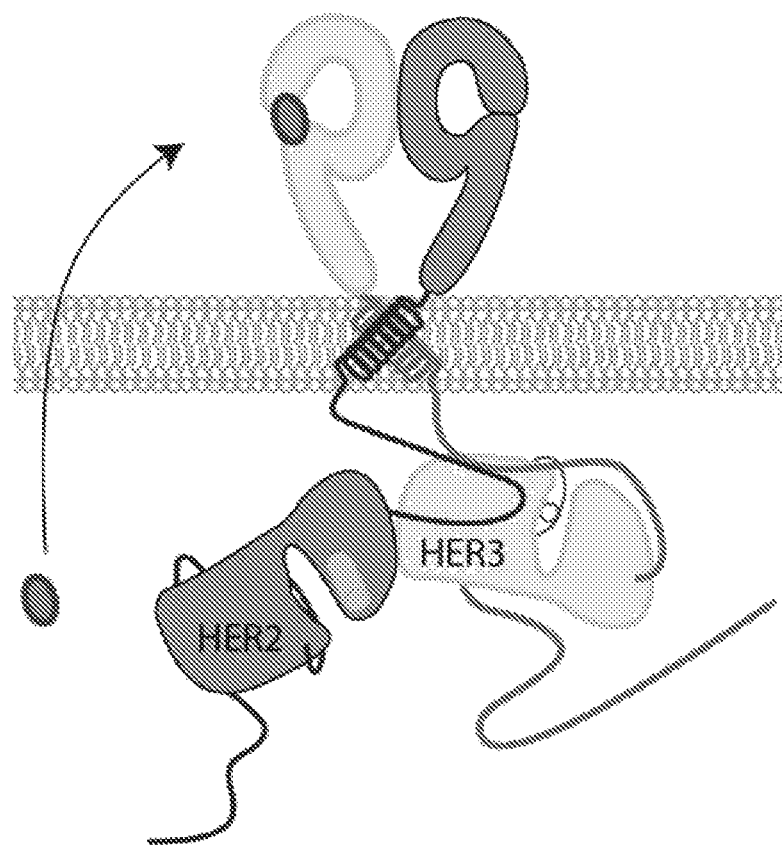
FIGS. 6A-6B.
Figure 6B:
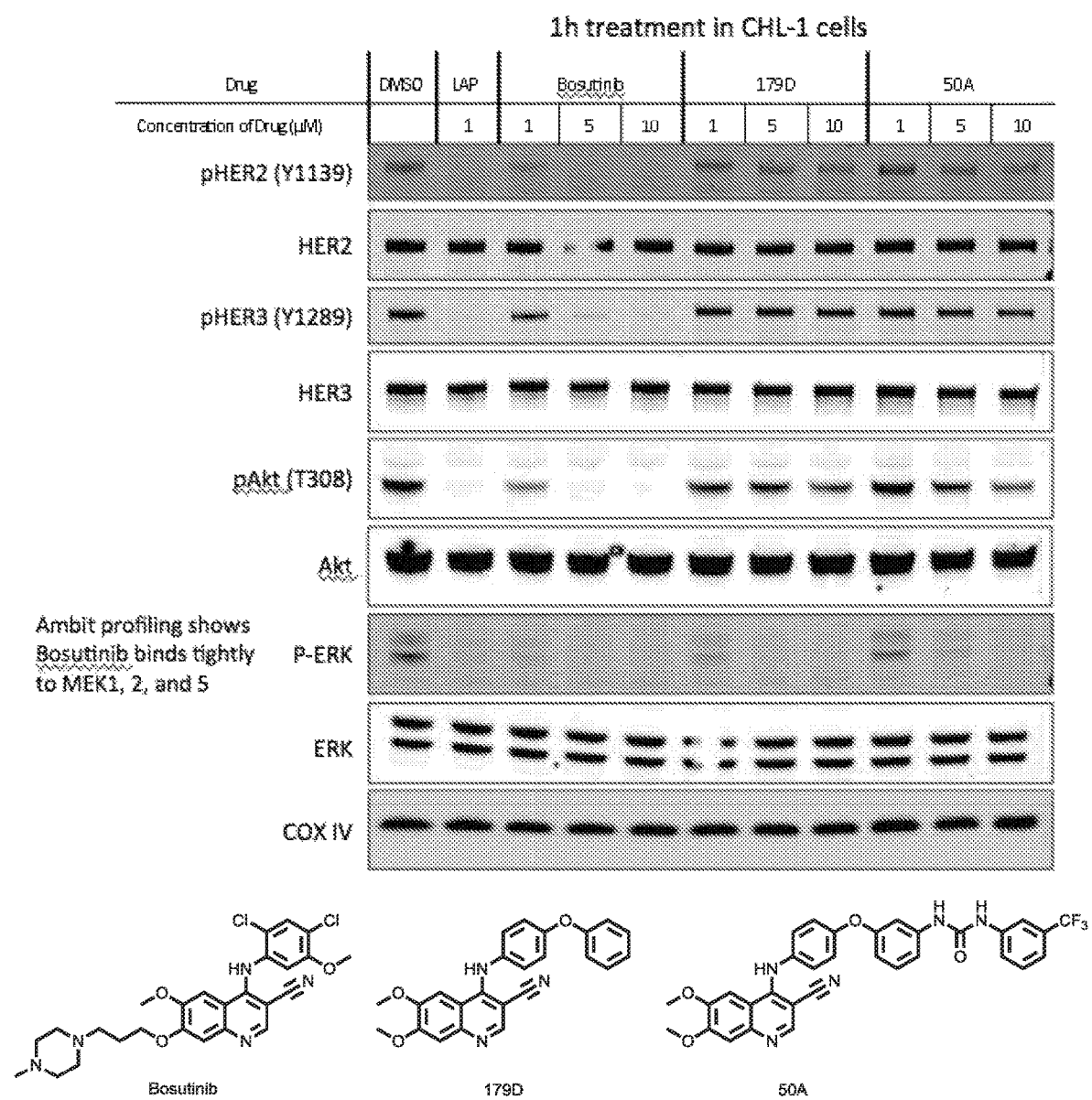
Figure 7:
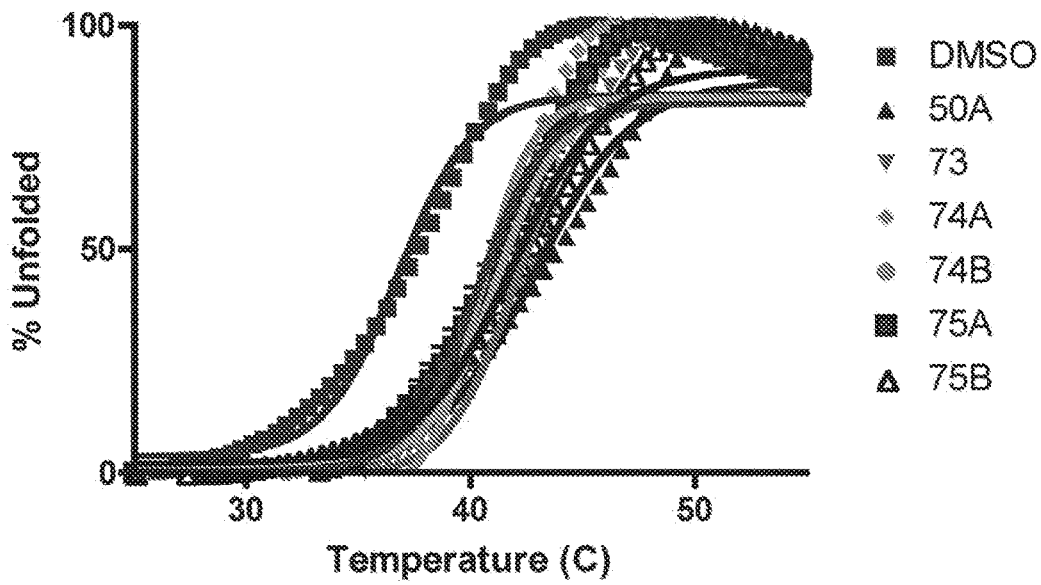
FIG. 7. Extended type II motif allows quinazolines to bind HER3.
Figure 7:
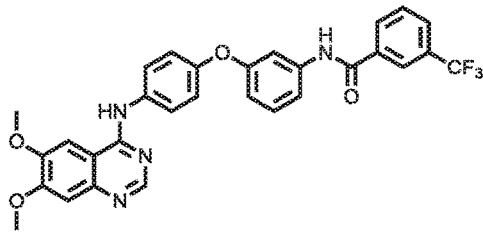
Figure 7:
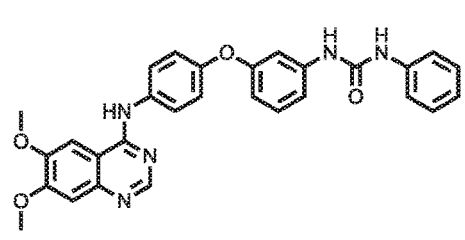
Figure 7:
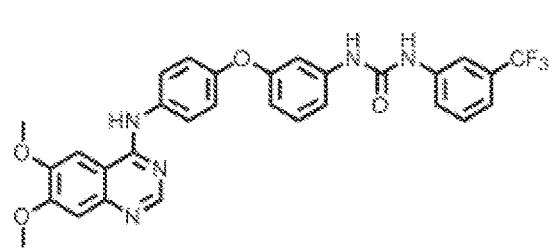
Figure 7:
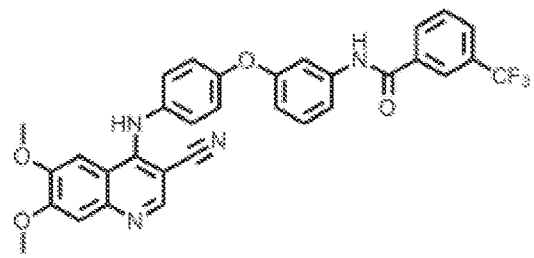
Figure 7:
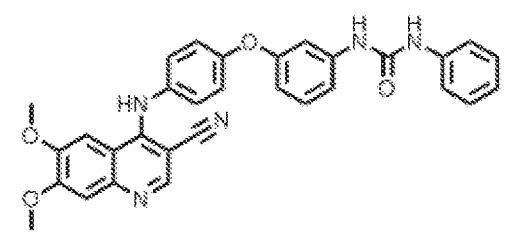
Figure 7:
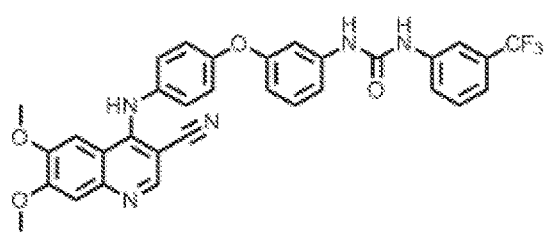
Figure 8:
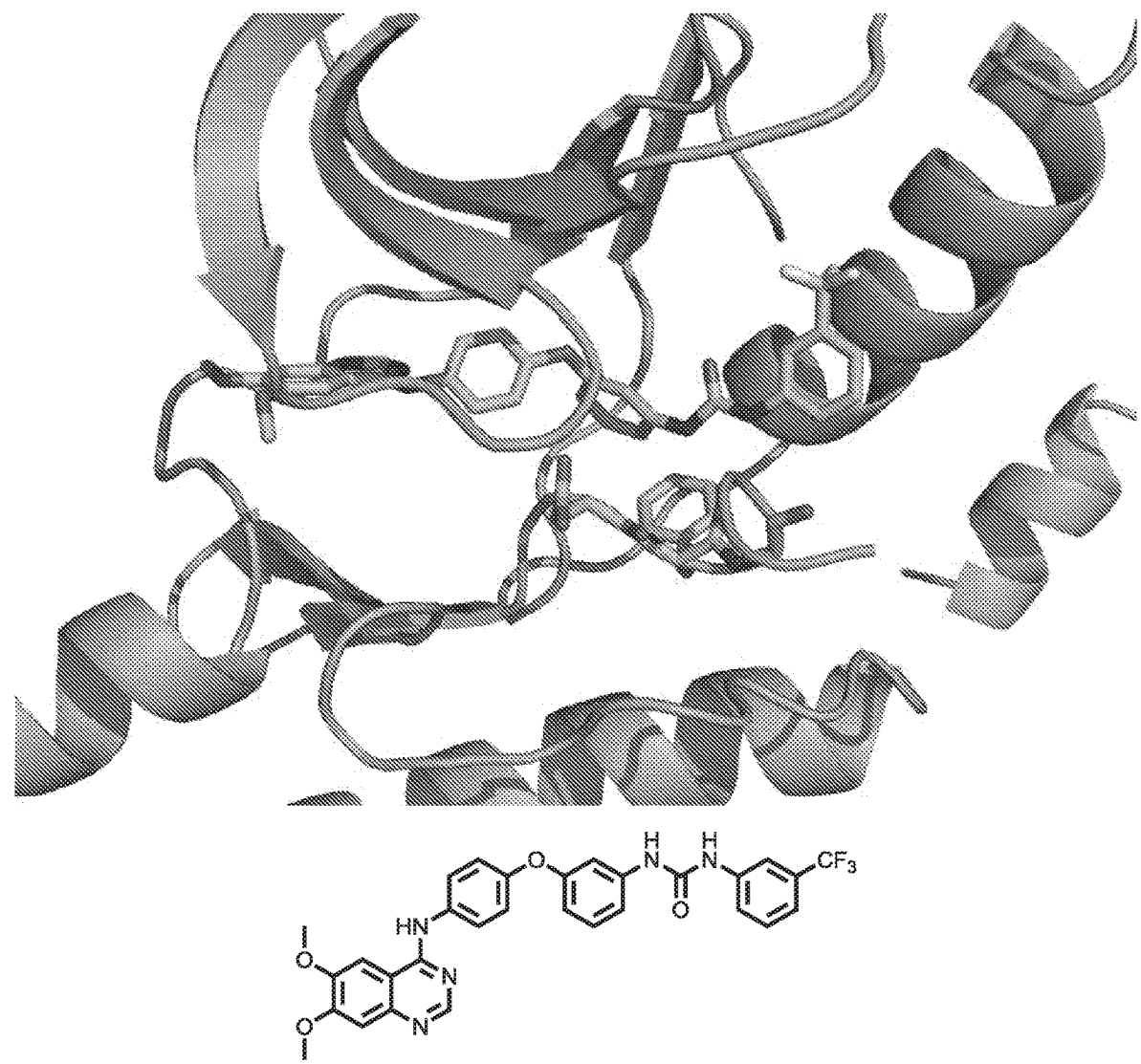
FIG. 8.
Figure 9A:
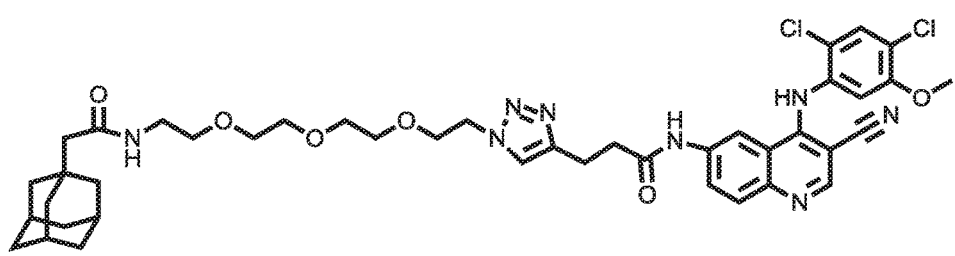
FIGS. 9A-9B. Depicted are chemical structures of compounds, which were designed to assess the potential of introducing biological activity into a HER3 binder.
Figure 9A:
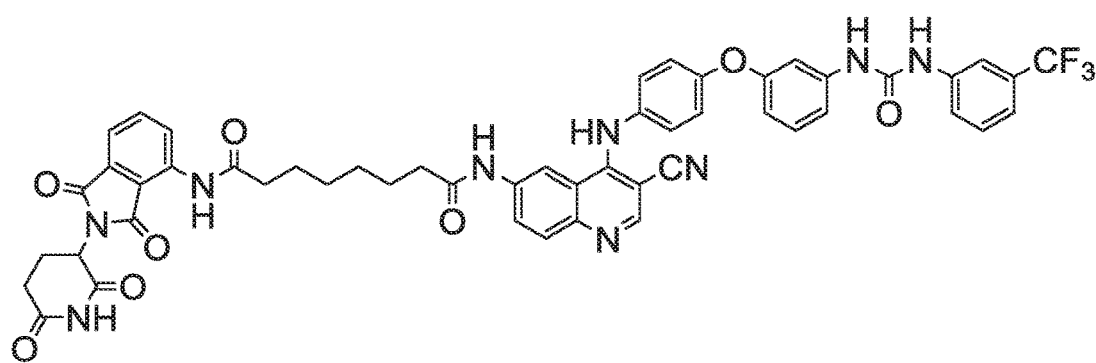
Figure 9A:
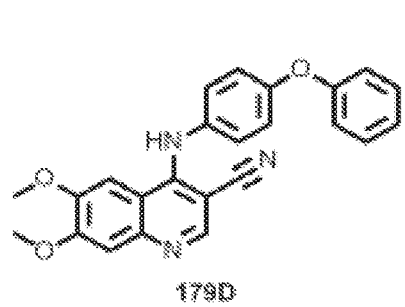
Figure 9A:
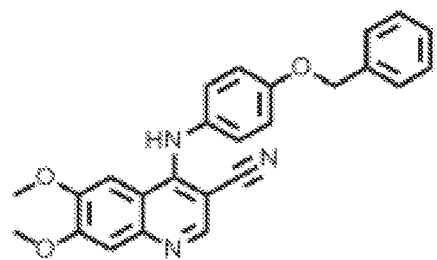
Figure 9B:
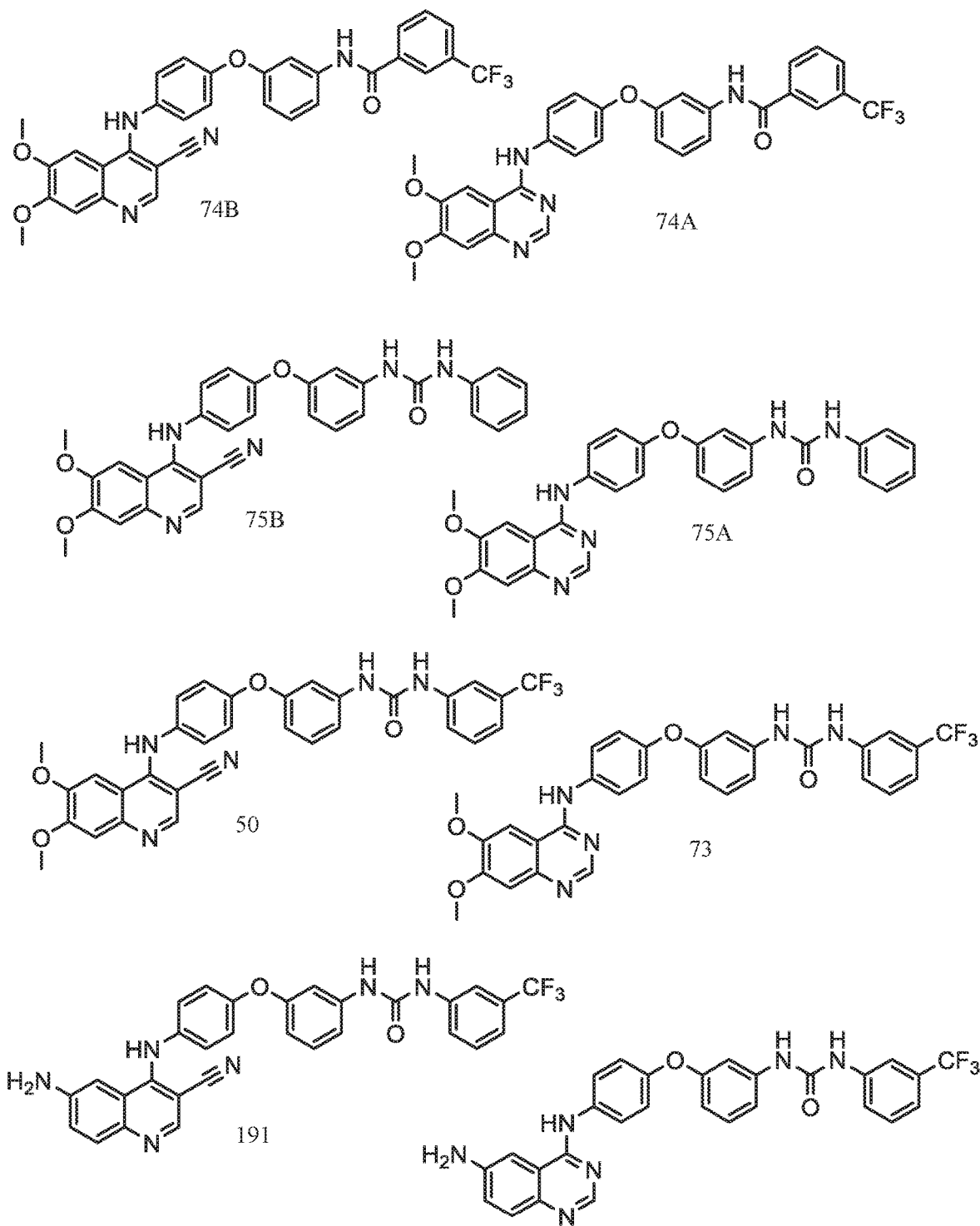

The abbreviations used herein have their conventional meaning within the chemical and biological arts. The chemical structures and formulae set forth herein are constructed according to the standard rules of chemical valency known in the chemical arts.

Where substituent groups are specified by their conventional chemical formulae, written from left to right, they equally encompass the chemically identical substituents that would result from writing the structure from right to left, e.g., —CH$_2$O— is equivalent to —OCH$_2$—.

The term "alkyl," by itself or as part of another substituent, means, unless otherwise stated, a straight (i.e., unbranched) or branched non-cyclic carbon chain (or carbon), or combination thereof, which may be fully saturated, mono- or polyunsaturated and can include di- and multivalent radicals, having the number of carbon atoms designated (i.e., $C_1$-$C_{10}$ means one to ten carbons). Examples of saturated hydrocarbon radicals include, but are not limited to, groups such as methyl, ethyl, n-propyl, isopropyl, n-butyl, t-butyl, isobutyl, sec-butyl, (cyclohexyl)methyl, homologs and isomers of, for example, n-pentyl, n-hexyl, n-heptyl, n-octyl, and the like. An unsaturated alkyl group is one having one or more double bonds or triple bonds. Examples of unsaturated alkyl groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propenyl, 3-butynyl, and the higher homologs and isomers. An alkoxy is an alkyl attached to the remainder of the molecule via an oxygen linker (—O—). An alkyl moiety may be an alkenyl moiety. An alkyl moiety may be an alkenyl moiety. An alkyl moiety may be fully saturated.

The term "alkylene," by itself or as part of another substituent, means, unless otherwise stated, a divalent radical derived from an alkyl, as exemplified, but not limited by, —CH$_2$CH$_2$CH$_2$CH$_2$—. Typically, an alkyl (or alkylene)

group will have from 1 to 24 carbon atoms, with those groups having 10 or fewer carbon atoms being preferred in the present invention. A "lower alkyl" or "lower alkylene" is a shorter chain alkyl or alkylene group, generally having eight or fewer carbon atoms. The term "alkenylene," by itself or as part of another substituent, means, unless otherwise stated, a divalent radical derived from art alkene.

The term "heteroalkyl," by itself or in combination with another term, means, unless otherwise stated, a stable straight or branched non-cyclic chain, or combinations thereof, including at least one carbon atom and at least one heteroatom (e.g., selected from the group consisting of O, N, P, Si, and S), and wherein the nitrogen and sulfur atoms may optionally be oxidized, and the nitrogen heteroatom may optionally be quaternized. The heteroatom(s) (e.g., O, N, P, S, and Si) may be placed at any interior position of the heteroalkyl group or at the position at which the alkyl group is attached to the remainder of the molecule. Examples include, but are not limited to: —$CH_2$—$CH_2$—O—$CH_3$, —$CH_2$—$CH_2$—NH—$CH_3$, —$CH_2$—$CH_2$—N($CH_3$)—$CH_3$, —$CH_2$—S—$CH_2$—$CH_3$, —$CH_2$—$CH_2$, —S(O)—$CH_3$, —$CH_2$—$CH_2$—S(O)$_2$—$CH_3$, —CH=CH—O—$CH_3$, —Si($CH_3$)$_3$, —$CH_2$—CH=N—$OCH_3$, —CH=CH—N($CH_3$)—$CH_3$, —O—$CH_3$, —O—$CH_2$—$CH_3$, and —CN. Up to two or three heteroatoms may be consecutive, such as, for example, —$CH_2$—NH—$OCH_3$ and —$CH_2$—O—Si($CH_3$)$_3$. A heteroalkyl moiety may include one heteroatom (e.g., O, N, S, Si, or P). A heteroalkyl moiety may include two optionally different heteroatoms (e.g., O, N, S, Si, or P). A heteroalkyl moiety may include three optionally different heteroatoms (e.g., O, N, S, Si, or P). A heteroalkyl moiety may include four optionally different heteroatoms (e.g., O, N, S, Si, or P). A heteroalkyl moiety may include five optionally different heteroatoms (e.g., O, N, S, Si, or P). A heteroalkyl moiety may include up to 8 optionally different heteroatoms (e.g., O, N, S, Si, or P).

Similarly, the term "heteroalkylene," by itself or as part of another substituent, means, unless otherwise stated, a divalent radical derived from heteroalkyl, as exemplified, but not limited by, —$CH_2$—$CH_2$—S—$CH_2$—$CH_2$— and —$CH_2$—S—$CH_2$—$CH_2$—NH—$CH_2$—. For heteroalkylene groups, heteroatoms can also occupy either or both of the chain termini (e.g., alkyleneoxy, alkylenedioxy, alkyleneamino, alkylenediamino, and the like). Still further, for alkylene and heteroalkylene linking groups, no orientation of the linking group is implied by the direction in which the formula of the linking group is written. For example, the formula —C(O)$_2$R'— represents both —C(O)$_2$R'— and —R'C(O)$_2$—. As described above, heteroalkyl groups, as used herein, include those groups that are attached to the remainder of the molecule through a heteroatom, such as —C(O)R', —C(O)NR', —NR'R", —OR', —SR', and/or —SO$_2$R'. Where "heteroalkyl" is recited, followed by recitations of specific heteroalkyl groups, such as —NR'R" or the like, it will be understood that the terms heteroalkyl and —NR'R" are not redundant or mutually exclusive. Rather, the specific heteroalkyl groups are recited to add clarity. Thus, the term "heteroalkyl" should not be interpreted herein as excluding specific heteroalkyl groups, such as —NR'R" or the like.

The terms "cycloalkyl" and "heterocycloalkyl," by themselves or in combination with other terms, mean, unless otherwise stated, non-aromatic cyclic versions of "alkyl" and "heteroalkyl," respectively, wherein the carbons making up the ring or rings do not necessarily need to be bonded to a hydrogen due to all carbon valencies participating in bonds with non-hydrogen atoms. Additionally, for heterocycloalkyl, a heteroatom can occupy the position at which the heterocycle is attached to the remainder of the molecule. Examples of cycloalkyl include, but are not limited to, cyclopropyl, cyclobutyl, cyclopentyl, cyclohexyl, 1-cyclohexenyl, 3-cyclohexenyl, cycloheptyl, 3-hydroxy-cyclobut-3-enyl-1,2, dione, 1H-1,2,4-triazolyl-5(4H)-one, 4H-1,2,4-triazolyl, and the like. Examples of heterocycloalkyl include, but are not limited to, 1-(1,2,5,6-tetrahydropyridyl), 1-piperidinyl, 2-piperidinyl, 3-piperidinyl, 4-morpholinyl, 3-morpholinyl, tetrahydrofuran-2-yl, tetrahydrofuran-3-yl, tetrahydrothien-2-yl, tetrahydrothien-3-yl, 1-piperazinyl, 2-piperazinyl, and the like. A "cycloalkylene" and a "heterocycloalkylene," alone or as part of another substituent, means a divalent radical derived from a cycloalkyl and heterocycloalkyl, respectively. A heterocycloalkyl moiety may include one ring heteroatom (e.g., O, N, S, Si, or P). A heterocycloalkyl moiety may include two optionally different ring heteroatoms (e.g., O, N, S, Si, or P). A heterocycloalkyl moiety may include three optionally different ring heteroatoms (e.g., O, N, S, Si, or P). A heterocycloalkyl moiety may include four optionally different ring heteroatoms (e.g., O, N, S, Si, or P). A heterocycloalkyl moiety may include five optionally different ring heteroatoms (e.g., O, N, S, Si, or P). A heterocycloalkyl moiety may include up to 8 optionally different ring heteroatoms (e.g., O, N, S, Si, or P).

The terms "halo" or "halogen," by themselves or as part of another substituent, mean, unless otherwise stated, a fluorine, chlorine, bromine, or iodine atom. Additionally, terms such as "haloalkyl" are meant to include monohaloalkyl and polyhaloalkyl. For example, the term "halo($C_1$-$C_4$) alkyl" includes, but is not limited to, fluoromethyl, difluoromethyl, trifluoromethyl, 2,2,2-trifluoroethyl, 4-chlorobutyl, 3-bromopropyl, and the like.

The term "aryl" means, unless otherwise stated, —C(O)R where R is a substituted or unsubstituted alkyl, substituted or unsubstituted cycloalkyl, substituted or unsubstituted heteroalkyl, substituted or unsubstituted heterocycloalkyl, substituted or unsubstituted aryl, or substituted or unsubstituted heteroaryl.

The term "aryl" means, unless otherwise stated, a polyunsaturated, aromatic, hydrocarbon substituent, which can be a single ring or multiple rings (preferably from 1 to 3 rings) that are fused together (i.e., a fused ring aryl) or linked covalently. A fused ring aryl refers to multiple rings fused together wherein at least one of the fused rings is an aryl ring. The term "heteroaryl" refers to aryl groups (or rings) that contain at least one heteroatom such as N, O, or S, wherein the nitrogen and sulfur atoms are optionally oxidized, and the nitrogen atom(s) are optionally quaternized. Thus, the term "heteroaryl" includes fused ring heteroaryl groups (i.e., multiple rings fused together wherein at least one of the fused rings is a heteroaromatic ring). A 5,6-fused ring heteroarylene refers to two rings fused together, wherein one ring has 5 members and the other ring has 6 members, and wherein at least one ring is a heteroaryl ring. Likewise, a 6,6-fused ring heteroarylene refers to two rings fused together, wherein one ring has 6 members and the other ring has 6 members, and wherein at least one ring is a heteroaryl ring. And a 6,5-fused ring heteroarylene refers to two rings fused together, wherein one ring has 6 members and the other ring has 5 members, and wherein at least one ring is a heteroaryl ring. A heteroaryl group can be attached to the remainder of the molecule through a carbon or heteroatom. Non-limiting examples of aryl and heteroaryl groups include phenyl, 1-naphthyl, 2-naphthyl, 4-biphenyl, 1-pyrrolyl, 2-pyrrolyl, 3-pyrrolyl, 3-pyrazolyl, 2-imidazolyl, 4-imidazolyl, pyrazinyl, 2-oxazolyl, 4-oxazolyl, 2-phenyl-4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl, 4-pyrimidyl, 5-benzothiazolyl, purinyl, 2-benzimidazolyl, 5-indolyl, 1-isoquinolyl, 5-isoquinolyl, 2-quinoxalinyl, 5-quinoxalinyl, 3-quinolyl, and 6-quinolyl. Substituents for each of the above noted aryl and heteroaryl ring systems are selected from the group of acceptable substituents described below. An "arylene" and a "heteroarylene," alone or as part of another substituent, mean a divalent radical derived from an aryl and heteroaryl, respectively. Non-limiting examples of aryl and heteroaryl groups include pyridinyl, pyrimidinyl, thiophenyl, thienyl, furanyl, indolyl, benzoxadiazolyl, benzodioxolyl, benzodioxanyl, thianaphthanyl, pyrrolopyridinyl, indazolyl, quinolinyl, quinoxalinyl, pyridopyrazinyl, quinazolinonyl, benzoisoxazolyl, imidazopyridinyl, benzofuranyl, benzothienyl, benzothiophenyl, phenyl, naphthyl, biphenyl, pyrrolyl, pyrazolyl, imidazolyl, pyrazinyl, oxazolyl, isoxazolyl, thiazolyl, furylthienyl, pyridyl, pyrimidyl, benzothiazolyl, purinyl, benzimidazolyl, isoquinolyl, thiadiazolyl, oxadiazolyl, pyrrolyl, diazolyl, triazolyl, tetrazolyl, benzothiadiazolyl, isothiazolyl, pyrazolopyrimidinyl, pyrrolopyrimidinyl, benzotriazolyl, benzoxazolyl, or quinolyl. The examples above may be substituted or unsubstituted and divalent radicals of each heteroaryl example above are non-limiting examples of heteroarylene. A heteroaryl moiety may include one ring heteroatom (e.g., O, N, or S). A heteroaryl moiety may include two optionally different ring heteroatoms (e.g., O, N, or S). A heteroaryl moiety may include three optionally different ring heteroatoms (e.g., O, N, or S). A heteroaryl moiety may include four optionally different ring heteroatoms (e.g., O, N, or S). A heteroaryl moiety may include five optionally different ring heteroatoms (e.g., O, N, or S). An aryl moiety may have a single ring. An aryl moiety may have two optionally different rings. An aryl moiety may have three optionally different rings. An aryl moiety may have four optionally different rings. A heteroaryl moiety may have one ring. A heteroaryl moiety may have two optionally different rings. A heteroaryl moiety may have three optionally different rings. A heteroaryl moiety may have four optionally different rings. A heteroaryl moiety may have five optionally different rings.

A fused ring heterocycloalkyl-aryl is an aryl fused to a heterocycloalkyl. A fused ring heterocycloalkyl-heteroaryl is a heteroaryl fused to a heterocycloalkyl. A fused ring heterocycloalkyl-cycloalkyl is a heterocycloalkyl fused to a cycloalkyl. A fused ring heterocycloalkyl-heterocycloalkyl is a heterocycloalkyl fused to another heterocycloalkyl. Fused ring heterocycloalkyl-aryl, fused ring heterocycloalkyl-heteroaryl, fused ring heterocycloalkyl-cycloalkyl, or fused ring heterocycloalkyl-heterocycloalkyl may each independently be unsubstituted or substituted with one or more of the substitutents described herein.

The term "oxo," as used herein, means an oxygen that is double bonded to a carbon atom.

The term "alkylsulfonyl," as used herein, means a moiety having the formula —S($O_2$)—R', where R' is a substituted or unsubstituted alkyl group as defined above. R' may have a specified number of carbons (e.g., "$C_1$-$C_4$ alkylsulfonyl").

Each of the above terms (e.g., "alkyl," "heteroalkyl,", "cycloalkyl", "heterocycloalkyl", "aryl," and "heteroaryl") includes both substituted and unsubstituted forms of the indicated radical. Preferred substituents for each type of radical are provided below.

Substituents for the alkyl and heteroalkyl radicals (including those groups often referred to as alkylene, alkenyl, heteroalkylene, heteroalkenyl, alkynyl, cycloalkyl, heterocycloalkyl, cycloalkenyl, and heterocycloalkenyl) can be one or more of a variety of groups selected from, but not limited to, —OR', =O, =NR', =N—OR', —NR'R", —SR', -halogen, —SiR'R"R'", —OC(O)R', —C(O)R', —$CO_2$R', —CONR'R", —OC(O)N R'R", —NR"C(O)R', —NR'—C(O)NR"R'", —NR"C(O)$_2$R', —NR—C(NR'R"R'")=NR"", —NR—C(NR'R")=NR'", —S(O)R', —S($O_2$)R', —S(O)$_2$NR'R", —NRS$O_2$R', —NR'NR"R'", —ONR'R", —NR'C=(O)NR"NR'"R"", —CN, —$NO_2$, in a number ranging from zero to (2m'+1), where m' is the total number of carbon atoms in such radical. R, R', R", R'", and R"" each preferably independently refer to hydrogen, substituted or unsubstituted heteroalkyl, substituted or unsubstituted cycloalkyl, substituted or unsubstituted heterocycloalkyl, substituted or unsubstituted aryl (e.g., aryl substituted with 1-3 halogens), substituted or unsubstituted heteroaryl, substituted or unsubstituted alkyl, alkoxy, or thioalkoxy groups, or arylalkyl groups. When a compound of the invention includes more than one R group, for example, each of the R groups is independently selected as are each R', R", R'", and R"" group when more than one of these groups is present. When R' and R" are attached to the same nitrogen atom, they can be combined with the nitrogen atom to form a 4-, 5-, 6-, or 7-membered ring. For example, —NR'R" includes, but is not limited to, 1-pyrrolidinyl and 4-morpholinyl. From the above discussion of substituents, one of skill in the art will understand that the term "alkyl" is meant to include groups including carbon atoms bound to groups other than hydrogen groups, such as haloalkyl (e.g., —$CF_3$ and —$CH_2CF_3$) and aryl (e.g., —C(O)$CH_3$, —C(O)$CF_3$, —C(O)$CH_2OCH_3$, and the like).

Similar to the substituents described for the alkyl radical, substituents for the aryl and heteroaryl groups are varied and are selected from, for example: —OR', —NR'R", —SR', -halogen, —SiR'R"R'", —OC(O)R', —C(O)R', —$CO_2$R', —CONR'R", —OC (O)NR'R", —NR"C(O)R', —NR'—C(O)NR"R'", —NR"C(O)$_2$R', —NR—C(NR'R"R'")=NR"", —NR—C(NR'R")=NR'", —S(O)R', —S($O_2$)R', —S(O)$_2$NR'R", —NRS$O_2$R', —NR'NR"R'", —ONR'R", —NR'C=(O)NR"NR'"R"", —CN, —$NO_2$, —R', —$N_3$, —CH(Ph)$_2$, fluoro($C_1$-$C_4$)alkoxy, and fluoro($C_1$-$C_4$)alkyl, in a number ranging from zero to the total number of open valences on the aromatic ring system; and where R', R", R'", and R"" are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl. When a compound of the invention includes more than one R group, for example, each of the R groups is independently selected as are each R', R", R'", and R"" groups when more than one of these groups is present.

Two or more substituents may optionally be joined to form aryl, heteroaryl, cycloalkyl, or heterocycloalkyl groups. Such so-called ring-forming substituents are typically, though not necessarily, found attached to a cyclic base structure. In one embodiment, the ring-forming substituents are attached to adjacent members of the base structure. For example, two ring-forming substituents attached to adjacent members of a cyclic base structure create a fused ring structure. In another embodiment, the ring-forming substituents are attached to a single member of the base structure. For example, two ring-forming substituents attached to a single member of a cyclic base structure create a spirocyclic structure. In yet another embodiment, the ring-forming substituents are attached to non-adjacent members of the base structure.

Two of the substituents on adjacent atoms of the aryl or heteroaryl ring may optionally form a ring of the formula -T-C(O)—(CRR')$_q$—U—, wherein T and U are independently —NR—, —O—, —CRR'—, or a single bond, and q is an integer of from 0 to 3. Alternatively, two of the substituents on adjacent atoms of the aryl or heteroaryl ring may optionally be replaced with a substituent of the formula -A-(CH$_2$)$_r$—B—, wherein A and B are independently —CRR'—, —O—, —NR—, —S—, —S(O)—, —S(O)$_2$—, —S(O)$_2$NR', or a single bond, and r is an integer of from 1 to 4. One of the single bonds of the new ring so formed may optionally be replaced with a double bond. Alternatively, two of the substituents on adjacent atoms of the aryl or heteroaryl ring may optionally be replaced with a substituent of the formula —(CRR')$_s$—X'—(C"R"R''')$_d$—, where s and d are independently integers of from 0 to 3, and X' is —O—, —NR'—, —S—, —S(O)—, —S(O)$_2$—, or —S(O)$_2$NR'—. The substituents R, R', R", and R''' are preferably independently selected from hydrogen, substituted or unsubstituted alkyl, substituted or unsubstituted heteroalkyl, substituted or unsubstituted cycloalkyl, substituted or unsubstituted heterocycloalkyl, substituted or unsubstituted aryl, and substituted or unsubstituted heteroaryl.

As used herein, the terms "heteroatom" or "ring heteroatom" are meant to include, oxygen (O), nitrogen (N), sulfur (S), phosphorus (P), and silicon (Si).

A "substituent group," as used herein, means a group selected from the following moieties:

(A) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (B) alkyl, heteroalkyl, cycloalkyl, heterocycloalkyl, aryl, heteroaryl, substituted with at least one substituent selected from:

(i) oxo, halogen, —CF$_3$, —CN, —OH, —NH$_2$, —COOH, —CONH$_2$, —NO$_2$, —SH—SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_2$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (ii) alkyl, heteroalkyl, cycloalkyl, heterocycloalkyl, aryl, heteroaryl, substituted with at least one substituent selected from:

(a) oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl, and (b) alkyl, heteroalkyl, cycloalkyl, heterocycloalkyl, aryl, heteroaryl, substituted with at least one substituent selected from: oxo, halogen, —CF$_3$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O)NH$_2$, —NHSO$_2$H, —NHC=(O)H, —NHC(O)—OH, —NHOH, —OCF$_3$, —OCHF$_2$, unsubstituted alkyl, unsubstituted heteroalkyl, unsubstituted cycloalkyl, unsubstituted heterocycloalkyl, unsubstituted aryl, unsubstituted heteroaryl.

A "size-limited substituent" or "size-limited substituent group," as used herein, means a group selected from all of the substituents described above for a "substituent group," wherein each substituted or unsubstituted alkyl is a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 10 membered heteroaryl.

A "lower substituent" or "lower substituent group," as used herein, means a group selected from all of the substituents described above for a "substituent group," wherein each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and each substituted or unsubstituted heteroaryl is a substituted or unsubstituted 5 to 9 membered heteroaryl.

In some embodiments, each substituted group described in the compounds herein is substituted with at least one substituent group. More specifically, in some embodiments, each substituted alkyl, substituted heteroalkyl, substituted cycloalkyl, substituted heterocycloalkyl, substituted aryl, substituted heteroaryl, substituted alkylene, substituted heteroalkylene, substituted cycloalkylene, substituted heterocycloalkylene, substituted arylene, and/or substituted heteroarylene described in the compounds herein are substituted with at least one substituent group. In other embodiments, at least one or all of these groups are substituted with at least one size-limited substituent group. In other embodiments, at least one or all of these groups are substituted with at least one lower substituent group.

In other embodiments of the compounds herein, each substituted or unsubstituted alkyl may be a substituted or unsubstituted $C_1$-$C_{20}$ alkyl, each substituted or unsubstituted heteroalkyl is a substituted or unsubstituted 2 to 20 membered heteroalkyl, each substituted or unsubstituted cycloalkyl is a substituted or unsubstituted $C_3$-$C_8$ cycloalkyl, each substituted or unsubstituted heterocycloalkyl is a substituted or unsubstituted 3 to 8 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 10 membered heteroaryl. In some embodiments of the compounds herein, each substituted or unsubstituted alkylene is a substituted or unsubstituted $C_1$-$C_{20}$ alkylene, each substituted or unsubstituted heteroalkylene is a substituted or unsubstituted 2 to 20 membered heteroalkylene, each substituted or unsubstituted cycloalkylene is a substituted or unsubstituted $C_3$-$C_8$ cycloalkylene, each substituted or unsubstituted heterocycloalkylene is a substituted or unsubstituted 3 to 8 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 10 membered heteroarylene.

In some embodiments, each substituted or unsubstituted alkyl is a substituted or unsubstituted $C_1$-$C_8$ alkyl, each substituted or unsubstituted heteroalkyl is a substituted or unsubstituted 2 to 8 membered heteroalkyl, each substituted or unsubstituted cycloalkyl is a substituted or unsubstituted $C_3$-$C_7$ cycloalkyl, each substituted or unsubstituted heterocycloalkyl is a substituted or unsubstituted 3 to 7 membered heterocycloalkyl, each substituted or unsubstituted aryl is a substituted or unsubstituted $C_6$-$C_{10}$ aryl, and/or each substituted or unsubstituted heteroaryl is a substituted or unsubstituted 5 to 9 membered heteroaryl. In some embodiments, each substituted or unsubstituted alkylene is a substituted or unsubstituted $C_1$-$C_8$ alkylene, each substituted or unsubstituted heteroalkylene is a substituted or unsubstituted 2 to 8 membered heteroalkylene, each substituted or unsubstituted cycloalkylene is a substituted or unsubstituted $C_3$-$C_7$ cycloalkylene, each substituted or unsubstituted heterocycloalkylene is a substituted or unsubstituted 3 to 7 membered heterocycloalkylene, each substituted or unsubstituted arylene is a substituted or unsubstituted $C_6$-$C_{10}$ arylene, and/or each substituted or unsubstituted heteroarylene is a substituted or unsubstituted 5 to 9 membered heteroarylene. In some embodiments, the compound is a chemical species set forth in the Examples section, figures, or tables below.

The term "pharmaceutically acceptable salts" is meant to include salts of the active compounds that are prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, lactic, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, e.g., Berge et al., *Journal of Pharmaceutical Science* 66:1-19 (1977)). Certain specific compounds of the present invention contain both basic and acidic functionalities that allow the compounds to be converted into either base or acid addition salts. Other pharmaceutically acceptable carriers known to those of skill in the art are suitable for the present invention. Salts tend to be more soluble in aqueous or other protonic solvents than are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Thus, the compounds of the present invention may exist as salts, such as with pharmaceutically acceptable acids. The present invention includes such salts. Examples of such salts include hydrochlorides, hydrobromides, sulfates, methanesulfonates, nitrates, maleates, acetates, citrates, fumarates, tartrates (e.g., (+)-tartrates, (−)-tartrates, or mixtures thereof including racemic mixtures), succinates, benzoates, and salts with amino acids such as glutamic acid. These salts may be prepared by methods known to those skilled in the art.

The neutral forms of the compounds are preferably regenerated by contacting the salt with a base or acid and isolating the parent compound in the conventional manner. The parent form of the compound differs from the various salt forms in certain physical properties, such as solubility in polar solvents.

Certain compounds of the present invention can exist in unsolvated forms as well as solvated forms, including hydrated forms. In general, the solvated forms are equivalent to unsolvated forms and are encompassed within the scope of the present invention. Certain compounds of the present invention may exist in multiple crystalline or amorphous forms. In general, all physical forms are equivalent for the uses contemplated by the present invention and are intended to be within the scope of the present invention.

As used herein, the term "salt" refers to acid or base salts of the compounds used in the methods of the present invention. Illustrative examples of acceptable salts are mineral acid (hydrochloric acid, hydrobromic acid, phosphoric acid, and the like) salts, organic acid (acetic acid, propionic acid, glutamic acid, citric acid and the like) salts, quaternary ammonium (methyl iodide, ethyl iodide, and the like) salts.

Certain compounds of the present invention possess asymmetric carbon atoms (optical or chiral centers) or double bonds; the enantiomers, racemates, diastereomers, tautomers, geometric isomers, stereoisometric forms that may be defined, in terms of absolute stereochemistry, as (R)- or (S)- or, as (D)- or (L)- for amino acids, and individual isomers are encompassed within the scope of the present invention. The compounds of the present invention do not include those which are known in art to be too unstable to synthesize and/or isolate. The present invention is meant to include compounds in racemic and optically pure forms. Optically active (R)- and (S)-, or (D)- and (L)-isomers may be prepared using chiral synthons or chiral reagents, or resolved using conventional techniques. When the compounds described herein contain olefinic bonds or other centers of geometric asymmetry, and unless specified otherwise, it is intended that the compounds include both E and Z geometric isomers.

As used herein, the term "isomers" refers to compounds having the same number and kind of atoms, and hence the same molecular weight, but differing in respect to the structural arrangement or configuration of the atoms.

The term "tautomer," as used herein, refers to one of two or more structural isomers which exist in equilibrium and which are readily converted from one isomeric form to another.

It will be apparent to one skilled in the art that certain compounds of this invention may exist in tautomeric forms, all such tautomeric forms of the compounds being within the scope of the invention.

Unless otherwise stated, structures depicted herein are also meant to include all stereochemical forms of the structure; i.e., the R and S configurations for each asymmetric center. Therefore, single stereochemical isomers as well as enantiomeric and diastereomeric mixtures of the present compounds are within the scope of the invention.

Unless otherwise stated, structures depicted herein are also meant to include compounds which differ only in the presence of one or more isotopically enriched atoms. For example, compounds having the present structures except for the replacement of a hydrogen by a deuterium or tritium, or the replacement of a carbon by $^{13}$C- or $^{14}$C-enriched carbon are within the scope of this invention.

The compounds of the present invention may also contain unnatural proportions of atomic isotopes at one or more of the atoms that constitute such compounds. For example, the compounds may be radiolabeled with radioactive isotopes, such as for example tritium ($^{3}$H), iodine-125 ($^{125}$I), or carbon-14 ($^{14}$C). All isotopic variations of the compounds of the present invention, whether radioactive or not, are encompassed within the scope of the present invention.

The symbol " " denotes the point of attachment of a chemical moiety to the remainder of a molecule or chemical formula.

The terms "a" or "an," as used in herein means one or more. In addition, the phrase "substituted with a[n]," as used herein, means the specified group may be substituted with one or more of any or all of the named substituents. For example, where a group, such as an alkyl or heteroaryl group, is "substituted with an unsubstituted $C_1$-$C_{20}$ alkyl, or unsubstituted 2 to 20 membered heteroalkyl," the group may contain one or more unsubstituted $C_1$-$C_{20}$ alkyls, and/or one or more unsubstituted 2 to 20 membered heteroalkyls. Moreover, where a moiety is substituted with an R substituent, the group may be referred to as "R-substituted." Where a moiety is R-substituted, the moiety is substituted with at least one R substituent and each R substituent is optionally different.

Descriptions of compounds of the present invention are limited by principles of chemical bonding known to those skilled in the art. Accordingly, where a group may be substituted by one or more of a number of substituents, such substitutions are selected so as to comply with principles of chemical bonding and to give compounds which are not inherently unstable and/or would be known to one of ordinary skill in the art as likely to be unstable under ambient conditions, such as aqueous, neutral, and several known physiological conditions. For example, a heterocycloalkyl or heteroaryl is attached to the remainder of the molecule via a ring heteroatom in compliance with principles of chemical bonding known to those skilled in the art thereby avoiding inherently unstable compounds.

The terms "treating" or "treatment" refers to any indicia of success in the treatment or amelioration of an injury, disease, pathology or condition, including any objective or subjective parameter such as abatement; remission; diminishing of symptoms or making the injury, pathology or condition more tolerable to the patient; slowing in the rate of degeneration or decline; making the final point of degeneration less debilitating; improving a patient's physical or mental well-being. The treatment or amelioration of symptoms can be based on objective or subjective parameters; including the results of a physical examination, neuropsychiatric exams, and/or a psychiatric evaluation. For example, certain methods herein treat diseases associated with HER3 activity. Certain methods described herein may treat diseases associated with HER3 activity (e.g., cancer) by inhibiting HER3 activity. For example, certain methods herein treat cancer. For example certain methods herein treat cancer by decreasing a symptom of cancer. Symptoms of cancer would be known or may be determined by a person of ordinary skill in the art. The term "treating" and conjugations thereof, include prevention of an injury, pathology, condition, or disease. In embodiments, treating does not include preventing.

An "effective amount" is an amount sufficient to accomplish a stated purpose (e.g. achieve the effect for which it is administered, treat a disease, reduce enzyme activity, increase enzyme activity, reduce protein function, reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug or prodrug is an amount of a drug or prodrug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. The exact amounts will depend on the purpose of the treatment, and will be ascertainable by one skilled in the art using known techniques see, e.g., Lieberman, *Pharmaceutical Dosage Forms* (vols. 1-3, 1992); Lloyd, *The Art. Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

The term "associated" or "associated with" in the context of a substance or substance activity or function associated with a disease (e.g. cancer) means that the disease is caused by (in whole or in part), or a symptom of the disease is caused by (in whole or in part) the substance or substance activity or function. As used herein, what is described as being associated with a disease, if a causative agent, could be a target for treatment of the disease. For example, a disease associated with HER3 activity may be treated with an agent (e.g. compound as described herein) effective for decreasing the level of HER3 activity.

"Control" or "control experiment" or "standard control" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects.

"Contacting" is used in accordance with its plain ordinary meaning and refers to the process of allowing at least two distinct species (e.g. chemical compounds including biomolecules, or cells) to become sufficiently proximal to react, interact or physically touch. It should be appreciated, however, that the resulting reaction product can be produced directly from a reaction between the added reagents or from an intermediate from one or more of the added reagents which can be produced in the reaction mixture. The term "contacting" may include allowing two species to react, interact, or physically touch, wherein the two species may be a compound as described herein and a protein or enzyme. In some embodiments contacting includes allowing a compound described herein to interact with a protein (e.g., HER3) or enzyme.

As defined herein, the term "inhibition", "inhibit", "inhibiting" and the like in reference to a protein-inhibitor (e.g. antagonist) interaction means negatively affecting (e.g. decreasing) the level of activity or function of the protein relative to the level of activity or function of the protein in the absence of the inhibitor. In some embodiments inhibition refers to reduction of a disease or symptoms of disease. Thus, inhibition may include, at least in part, partially or totally blocking stimulation, decreasing, preventing, or delaying activation, or inactivating, desensitizing, or down-regulating signal transduction or enzymatic activity or the amount of a protein.

As defined herein, the term "activation", "activate", "activating" and the like in reference to a protein-activator (e.g. agonist) interaction means positively affecting (e.g. increasing) the activity or function of the protein relative to the activity or function of the protein in the absence of the activator (e.g. compound described herein). Thus, activation may include, at least in part, partially or totally increasing stimulation, increasing or enabling activation, or activating, sensitizing, or up-regulating signal transduction or enzymatic activity or the amount of a protein decreased in a disease. Activation may include, at least in part, partially or totally increasing stimulation, increasing or enabling activation, or activating, sensitizing, or up-regulating signal transduction or enzymatic activity or the amount of a protein.

The term "modulator" refers to a composition that increases or decreases the level of a target molecule or the function of a target molecule. In embodiments, a modulator is an anti-cancer agent. In embodiments, a modulator is a HER3 antagonist. In embodiments, a modulator is a HER3 agonist.

"Anti-cancer agent" or "anti-cancer drug" is used in accordance with its plain ordinary meaning and refers to a composition (e.g. compound, drug, antagonist, inhibitor, modulator) having antineoplastic properties or the ability to inhibit the growth or proliferation of cells. In some embodiments, an anti-cancer agent is a chemotherapeutic. In some embodiments, an anti-cancer agent is an agent approved by the FDA or similar regulatory agency of a country other than the USA, for treating cancer. Examples of anti-cancer agents include, but are not limited to, anti-androgens (e.g., Casodex, Flutamide, MDV3100, or ARN-509), MEK (e.g. MEK1, MEK2, or MEK1 and MEK2) inhibitors (e.g. XL518, CI-1040, PD035901, selumetinib/AZD6244, GSK1120212/trametinib, GDC-0973, ARRY-162, ARRY-300, AZD8330, PD0325901, U0126, PD98059, TAK-733, PD318088, AS703026, BAY 869766), alkylating agents (e.g., cyclophosphamide, ifosfamide, chlorambucil, busulfan, melphalan, mechlorethamine, uramustine, thiotepa, nitrosoureas, nitrogen mustards (e.g., mechloroethamine, cyclophosphamide, chlorambucil, meiphalan), ethylenimine and methylmelamines (e.g., hexamethylmelamine, thiotepa), alkyl sulfonates (e.g., busulfan), nitrosoureas (e.g., carmustine, lomustine, semustine, streptozocin), triazenes (decarbazine)), anti-metabolites (e.g., 5-azathioprine, leucovorin, capecitabine, fludarabine, gemcitabine, pemetrexed, raltitrexed, folic acid analog (e.g., methotrexate), pyrimidine analogs (e.g., fluorouracil, floxouridine, Cytarabine), purine analogs (e.g., mercaptopurine, thioguanine, pentostatin), etc.), plant alkaloids (e.g., vincristine, vinblastine, vinorelbine, vindesine, podophyllotoxin, paclitaxel, docetaxel, etc.), topoisomerase inhibitors (e.g., irinotecan, topotecan, amsacrine, etoposide (VP16), etoposide phosphate, teniposide, etc.), antitumor antibiotics (e.g., doxorubicin, adriamycin, daunorubicin, epirubicin, actinomycin, bleomycin, mitomycin, mitoxantrone, plicamycin, etc.), platinum-based compounds (e.g. cisplatin, oxaloplatin, carboplatin), anthracenedione (e.g., mitoxantrone), substituted urea (e.g., hydroxyurea), methyl hydrazine derivative (e.g., procarbazine), adrenocortical suppressant (e.g., mitotane, aminoglutethimide), epipodophyllotoxins (e.g., etoposide), antibiotics (e.g., daunorubicin, doxorubicin, bleomycin), enzymes (e.g., L-asparaginase), inhibitors of mitogen-activated protein kinase signaling (e.g. U0126, PD98059, PD184352, PD0325901, ARRY-142886, SB239063, SP600125, BAY 43-9006, wortmannin, or LY294002), mTOR inhibitors, antibodies (e.g., rituxan), 5-aza-2'-deoxycytidine, doxorubicin, vincristine, etoposide, gemcitabine, imatinib (Gleevec®) geldanamycin, 17-N-Allylamino-17-Demethoxygeldanamycin (17-AAG), bortezomib, trastuzumab, anastrozole; angiogenesis inhibitors; antiandrogen, antiestrogen; antisense oligonucleotides; apoptosis gene modulators; apoptosis regulators; arginine deaminase; BCR/ABL antagonists; beta lactam derivatives; bFGF inhibitor; bicalutamide; camptothecin derivatives; casein kinase inhibitors (ICOS); clomifene analogues; cytarabine dacliximab; dexamethasone; estrogen agonists; estrogen antagonists; etanidazole; etoposide phosphate; exemestane; fadrozole; finasteride; fludarabine; fluorodaunorunicin hydrochloride; gadolinium texaphyrin; gallium nitrate; gelatinase inhibitors; gemcitabine; glutathione inhibitors; hepsulfam; immunostimulant peptides; insulin-like growth factor-1 receptor inhibitor; interferon agonists; interferons; interleukins; letrozole; leukemia inhibiting factor; leukocyte alpha interferon; leuprolide+estrogen+progesterone; leuprorelin; matrilysin inhibitors; matrix metalloproteinase inhibitors; MIF inhibitor; mifepristone; mismatched double stranded RNA; monoclonal antibody; mycobacterial cell wall extract; nitric oxide modulators; oxaliplatin; panomifene; pentrozole; phosphatase inhibitors; plasminogen activator inhibitor; platinum complex; platinum compounds; prednisone; proteasome inhibitors; protein A-based immune modulator; protein kinase C inhibitor; protein tyrosine phosphatase inhibitors; purine nucleoside phosphorylase inhibitors; ras farnesyl protein transferase inhibitors; ras inhibitors; ras-GAP inhibitor; ribozymes; signal transduction inhibitors; signal transduction modulators; single chain antigen-binding protein; stem cell inhibitor; stem-cell division inhibitors; stromelysin inhibitors; synthetic glycosaminoglycans; tamoxifen methiodide; telomerase inhibitors; thyroid stimulating hormone; translation inhibitors; tyrosine kinase inhibitors; urokinase receptor antagonists; steroids (e.g., dexamethasone), finasteride, aromatase inhibitors, gonadotropin-releasing hormone agonists (GnRH) such as goserelin or leuprolide, adrenocorticosteroids (e.g., prednisone), progestins (e.g., hydroxyprogesterone caproate, megestrol acetate, medroxyprogesterone acetate), estrogens (e.g., diethylstilbestrol, ethinyl estradiol), antiestrogen (e.g., tamoxifen), androgens (e.g., testosterone propionate, fluoxymesterone), antiandrogen (e.g., flutamide), immunostimulants (e.g., Bacillus Calmette-Guérin (BCG), levamisole, interleukin-2, alpha-interferon, etc.), monoclonal antibodies (e.g., anti-CD20, anti-HER2, anti-CD52, anti-HLA-DR, and anti-VEGF monoclonal antibodies), immunotoxins (e.g., anti-CD33 monoclonal antibody-calicheamicin conjugate, anti-CD22 monoclonal antibody-pseudomonas exotoxin conjugate, etc.), radioimmunotherapy (e.g., anti-CD20 monoclonal antibody conjugated to $^{111}$In, $^{90}$Y, or $^{131}$I, etc.), triptolide, homoharringtonine, dactinomycin, doxorubicin, epirubicin, topotecan, itraconazole, vindesine, cerivastatin, vincristine, deoxyadenosine, sertraline, pitavastatin, irinotecan, clofazimine, 5-nonyloxytryptamine, vemurafenib, dabrafenib, erlotinib, gefitinib, EGFR inhibitors, epidermal growth factor receptor (EGFR)-targeted therapy or therapeutic (e.g. gefitinib (Iressa™), erlotinib (Tarceva™), cetuximab (Erbitux™), lapatinib (Tykerb™), panitumumab (Vectibix™), vandetanib (Caprelsa™), afatinib/BIBW2992, CI-1033/canertinib, neratinib/HKI-272, CP-724714, TAK-285, AST-1306, ARRY334543, ARRY-380, AG-1478, dacomitinib/PF299804, OSI-420/desmethyl erlotinib, AZD8931, AEE788, pelitinib/EKB-569, CUDC-101, WZ8040, WZ4002, WZ3146, AG-490, XL647, PD153035, BMS-599626), sorafenib, imatinib, sunitinib, dasatinib, pyrrolo benzodiazepines (e.g. tomaymycin), carboplatin, CC-1065 and CC-1065 analogs including amino-CBIs, nitrogen mustards (such as chlorambucil and melphalan), dolastatin and dolastatin analogs (including auristatins: eg. monomethyl auristatin E), anthracycline antibiotics (such as doxorubicin, daunorubicin, etc.), duocarmycins and duocarmycin analogs, enediynes (such as neocarzinostatin and calicheamicins), leptomycin derivatives, maytansinoids and maytansinoid analogs (e.g. mertansine), methotrexate, mitomycin C, taxoids, vinca alkaloids (such as vinblastine and vincristine), epothilones (e.g. epothilone B), camptothecin and its clinical analogs topotecan and irinotecan, or the like.

"Chemotherapeutic" or "chemotherapeutic agent" is used in accordance with its plain ordinary meaning and refers to a chemical composition or compound having antineoplastic properties or the ability to inhibit the growth or proliferation of cells.

"Patient" or "subject in need thereof" or "subject" refers to a living organism suffering from or prone to a disease or condition that can be treated by administration of a compound or pharmaceutical composition or by a method, as provided herein. Non-limiting examples include humans, other mammals, bovines, rats, mice, dogs, monkeys, goat, sheep, cows, deer, and other non-mammalian animals. In some embodiments, a patient is human. In some embodiments, a subject is human.

"Disease" or "condition" refer to a state of being or health status of a patient or subject capable of being treated with a compound, pharmaceutical composition, or method provided herein. In some embodiments, the disease is a disease having the symptom of cell hyperproliferation. In some embodiments, the disease is a disease having the symptom of an aberrant level of HER3 activity. In some embodiments, the disease is a cancer. In some further instances, "cancer" refers to human cancers and carcinomas, sarcomas, adenocarcinomas, lymphomas, leukemias, etc., including solid and lymphoid cancers, kidney, breast, lung, bladder, colon, ovarian, prostate, pancreas, stomach, brain, head and neck, skin, uterine, testicular, glioma, esophagus, and liver cancer, including hepatocarcinoma, lymphoma, including B-acute lymphoblastic lymphoma, non-Hodgkin's lymphomas (e.g., Burkitt's, Small Cell, and Large Cell lymphomas), Hodgkin's lymphoma, leukemia (including AML, ALL, and CML), or multiple myeloma. In embodiments, the disease is brain cancer. In embodiments, the disease is neuroblastoma. In embodiments, the disease is glioblastoma.

As used herein, the term "cancer" refers to all types of cancer, neoplasm or malignant tumors found in mammals (e.g. humans), including leukemia, carcinomas and sarcomas. Exemplary cancers that may be treated with a compound or method provided herein include cancer of the prostate, thyroid, endocrine system, brain, breast, cervix, colon, head & neck, liver, kidney, lung, non-small cell lung, melanoma, mesothelioma, ovary, sarcoma, stomach, uterus, Medulloblastoma, colorectal cancer, pancreatic cancer. Additional examples may include, Hodgkin's Disease, Non-Hodgkin's Lymphoma, multiple myeloma, neuroblastoma, glioma, glioblastoma multiforme, ovarian cancer, rhabdomyosarcoma, primary thrombocytosis, primary macroglobulinemia, primary brain tumors, cancer, malignant pancreatic insulanoma, malignant carcinoid, urinary bladder cancer, premalignant skin lesions, testicular cancer, lymphomas, thyroid cancer, neuroblastoma, esophageal cancer, genitourinary tract cancer, malignant hypercalcemia, endometrial cancer, adrenal cortical cancer, neoplasms of the endocrine or exocrine pancreas, medullary thyroid cancer, medullary thyroid carcinoma, melanoma, colorectal cancer, papillary thyroid cancer, hepatocellular carcinoma, or prostate cancer.

The term "leukemia" refers broadly to progressive, malignant diseases of the blood-forming organs and is generally characterized by a distorted proliferation and development of leukocytes and their precursors in the blood and bone marrow. Leukemia is generally clinically classified on the basis of (1) the duration and character of the disease-acute or chronic; (2) the type of cell involved; myeloid (myelogenous), lymphoid (lymphogenous), or monocytic; and (3) the increase or non-increase in the number abnormal cells in the blood-leukemic or aleukemic (subleukemic). Exemplary leukemias that may be treated with a compound or method provided herein include, for example, acute nonlymphocytic leukemia, chronic lymphocytic leukemia, acute granulocytic leukemia, chronic granulocytic leukemia, acute promyelocytic leukemia, adult T-cell leukemia, aleukemic leukemia, a leukocythemic leukemia, basophylic leukemia, blast cell leukemia, bovine leukemia, chronic myelocytic leukemia, leukemia cutis, embryonal leukemia, eosinophilic leukemia, Gross' leukemia, hairy-cell leukemia, hemoblastic leukemia, hemocytoblastic leukemia, histiocytic leukemia, stem cell leukemia, acute monocytic leukemia, leukopenic leukemia, lymphatic leukemia, lymphoblastic leukemia, lymphocytic leukemia, lymphogenous leukemia, lymphoid leukemia, lymphosarcoma cell leukemia, mast cell leukemia, megakaryocytic leukemia, micromyeloblastic leukemia, monocytic leukemia, myeloblastic leukemia, myelocytic leukemia, myeloid granulocytic leukemia, myelomonocytic leukemia, Naegeli leukemia, plasma cell leukemia, multiple myeloma, plasmacytic leukemia, promyelocytic leukemia, Rieder cell leukemia, Schilling's leukemia, stem cell leukemia, subleukemic leukemia, or undifferentiated cell leukemia.

The term "sarcoma" generally refers to a tumor which is made up of a substance like the embryonic connective tissue and is generally composed of closely packed cells embedded in a fibrillar or homogeneous substance. Sarcomas that may be treated with a compound or method provided herein include a chondrosarcoma, fibrosarcoma, lymphosarcoma, melanosarcoma, myxosarcoma, osteosarcoma, Abemethy's sarcoma, adipose sarcoma, liposarcoma, alveolar soft part sarcoma, ameloblastic sarcoma, botryoid sarcoma, chloroma sarcoma, chorio carcinoma, embryonal sarcoma, Wilms' tumor sarcoma, endometrial sarcoma, stromal sarcoma, Ewing's sarcoma, fascial sarcoma, fibroblastic sarcoma, giant cell sarcoma, granulocytic sarcoma, Hodgkin's sarcoma, idiopathic multiple pigmented hemorrhagic sarcoma, immunoblastic sarcoma of B cells, lymphoma, immunoblastic sarcoma of T-cells, Jensen's sarcoma, Kaposi's sarcoma, Kupffer cell sarcoma, angiosarcoma, leukosarcoma, malignant mesenchymoma sarcoma, parosteal sarcoma, reticulocytic sarcoma, Rous sarcoma, serocystic sarcoma, synovial sarcoma, or telangiectaltic sarcoma.

The term "melanoma" is taken to mean a tumor arising from the melanocytic system of the skin and other organs. Melanomas that may be treated with a compound or method provided herein include, for example, acral-lentiginous melanoma, amelanotic melanoma, benign juvenile melanoma, Cloudman's melanoma, S91 melanoma, Harding-Passey melanoma, juvenile melanoma, lentigo maligna melanoma, malignant melanoma, nodular melanoma, subungal melanoma, or superficial spreading melanoma.

The term "carcinoma" refers to a malignant new growth made up of epithelial cells tending to infiltrate the surrounding tissues and give rise to metastases. Exemplary carcinomas that may be treated with a compound or method provided herein include, for example, medullary thyroid carcinoma, familial medullary thyroid carcinoma, acinar carcinoma, acinous carcinoma, adenocystic carcinoma, adenoid cystic carcinoma, carcinoma adenomatosum, carcinoma of adrenal cortex, alveolar carcinoma, alveolar cell carcinoma, basal cell carcinoma, carcinoma basocellulare, basaloid carcinoma, basosquamous cell carcinoma, bronchioalveolar carcinoma, bronchiolar carcinoma, bronchogenic carcinoma, cerebriform carcinoma, cholangiocellular carcinoma, chorionic carcinoma, colloid carcinoma, comedo carcinoma, corpus carcinoma, cribriform carcinoma, carcinoma en cuirasse, carcinoma cutaneum, cylindrical carcinoma, cylindrical cell carcinoma, duct carcinoma, carcinoma durum, embryonal carcinoma, encephaloid carcinoma, epiermoid carcinoma, carcinoma epitheliale adenoides, exophytic carcinoma, carcinoma ex ulcere, carcinoma fibrosum, gelatiniforni carcinoma, gelatinous carcinoma, giant cell carcinoma, carcinoma gigantocellulare, glandular carcinoma, granulosa cell carcinoma, hair-matrix carcinoma, hematoid carcinoma, hepatocellular carcinoma, Hurthle cell carcinoma, hyaline carcinoma, hypernephroid carcinoma, infantile embryonal carcinoma, carcinoma in situ, intraepidermal carcinoma, intraepithelial carcinoma, Krompecher's carcinoma, Kulchitzky-cell carcinoma, large-cell carcinoma, lenticular carcinoma, carcinoma lenticulare, lipomatous carcinoma, lymphoepithelial carcinoma, carcinoma medullare, medullary carcinoma, melanotic carcinoma, carcinoma molle, mucinous carcinoma, carcinoma muciparum, carcinoma mucocellulare, mucoepidermoid carcinoma, carcinoma mucosum, mucous carcinoma, carcinoma myxomatodes, nasopharyngeal carcinoma, oat cell carcinoma, carcinoma ossificans, osteoid carcinoma, papillary carcinoma, periportal carcinoma, preinvasive carcinoma, prickle cell carcinoma, pultaceous carcinoma, renal cell carcinoma of kidney, reserve cell carcinoma, carcinoma sarcomatodes, schneiderian carcinoma, scirrhous carcinoma, carcinoma scroll, signet-ring cell carcinoma, carcinoma simplex, small-cell carcinoma, solanoid carcinoma, spheroidal cell carcinoma, spindle cell carcinoma, carcinoma spongiosum, squamous carcinoma, squamous cell carcinoma, string carcinoma, carcinoma telangiectaticum, carcinoma telangiectodes, transitional cell carcinoma, carcinoma tuberosum, tuberous carcinoma, verrucous carcinoma, or carcinoma villosum.

The term "signaling pathway" as used herein refers to a series of interactions between cellular and optionally extracellular components (e.g. proteins, nucleic acids, small molecules, ions, lipids) that conveys a change in one component to one or more other components, which in turn may convey a change to additional components, which is optionally propagated to other signaling pathway components.

The term "aberrant" as used herein refers to different from normal. When used to describe enzymatic activity, aberrant refers to activity that is greater or less than a normal control or the average of normal non-diseased control samples. Aberrant activity may refer to an amount of activity that results in a disease, wherein returning the aberrant activity to a normal or non-disease-associated amount (e.g. by administering a compound or using a method as described herein), results in reduction of the disease or one or more disease symptoms.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 10 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, *Adv. Appl. Math.* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci. USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., *Current Protocols in Molecular Biology* (Ausubel et al., eds. 1995 supplement)).

Twenty amino acids are commonly found in proteins. Those amino acids can be grouped into nine classes or groups based on the chemical properties of their side chains. Substitution of one amino acid residue for another within the same class or group is referred to herein as a "conservative" substitution. Conservative amino acid substitutions can frequently be made in a protein without significantly altering the conformation or function of the protein. Substitution of one amino acid residue for another from a different class or group is referred to herein as a "non-conservative" substitution. In contrast, non-conservative amino acid substitutions tend to modify conformation and function of a protein.

Example of Amino Acid Classification

| | |
|---|---|
| Small/Aliphatic residues: | Gly, Ala, Val, Leu, Ile |
| Cyclic Imino Acid: | Pro |
| Hydroxyl-containing Residues: | Ser, Thr |
| Acidic Residues: | Asp, Glu |
| Amide Residues: | Asn, Gln |
| Basic Residues: | Lys, Arg |
| Imidazole Residue: | His |
| Aromatic Residues: | Phe, Tyr, Trp |
| Sulfur-containing Residues: | Met, Cys |

In some embodiments, the conservative amino acid substitution comprises substituting any of glycine (G), alanine (A), isoleucine (I), valine (V), and leucine (L) for any other of these aliphatic amino acids; serine (S) for threonine (T) and vice versa; aspartic acid (D) for glutamic acid (E) and vice versa; glutamine (Q) for asparagine (N) and vice versa; lysine (K) for arginine (R) and vice versa; phenylalanine (F), tyrosine (Y) and tryptophan (W) for any other of these aromatic amino acids; and methionine (M) for cysteine (C) and vice versa. Other substitutions can also be considered conservative, depending on the environment of the particular amino acid and its role in the three-dimensional structure of the protein. For example, glycine (G) and alanine (A) can frequently be interchangeable, as can alanine (A) and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pKs of these two amino acid residues are not significant. Still other changes can be considered "conservative" in particular environments (see, e.g., BIOCHEMISTRY at pp. 13-15, 2nd ed. Lubert Stryer ed. (Stanford University); Henikoff et al., *Proc. Nat'l Acad. Sci. USA* (1992) 89:10915-10919; Lei et al., *J. Biol. Chem.* (1995) 270(20):11882-11886).

"Polypeptide," "peptide," and "protein" are used herein interchangeably and mean any peptide-linked chain of amino acids, regardless of length or post-translational modification. As noted below, the polypeptides described herein can be, e.g., wild-type proteins, biologically-active fragments of the wild-type proteins, or variants of the wild-type proteins or fragments. Variants, in accordance with the disclosure, can contain amino acid substitutions, deletions, or insertions. The substitutions can be conservative or non-conservative.

Following expression, the proteins can be isolated. The term "purified" or "isolated" as applied to any of the proteins described herein refers to a polypeptide that has been separated or purified from components (e.g., proteins or other naturally-occurring biological or organic molecules) which naturally accompany it, e.g., other proteins, lipids, and nucleic acid in a cell expressing the proteins. Typically, a polypeptide is purified when it constitutes at least 60 (e.g., at least 65, 70, 75, 80, 85, 90, 92, 95, 97, or 99) %, by weight, of the total protein in a sample.

An amino acid residue in a protein "corresponds" to a given residue when it occupies the same essential structural position within the protein as the given residue. For example, a selected residue in a selected protein corresponds to a particular amino acid in HER3 when the selected residue occupies the same essential spatial or other structural relationship as particular amino acid in HER3. In some embodiments, where a selected protein is aligned for maximum homology with the human HER3 protein, the position in the aligned selected protein aligning with a particular reside is said to correspond to that particular reside. Instead of a primary sequence alignment, a three dimensional structural alignment can also be used, e.g., where the structure of the selected protein is aligned for maximum correspondence with the human HER3 protein and the overall structures compared. In this case, an amino acid that occupies the same essential position as a particular reside in the structural model is said to correspond to the particular reside.

"Pharmaceutically acceptable excipient" and "pharmaceutically acceptable carrier" refer to a substance that aids the administration of an active agent to and absorption by a subject and can be included in the compositions of the present invention without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethylcellulose, polyvinyl pyrrolidine, and colors, and the like. Such preparations can be sterilized and, if desired, mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the invention. One of skill in the art will recognize that other pharmaceutical excipients are useful in the present invention.

The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

As used herein, the term "administering" means oral administration, administration as a suppository, topical contact, intravenous, parenteral, intraperitoneal, intramuscular, intralesional, intrathecal, intracranial, intranasal or subcutaneous administration, or the implantation of a slow-release device, e.g., a mini-osmotic pump, to a subject. Administration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches. etc. By "co-administer" it is meant that a composition described herein is administered at the same time, just prior to, or just after the administration of one or more additional therapies (e.g. anti-cancer agent). The compound of the invention can be administered alone or can be coadministered to the patient. Coadministration is meant to include simultaneous or sequential administration of the compound individually or in combination (more than one compound or agent). Thus, the preparations can also be combined, when desired, with other active substances (e.g. to reduce metabolic degradation, to increase degradation of a prodrug and release of the drug, detectable agent). The compositions of the present invention can be delivered by transdermally, by a topical route, formulated as applicator sticks, solutions, suspensions, emulsions, gels, creams, ointments, pastes, jellies, paints, powders, and aerosols. Oral preparations include tablets, pills, powder, dragees, capsules, liquids, lozenges, cachets, gels, syrups, slurries, suspensions, etc., suitable for ingestion by the patient. Solid form preparations include powders, tablets, pills, capsules, cachets, suppositories, and dispersible granules. Liquid form preparations include solutions, suspensions, and emulsions, for example, water or water/propylene glycol solutions. The compositions of the present invention may additionally include components to provide sustained release and/or comfort. Such components include high molecular weight, anionic mucomimetic polymers, gelling polysaccharides and finely-divided drug carrier substrates. These components are discussed in greater detail in U.S. Pat. Nos. 4,911,920; 5,403,841; 5,212,162; and 4,861,760. The entire contents of these patents are incorporated herein by reference in their entirety for all purposes. The compositions of the present invention can also be delivered as microspheres for slow release in the body. For example, microspheres can be administered via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). In another embodiment, the formulations of the compositions of the present invention can be delivered by the use of liposomes which fuse with the cellular membrane or are endocytosed, i.e., by employing receptor ligands attached to the liposome, that bind to surface membrane protein receptors of the cell resulting in endocytosis. By using liposomes, particularly where the liposome surface carries receptor ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989). The compositions of the present invention can also be delivered as nanoparticles.

Pharmaceutical compositions provided by the present invention include compositions wherein the active ingredient (e.g. compounds described herein, including embodiments or examples) is contained in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., reducing, eliminating, or slowing the progression of disease symptoms (e.g. symptoms of cancer or aberrant HER3 activity). Determination of a therapeutically effective amount of a compound of the invention is well within the capabilities of those skilled in the art, especially in light of the detailed disclosure herein.

The dosage and frequency (single or multiple doses) administered to a mammal can vary depending upon a variety of factors, for example, whether the mammal suffers from another disease, and its route of administration; size, age, sex, health, body weight, body mass index, and diet of the recipient; nature and extent of symptoms of the disease being treated (e.g. symptoms of cancer), kind of concurrent treatment, complications from the disease being treated or other health-related problems. Other therapeutic regimens or agents can be used in conjunction with the methods and compounds of Applicants' invention. Adjustment and manipulation of established dosages (e.g., frequency and duration) are well within the ability of those skilled in the art.

For any compound described herein, the therapeutically effective amount can be initially determined from cell culture assays. Target concentrations will be those concentrations of active compound(s) that are capable of achieving the methods described herein, as measured using the methods described herein or known in the art.

As is well known in the art, therapeutically effective amounts for use in humans can also be determined from animal models. For example, a dose for humans can be formulated to achieve a concentration that has been found to be effective in animals. The dosage in humans can be adjusted by monitoring compounds effectiveness and adjusting the dosage upwards or downwards, as described above. Adjusting the dose to achieve maximal efficacy in humans based on the methods described above and other methods is well within the capabilities of the ordinarily skilled artisan.

Dosages may be varied depending upon the requirements of the patient and the compound being employed. The dose administered to a patient, in the context of the present invention should be sufficient to effect a beneficial therapeutic response in the patient over time. The size of the dose also will be determined by the existence, nature, and extent of any adverse side-effects. Determination of the proper dosage for a particular situation is within the skill of the practitioner. Generally, treatment is initiated with smaller dosages which are less than the optimum dose of the compound. Thereafter, the dosage is increased by small increments until the optimum effect under circumstances is reached.

Dosage amounts and intervals can be adjusted individually to provide levels of the administered compound effective for the particular clinical indication being treated. This will provide a therapeutic regimen that is commensurate with the severity of the individual's disease state.

Utilizing the teachings provided herein, an effective prophylactic or therapeutic treatment regimen can be planned that does not cause substantial toxicity and yet is effective to treat the clinical symptoms demonstrated by the particular patient. This planning should involve the careful choice of active compound by considering factors such as compound potency, relative bioavailability, patient body weight, presence and severity of adverse side effects, preferred mode of administration and the toxicity profile of the selected agent.

The compounds described herein can be used in combination with one another, with other active agents known to be useful in treating cancer, or with adjunctive agents that may not be effective alone, but may contribute to the efficacy of the active agent.

In some embodiments, co-administration includes administering one active agent within 0.5, 2, 4, 6, 8, 10, 12, 16, 20, or 24 hours of a second active agent. Co-administration includes administering two active agents simultaneously, approximately simultaneously (e.g., within about 1, 5, 10, 15, 20, or 30 minutes of each other), or sequentially in any order. In some embodiments, co-administration can be accomplished by co-formulation, i.e., preparing a single pharmaceutical composition including both active agents. In other embodiments, the active agents can be formulated separately. In another embodiment, the active and/or adjunctive agents may be linked or conjugated to one another. In some embodiments, the compounds described herein may be combined with treatments for cancer such as radiation or surgery.

As used herein, the term "about" means a range of values including the specified value, which a person of ordinary skill in the art would consider reasonably similar to the specified value. In embodiments, about means within a standard deviation using measurements generally acceptable in the art. In embodiments, about means a range extending to +/−10% of the specified value. In embodiments, about includes the specified value.

The term "Receptor tyrosine-protein kinase erbB-3", "human epidermal growth factor receptor 3", "ERBB3", or "HER3" refers to a pseudokinase (reduced activity or inactive kinase) that s a member of the epidermal growth factor receptor (EGFR/ERBB) family of receptor tyrosine kinases. The term "HER3" may refer to the nucleotide sequence or protein sequence of human HER3 (e.g., Entrez 2065, Uniprot P21860, RefSeq NM_001982, or RefSeq NP_001973). The term "HER3" includes both the wild-type form of the nucleotide sequences or proteins as well as any mutants thereof. In some embodiments, "HER3" is wild-type HER3 receptor. In some embodiments, "HER3" is one or more mutant forms. The term "HER3" XYZ refers to a nucleotide sequence or protein of a mutant HER3 wherein the Y numbered amino acid of HER3 that normally has an X amino acid in the wildtype, instead has a Z amino acid in the mutant. In embodiments, an HER3 is the human HER3. In embodiments, the HER3 has the nucleotide sequence corresponding to reference number GI:317171925. In embodiments, the HER3 has the nucleotide sequence corresponding to RefSeq NM_001982.3. In embodiments, the HER3 has the protein sequence corresponding to reference number GI:54792100. In embodiments, the HER3 has the protein sequence corresponding to RefSeq NP_001973.2. In embodiments, the HER3 has the following amino acid sequence:

```
                                          (SEQ ID NO: 1)
MRANDALQVLGLLFSLARGSEVGNSQAVCPGTLNGLSVTGDAENQYQT

LYKLYERCEVVMGNLEIVLTGHNADLSFLQWIREVTGYVLVAMNEFST

LPLPNLRVVRGTQVYDGKFAIFVMLNYNTNSSHALRQLRLTQLTEILS
```

-continued
```
GGVYIEKNDKLCHMDTIDWRDIVRDRDAEIVVKDNGRSCPPCHEVCKG

RCWGPGSEDCQTLTKTICAPQCNGHCFGPNPNQCCHDECAGGCSGPQD

TDCFACRHFNDSGACVPRCPQPLVYNKLTFQLEPNPHTKYQYGGVCVA

SCPHNFVVDQTSCVRACPPDKMEVDKNGLKMCEPCGGLCPKACEGTGS

GSRFQTVDSSNIDGFVNCTKILGNLDFLITGLNGDPWHKIPALDPEKL

NVFRTVREITGYLNIQSWPPHMHNFSVFSNLTTIGGRSLYNRGFSLLI

MKNLNVTSLGFRSLKEISAGRIYISANRQLCYHHSLNWTKVLRGPTEE

RLDIKHNRPRRDCVAEGKVCDPLCSSGGCWGPGPGQCLSCRNYSRGGV

CVTHCNFLNGEPREFAHEAECFSCHPECQPMEGTATCNGSGSDTCAQC

AHFRDGPHCVSSCPHGVLGAKGPIYKYPDVGNECRPCHENCTQGCKGP

ELQDCLGQTLVLIGKTHLTMALTVIAGLVVIFMMLGGTFLYWRGRRIQ

NKRAMRRYLERGESIEPLDPSEKANKVLARIFKETELRKLKVLGSGVF

GTVHKGVWIPEGESIKIPVCIKVIEDKSGRQSFQAVTDHMLAIGSLDH

AHIVRLLGLCPGSSLQLVTQYLPLGSLLDHVRQHRGALGPQLLLNWGV

QIAKGMYYLEEHGMVHRNLAARNVLLKSPSQVQVADFGVADLLPPDDK

QLLYSEAKTPIKWMALESIHFGKYTHQSDVWSYGVTVWELMTFGAEPY

AGLRLAEVPDLLEKGERLAQPQICTIDVYMVMVKCWMIDENIRPTFKE

LANEFTRMARDPPRYLVIKRESGPGIAPGPEPHGLTNKKLEEVELEPE

LDLDLDLEAEEDNLATTTLGSALSLPVGTLNRPRGSQSLLSPSSGYMP

MNQGNLGESCQESAVSGSSERCPRPVSLHPMPRGCLASESSEGHVTGS

EAELQEKVSMCRSRSRSRSPRPRGDSAYHSQRHSLLTPVTPLSPPGLE

EEDVNGYVMPDTHLKGTPSSREGTLSSVGLSSVLGTEEEDEDEEYEYM

NRRRRHSPPHPPRPSSLEELGYEYMDVGSDLSASLGSTQSCPLHPVPI

MPTAGTTPDEDYEYMNRQRDGGGPGGDYAAMGACPASEQGYEEMRAFQ

GPGHQAPHVHYARLKTLRSLEATDSAFDNPDYWHSRLFPKANAQRT.
```

In embodiments, the HER3 is a mutant HER3. In embodiments, the mutant HER3 is associated with a disease that is not associated with wildtype HER3. In embodiments, the HER3 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above. In embodiments, the HER3 is a variant of the sequence above, including a shorter variant or mutated variant. In embodiments, the mutant HER3 is a splice variant. In embodiments, the mutant HER3 is a splice variant with aberrant activity relative to the wildtype HER3. In embodiments, the mutant HER3 is a truncated splice variant with aberrant activity relative to the wildtype HER3. In embodiments, the mutant HER3 is a splice variant lacking a portion of the wildtype HER3 with aberrant activity relative to the wildtype HER3. In embodiments, the HER3 is described in Cancer Cell (2013) May 13 23, 603-617, which is herein incorporated in its entirety for all purposes.

The term "Receptor tyrosine-protein kinase erbB-2", "human epidermal growth factor receptor 2", "CD340", "ERBB2", "neu", "HER2/neu", or "HER2" refers to a member of the epidermal growth factor receptor (EGFR/ERBB) family of receptor tyrosine kinases. The term "HER2" may refer to the nucleotide sequence or protein sequence of human HER2 (e.g., Entrez 2064, Uniprot P04626, RefSeq NM_004448, or RefSeq NP_004439). The term "HER2" includes both the wild-type form of the nucleotide sequences or proteins as well as any mutants thereof. In some embodiments, "HER2" is wild-type HER3 receptor. In some embodiments, "HER2" is one or more mutant forms. The term "HER2" XYZ refers to a nucleotide sequence or protein of a mutant HER2 wherein the Y numbered amino acid of HER2 that normally has an X amino acid in the wildtype, instead has a Z amino acid in the mutant. In embodiments, an HER2 is the human HER2. In embodiments, the HER2 has the nucleotide sequence corresponding to reference number GI:584277099. In embodiments, the HER2 has the nucleotide sequence corresponding to RefSeq NM_004448.3. In embodiments, the HER2 has the protein sequence corresponding to reference number GI:54792096. In embodiments, the HER2 has the protein sequence corresponding to RefSeq NP_004439.2. In embodiments, the HER2 has the following amino acid sequence:

```
                                            (SEQ ID NO: 2)
MELAALCRWGLLLALLPPGAASTQVCTGTDMKLRLPASPETHLDMLRH

LYQGCQVVQGNLELTYLPTNASLSFLQDIQEVQGYVLIAHNQVRQVPL

QRLRIVRGTQLFEDNYALAVLDNGDPLNNTTPVTGASPGGLRELQLRS

LTEILKGGVLIQRNPQLCYQDTILWKDIFHKNNQLALTLIDTNRSRAC

HPCSPMCKGSRCWGESSEDCQSLTRTVCAGGCARCKGPLPTDCCHEQC

AAGCTGPKHSDCLACLHFNHSGICELHCPALVTYNTDTFESMPNPEGR

YTFGASCVTACPYNYLSTDVGSCTLVCPLHNQEVTAEDGTQRCEKCSK

PCARVCYGLGMEHLREVRAVTSANIQEFAGCKKIFGSLAFLPESFDGD

PASNTAPLQPEQLQVFETLEEITGYLYISAWPDSLPDLSVFQNLQVIR

GRILHNGAYSLTLQGLGISWLGLRSLRELGSGLALIHHNTHLCFVHTV

PWDQLFRNPHQALLHTANRPEDECVGEGLACHQLCARGHCWGPGPTQC

VNCSQFLRGQECVEECRVLQGLPREYVNARHCLPCHPECQPQNGSVTC

FGPEADQCVACAHYKDPPFCVARCPSGVKPDLSYMPIWKFPDEEGACQ

PCPINCTHSCVDLDDKGCPAEQRASPLTSIISAVVGILLVVVLGVVFG

ILIKRRQQKIRKYTMRRLLQETELVEPLTPSGAMPNQAQMRILKETEL

RKVKVLGSGAFGTVYKGIWIPDGENVKIPVAIKVLRENTSPKANKEIL

DEAYVMAGVGSPYVSRLLGICLTSTVQLVTQLMPYGCLLDHVRENRGR

LGSQDLLNWCMQIAKGMSYLEDVRLVHRDLAARNVLVKSPNHVKITDF

GLARLLDIDETEYHADGGKVPIKWMALESILRRRFTHQSDVWSYGVTV

WELMTFGAKPYDGIPAREIPDLLEKGERLPQPPICTIDVYMIMVKCWM

IDSECRPRFRELVSEFSRMARDPQRFVVIQNEDLGPASPLDSTFYRSL

LEDDDMGDLVDAEEYLVPQQGFFCPDPAPGAGGMVHHRHRSSSTRSGG

GDLTLGLEPSEEEAPRSPLAPSEGAGSDVFDGDLGMGAAKGLQSLPTH

DPSPLQRYSEDPTVPLPSETDGYVAPLTCSPQPEYVNQPDVRPQPPSP

REGPLPAARPAGATLERPKTLSPGKNGVVKDVFAFGGAVENPEYLTPQ

GGAAPQPHPPPAFSPAFDNLYYWDQDPPERGAPPSTFKGTPTAENPEY

LGLDVPV.
```

In embodiments, the HER2 is a mutant HER2. In embodiments, the mutant HER2 is associated with a disease that is not associated with wildtype HER2. In embodiments, the HER2 includes at least one amino acid mutation (e.g., 1, 2, 3, 4, 5, 6, 7, 8, 9, 10, 11, 12, 13, 14, 15, 16, 17, 18, 19, 20, 21, 22, 23, 24, 25, 26, 27, 28, 29, or 30 mutations) compared to the sequence above. In embodiments, the HER2 is a variant of the sequence above, including a shorter variant or mutated variant. In embodiments, the mutant HER2 is a splice variant. In embodiments, the mutant HER2 is a splice variant with aberrant activity relative to the wildtype HER2. In embodiments, the mutant HER2 is a truncated splice variant with aberrant activity relative to the wildtype HER2. In embodiments, the mutant HER2 is a splice variant lacking a portion of the wildtype HER2 with aberrant activity relative to the wildtype HER2.

The term "ligand" is used in accordance with its plain ordinary meaning and refers to a molecule (e.g., compound as described herein) capable of binding to another molecule (e.g., protein, receptor, enzyme, target, or cell). In embodiments, a ligand is a modulator, inhibitor, activator, agonist, or antagonist.

Provided herein are agents (e.g. compounds, drugs, therapeutic agents) that may be in a prodrug form. Prodrugs of the compounds described herein are those compounds that readily undergo chemical changes under select physiological conditions to provide the final agents (e.g. compounds, drugs, therapeutic agents). Additionally, prodrugs can be converted to agents (e.g. compounds, drugs, therapeutic agents) by chemical or biochemical methods in an ex vivo environment. Prodrugs described herein include compounds that readily undergo chemical changes under select physiological conditions to provide agents (e.g. compounds, drugs, prophylactic agents, therapeutic agents) to a biological system (e.g. in a subject, in a cancer cell, in the extracellular space near a cancer cell). For example, physiologically hydrolyzable esters or amides are esters or amides, respectively, that are hydrolyzed to the corresponding hydroxyl and carboxylic acid portions of the ester, or the corresponding amine and carboxylic acid portions of the amide, by a chemical or enzymatic reaction (e.g., esterase or amidase or protease) following administration to a subject.

"Analog" and "analogue" are used interchangeably and are used in accordance with their plain ordinary meaning within Chemistry and Biology and refers to a chemical compound that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof or but differs in one or more components (e.g., different substituent(s), addition of substituent(s), removal of substituent(s)). Accordingly, an analog is a compound that is similar or comparable in function and appearance but not in structure or origin to a reference compound.

The term "derivative" is used in accordance with its plain ordinary meaning in Chemistry and refers to a compound that is derived (e.g., a product made from a reactant) from a similar compound by a chemical or physical process. "Derivative" is used in accordance with its plain ordinary meaning within Chemistry and Biology and refers to a compound (e.g., chemical) that is structurally similar to another compound (i.e., a so-called "reference" compound) but differs in composition, e.g., in the replacement of one atom by an atom of a different element, or in the presence of a particular functional group, or the replacement of one functional group by another functional group, or the absolute stereochemistry of one or more chiral centers of the reference compound, including isomers thereof; and the derivative is a compound that was derived from the reference compound through one or more chemical reaction(s) or the reference compound was derived from the derivative through one or more chemical reaction(s). Accordingly, a derivative is a compound that is similar or comparable in function and appearance but not in structure or origin to a reference compound. In embodiments of a derivative, an original substituent (e.g., substituent group) of a reference compound is replaced with an alternative substituent (e.g., substituent group), wherein the alternative substituent (e.g., substituent group) is different from the original substituent (e.g., substituent group). In embodiments of a derivative, a plurality of original substituents substituent groups) of a reference compound are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a reference compound is replaced with a substituent (e.g., substituent group). In embodiments of a derivative, a plurality of hydrogen atoms of a reference compound are replaced with a plurality of substituents (e.g., substituent groups), wherein the substituents (e.g., substituent groups) are each optionally different.

The term "HER3 activity" is used in accordance with its plain ordinary meaning and refers to the function or activity of the HER3 protein. Examples of HER3 activity include dimerization (e.g., heterodimerization or activation of the activity of a protein upon dimerization with HER3 (e.g., EGFR activity, HER2 activity, HER4 activity, or c-MET activity). In embodiments, HER3 activity is increasing or activating activity of a protein interacting with HER3 (e.g., PI3K activity, MEK activity, MAPK activity, RAF activity, BRAF activity, AKT activity, RAS activity, or KRAS activity). In embodiments HER3 activity is activation or increasing of activity of a signaling pathway by HER3 or activation of a component of a signaling pathway by HER3 (e.g., directly or through intervening components of the signaling pathway). In embodiments HER3 activity is activation of kinase activity of a protein that interacts (e.g., directly contacting HER3 or interactions with HER3 through intermediates) with HER3 (e.g., EGFR, HER2, HER4, c-MET, PI3K, MEK, MAPK, RAF, BRAF, AKT, RAS, or KRAS).

The term "degradation-increasing moiety" is used in accordance with its plain ordinary meaning and refers to a moiety capable of increasing the degradation of a protein or other biological molecule (e.g., including by binding to the protein or other biological molecule or by binding to the protein or other biological molecule through a second moiety bonded to the degradation-increasing moiety (e.g., wherein the degradation-increasing moiety and second moiety are a compound described herein and the protein or other biological molecule bound to the compound described herein is a HER protein, for example HER3, and the HER protein (e.g., HER3) is degraded more than control (e.g., degradation in the absence of the compound including the degradation-increasing moiety)). In embodiments, a degradation-increasing moiety increases the interaction of a protein to be degraded with a cell's protein degradation components (e.g., ubiquitin ligase(s), proteasome, E3 ubiquitin ligase (e.g., cereblon, HECT, RING-finger, U-box, PHD-finger, APC, SCF complex (Skp1-Cullin-F-box protein complex), E3A, mdm2, EDD1, SOCS, LNXp80, CBX4, HACE1, CBLL1, HECTD1, HECTD2, HECTD3, HECW1, HECW2, HERC1, HERC2, HERC3, HERC4, HUWE1, ITCH, NEDD4, NEDD4L, PPIL2, PRPF19, PIAS1, PIAS2, PIAS3, PIAS4, RANBP2, RNF4, RBX1, SMURF1, SMURF2, STUB1, TOPORS, TRIP12, UBE3A, UBE3B, UBE3C, UBE4A, UBE4B, UBOX5, UBR5, WWP1, WWP2, VHL, or VHL-cullin-RING-ligase complex). In embodiments, the degradation-increasing moiety binds (e.g., directly or through another moiety bonded to the degradation-increasing moiety (e.g., another portion of a compound that includes a degradation-increasing moiety)) to the protein to be degraded and a component of the cell's protein degradation effectors (e.g., E3 ubiquitin ligase). In embodiments, the degradation-increasing moiety is a thalidomide moiety or an analog, derivative, or prodrug thereof; phthalimide moiety or an analog, derivative, or prodrug thereof; adamantyl or an analog, derivative, or prodrug thereof; an IκBα phosphopeptide moiety or an analog, derivative, or prodrug thereof; nutlin moiety or an analog, derivative, or prodrug thereof; HIF-1α pentapeptide moiety or an analog, derivative, or prodrug thereof; or

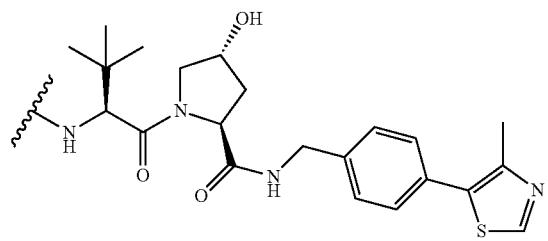 [SMILES: *N[C@H](C(=O)N1C[C@H](O)C[C@H]1C(=O)NCc1ccc(-c2scnc2C)cc1)C(C)(C)C]

or an analog, derivative, or prodrug thereof. In embodiments, the degradation-increasing moiety is described in Bioorg. Med. Chem. Lett (2008) 18 5904-5908; Cancer Cell (2011) August 16, 20, 158-172; Nat Chem Biol (2014) December vol 10, 1006-1012; Nat Chem Biol (2015) August vol 11 611-617; Oncogene (2008) 27, 7201-7211; P. Natl Acad Sci USA (2001) July 17, vol. 98(15) 8554-8559; Science (2015) 348, 1376-1381; U.S. Pat. Nos. 7,208,157; 7,041,298; US publ. no. 20150119435; US publ. no. 20040038358; or US publ. no. 20020068063, all of which are herein incorporated by reference in their entirely and for all purposes.

B. Compounds

In an aspect is provided a compound having the formula:

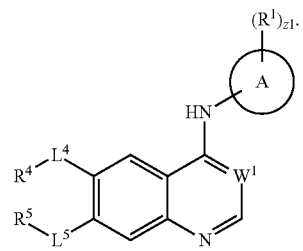

Ring A is aryl or heteroaryl. $W^1$ is N or $C(R^6)$. $R^1$ is independently a halogen, $-CX^1_3$, $-CHX^1_2$, $-CH_2X^1$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-$ OR$^9$, —NR$^7$OR$^9$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^1$ substituents may optionally be joined to form a substituted or unsubstituted cycloalkyl, substituted or unsubstituted heterocycloalkyl substituted or unsubstituted aryl, or substituted or unsubstituted heteroaryl, R$^4$ is independently a hydrogen, halogen, —CX$^4_3$, —CHX$^4_2$, —CH$_2$X$^4$, —CN, —OH, —COOH, —CONH$_2$, —NO$_2$, —SH, —SO$_3$H, —SO$_4$H, —SO$_2$NH$_2$, —NHC═(O)NHNH$_2$, —NHC═(O)NH$_2$, —NHSO$_2$H, —NHC═(O)H, —NHC(O)—OH, —NHOH, —OCX$^4_3$, —OCHX$^4_2$, —OCH$_2$X$^4_2$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^5$ is independently a hydrogen, halogen, —CX$^5_3$, —CHX$^5_2$, —CH$_2$X$^5$, —CN, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^5_3$, —OCHX$^5_2$, —OCH$_2$X$^5$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted or substituted or unsubstituted heteroaryl. R$^6$ is independently a hydrogen, halogen, —CX$^6_3$, —CHX$^6_2$, —CH$_2$X$^6$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^6_3$, —OCHX$^6_2$, —OCH$_2$X$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. R$^7$, R$^8$, R$^9$, and R$^{10}$ are independently hydrogen, halogen, —CX$^A_3$, —CHX$^A_2$, —CH$_2$X$^A$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC═(O)NHNH$_2$, —NHC═(O)NH$_2$, —NHSO$_2$H, —NHC═(O)H, —NHC(O)—OH, —NHOH, —OCX$^A_3$, —OCHX$^A_2$, —OCH$_2$X$^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl. L$^4$ is a bond or a divalent linker. L$^5$ is a bond or a divalent linker. z1 is independently an integer from 0 to 7. m1 and v1 are independently 1 or 2. n1 is independently an integer from 0 to 4. X$^1$, X$^4$, X$^5$, X$^6$, and X$^A$ are independently —Cl, —Br, —I, or —F. In embodiments, one of R$^4$ and R$^5$ is a degradation-increasing moiety (e.g., as described herein, including in an embodiment). In embodiments, R$^4$ is a degradation-increasing moiety (e.g., as described herein, including in an embodiment). In embodiments, R$^5$ is a degradation-increasing moiety (e.g., as described herein, including in an embodiment). In embodiments, R$^4$ and R$^5$ are independently an optionally different degradation-increasing moiety (e.g., as described herein, including in an embodiment). In embodiments, R$^4$ is a degradation-increasing moiety selected from a thalidomide moiety or an analog, derivative, or prodrug thereof; phthalimide moiety or an analog, derivative, or prodrug thereof; adamantyl or an analog, derivative, or prodrug thereof; an IκBα phosphopeptide moiety or an analog, derivative, or prodrug thereof; nutlin moiety or an analog, derivative, or prodrug thereof; and HIF-1α pentapeptide moiety or an analog, derivative, or prodrug thereof; and

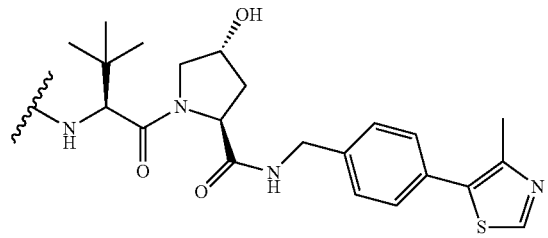 [SMILES: *N[C@H](C(=O)N1C[C@H](O)C[C@H]1C(=O)NCc1ccc(-c2scnc2C)cc1)C(C)(C)C]

or an analog, derivative, or prodrug thereof. In embodiments, R$^5$ is a degradation-increasing moiety selected from a thalidomide moiety or an analog, derivative, or prodrug thereof; phthalimide moiety or an analog, derivative, or prodrug thereof; adamantyl or an analog, derivative, or prodrug thereof; an IκBα phosphopeptide moiety or an analog, derivative, or prodrug thereof; nutlin moiety or an analog, derivative, or prodrug thereof; and HIF-1α pentapeptide moiety or an analog, derivative, or prodrug thereof; and

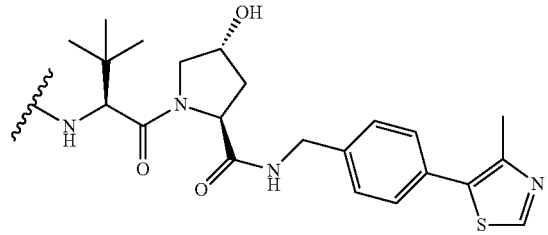 [SMILES: *N[C@H](C(=O)N1C[C@H](O)C[C@H]1C(=O)NCc1ccc(-c2scnc2C)cc1)C(C)(C)C]

or an analog, derivative, or prodrug thereof.

In an aspect is provided a compound having the formula:

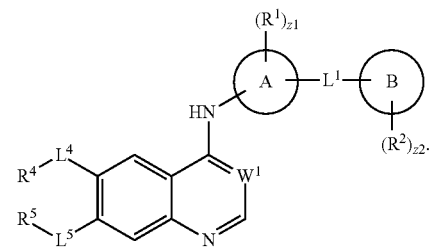

Ring A is aryl or heteroaryl. Ring B is aryl or heteroaryl. W$^1$ is N or C(R$^6$). R$^1$ is independently a halogen, —CX$^1_3$, —CHX$^1_2$, —CH$_2$X$^1$, —CN, —SO$_{n1}$R$^{10}$, —SO$_{v1}$NR$^7$R$^8$, —NHNH$_2$, —ONR$^7$R$^8$, —NHC═(O)NHNH$_2$, —NHC═(O)NR$^7$R$^8$, —N(O)$_{m1}$, —NR$^7$R$^8$, —C(O)R$^9$, —C(O)—OR$^9$, —C(O)NR$^7$R$^8$, —OR$^{10}$, —NR$^7$SO$_2$R$^{10}$, —NR$^7$C═(O)R$^9$, —NR$^7$C(O)—OR$^9$, —NR$^7$OR$^9$, —OCX$^1_3$, —OCHX$^1_2$, —OCH$_2$X$^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl. $R^2$ is independently a halogen, $-CX^2_3$, $-CHX^2_2$, $-CH_2X^2$, $-CN$, $-SO_{n2}R^{14}$, $-SO_{v2}NR^{11}R^{12}$, $-NHNH_2$, $-ONR^{11}R^{12}$, $-NHC=(O)NHNR^{11}R^{12}$, $-NHC=(O)NR^{11}R^{12}$, $-N(O)_{m2}$, $-NR^{11}R^{12}$, $-C(O)R^{13}$, $-C(O)-OR^9$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^2_3$, $-OCHX^2_2$, $-OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl. $R^4$ is independently a hydrogen, halogen, $-CX^4_3$, $-CHX^4_2$, $-CH_2X^4$, $-CN$, $-OH$, $-NH_2$, $-COOH$, $-CONH_2$, $-NO_2$, $-SH$, $-SO_4H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, $-OCH_2X^4$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^5$ is independently a hydrogen, halogen, $-CX^5_3$, $-CHX^5_2$, $-CH_2X^5$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^5_3$, $-OCHX^5_2$, $-OCH_2X^5$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^6$ is independently a hydrogen, halogen, $-CX^6_3$, $-CHX^6_2$, $-CH_2X^6$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^6_3$, $-OCHX^6_2$, $-OCH_2X^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl. $R^7$, $R^8$, $R^9$, $R^{10}$, $R^{11}$, $R^{12}$, $R^{13}$, and $R^{14}$ are independently hydrogen, halogen, $-CX^4_3$, $-CHX^4_2$, $-CH_2X^4$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, $-OCH_2X^4$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl. $L^1$ is a bond, $-O-$, $-NH-$, $-C(O)-$, $-C(O)NH-$, $-NHC(O)-$, $-C(O)O-$, $-OC(O)-$, $-NHC(O)NH-$, $-S-$, substituted or unsubstituted alkylene or substituted or unsubstituted heteroalkylene. $L^4$ is a bond or a divalent linker. $L^5$ is a bond or a divalent linker. z1 and z2 are independently an integer from 0 to 7. m1, m2, v1, and v2 are independently 1 or 2. n1 and n2 are independently an integer from 0 to 4. $X^1$, $X^2$, $X^4$, $X^5$, $X^6$, and $X^A$ are independently $-Cl$, $-Br$, $-I$, or $-F$.

In embodiments, the compound has the formula:

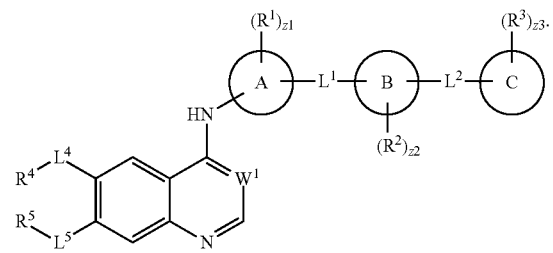

Ring A, Ring B, $W^1$, $R^1$, $R^2$, $R^4$, $R^5$, $L^1$, $L^4$, $L^5$, $X^1$, $X^2$, $X^4$, $X^5$, $X^6$, $X^A$, z1, and z2 are as described herein.

Ring C is cycloalkyl, heterocycloalkyl, aryl, or heteroaryl. In embodiments, ring C is $C_3$-$C_6$ cycloalkyl, 3 to 6 membered heterocycloalkyl, phenyl, or 5 to 6 membered heteroaryl. $R^3$ is independently a halogen, $-CX^3_3$, $-CHX^3_2$, $-CH_2X^3$, $-CN$, $-SO_{n3}R^{18}$, $-SO_{v3}NR^{15}R^{16}$, $-NHNH_2$, $-ONR^{15}R^{16}$, $-NHC=(O)NHNR^{15}R^{16}$, $-NHC=(O)NR^{15}R^{16}$, $-N(O)_{m3}$, $-NR^{15}R^{16}$, $-C(O)R^{17}$, $-C(O)-OR^{17}$, $-C(O)NR^{15}R^{16}$, $-OR^{18}$, $-NR^{15}SO_2R^{17}$, $-NR^{15}C=(O)R^{17}$, $-NR^{15}C(O)-OR^{17}$, $-NR^{15}OR^{17}$, $-OCX^3_3$, $-OCHX^3_2$, $-OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl. $R^{15}$, $R^{16}$, $R^{17}$, and $R^{18}$ are independently hydrogen, halogen, $-CX^A_3$, $-CHX^A_2$, $-CH_2X^A$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^A_3$, $-OCHX^A_2$, $-OCH_2X^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl. $L^2$ is a bond, $-O-$, $-NH-$, $-C(O)-$, $-C(O)NH-$, $-NHC(O)-$, $-C(O)O-$, $-OC(O)-$, $-NHC(O)NH-$, $-S-$, substituted or unsubstituted alkylene or substituted or unsubstituted heteroalkylene. In embodiments, $L^2$ is a bond, $-O-$, $-NH-$, $-C(O)-$, $-C(O)NH-$, $-NHC(O)-$, $-C(O)O-$, $-OC(O)-$, $-NHC(O)NH-$, $-S-$, substituted or unsubstituted $C_1$-$C_3$ alkylene or substituted or unsubstituted 2 to 3 membered heteroalkylene. z3 is independently an integer from 0 to 5. m3 is independently 1 or 2. v3 is independently 1 or 2. n3 s independently an integer from 0 to 4. $X^3$ is independently $-Cl$, $-Br$, $-I$, or $-F$.

In embodiments, Ring A is phenyl. In embodiments, Ring A is a 5 to 6 membered heteroaryl. In embodiments, Ring A is a thienyl. In embodiments, Ring A is a 2-thienyl. In embodiments, Ring A is a 3-thienyl. In embodiments, Ring A is a pyridyl. In embodiments, Ring A is a 2-pyridyl. In embodiments, Ring A is a 3-pyridyl. In embodiments, Ring A is a 4-pyridyl. In embodiments, Ring A is a napththyl. In embodiments, Ring A is a 1-napththyl. In embodiments, Ring A is a 2-napththyl. In embodiments, Ring A is a quinolinyl. In embodiments, Ring A is a isoquinolinyl. In embodiments, Ring A is a 1-isoquinolinyl. In embodiments, Ring A is a 3-isoquinolinyl. In embodiments, Ring A is a 4-isoquinolinyl. In embodiments, Ring A is phenyl or 5 or 6 membered heteroaryl. In embodiments, the numbering of Ring A in this paragraph (e.g., 2-thienyl, 1-isoquinolinyl, etc.) refers the attachment point of the —NH— linker that connects Ring A to the fused ring moiety (i.e. the fused ring that contains $W^1$).

In embodiments,

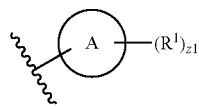

is

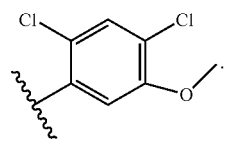 [SMILES: *c1cc(OC)c(Cl)cc1Cl]

In embodiments,

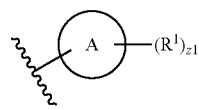

is

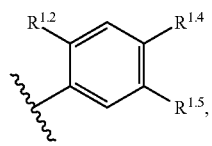

wherein $R^{1.2}$ and $R^{1.4}$ are halogen, and $R^{1.5}$ is unsubstituted methoxy. In embodiments, z1 is 0. In embodiments, Ring A is aryl when z1 is non-zero. In embodiments, Ring A is a heteroaryl when z1 is non-zero. In embodiments, Ring A is a aryl (e.g., $C_6$-$C_{10}$ or phenyl) or 5 to 6 membered heteroaryl when z1 is non-zero. In embodiments, Ring A is aryl (e.g., $C_6$-$C_{10}$ or phenyl) when z1 is non-zero. In embodiments, Ring A is 5 to 6 membered heteroaryl when z1 is non-zero.

In embodiments, Ring B is phenyl. In embodiments, Ring B is a 5 to 6 membered heteroaryl. In embodiments, Ring B is a thienyl. In embodiments, Ring B is a 2-thienyl. In embodiments, Ring B is a 3-thienyl. In embodiments, Ring B is a pyridyl. In embodiments, Ring B is a 2-pyridyl. In embodiments, Ring B is a 3-pyridyl. In embodiments, Ring B is a 4-pyridyl. In embodiments, Ring B is a napththyl. In embodiments, Ring B is a 1-napththyl. In embodiments, Ring B is a 2-napththyl. In embodiments, Ring B is a quinolinyl. In embodiments, Ring B is a isoquinolinyl. In embodiments, Ring B is a 1-isoquinolinyl. In embodiments, Ring B is a 3-isoquinolinyl. In embodiments, Ring B is a 4-isoquinolinyl. In embodiments, Ring B is phenyl or 5 or 6 membered heteroaryl. In embodiments, the numbering of Ring B in this paragraph (e.g., 2-thienyl, 1-isoquinolinyl, etc.) refers the attachment point of the $L^1$ linker that connects Ring B to Ring A.

In embodiments, Ring B is

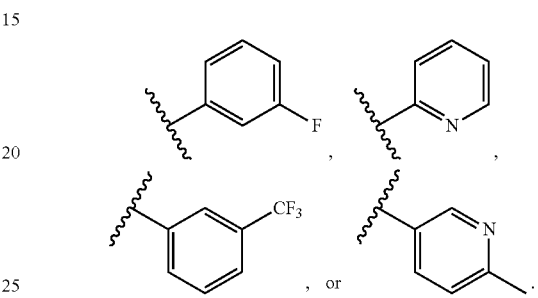

, or

In embodiments, Ring B is

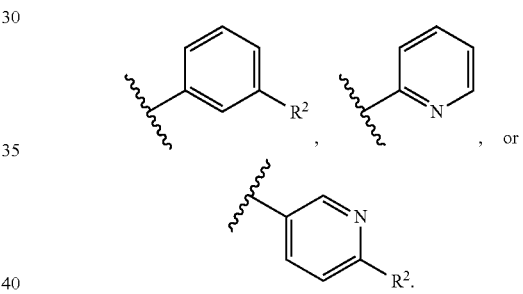

, or

In embodiments, Ring B is

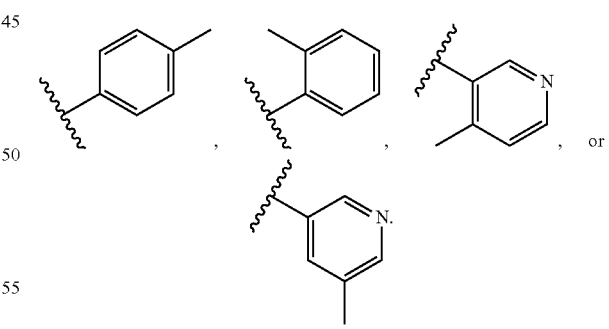

, or

In embodiments, Ring B is

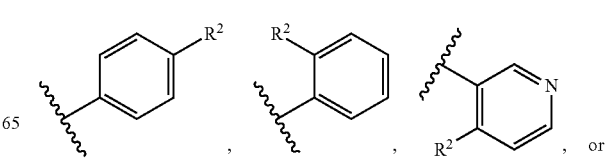

, or

-continued

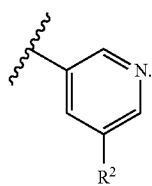

In embodiments, Ring B is a substituted aryl or substituted heteroaryl. In embodiments, Ring B is a substituted aryl. In embodiments, Ring B is a substituted heteroaryl. In embodiments, Ring B is a substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, Ring B is pyridyl when z2 is 1. In embodiments, Ring B is pyridyl when z2 is 2.

In embodiments,

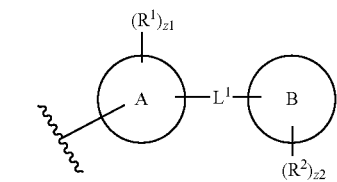

is

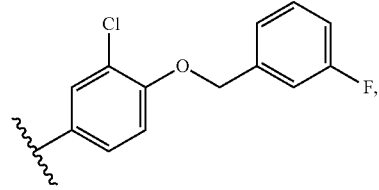

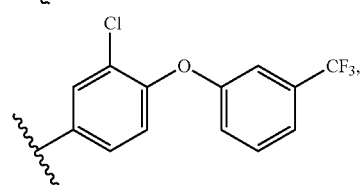

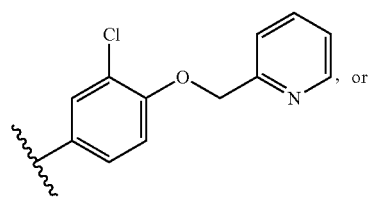

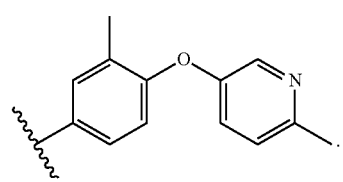

In embodiments,

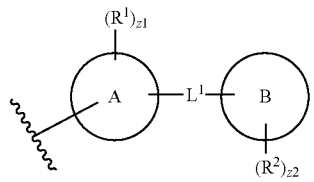

is

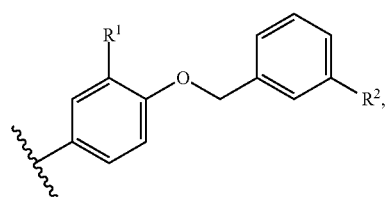

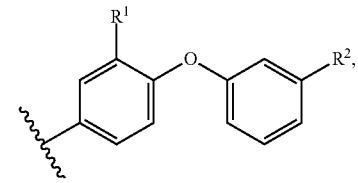

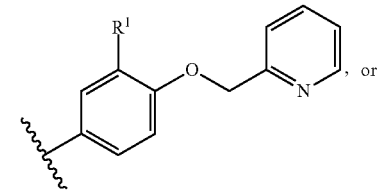, or

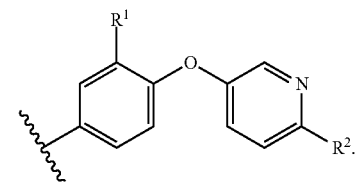

In embodiments,

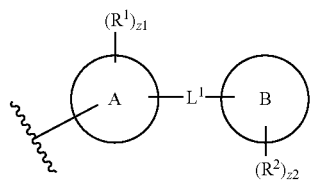

is

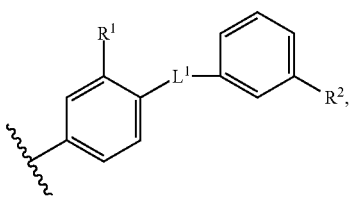

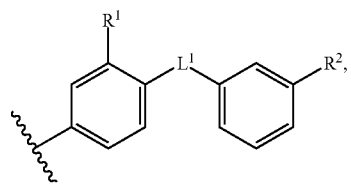
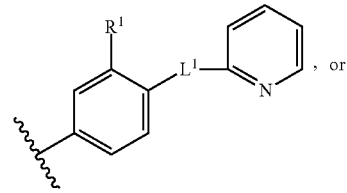, or
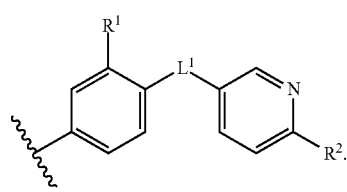
In embodiments,
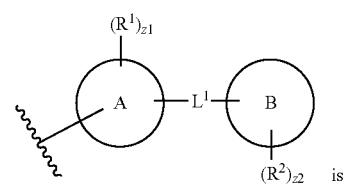
is
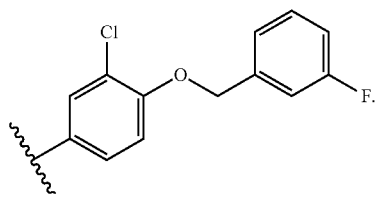
In embodiments,
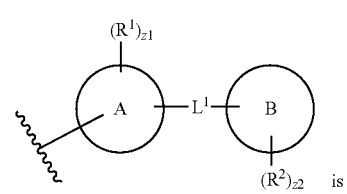
is
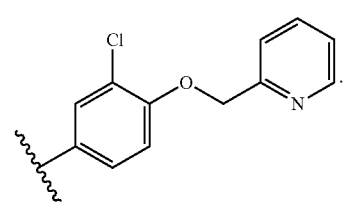
In embodiments,
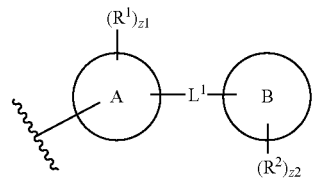
is
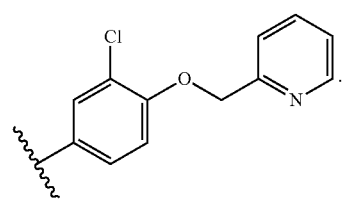 [SMILES: *c1ccc(OCc2ccccn2)c(Cl)c1]
In embodiments,
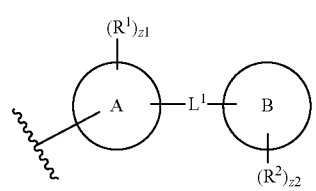
is
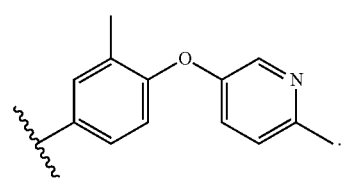 [SMILES: *c1ccc(Oc2ccc(C)nc2)c(C)c1]
In embodiments,
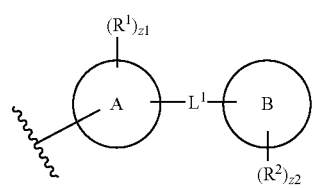
is
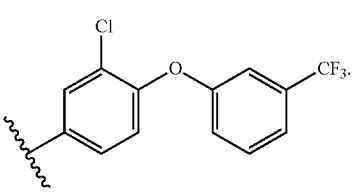 [SMILES: *c1ccc(Oc2cccc(C(F)(F)F)c2)c(Cl)c1]

In embodiments,
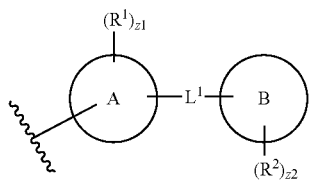
is
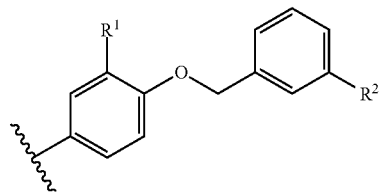
when W¹ is N. In embodiments,
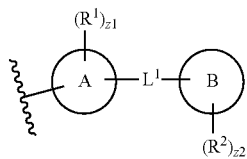
is
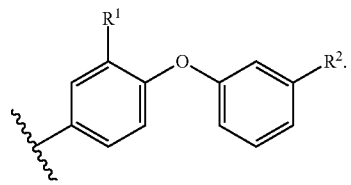
In embodiments,
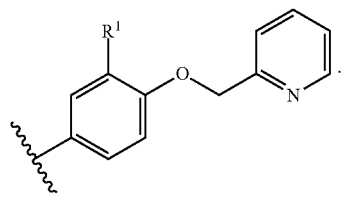
is
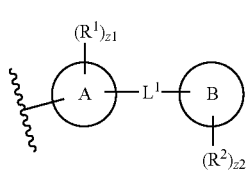
In embodiments,
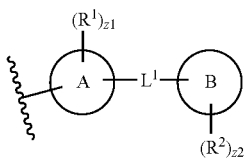
is
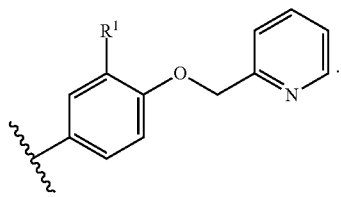
In embodiments,
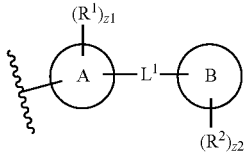
is
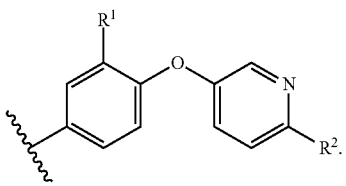
In embodiments,
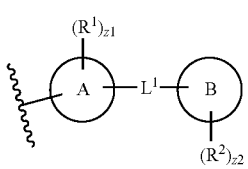
is
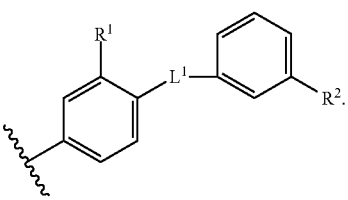

In embodiments,

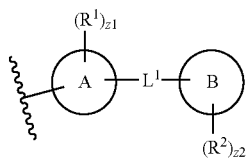

is

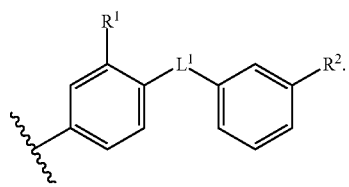

In embodiments,

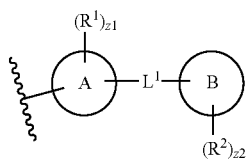

is

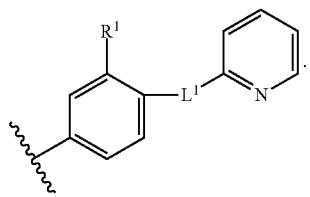

In embodiments,

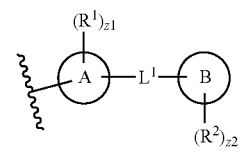

is

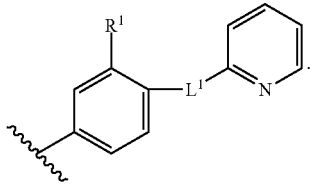

In embodiments,

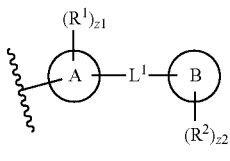

is

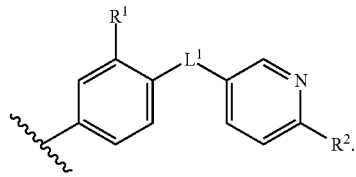

In embodiments, Ring C is cycloalkyl. In embodiments, Ring C is heterocycloalkyl. In embodiments, Ring C is aryl. In embodiments, Ring C is heteroaryl. In embodiments, Ring C is phenyl. In embodiments, Ring C is a 5 to 6 membered heteroaryl. In embodiments, Ring C is a thienyl. In embodiments, Ring C is a 2-thienyl. In embodiments, Ring C is a 3-thienyl. In embodiments, Ring C is a pyridyl. In embodiments, Ring C is a 2-pyridyl. In embodiments, Ring C is a 3-pyridyl. In embodiments, Ring C is a 4-pyridyl. In embodiments, Ring C is a $C_3$-$C_6$ cycloalkyl. In embodiments, Ring C is a $C_3$ cycloalkyl. In embodiments, Ring C is a $C_4$ cycloalkyl. In embodiments, Ring C is a $C_5$ cycloalkyl. In embodiments, Ring C is a $C_6$ cycloalkyl. In embodiments, Ring C is a 3 membered heterocycloalkyl. In embodiments, Ring C is a 4 membered heterocycloalkyl. In embodiments, Ring C is a 5 membered heterocycloalkyl. In embodiments, Ring C is a 6 membered heterocycloalkyl. In embodiments, the numbering of Ring C in this paragraph (e.g., 2-thienyl, 1-isoquinolinyl, etc.) refers the attachment point of the $L^2$ linker that connects Ring C to Ring B.

In embodiments,

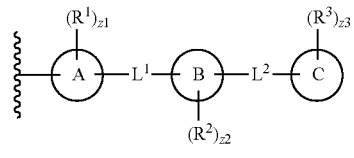

is

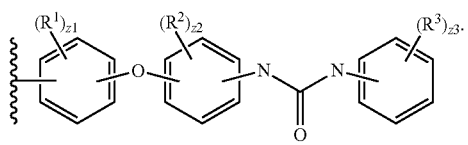

In embodiments,
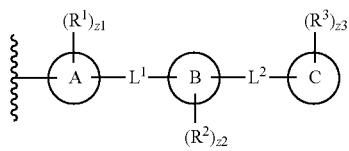
is
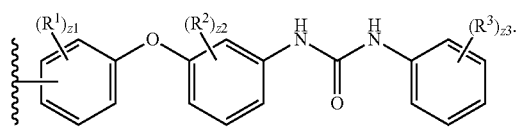
In embodiments,
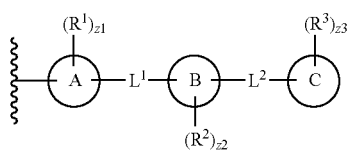
is
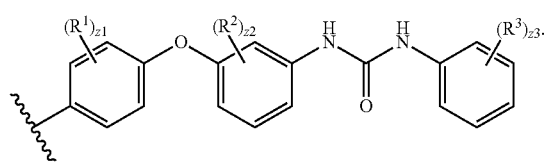
In embodiments,
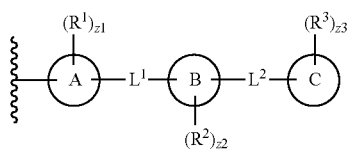
is
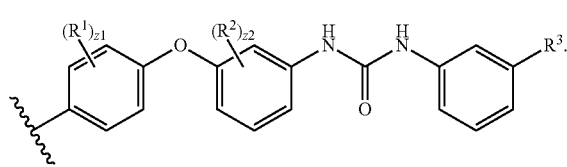
In embodiments,
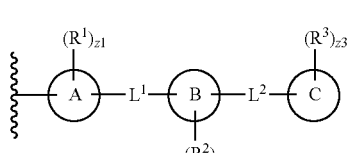
is
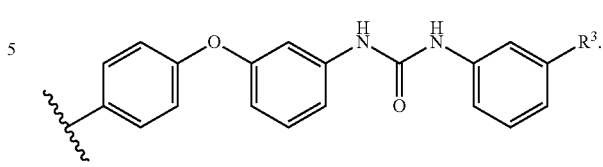
In embodiments,
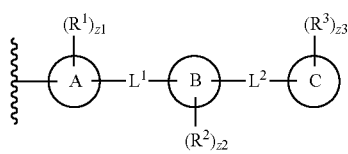
is
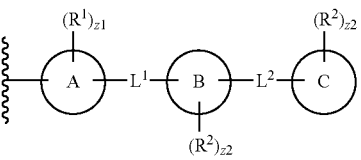
In embodiments,
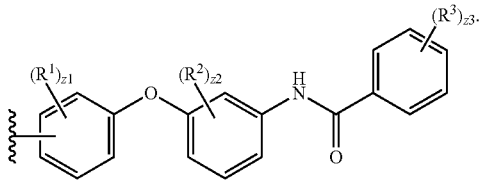
is
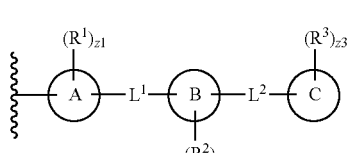
In embodiments,
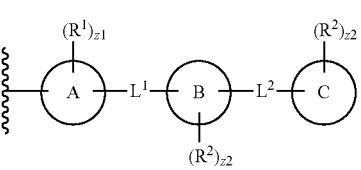

is

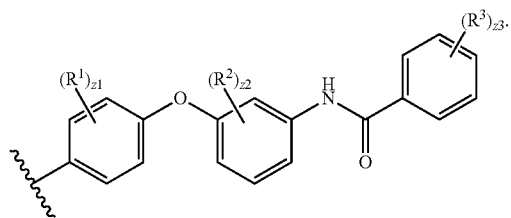

In embodiments,

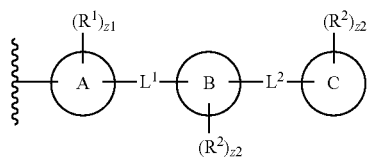

is

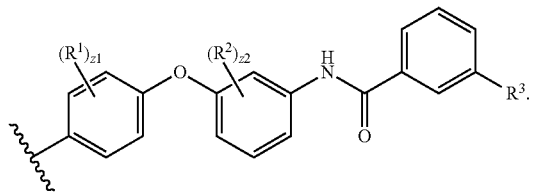

In embodiments,

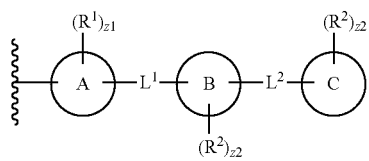

is

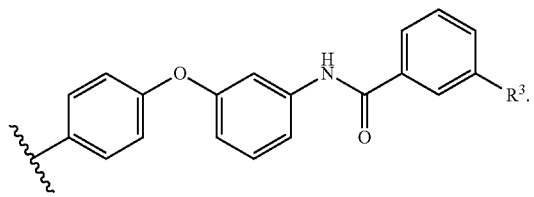

In embodiments, $R^1$ is independently a halogen, $-CX^1_3$, $-CHX^1_2$, $-CH_2X^1$, $-CN$, $-OH$, $-NH_2$, $-COOH$, $-CONH_2$, $-NO_2$, $-SH$, substituted or unsubstituted $C_1$-$C_4$ alkyl, or substituted or unsubstituted 2 to 4 membered heteroalkyl. In embodiments, $R^1$ is independently halogen, $-CF_3$, $-CHF_2$, $-OCF_3$, $-OCHF_2$, substituted or unsubstituted $C_1$-$C_3$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^1$ is independently halogen, $-CF_3$, $-OH$, $-NH_2$, $-SH$, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^1$ is independently halogen, $-OH$, $-NH_2$, $-SH$, unsubstituted $C_1$-$C_4$ alkyl, or unsubstituted 2 to 4 membered heteroalkyl. In embodiments, $R^1$ is independently halogen, $-OH$, unsubstituted methyl, or unsubstituted methoxy. In embodiments, $R^1$ is independently halogen. In embodiments, $R^1$ is independently $-CF_3$. In embodiments, $R^1$ is independently $-CHF_2$. In embodiments, $R^1$ is independently $-CH_2F$. In embodiments, $R^1$ is independently $-OCF_3$. In embodiments, $R^1$ is independently $-OCHF_2$. In embodiments, $R^1$ is independently $-OCH_2F$. In embodiments, $R^1$ is independently substituted or unsubstituted $C_1$-$C_8$ alkyl. In embodiments, $R^1$ is independently substituted or unsubstituted 2 to 8 membered heteroalkyl. In embodiments, $R^1$ is independently substituted or unsubstituted $C_3$-$C_8$ cycloalkyl. In embodiments, $R^1$ is independently substituted or unsubstituted 3 to 8 membered heterocycloalkyl. In embodiments, $R^1$ is independently substituted or unsubstituted $C_6$-$C_{10}$ aryl. In embodiments, $R^1$ is independently substituted or unsubstituted 5 to 10 membered heteroaryl. In embodiments, $R^1$ is independently $-OH$. In embodiments, $R^1$ is independently $-NH_2$. In embodiments, $R^1$ is independently $-SH$. In embodiments, $R^1$ is independently substituted or unsubstituted $C_1$-$C_4$ alkyl. In embodiments, $R^1$ is independently substituted or unsubstituted 2 to 4 membered heteroalkyl. In embodiments, $R^1$ is independently substituted or unsubstituted $C_3$-$C_6$ cycloalkyl. In embodiments, $R^1$ is independently substituted or unsubstituted 3 to 6 membered heterocycloalkyl. In embodiments, $R^1$ is independently substituted or unsubstituted phenyl. In embodiments, $R^1$ is independently substituted or unsubstituted 5 to 6 membered heteroaryl. In embodiments, $R^1$ is independently substituted $C_1$-$C_8$ alkyl. In embodiments, $R^1$ is independently substituted 2 to 8 membered heteroalkyl. In embodiments, $R^1$ is independently substituted $C_3$-$C_8$ cycloalkyl. In embodiments, $R^1$ is independently substituted 3 to 8 membered heterocycloalkyl. In embodiments, $R^1$ is independently substituted $C_6$-$C_{10}$ aryl. In embodiments, $R^1$ is independently substituted 5 to 10 membered heteroaryl. In embodiments, $R^1$ is independently substituted $C_1$-$C_4$ alkyl. In embodiments, $R^1$ is independently substituted 2 to 4 membered heteroalkyl. In embodiments, $R^1$ is independently substituted $C_3$-$C_6$ cycloalkyl. In embodiments, $R^1$ is independently substituted 3 to 6 membered heterocycloalkyl. In embodiments, $R^1$ is independently substituted phenyl. In embodiments, $R^1$ is independently substituted 5 to 6 membered heteroaryl. In embodiments, $R^1$ is independently unsubstituted $C_1$-$C_8$ alkyl. In embodiments, $R^1$ is independently unsubstituted 2 to 8 membered heteroalkyl. In embodiments, $R^1$ is independently unsubstituted $C_3$-$C_8$ cycloalkyl. In embodiments, $R^1$ is independently unsubstituted 3 to 8 membered heterocycloalkyl. In embodiments, $R^1$ is independently unsubstituted $C_6$-$C_{10}$ aryl. In embodiments, $R^1$ is independently unsubstituted 5 to 10 membered heteroaryl. In embodiments, $R^1$ is independently unsubstituted $C_1$-$C_4$ alkyl. In embodiments, $R^1$ is independently unsubstituted 2 to 4 membered heteroalkyl. In embodiments, $R^1$ is independently unsubstituted $C_3$-$C_6$ cycloalkyl. In embodiments, $R^1$ is independently unsubstituted 3 to 6 membered heterocycloalkyl. In embodiments, $R^1$ is independently unsubstituted phenyl. In embodiments, $R^1$ is independently unsubstituted 5 to 6 membered heteroaryl. In embodiments, $R^1$ is independently unsubstituted methyl. In embodiments, $R^1$ is independently unsubstituted ethyl. In embodiments, $R^1$ is independently unsubstituted isopropyl. In embodiments, $R^1$ is independently unsubstituted tert-butyl. In embodiments, $R^1$ is independently unsubstituted methoxy. In embodiments, $R^1$ is independently unsubstituted ethoxy. In embodiments, $R^1$ is independently —F. In embodiments, $R^1$ is independently —Cl. In embodiments, $R^1$ is independently —Br. In embodiments, $R^1$ is independently —I. In embodiments, $R^1$ is independently hydrogen.

In embodiments, z1 is 1. In embodiments, z1 is 0. In embodiments, z1 is 2. In embodiments, z1 is 3. In embodiments, z1 is 4. In embodiments, z1 is an integer from 0 to 4. In embodiments, z1 and z2 are 0. In embodiments, z1 is an integer from 0 to 1.

In embodiments, $R^2$ is independently a halogen, —$CX^2_3$, —$CHX^2_2$, —$CH_2X^2$, —CN, —OH, —$NH_2$, —COOH, —$CONH_2$, —$NO_2$, —SH, substituted or unsubstituted $C_1$-$C_4$ alkyl, or substituted or unsubstituted 2 to 4 membered heteroalkyl. In embodiments, $R^2$ is independently halogen, —$CF_3$, —$CHF_2$, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^2$ is independently halogen, —$CF_3$, —OH, —$NH_2$, —SH, substituted or unsubstituted $C_1$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^2$ is independently halogen, —OH, —$NH_2$, —SH, unsubstituted $C_1$-$C_4$ alkyl, or unsubstituted 2 to 4 membered heteroalkyl. In embodiments, $R^2$ is independently halogen, —OH, unsubstituted methyl, or unsubstituted methoxy. In embodiments, $R^2$ is independently halogen. In embodiments, $R^2$ is independently —$CF_3$. In embodiments, $R^2$ is independently —$CHF_2$. In embodiments, $R^2$ is independently —$CH_2F$. In embodiments, $R^2$ is independently —$OCF_3$. In embodiments, $R^2$ is independently —$OCHF_2$. In embodiments, $R^2$ is independently —$OCH_2F$. In embodiments, $R^2$ is independently substituted or unsubstituted $C_1$-$C_8$ alkyl. In embodiments, $R^2$ is independently substituted or unsubstituted 2 to 8 membered heteroalkyl. In embodiments, $R^2$ is independently substituted or unsubstituted $C_3$-$C_8$ cycloalkyl. In embodiments, $R^2$ is independently substituted or unsubstituted 3 to 8 membered heterocycloalkyl. In embodiments, $R^2$ is independently substituted or unsubstituted $C_6$-$C_{10}$ aryl. In embodiments, $R^2$ is independently substituted or unsubstituted 5 to 10 membered heteroaryl. In embodiments, $R^2$ is independently —OH. In embodiments, $R^2$ is independently —$NH_2$. In embodiments, $R^2$ is independently —SH. In embodiments, $R^2$ is independently substituted or unsubstituted $C_1$-$C_4$ alkyl. In embodiments, $R^2$ is independently substituted or unsubstituted 2 to 4 membered heteroalkyl. In embodiments, $R^2$ is independently substituted or unsubstituted $C_3$-$C_6$ cycloalkyl. In embodiments, $R^2$ is independently substituted or unsubstituted 3 to 6 membered heterocycloalkyl. In embodiments, $R^2$ is independently substituted or unsubstituted phenyl. In embodiments, $R^2$ is independently substituted or unsubstituted 5 to 6 membered heteroaryl. In embodiments, $R^2$ is independently substituted $C_1$-$C_8$ alkyl. In embodiments, $R^2$ is independently substituted 2 to 8 membered heteroalkyl. In embodiments, $R^2$ is independently substituted $C_3$-$C_8$ cycloalkyl. In embodiments, $R^2$ is independently substituted 3 to 8 membered heterocycloalkyl. In embodiments, $R^2$ is independently substituted $C_6$-$C_{10}$ aryl. In embodiments, $R^2$ is independently substituted 5 to 10 membered heteroaryl. In embodiments, $R^2$ is independently substituted $C_1$-$C_4$ alkyl. In embodiments, $R^2$ is independently substituted 2 to 4 membered heteroalkyl. In embodiments, $R^2$ is independently substituted $C_3$-$C_6$ cycloalkyl. In embodiments, $R^2$ is independently substituted 3 to 6 membered heterocycloalkyl. In embodiments, $R^2$ is independently substituted phenyl. In embodiments, $R^2$ is independently substituted 5 to 6 membered heteroaryl. In embodiments, $R^2$ is independently unsubstituted $C_1$-$C_8$ alkyl. In embodiments, $R^2$ is independently unsubstituted 2 to 8 membered heteroalkyl. In embodiments, $R^2$ is independently unsubstituted $C_3$-$C_8$ cycloalkyl. In embodiments, $R^2$ is independently unsubstituted 3 to 8 membered heterocycloalkyl. In embodiments, $R^2$ is independently unsubstituted $C_6$-$C_{10}$ aryl. In embodiments, $R^2$ is independently unsubstituted 5 to 10 membered heteroaryl. In embodiments, $R^2$ is independently unsubstituted $C_1$-$C_4$ alkyl. In embodiments, $R^2$ is independently unsubstituted 2 to 4 membered heteroalkyl. In embodiments, $R^2$ is independently unsubstituted $C_3$-$C_6$ cycloalkyl. In embodiments, $R^2$ is independently unsubstituted 3 to 6 membered heterocycloalkyl. In embodiments, $R^2$ is independently unsubstituted phenyl. In embodiments, $R^2$ is independently unsubstituted 5 to 6 membered heteroaryl. In embodiments, $R^2$ is independently unsubstituted methyl. In embodiments, $R^2$ is independently unsubstituted ethyl. In embodiments, $R^2$ is independently unsubstituted isopropyl. In embodiments, $R^2$ is independently unsubstituted tert-butyl. In embodiments, $R^2$ is independently unsubstituted methoxy. In embodiments, $R^2$ is independently unsubstituted ethoxy. In embodiments, $R^2$ is independently —F. In embodiments, $R^2$ is independently —Cl. In embodiments, $R^2$ is independently —Br. In embodiments, $R^2$ is independently —I. In embodiments, $R^2$ is independently hydrogen.

In embodiments, z2 is 1. In embodiments, z2 is 0. In embodiments, z2 is 2. In embodiments, z2 is 3. In embodiments, z2 is 4. In embodiments, z2 is 5. In embodiments, z2 is an integer from 0 to 4. In embodiments, z2 is an integer from 0 to 1.

In embodiments, $R^3$ is independently a halogen, —$CX^3_3$, —$CHX^3_2$, —$CH_2X^3$, —CN, —OH, —$NH_2$, —COOH, —$CONH_2$, —$NO_2$, —SH, substituted or unsubstituted $C_1$-$C_4$ alkyl, or substituted or unsubstituted 2 to 4 membered heteroalkyl. In embodiments, $R^3$ is independently halogen, —$CF_3$, —$CHF_2$, —$CH_2F$, —$OCHF_2$, —$OCHF_2$, —$OCH_2F$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^3$ is independently halogen, —$CF_3$, —$CHF_2$, —$OCF_3$, —$OCHF_2$, substituted or unsubstituted $C_1$-$C_8$ alkyl, substituted or unsubstituted 2 to 8 membered heteroalkyl, substituted or unsubstituted $C_3$-$C_8$ cycloalkyl, substituted or unsubstituted 3 to 8 membered heterocycloalkyl, substituted or unsubstituted $C_6$-$C_{10}$ aryl, or substituted or unsubstituted 5 to 10 membered heteroaryl. In embodiments, $R^3$ is independently halogen, —$CF_3$, —OH, —$NH_2$, —SH, substituted or unsubstituted $C_3$-$C_4$ alkyl, substituted or unsubstituted 2 to 4 membered heteroalkyl, substituted or unsubstituted $C_3$-$C_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^3$ is independently halogen, —OH, —NH$_2$, —SH, unsubstituted C$_1$-C$_4$ alkyl, or unsubstituted 2 to 4 membered heteroalkyl. In embodiments, $R^3$ is independently halogen, —OH, unsubstituted methyl, or unsubstituted methoxy. In embodiments, $R^3$ is independently halogen. In embodiments, $R^3$ is independently —CF$_3$. In embodiments, $R^3$ is independently —CHF$_2$. In embodiments, $R^3$ is independently —CH$_2$F. In embodiments, $R^3$ is independently —OCF$_3$. In embodiments, $R^3$ is independently —OCHF$_2$. In embodiments, $R^3$ is independently —OCH$_2$F. In embodiments, $R^3$ is independently substituted or unsubstituted C$_1$-C$_8$ alkyl. In embodiments, $R^3$ is independently substituted or unsubstituted 2 to 8 membered heteroalkyl. In embodiments, $R^3$ is independently substituted or unsubstituted C$_3$-C$_8$ cycloalkyl. In embodiments, $R^3$ is independently substituted or unsubstituted 3 to 8 membered heterocycloalkyl. In embodiments, $R^3$ is independently substituted or unsubstituted C$_6$-C$_{10}$ aryl. In embodiments, $R^3$ is independently substituted or unsubstituted 5 to 10 membered heteroaryl. In embodiments, $R^3$ is independently —OH. In embodiments, $R^3$ is independently —NH$_2$. In embodiments, $R^3$ is independently —SH. In embodiments, $R^3$ is independently substituted or unsubstituted C$_1$-C$_4$ alkyl. In embodiments, $R^3$ is independently substituted or unsubstituted 2 to 4 membered heteroalkyl. In embodiments, $R^3$ is independently substituted or unsubstituted C$_3$-C$_6$ cycloalkyl. In embodiments, $R^3$ is independently substituted or unsubstituted 3 to 6 membered heterocycloalkyl. In embodiments, $R^3$ is independently substituted or unsubstituted phenyl. In embodiments, $R^3$ is independently substituted or unsubstituted 5 to 6 membered heteroaryl. In embodiments, $R^3$ is independently substituted C$_1$-C$_8$ alkyl. In embodiments, $R^3$ is independently substituted 2 to 8 membered heteroalkyl. In embodiments, $R^3$ is independently substituted C$_3$-C$_8$ cycloalkyl. In embodiments, $R^3$ is independently substituted 3 to 8 membered heterocycloalkyl. In embodiments, $R^3$ is independently substituted C$_6$-C$_{10}$ aryl. In embodiments, $R^3$ is independently substituted 5 to 10 membered heteroaryl. In embodiments, $R^3$ is independently substituted C$_1$-C$_4$ alkyl. In embodiments, $R^3$ is independently substituted 2 to 4 membered heteroalkyl. In embodiments, $R^3$ is independently substituted C$_3$-C$_6$ cycloalkyl. In embodiments, $R^3$ is independently substituted 3 to 6 membered heterocycloalkyl. In embodiments, $R^3$ is independently substituted phenyl. In embodiments, $R^3$ is independently substituted 5 to 6 membered heteroaryl. In embodiments, $R^3$ is independently unsubstituted C$_1$-C$_8$ alkyl. In embodiments, $R^3$ is independently unsubstituted 2 to 8 membered heteroalkyl. In embodiments, $R^3$ is independently unsubstituted C$_3$-C$_8$ cycloalkyl. In embodiments, $R^3$ is independently unsubstituted 3 to 8 membered heterocycloalkyl. In embodiments, $R^3$ is independently unsubstituted C$_6$-C$_{10}$ aryl. In embodiments, $R^3$ is independently unsubstituted 5 to 10 membered heteroaryl. In embodiments, $R^3$ is independently unsubstituted C$_1$-C$_4$ alkyl. In embodiments, $R^3$ is independently unsubstituted 2 to 4 membered heteroalkyl. In embodiments, $R^3$ is independently unsubstituted C$_3$-C$_6$ cycloalkyl. In embodiments, $R^3$ is independently unsubstituted 3 to 6 membered heterocycloalkyl. In embodiments, $R^3$ is independently unsubstituted phenyl. In embodiments, $R^3$ is independently unsubstituted 5 to 6 membered heteroaryl. In embodiments, $R^3$ is independently unsubstituted methyl. In embodiments, $R^3$ is independently unsubstituted ethyl. In embodiments, $R^3$ is independently unsubstituted isopropyl. In embodiments, $R^3$ is independently unsubstituted tert-butyl. In embodiments, $R^3$ is independently unsubstituted methoxy. In embodiments, $R^3$ is independently unsubstituted ethoxy. In embodiments, $R^3$ is independently —F. In embodiments, $R^3$ is independently —Cl. In embodiments, $R^3$ is independently —Br. In embodiments, $R^3$ is independently —I. In embodiments, $R^3$ is independently hydrogen. In embodiments, $R^3$ is —CF$_3$. In embodiments, $R^3$ is a halogen.

In embodiments, z3 is 1. In embodiments, z3 is 0. In embodiments, z3 is 2. In embodiments, z3 is 3. In embodiments, z3 is 4. In embodiments, z3 is 5.

In embodiments, $R^4$ is independently halogen, —CF$_3$, —CHF$_2$, —CH$_2$F, —OCF$_3$, —OCHF$_2$, —OCH$_2$F, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl. In embodiments, $R^4$ is independently halogen, —CF$_3$, —CHF$_2$, —OCF$_3$, —OCHF$_2$, substituted or unsubstituted C$_1$-C$_8$ alkyl, substituted or unsubstituted 2 to 8 membered heteroalkyl, substituted or unsubstituted C$_3$-C$_8$ cycloalkyl, substituted or unsubstituted 3 to 8 membered heterocycloalkyl, substituted or unsubstituted C$_6$-C$_{10}$ aryl, or substituted or unsubstituted 5 to 10 membered heteroaryl. In embodiments, $R^4$ is independently halogen, —CF$_3$, —OH, —NH$_2$, —SH, substituted or unsubstituted C$_1$-C$_4$ alkyl, substituted or unsubstituted 2 to 4 membered heteroalkyl, substituted or unsubstituted C$_3$-C$_6$ cycloalkyl, substituted or unsubstituted 3 to 6 membered heterocycloalkyl, substituted or unsubstituted phenyl, or substituted or unsubstituted 5 to 6 membered heteroaryl. In embodiments, $R^4$ is independently halogen, —OH, —NH$_2$, —SH, unsubstituted C$_1$-C$_4$ alkyl, or unsubstituted 2 to 4 membered heteroalkyl. In embodiments, $R^4$ is independently halogen, —OH, unsubstituted methyl, or unsubstituted methoxy. In embodiments, $R^4$ is independently halogen. In embodiments, $R^4$ is independently —CF$_3$. In embodiments, $R^4$ is independently —CHF$_2$. In embodiments, $R^4$ is independently —CH$_2$F. In embodiments, $R^4$ is independently —OCF$_3$. In embodiments, $R^4$ is independently —OCHF$_2$. In embodiments, $R^4$ is independently —OCH$_2$F. In embodiments, $R^4$ is independently substituted or unsubstituted C$_1$-C$_8$ alkyl. In embodiments, $R^4$ is independently substituted or unsubstituted 2 to 8 membered heteroalkyl. In embodiments, $R^4$ is independently substituted or unsubstituted C$_3$-C$_8$ cycloalkyl. In embodiments, $R^4$ is independently substituted or unsubstituted 3 to 8 membered heterocycloalkyl. In embodiments, $R^4$ is independently substituted or unsubstituted C$_6$-C$_{10}$ aryl. In embodiments, $R^4$ is independently substituted or unsubstituted 5 to 10 membered heteroaryl. In embodiments, $R^4$ is independently —OH. In embodiments, $R^4$ is independently —NH$_2$. In embodiments, $R^4$ is independently —SH. In embodiments, $R^4$ is independently substituted or unsubstituted C$_1$-C$_4$ alkyl. In embodiments, $R^4$ is independently substituted or unsubstituted 2 to 4 membered heteroalkyl. In embodiments, $R^4$ is independently substituted or unsubstituted C$_3$-C$_6$ cycloalkyl. In embodiments, $R^4$ is independently substituted or unsubstituted 3 to 6 membered heterocycloalkyl. In embodiments, $R^4$ is independently substituted or unsubstituted phenyl. In embodiments, $R^4$ is independently substituted or unsubstituted 5 to 6 membered heteroaryl. In embodiments, $R^4$ is independently substituted C$_1$-C$_8$ alkyl. In embodiments, $R^4$ is independently substituted 2 to 8 membered heteroalkyl. In embodiments, $R^4$ is independently substituted C$_3$-C$_8$ cycloalkyl. In embodiments, $R^4$ is independently substituted 3 to 8 membered heterocycloalkyl. In embodiments, $R^4$ is independently substituted C$_6$-C$_{10}$ aryl. In embodiments, $R^4$ is independently substituted 5 to 10 membered heteroaryl. In embodiments, $R^4$ is independently substituted $C_1$-$C_4$ alkyl. In embodiments, $R^4$ is independently substituted 2 to 4 membered heteroalkyl. In embodiments, $R^4$ is independently substituted $C_3$-$C_6$ cycloalkyl. In embodiments, $R^4$ is independently substituted 3 to 6 membered heterocycloalkyl. In embodiments, $R^4$ is independently substituted phenyl. In embodiments, $R^4$ is independently substituted 5 to 6 membered heteroaryl. In embodiments, $R^4$ is independently unsubstituted $C_1$-$C_8$ alkyl. In embodiments, $R^4$ is independently unsubstituted 2 to 8 membered heteroalkyl. In embodiments, $R^4$ is independently unsubstituted $C_3$-$C_8$ cycloalkyl. In embodiments, $R^4$ is independently unsubstituted 3 to 8 membered heterocycloalkyl. In embodiments, $R^4$ is independently unsubstituted $C_6$-$C_{10}$ aryl. In embodiments, $R^4$ is independently unsubstituted 5 to 10 membered heteroaryl. In embodiments, $R^4$ is independently unsubstituted $C_1$-$C_4$ alkyl. In embodiments, $R^4$ is independently unsubstituted 2 to 4 membered heteroalkyl. In embodiments, $R^4$ is independently unsubstituted $C_3$-$C_6$ cycloalkyl. In embodiments, $R^4$ is independently unsubstituted 3 to 6 membered heterocycloalkyl. In embodiments, $R^4$ is independently unsubstituted phenyl. In embodiments, $R^4$ is independently unsubstituted 5 to 6 membered heteroaryl. In embodiments, $R^4$ is —$NH_2$.

In embodiments, -$L^4$-$R^4$ is unsubstituted methoxy.

In embodiments, -$L^4$-$R^4$ is

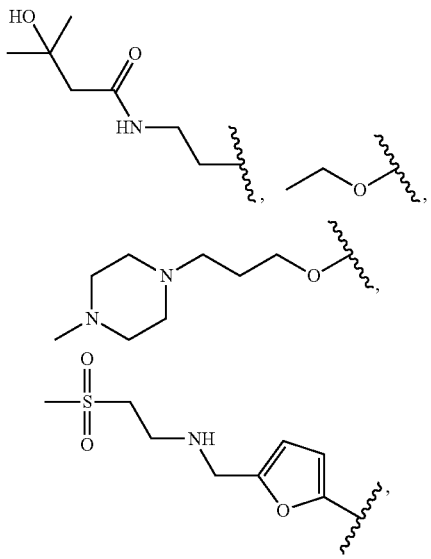

,

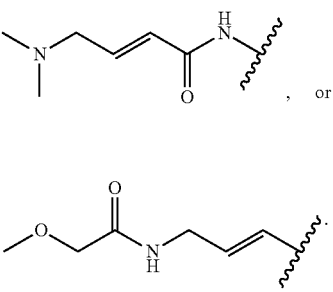

.

In embodiments, -$L^4$-$R^4$ is

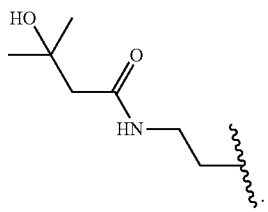 [SMILES: *CCNC(=O)CC(C)(C)O]

In embodiments, -$L^4$-$R^4$ is

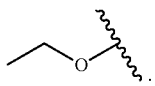

.

In embodiments, -$L^4$-$R^4$ is

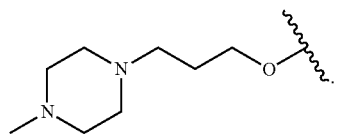 [SMILES: *OCCCN1CCN(C)CC1]

.

In embodiments, -$L^4$-$R^4$ is

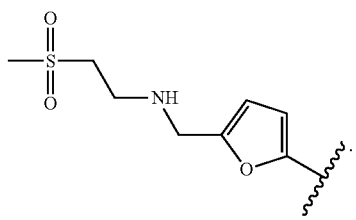 [SMILES: *c1ccc(CNCCS(C)(=O)=O)o1]

In embodiments, -$L^4$-$R^4$ is

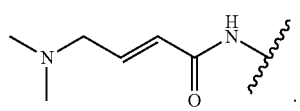 [SMILES: *NC(=O)/C=C/CN(C)C]

In embodiments, -$L^4$-$R^4$ is

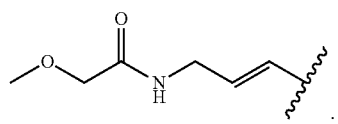 [SMILES: */C=C/CNC(=O)COC]

In embodiments, -$L^4$-$R^4$ is substituted or unsubstituted 5 to 10 membered heteroalkyl. In embodiments, -$L^4$-$R^4$ is substituted or unsubstituted 6 to 10 membered heteroalkyl. In embodiments, -$L^4$-$R^4$ is substituted or unsubstituted 7 to 10 membered heteroalkyl. In embodiments, -$L^4$-$R^4$ is substituted or unsubstituted 7 to 9 membered heteroalkyl. In embodiments, -$L^4$-$R^4$ is substituted or unsubstituted 5 membered heteroaryl. In embodiments, -$L^4$-$R^4$ is substituted or unsubstituted 5 to 6 membered heteroaryl. In embodiments, -$L^4$-$R^4$ is substituted or unsubstituted 4 to 6 membered heteroaryl. In embodiments, -L⁴-R⁴ is substituted or unsubstituted heteroaryl. In embodiments, -L⁴-R⁴ is substituted 5 membered heteroaryl. In embodiments, -L⁴-R⁴ is substituted 5 to 6 membered heteroaryl. In embodiments, -L⁴-R⁴ is substituted 4 to 6 membered heteroaryl. In embodiments, -L⁴-R⁴ is substituted heteroaryl. In embodiments, -L⁴-R⁴ is unsubstituted 5 membered heteroaryl. In embodiments, -L⁴-R⁴ is unsubstituted 5 to 6 membered heteroaryl. In embodiments, -L⁴-R⁴ is unsubstituted heteroaryl. In embodiments, -L⁴-R⁴ is unsubstituted 4 to 6 membered heteroaryl.

In embodiments, -L⁴-R⁴ is

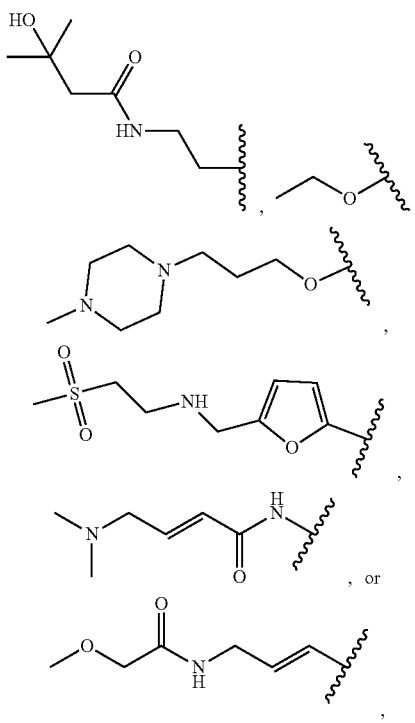

when R⁵ is a degradation-increasing moiety. In embodiments, -L⁴-R⁴ is

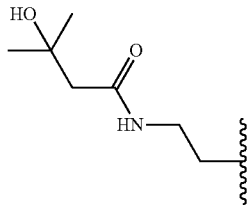 [SMILES: *CCNC(=O)CC(C)(C)O]

when R⁵ is a degradation-increasing moiety. In embodiments, -L⁴-R⁴ is

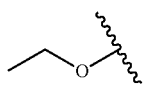

when R⁵ is a degradation-increasing moiety. In embodiments, -L⁴-R⁴ is

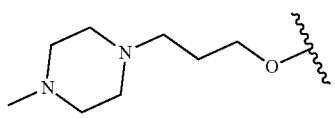 [SMILES: *OCCCN1CCN(C)CC1]

when R⁵ is a degradation-increasing moiety. In embodiments, -L⁴-R⁴ is

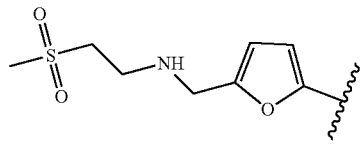 [SMILES: *c1ccc(CNCCS(C)(=O)=O)o1]

when R⁵ is a degradation-increasing moiety. In embodiments, -L⁴-R⁴ is

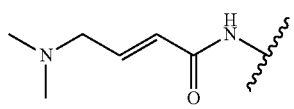 [SMILES: *NC(=O)/C=C/CN(C)C]

when R⁵ is a degradation-increasing moiety. In embodiments, -L⁴-R⁴ is

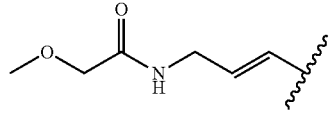 [SMILES: */C=C/CNC(=O)COC]

when R⁵ is a degradation-increasing moiety.

In embodiments, R⁴ is a degradation-increasing moiety. In embodiments, the degradation-increasing moiety is thalidomide moiety or an analog, derivative, or prodrug thereof; phthalimide moiety or an analog, derivative, or prodrug thereof; adamantyl or an analog, derivative, or prodrug thereof; an IκBα phosphopeptide moiety or an analog, derivative, or prodrug thereof; nutlin moiety or an analog, derivative, or prodrug thereof; HIF-1α pentapeptide moiety or an analog, derivative, or prodrug thereof; or

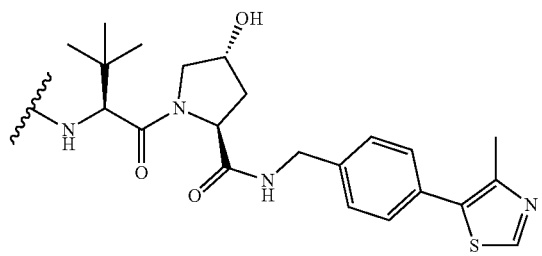 [SMILES: *N[C@H](C(=O)N1C[C@H](O)C[C@H]1C(=O)NCc1ccc(-c2scnc2C)cc1)C(C)(C)C]

or an analog, derivative, or prodrug thereof. In embodiments, the degradation-increasing moiety is thalidomide moiety or an analog, derivative, or prodrug thereof. In embodiments, R⁴ is

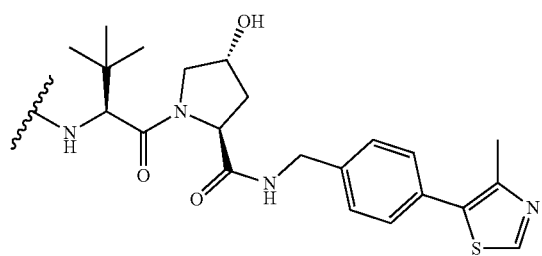 [SMILES: *N[C@H](C(=O)N1C[C@H](O)C[C@H]1C(=O)NCc1ccc(-c2scnc2C)cc1)C(C)(C)C]

or an analog, derivative, or prodrug thereof. In embodiments, R⁴ is

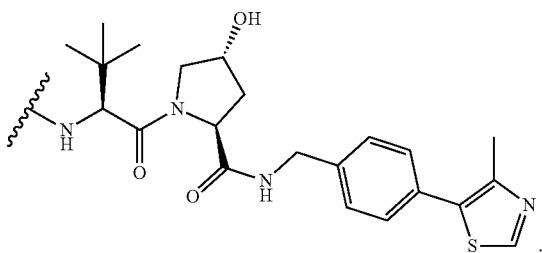 [SMILES: *N[C@H](C(=O)N1C[C@H](O)C[C@H]1C(=O)NCc1ccc(-c2scnc2C)cc1)C(C)(C)C]

In embodiments, R⁴ is a thalidomide moiety or an analog, derivative, or prodrug thereof. In embodiments, R⁴ is a thalidomide moiety. In embodiments, R⁴ is a lenalidomide moiety. In embodiments, R⁴ is a pomalidomide moiety. In embodiments, R⁴ is

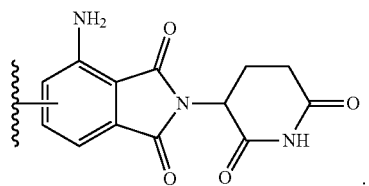

In embodiments, R⁴ is

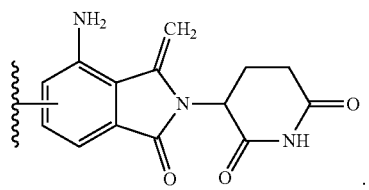

In embodiments, R⁴ is

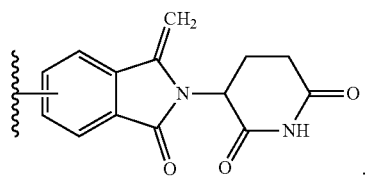

In embodiments, R⁴ is

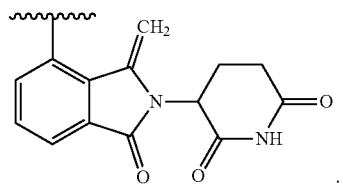 [SMILES: *c1cccc2c1C(=C)N(C1CCC(=O)NC1=O)C2=O]

In embodiments, R⁴ is

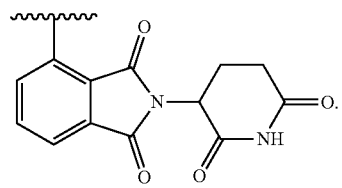 [SMILES: *c1cccc2c1C(=O)N(C1CCC(=O)NC1=O)C2=O]

In embodiments, R⁴ is a phthalimide moiety or an analog, derivative, or prodrug thereof. In embodiments, R⁴ is

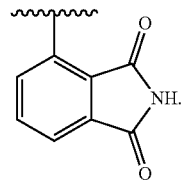 [SMILES: *c1cccc2c1C(=O)NC2=O]

In embodiments, R⁴ is

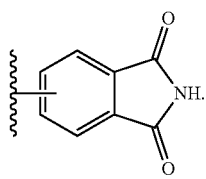

In embodiments, R⁴ is a phthalimide moiety. In embodiments, R⁴ includes a thalidomide moiety or an analog, derivative, or prodrug thereof. In embodiments, R⁴ includes a thalidomide moiety. In embodiments, R⁴ includes a lenalidomide moiety. In embodiments, R⁴ includes a pomalidomide moiety. In embodiments, R⁴ includes a phthalimide moiety or an analog, derivative, or prodrug thereof. In embodiments, R⁴ includes a phthalimide moiety.

In embodiments, R⁴ is adamantyl or an analog, derivative, or prodrug thereof. In embodiments, R⁴ is substituted adamantyl or an analog, derivative, or prodrug thereof. In embodiments, R⁴ is adamantyl. In embodiments, R⁴ is substituted adamantyl.

In embodiments, R⁴ is a phosphopeptide including a sequence of IκBα, or an analog, derivative, or prodrug thereof. In embodiments, R⁴ is a phosphopeptide consisting of a sequence of IκBα, or an analog, derivative, or prodrug thereof. In embodiments, R⁴ is -RAEDS*GNES*EGE (SEQ ID NO:3) or a derivative thereof (e.g., including one, two or three substitutions (e.g., conservative substitutions), wherein S* is a phosphoserine. In embodiments, R⁴ is -RAEDS*GNES*EGE (SEQ ID NO:3). In embodiments, R⁴ is -G$_{0-10}$RAEDS*GNES*EGE (SEQ ID NO:4) or a derivative thereof (e.g., including one, two or three substitutions (e.g., conservative substitutions), wherein S* is a phosphoserine. In embodiments, $R^4$ is -$G_{0-10}$RAEDS*GNES*EGE (SEQ ID NO:4). In embodiments, $R^4$ is -DRIIDS*GLDS*M (SEQ ID NO:5) or a derivative thereof (e.g., including one, two or three substitutions (e.g., conservative substitutions), wherein S* is a phosphoserine. In embodiments, $R^4$ is -DRIIDS*GLDS*M (SEQ ID NO:5). In embodiments, $R^4$ is -$G_{0-10}$DRIIDS*GLDS*M (SEQ NO:6) or a derivative thereof (e.g., including one, two or three substitutions (e.g., conservative substitutions), wherein S* is a phosphoserine. In embodiments, $R^4$ is -$G_{0-10}$DRIIDS*GLDS*M (SEQ ID NO:6). "IκBα" is used in accordance with its well understood meaning and refers to a protein that inhibits NF-κB transcription factor. In embodiments, phosphopeptide including a sequence of IκBα is as described in P. Natl Acad Sci USA (2001) July 17, vol. 98(15) 8554-8559. In embodiments, $R^4$ includes a phosphopeptide including a sequence of IκBα, or an analog, derivative, or prodrug thereof. In embodiments, $R^4$ includes a phosphopeptide consisting of a sequence of IκBα, or an analog, derivative, or prodrug thereof. In embodiments, $R^4$ includes -RAEDS*GNES*EGE (SEQ ID NO:3) or a derivative thereof (e.g., including one, two or three substitutions (e.g., conservative substitutions), wherein S* is a phosphoserine. In embodiments, $R^4$ includes -RAEDS*GNES*EGE (SEQ ID NO:3). In embodiments, $R^4$ is $G_{0-10}$RAEDS*GNES*EGE (SEQ ID NO:4) or a derivative thereof (e.g., including one, two or three substitutions (e.g., conservative substitutions), wherein S* is a phosphoserine. In embodiments, $R^4$ includes -$G_{0-10}$RAEDS*GNES*EGE (SEQ ID NO:4). In embodiments, $R^4$ includes -DRIIDS*GLDS*M (SEQ ID NO:5) or a derivative thereof (e.g., including one, two or three substitutions (e.g., conservative substitutions), wherein S* is a phosphoserine. In embodiments, $R^4$ includes -DRIIDS*GLDS*M (SEQ ID NO:5). In embodiments, $R^4$ includes -$G_{0-10}$DRIIDS*GLDS*M (SEQ ID NO:6) or a derivative thereof (e.g., including one, two or three substitutions (e.g., conservative substitutions), wherein S* is a phosphoserine. In embodiments, $R^4$ includes -$G_{0-10}$DRIIDS*GLDS*M (SEQ ID NO:6).

In embodiments, $R^4$ is a nutlin moiety or an analog, derivative, or prodrug thereof. In embodiments, $R^4$ is a nutlin-3 moiety or an analog, derivative, or prodrug thereof. In embodiments, $R^4$ is a (±)-4-[4,5-Bis(4-chlorophenyl)-2-(2-isopropoxy-4-methoxy-phenyl)-4,5-dihydro-imidazole-1 1-carbonyl]-piperazin-2-one moiety. In embodiments, $R^4$ is a (−)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^4$ is a (+)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^4$ is a nutlin moiety. In embodiments, $R^4$ is a nutlin-3 moiety. "Nutlin" and "nutlin-3" are used in accordance with their well understood meaning and refer to cis-imidazoline analogs. In embodiments, nutlin or nutlin-3 is as described in Bioorg. Med. Chem. Lett (2008) 18 5904-5908. In embodiments, $R^4$ includes a nutlin moiety or an analog, derivative, or prodrug thereof. In embodiments, $R^4$ includes a nutlin-3 moiety or an analog, derivative, or prodrug thereof. In embodiments, $R^4$ includes a (±)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^4$ includes a (−)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^4$ includes a (+)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^4$ includes a nutlin moiety.

In embodiments, $R^4$ is a hydroxyproline containing HIF-1α pentapeptide moiety or an analog, derivative, or prodrug thereof. In embodiments, $R^4$ is -LAP*YI or a derivative thereof (e.g., including one, two or three substitutions (e.g., conservative substitutions), wherein P* is a hydroxyproline. In embodiments, $R^4$ is -$G_{0-10}$LAP*YI or a derivative thereof (e.g., including one, two or three substitutions (e.g., conservative substitutions), wherein P* is a hydroxyproline. In embodiments, $R^4$ is -LAP*YI. In embodiments, $R^4$ is -$G_{0-10}$LAP*YI. "HIF-1α" is used in accordance with its well understood meaning and refers to the hypoxia-inducible factor 1-alpha transcription factor. In embodiments, HIF-1α is as described in Oncogene (2008) 27, 7201-7211. In embodiments, $R^4$ includes a hydroxyproline containing HIF-1α pentapeptide moiety or an analog, derivative, or prodrug thereof. In embodiments, $R^4$ includes -LAP*YI or a derivative thereof (e.g., including one, two or three substitutions (e.g., conservative substitutions), wherein P* is a hydroxyproline. In embodiments, $R^4$ includes -$G_{0-10}$LAP*YI or a derivative thereof (e.g., including one, two or three substitutions (e.g., conservative substitutions), wherein P* is a hydroxyproline. In embodiments, $R^4$ includes -LAP*YI. In embodiments, $R^4$ includes -$G_{0-10}$LAP*YI.

In embodiments, $R^4$ is a degradation-increasing moiety. In embodiments, the degradation-increasing moiety is a thalidomide moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is a thalidomide moiety. In embodiments of a derivative, an original substituent (e.g., substituent group) of a thalidomide moiety is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of a thalidomide moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a thalidomide moiety is replaced with a substituent (e.g., substituent group). In embodiments of a derivative, a plurality of hydrogen atoms of a thalidomide moiety are replaced with a plurality of substituents (e.g., substituent groups), wherein the substituents (e.g., substituent groups) are each optionally different.

In embodiments, $R^4$ is a degradation-increasing moiety. In embodiments, the degradation-increasing moiety is a phthalimide moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is a phthalimide moiety. In embodiments of a derivative, an original substituent (e.g., substituent group) of a phthalimide moiety is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of a phthalimide moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a phthalimide moiety is replaced with a substituent (e.g., substituent group). In embodiments of a derivative, a plurality of hydrogen atoms of a phthalimide moiety are replaced with a plurality of substituents (e.g., substituent groups), wherein the substituents (e.g., substituent groups) are each optionally different.

In embodiments, $R^4$ is a degradation-increasing moiety. In embodiments, the degradation-increasing moiety is adamantyl or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is adamantyl. In embodiments of a derivative, an original substituent (e.g., substituent group) of adamantyl is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of adamantyl are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of adamantyl is replaced with a substituent (e.g., substituent group). In embodiments of a derivative, a plurality of hydrogen atoms of adamantyl are replaced with a plurality of substituents (e.g., substituent groups), wherein the substituents (e.g., substituent groups) are each optionally different.

In embodiments, $R^4$ is a degradation-increasing moiety. In embodiments, the degradation-increasing moiety is an IκBα phosphopeptide moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is an IκBα phosphopeptide moiety. In embodiments of a derivative, an original substituent (e.g., substituent group) of an IκBα phosphopeptide moiety is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of an IκBα phosphopeptide moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of an IκBα phosphopeptide moiety is replaced with a substituent (e.g., substituent group). In embodiments of a derivative, a plurality of hydrogen atoms of an IκBα phosphopeptide moiety are replaced with a plurality of substituents (e.g., substituent groups), wherein the substituents (e.g., substituent groups) are each optionally different.

In embodiments, $R^4$ is a degradation-increasing moiety. In embodiments, the degradation-increasing moiety is a nutlin moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is a nutlin moiety. In embodiments of a derivative, an original substituent (e.g., substituent group) of a nutlin moiety is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of a nutlin moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a nutlin moiety is replaced with a substituent (e.g., substituent group). In embodiments of a derivative, a plurality of hydrogen atoms of a nutlin moiety are replaced with a plurality of substituents (e.g., substituent groups), wherein the substituents (e.g., substituent groups) are each optionally different.

In embodiments, $R^4$ is a degradation-increasing moiety. In embodiments, the degradation-increasing moiety is a HIF-1α pentapeptide moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is a HIF-1α pentapeptide moiety. In embodiments of a derivative, an original substituent (e.g., substituent group) of a HIF-1α pentapeptide moiety is replaced with an alternative substituent (e.g., substituent group), wherein the alternative substituent (e.g., substituent group) is different from the original substituent (e.g., substituent group). In embodiments of a derivative, a plurality of original substituents substituent groups) of a HIF-1α pentapeptide moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a HIF-1α pentapeptide moiety is replaced with a substituent (e.g., substituent group). In embodiments of a derivative, a plurality of hydrogen atoms of a HIF-1α pentapeptide moiety are replaced with a plurality of substituents (e.g., substituent groups), wherein the substituents (e.g., substituent groups) are each optionally different.

In embodiments, R⁴ is a degradation-increasing moiety. In embodiments, the degradation-increasing moiety is

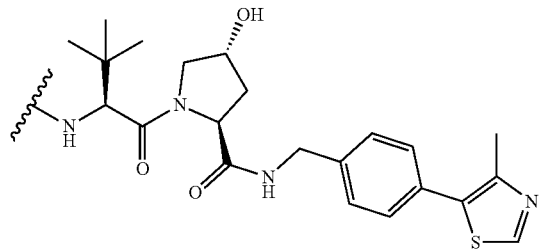 [SMILES: *N[C@H](C(=O)N1C[C@H](O)C[C@H]1C(=O)NCc1ccc(-c2scnc2C)cc1)C(C)(C)C]

or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is

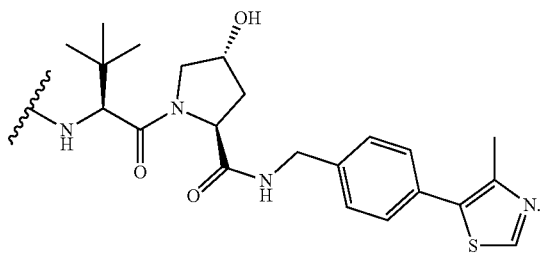 [SMILES: *N[C@H](C(=O)N1C[C@H](O)C[C@H]1C(=O)NCc1ccc(-c2scnc2C)cc1)C(C)(C)C]

In embodiments of a derivative, an original substituent (e.g., substituent group) of

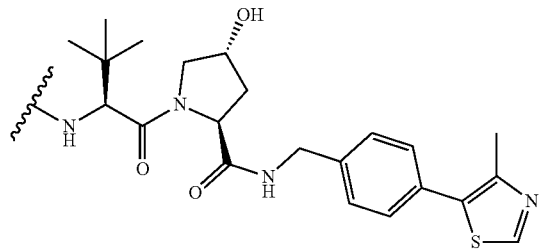 [SMILES: *N[C@H](C(=O)N1C[C@H](O)C[C@H]1C(=O)NCc1ccc(-c2scnc2C)cc1)C(C)(C)C]

is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of

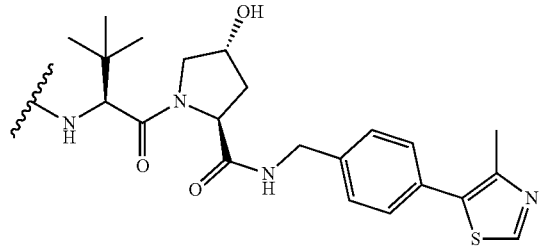 [SMILES: *N[C@H](C(=O)N1C[C@H](O)C[C@H]1C(=O)NCc1ccc(-c2scnc2C)cc1)C(C)(C)C]

are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of

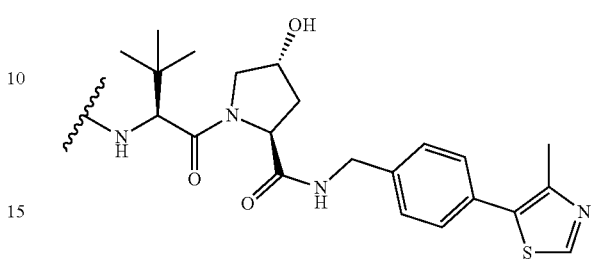

is replaced with a substituent (e.g., substituent group). In embodiments of a derivative, a plurality of hydrogen atoms of

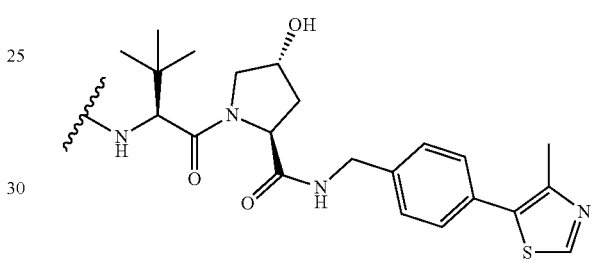

are replaced with a plurality of substituents (e.g., substituent groups), wherein the substituents substituent groups) are each optionally different.

In embodiments, R⁵ is independently halogen, —CF₃, —CHF₂, —CH₂F, —OCF₃, —OCHF₂, —OCH₂F, substituted or unsubstituted C₁-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted C₆-C₁₀ aryl, or substituted or unsubstituted 5 to 10 membered heteroaryl. In embodiments, R⁵ is independently halogen, —CF₃, —CHF₂, —OCF₃, —OCHF₂, substituted or unsubstituted C₁-C₈ alkyl, substituted or unsubstituted 2 to 8 membered heteroalkyl, substituted or unsubstituted C₃-C₈ cycloalkyl, substituted or unsubstituted 3 to 8 membered heterocycloalkyl, substituted or unsubstituted C₆-C₁₀ aryl, or substituted or unsubstituted 5 to 10 membered heteroaryl. In embodiments, R⁵ is independently halogen, —CF₃, —OH, —NH₂, —SH, substituted or unsubstituted C₁-C₄ alkyl, substituted or unsubstituted 2 to 4 membered heteroalkyl, substituted or unsubstituted C₃-C₆ cycloalkyl, substituted or unsubstituted 3 to 6 membered heterocycloalkyl, substituted or unsubstituted phenyl, or substituted or unsubstituted 5 to 6 membered heteroaryl. In embodiments, R⁵ is independently halogen, —OH, —NH₂, —SH, unsubstituted C₁-C₄ alkyl, or unsubstituted 2 to 4 membered heteroalkyl. In embodiments, R⁵ is independently halogen, —OH, unsubstituted methyl, or unsubstituted methoxy. In embodiments, R⁵ is independently halogen. In embodiments, R⁵ is independently —CF₃. In embodiments, R⁵ is independently —CHF₂. In embodiments, R⁵ is independently —CH₂F. In embodiments, R⁵ is independently —OCF₃. In embodiments, R⁵ is independently —OCHF₂. In embodiments, R⁵ is independently —OCH₂F. In embodiments, R⁵ is independently substituted or unsubstituted C₁-C₈ alkyl. In embodiments, R⁵ is independently substituted or unsubstituted 2 to 8 membered heteroalkyl. In embodiments, R⁵ is independently substituted or unsubstituted C₃-C₈ cycloalkyl. In embodiments, R⁵ is independently substituted or unsubstituted 3 to 8 membered heterocycloalkyl. In embodiments, R⁵ is independently substituted or unsubstituted C₆-C₁₀ aryl. In embodiments, R⁵ is independently substituted or unsubstituted 5 to 10 membered heteroaryl. In embodiments, R⁵ is independently —OH. In embodiments, R⁵ is independently —NH₂. In embodiments, R⁵ is independently —SH. In embodiments, R⁵ is independently substituted or unsubstituted C₁-C₄ alkyl. In embodiments, R⁵ is independently substituted or unsubstituted 2 to 4 membered heteroalkyl. In embodiments, R⁵ is independently substituted or unsubstituted C₃-C₆ cycloalkyl. In embodiments, R⁵ is independently substituted or unsubstituted 3 to 6 membered heterocycloalkyl. In embodiments, R⁵ is independently substituted or unsubstituted phenyl. In embodiments, R⁵ is independently substituted or unsubstituted 5 to 6 membered heteroaryl. In embodiments, R⁵ is independently substituted C₁-C₈ alkyl. In embodiments, R⁵ is independently substituted 2 to 8 membered heteroalkyl. In embodiments, R⁵ is independently substituted C₃-C₈ cycloalkyl. In embodiments, R⁵ is independently substituted 3 to 8 membered heterocycloalkyl. In embodiments, R⁵ is independently substituted C₆-C₁₀ aryl. In embodiments, R⁵ is independently substituted 5 to 10 membered heteroaryl. In embodiments, R⁵ is independently substituted C₁-C₄ alkyl. In embodiments, R⁵ is independently substituted to 4 membered heteroalkyl. In embodiments, R⁵ is independently substituted C₃-C₆ cycloalkyl. In embodiments, R⁵ is independently substituted 3 to 6 membered heterocycloalkyl. In embodiments, R⁵ is independently substituted phenyl. In embodiments, R⁵ is independently substituted 5 to 6 membered heteroaryl. In embodiments, R⁵ is independently unsubstituted C₁-C₈ alkyl. In embodiments, R⁵ is independently unsubstituted 2 to 8 membered heteroalkyl. In embodiments, R⁵ is independently unsubstituted C₃-C₈ cycloalkyl. In embodiments, R⁵ is independently unsubstituted 3 to 8 membered heterocycloalkyl. In embodiments, R⁵ is independently unsubstituted C₆-C₁₀ aryl. In embodiments, R⁵ is independently unsubstituted 5 to 10 membered heteroaryl. In embodiments, R⁵ is independently unsubstituted C₁-C₄ alkyl. In embodiments, R⁵ is independently unsubstituted 2 to 4 membered heteroalkyl. In embodiments, R⁵ is independently unsubstituted C₃-C₆ cycloalkyl. In embodiments, R⁵ is independently unsubstituted 3 to 6 membered heterocycloalkyl. In embodiments, R⁵ is independently unsubstituted phenyl. In embodiments, R⁵ is independently unsubstituted 5 to 6 membered heteroaryl. In embodiments, R⁵ is —NH₂.

In embodiments, -L⁵-R⁵ is unsubstituted methoxy.

In embodiments, -L⁵-R⁵ is

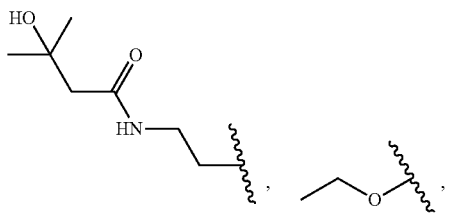

-continued

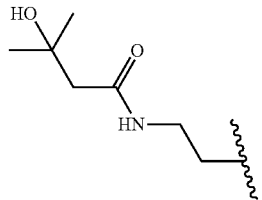

In embodiments, -L⁵-R⁵ is substituted or unsubstituted 5 to 10 membered heteroalkyl. In embodiments, -L⁵-R⁵ is substituted or unsubstituted 6 to 10 membered heteroalkyl. In embodiments, -L⁵-R⁵ is substituted or unsubstituted 7 to 10 membered heteroalkyl. In embodiments, -L⁵-R⁵ is substituted or unsubstituted 7 to 9 membered heteroalkyl. In embodiments, -L⁵-R⁵ is substituted or unsubstituted 5 membered heteroaryl. In embodiments, -L⁵-R⁵ is substituted or unsubstituted 5 to 6 membered heteroaryl. In embodiments, -L⁵-R⁵ is substituted or unsubstituted 4 to 6 membered heteroaryl. In embodiments, -L⁵-R⁵ is substituted or unsubstituted heteroaryl. In embodiments, -L⁵-R⁵ is substituted 5 membered heteroaryl. In embodiments, -L⁵-R⁵ is substituted 5 to 6 membered heteroaryl. In embodiments, -L⁵-R⁵ is substituted 4 to 6 membered heteroaryl. In embodiments, -L⁵-R⁵ is substituted heteroaryl. In embodiments, -L⁵-R⁵ is unsubstituted 5 membered heteroaryl. In embodiments, -L⁵-R⁵ is unsubstituted 5 to 6 membered heteroaryl. In embodiments, -L⁵-R⁵ is unsubstituted heteroaryl. In embodiments, -L⁵-R⁵ is unsubstituted 4 to 6 membered heteroaryl.

In embodiments, -L⁵-R⁵ is

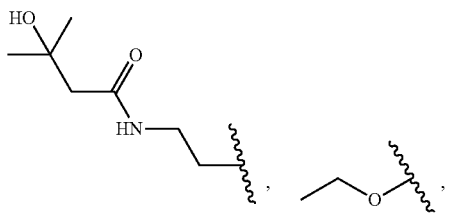

In embodiments, -L⁵-R⁵ is

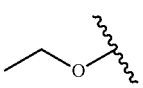 [SMILES: *OCC]

In embodiments, -L⁵-R⁵ is

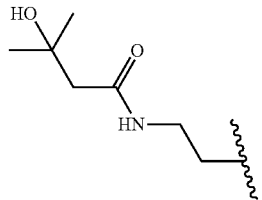

In embodiments, -L$^5$-R$^5$ is

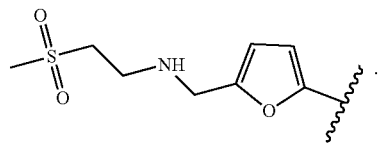 [SMILES: *c1ccc(CNCCS(C)(=O)=O)o1]

In embodiments, -L$^5$-R$^5$ is

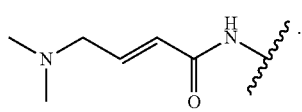 [SMILES: *NC(=O)/C=C/CN(C)C]

In embodiments, -L$^5$-R$^5$ is

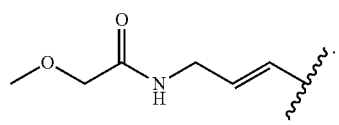 [SMILES: */C=C/CNC(=O)COC]

In embodiments, -L$^5$-R$^5$ is

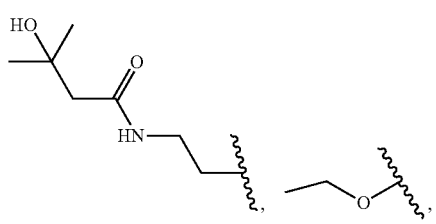

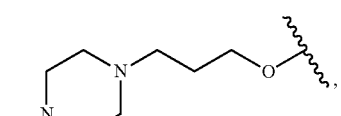

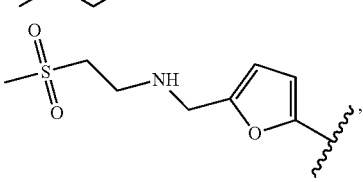

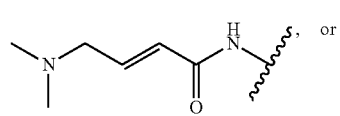 or

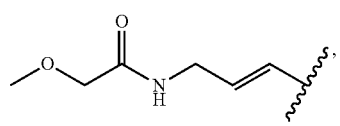

when R$^4$ is a degradation-increasing moiety. In embodiments, -L$^5$-R$^5$ is

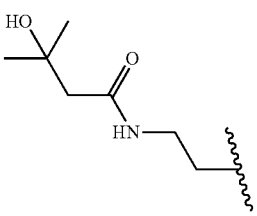 [SMILES: *CCNC(=O)CC(C)(C)O]

when R$^4$ is a degradation-increasing moiety. In embodiments, -L$^5$-R$^5$ is

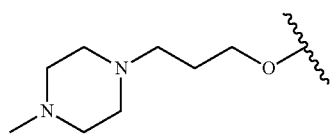 [SMILES: *OCCCN1CCN(C)CC1]

when R$^4$ is a degradation-increasing moiety. In embodiments, -L$^5$-R$^5$ is

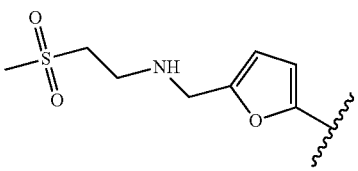 [SMILES: *c1ccc(CNCCS(C)(=O)=O)o1]

when R$^4$ is a degradation-increasing moiety. In embodiments, -L$^5$-R$^5$ is

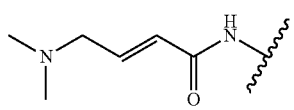 [SMILES: *NC(=O)/C=C/CN(C)C]

when R$^4$ is a degradation-increasing moiety. In embodiments, -L$^5$-R$^5$ is

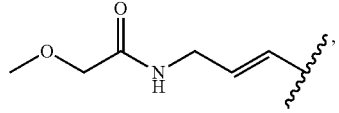 [SMILES: */C=C/CNC(=O)COC]

when R$^4$ is a degradation-increasing moiety.

In embodiments, R$^5$ is a degradation-increasing moiety. In embodiments, the degradation-increasing moiety is thalidomide moiety or an analog, derivative, prodrug thereof; phthalimide moiety or an analog, derivative, or prodrug thereof; adamantyl or an analog, derivative, or prodrug thereof; an IκBα phosphopeptide moiety or an analog, derivative, or prodrug thereof; nutlin moiety or an analog, derivative, or prodrug thereof; HIF-1α pentapeptide moiety or an analog, derivative, or prodrug thereof; or

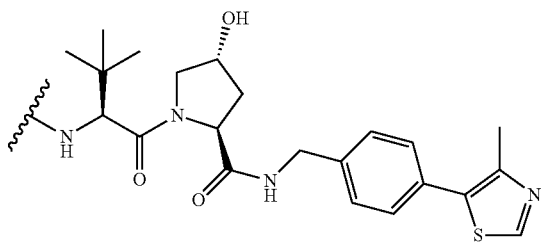 [SMILES: *N[C@H](C(=O)N1C[C@H](O)C[C@H]1C(=O)NCc1ccc(-c2scnc2C)cc1)C(C)(C)C]

or an analog, derivative, or prodrug thereof. In embodiments, the degradation-increasing moiety is thalidomide moiety or an analog, derivative, or prodrug thereof. In embodiments, $R^5$ is

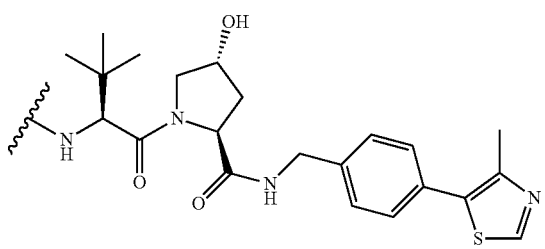 [SMILES: *N[C@H](C(=O)N1C[C@H](O)C[C@H]1C(=O)NCc1ccc(-c2scnc2C)cc1)C(C)(C)C]

or an analog, derivative, or prodrug thereof. In embodiments, $R^5$ is

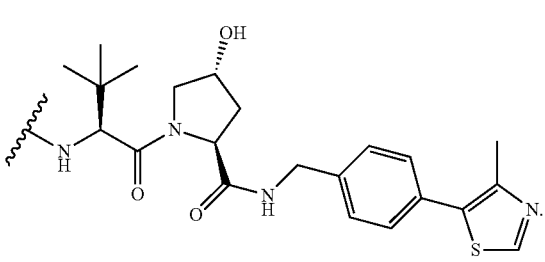 [SMILES: *N[C@H](C(=O)N1C[C@H](O)C[C@H]1C(=O)NCc1ccc(-c2scnc2C)cc1)C(C)(C)C]

In embodiments, $R^5$ is a thalidomide moiety or an analog, derivative, or prodrug thereof. In embodiments, $R^5$ is a thalidomide moiety. In embodiments, $R^5$ is a lenalidomide moiety. In embodiments, $R^5$ is a pomalidomide moiety. In embodiments, $R^5$ is

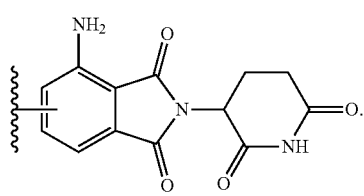

In embodiments, $R^5$ is

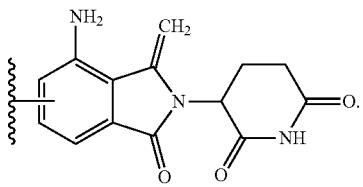

In embodiments, $R^5$ is

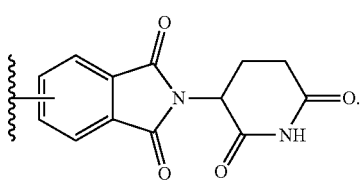

In embodiments, $R^5$ is

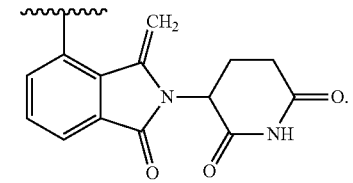 [SMILES: *c1cccc2c1C(=C)N(C1CCC(=O)NC1=O)C2=O]

In embodiments, $R^5$ is

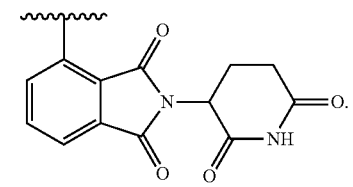 [SMILES: *c1cccc2c1C(=O)N(C1CCC(=O)NC1=O)C2=O]

In embodiments, $R^5$ is a phthalimide moiety or an analog, derivative, or prodrug thereof. In embodiments, $R^5$ is

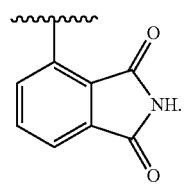 [SMILES: *c1cccc2c1C(=O)NC2=O]

In embodiments, $R^5$ is

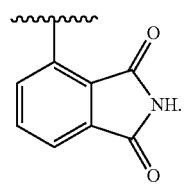 [SMILES: *c1cccc2c1C(=O)NC2=O]

In embodiments, $R^5$ is a phthalimide moiety. In embodiments, $R^5$ includes a thalidomide moiety or an analog, derivative, or prodrug thereof. In embodiments, $R^5$ includes a thalidomide moiety. In embodiments, $R^5$ includes a lenalidomide moiety. In embodiments, $R^5$ includes a pomalidomide moiety. In embodiments, $R^5$ includes a phthalimide moiety or an analog, derivative, or prodrug thereof. In embodiments, $R^5$ includes a phthalimide moiety.

In embodiments, $R^5$ is adamantyl or an analog, derivative, or prodrug thereof. In embodiments, $R^5$ is substituted adamantyl or an analog, derivative, or prodrug thereof. In embodiments, $R^5$ is adamantyl. In embodiments, $R^5$ is substituted adamantyl. In embodiments, $R^5$ is adamantyl. In embodiments, $R^5$ is substituted adamantyl.

In embodiments, $R^5$ is a phosphopeptide consisting of a sequence of IκBα, or an analog, derivative, or prodrug thereof. In embodiments, $R^5$ is -RAEDS*GNES*EGE (SEQ ID NO:3) or a derivative thereof (e.g., including one, two or three substitutions (e.g., conservative substitutions), wherein S* is a phosphoserine. In embodiments, $R^5$ is -RAEDS*GNES*EGE (SEQ ID NO:3). In embodiments, $R^5$ is -$G_{0-10}$RAEDS*GNES*EGE (SEQ ID NO:4) or a derivative thereof (e.g., including one, two or three substitutions (e.g., conservative substitutions), wherein S* is a phosphoserine. In embodiments, $R^5$ is $G_{0-10}$RAEDS*GNES*EGE (SEQ ID NO:4). In embodiments, $R^5$ is -DRIIDS*GLDS*M (SEQ ID NO:5) or a derivative thereof (e.g., including one, two or three substitutions (e.g., conservative substitutions), wherein S* is a phosphoserine. In embodiments, $R^5$ is -DRIIDS*GLDS*M (SEQ ID NO:5). In embodiments, $R^5$ is $G_{0-10}$DRIIDS*GLDS*M (SEQ ID NO:6) or a derivative thereof (e.g., including one, two or three substitutions (e.g., conservative substitutions), wherein S* is a phosphoserine. In embodiments, $R^5$ is -$G_{0-10}$DRIIDS*GLDS*M (SEQ ID NO:6). "IκBα" is used in accordance with its well understood meaning and refers to a protein that inhibits NF-κB transcription factor. In embodiments, phosphopeptide including a sequence of IκBα is as described in P. Natl Acad Sci USA (2001) July 17, vol. 98(15) 8554-8559. In embodiments, $R^5$ includes a phosphopeptide including a sequence of IκBα, or an analog, derivative, or prodrug thereof. In embodiments, $R^5$ includes a phosphopeptide consisting of a sequence of IκBα, or an analog, derivative, or prodrug thereof. In embodiments, $R^5$ includes -RAEDS*GNES*EGE (SEQ ID NO:3) or a derivative thereof (e.g., including one, two or three substitutions (e.g., conservative substitutions), wherein S* is a phosphoserine. In embodiments, $R^5$ includes -RAEDS*GNES*EGE (SEQ ID NO:3). In embodiments, $R^5$ is -$G_{0-10}$RAEDS*GNES*EGE (SEQ ID NO:4) or a derivative thereof (e.g., including one, two or three substitutions (e.g., conservative substitutions), wherein S* is a phosphoserine. In embodiments, $R^5$ includes -$G_{0-10}$RAEDS*GNES*EGE (SEQ ID NO:4). In embodiments, $R^5$ includes -DRIIDS*GLDS*M (SEQ ID NO:5) or a derivative thereof (e.g., including one, two or three substitutions (e.g., conservative substitutions), wherein S* is a phosphoserine. In embodiments, $R^5$ includes -DRIIDS*GLDS*M (SEQ NO:5). In embodiments, $R^5$ includes $G_{0-10}$DRIIDS*GLDS*M (SEQ ID NO:6) or a derivative thereof (e.g., including one, two or three substitutions (e.g., conservative substitutions), wherein S* is a phosphoserine. In embodiments, $R^5$ includes -$G_{0-10}$DRIIDS*GLDS*M (SEQ ID NO:6).

In embodiments, $R^5$ is a nutlin moiety or an analog, derivative, or prodrug thereof. In embodiments, $R^5$ is a nutlin-3 moiety or an analog, derivative, or prodrug thereof. In embodiments, $R^5$ is a (±)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^5$ is a (−)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^5$ is a (+)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^5$ is a nutlin moiety. In embodiments, $R^5$ is a nutlin-3 moiety. "Nutlin" and "nutlin-3" are used in accordance with their well understood meaning and refer to cis-imidazoline analogs. In embodiments, nutlin or nutlin-3 is as described in Bioorg. Med. Chem. Lett (2008) 18 5904-5908. In embodiments, $R^5$ includes a nutlin moiety or an analog, derivative, or prodrug thereof. In embodiments, $R^5$ includes a nutlin-3 moiety or an analog, derivative, or prodrug thereof. In embodiments, $R^5$ includes a (±)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^5$ includes a (−)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^5$ includes a (+)-4-[4,5-Bis(4-chlorophenyl)-2-(2-isopropoxy-4-methoxy-phenyl)-4,5-dihydro-imidazole-1-carbonyl]-piperazin-2-one moiety. In embodiments, $R^5$ includes a nutlin moiety.

In embodiments, $R^5$ is a hydroxyproline containing HIF-1α pentapeptide moiety or an analog, derivative, or prodrug thereof. In embodiments, $R^5$ is -LAP*YI or a derivative thereof (e.g., including one, two or three substitutions (e.g., conservative substitutions), wherein P* is a hydroxyproline. In embodiments, $R^5$ is -LAP*YI. In embodiments, $R^5$ is -$G_{0-10}$LAP*YI or a derivative thereof (e.g., including one, two or three substitutions (e.g., conservative substitutions), wherein P* is a hydroxyproline. In embodiments, $R^5$ is -$G_{0-10}$LAP*YI. "HIF-1α" is used in accordance with its well understood meaning and refers to the hypoxia-inducible factor 1-alpha transcription factor. In embodiments, HIF-1α is as described in Oncogene (2008) 27, 7201-7211. In embodiments, $R^5$ includes a hydroxyproline containing HIF-1α pentapeptide moiety or an analog, derivative, or prodrug thereof. In embodiments, $R^5$ includes -LAP*YI or a derivative thereof (e.g., including one, two or three substitutions (e.g., conservative substitutions), wherein P* is a hydroxyproline. In embodiments, $R^5$ includes -$G_{0-10}$LAP*YI or a derivative thereof (e.g., including one, two or three substitutions (e.g., conservative substitutions), wherein P* is a hydroxyproline. In embodiments, $R^5$ includes -LAP*YI. In embodiments, $R^5$ includes -$G_{0-10}$LAP*YI.

In embodiments, $R^5$ is a degradation-increasing moiety. In embodiments, the degradation-increasing moiety is a thalidomide moiety or a derivative, analog, or prodrug thereof. In embodiments, the degradation-increasing moiety is an analog thereof. In embodiments, the degradation-increasing moiety is a derivative thereof in embodiments, the degradation-increasing moiety is a prodrug thereof (e.g., a physiologically hydrolyzable ester thereof or a physiologically hydrolyzable amide thereof). In embodiments, the degradation-increasing moiety is a thalidomide moiety. In embodiments of a derivative, an original substituent (e.g., substituent group) of a thalidomide moiety is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of a thalidomide moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a thalidomide moiety is replaced with a substituent (e.g., substituent group). In embodiments of a derivative, a plurality of hydrogen atoms of a thalidomide moiety are replaced with a plurality of substituents (e.g., substituent groups), wherein the substituents (e.g., substituent groups) are each optionally different.

In embodiments, $R^5$ is a degradation-increasing moiety. In embodiments, the degradation-increasing moiety is a phthalimide moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is a phthalimide moiety. In embodiments of a derivative, an original substituent (e.g., substituent group) of a phthalimide moiety is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of a phthalimide moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a phthalimide moiety is replaced with a substituent (e.g., substituent group). In embodiments of a derivative, a plurality of hydrogen atoms of a phthalimide moiety are replaced with a plurality of substituents (e.g., substituent groups), wherein the substituents (e.g., substituent groups) are each optionally different.

In embodiments, $R^5$ is a degradation-increasing moiety. In embodiments, the degradation-increasing moiety is adamantyl or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is adamantyl. In embodiments of a derivative, an original substituent (e.g., substituent group) of adamantyl is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of adamantyl are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of adamantyl is replaced with a substituent (e.g., substituent group). In embodiments of a derivative, a plurality of hydrogen atoms of adamantyl are replaced with a plurality of substituents (e.g., substituent groups), wherein the substituents (e.g., substituent groups) are each optionally different.

In embodiments, $R^5$ is a degradation-increasing moiety. In embodiments, the degradation-increasing moiety is an IκBα phosphopeptide moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is an IκBα phosphopeptide moiety. In embodiments of a derivative, an original substituent (e.g., substituent group) of an IκBα phosphopeptide moiety is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of an IκBα phosphopeptide moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of an IκBα phosphopeptide moiety is replaced with a substituent (e.g., substituent group). In embodiments of a derivative, a plurality of hydrogen atoms of an IκBα phosphopeptide moiety are replaced with a plurality of substituents (e.g., substituent groups), wherein the substituents (e.g., substituent groups) are each optionally different.

In embodiments, $R^5$ is a degradation-increasing moiety. In embodiments, the degradation-increasing moiety is a nutlin moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is a nutlin moiety. In embodiments of a derivative, an original substituent (e.g., substituent group) of a nutlin moiety is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of a nutlin moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a nutlin moiety is replaced with a substituent (e.g., substituent group). In embodiments of a derivative, a plurality of hydrogen atoms of a nutlin moiety are replaced with a plurality of substituents (e.g., substituent groups), wherein the substituents (e.g., substituent groups) are each optionally different.

In embodiments, $R^5$ is a degradation-increasing moiety. In embodiments, the degradation-increasing moiety is a HIF-1α pentapeptide moiety or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is a HIF-1α pentapeptide moiety. In embodiments of a derivative, an original substituent (e.g., substituent group) of a HIF-1α pentapeptide moiety is replaced with an alternative substituent (e.g., substituent group), wherein the alternative substituent (e.g., substituent group) is different from the original substituent (e.g., substituent group). In embodiments of a derivative, a plurality of original substituents substituent groups) of a HIF-1α pentapeptide moiety are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of a HIF-1α pentapeptide moiety is replaced with a substituent (e.g., substituent group). In embodiments of a derivative, a plurality of hydrogen atoms of a HIF-1α pentapeptide moiety are replaced with a plurality of substituents (e.g., substituent groups), wherein the substituents (e.g., substituent groups) are each optionally different.

In embodiments, $R^5$ is a degradation-increasing moiety. In embodiments, the degradation-increasing moiety is

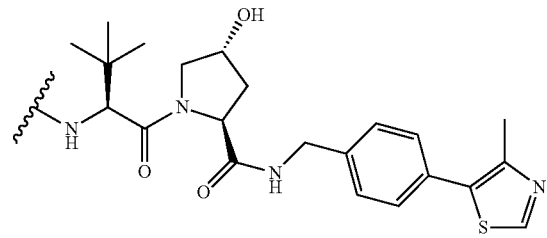 [SMILES: *N[C@H](C(=O)N1C[C@H](O)C[C@H]1C(=O)NCc1ccc(-c2scnc2C)cc1)C(C)(C)C]

or a derivative, analog, or prodrug thereof. In embodiments, the degradation-increasing moiety is an analog thereof. In embodiments, the degradation-increasing moiety is a derivative thereof. In embodiments, the degradation-increasing moiety is a prodrug thereof (e.g., a physiologically hydrolyzable ester thereof or a physiologically hydrolyzable amide thereof). In embodiments, the degradation-increasing moiety is

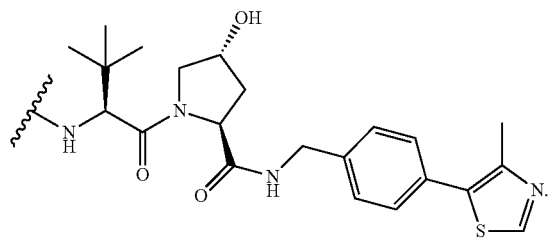 [SMILES: *N[C@H](C(=O)N1C[C@H](O)C[C@H]1C(=O)NCc1ccc(-c2scnc2C)cc1)C(C)(C)C]

In embodiments of a derivative, an original substituent (e.g., substituent group) of

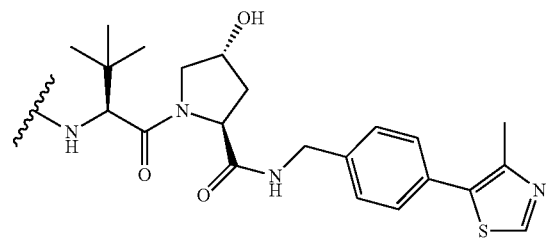 [SMILES: *N[C@H](C(=O)N1C[C@H](O)C[C@H]1C(=O)NCc1ccc(-c2scnc2C)cc1)C(C)(C)C]

is replaced with an alternative substituent (e.g., substituent group), wherein the alternative substituent (e.g., substituent group) is different from the original substituent (e.g., substituent group). In embodiments of a derivative, a plurality of original substituents (e.g., substituent groups) of

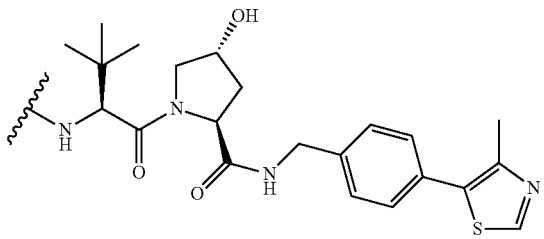 [SMILES: *N[C@H](C(=O)N1C[C@H](O)C[C@H]1C(=O)NCc1ccc(-c2scnc2C)cc1)C(C)(C)C]

are replaced with a plurality of alternative substituents (e.g., substituent groups), wherein the alternative substituents (e.g., substituent groups) are each optionally different and each alternative substituent (e.g., substituent group) is different from the original substituent (e.g., substituent group) it replaces. In embodiments of a derivative, a hydrogen atom of

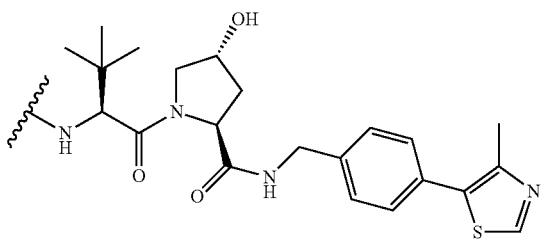 [SMILES: *N[C@H](C(=O)N1C[C@H](O)C[C@H]1C(=O)NCc1ccc(-c2scnc2C)cc1)C(C)(C)C]

is replaced with a substituent (e.g., substituent group). In embodiments of a derivative, a plurality of hydrogen atoms of

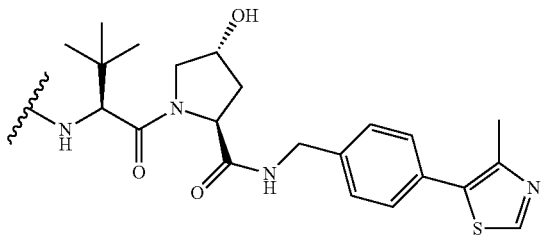 [SMILES: *N[C@H](C(=O)N1C[C@H](O)C[C@H]1C(=O)NCc1ccc(-c2scnc2C)cc1)C(C)(C)C]

are replaced with a plurality of substituents (e.g., substituent groups), wherein the substituents substituent groups) are each optionally different.

In embodiments, $R^6$ is independently a hydrogen, halogen, —CN, —OH, —NH$_2$, —COOH, —CONH$_2$, —NO$_2$, —SH, substituted or unsubstituted C$_1$-C$_4$ alkyl, or substituted or unsubstituted 2 to 4 membered heteroalkyl. In embodiments, $R^6$ is —CN. In embodiments, $R^6$ is independently a hydrogen.

In embodiments, $W^1$ is N. In embodiments, $W^1$ is C(R$^6$). In embodiments, $L^1$ is a bond, —O—, —NH—, —C(O)—, —C(O)NH—, —NHC(O)—, —C(O)O—, —OC(O)—, —NHC(O)NH—, —S—, substituted or unsubstituted C$_1$-C$_3$ alkylene or substituted or unsubstituted 2 to 3 membered heteroalkylene. In embodiments, $L^1$ is —O—, substituted or unsubstituted $C_1$-$C_3$ alkylene or substituted or unsubstituted 2 to 3 membered heteroalkylene. In embodiments, $L^1$ is —O—. In embodiments, $L^1$ is a bond. In embodiments, $L^1$ is —OCH$_2$—. In embodiments, $L^1$ is —CH$_2$O—.

In embodiments, $L^2$ is a bond, —O—, —NH—, —C(O)—, —C(O)NH—, —NHC(O)—, —C(O)O—, —OC(O)—, —NHC(O)NH—, —S—, substituted or unsubstituted $C_1$-$C_3$ alkylene or substituted or unsubstituted 2 to 3 membered heteroalkylene. In embodiments, $L^2$ is a bond. In embodiments, $L^2$ is —C(O)NH—. In embodiments, $L^2$ is —NHC(O)—. In embodiments, $L^2$ is —NHC(O)NH—. In embodiments, $L^2$ is —OCH$_2$—. In embodiments, $L^2$ is —CH$_2$O—.

In embodiments, the linker (e.g., linker that forms a divalent linker such as $L^4$ and/or $L^5$) is a polyethylene glycol linker. In embodiments, the linker (e.g., linker that forms a divalent linker such as $L^4$ and/or $L^5$) is hydrophilic. In embodiments, the linker (e.g., linker that forms a divalent linker such as $L^4$ and/or $L^5$) is hydrophobic. In embodiments, the linker (e.g., linker that forms a divalent linker such as $L^4$ and/or $L^5$) includes a disulfide bond. In embodiments, the linker (e.g., linker that forms a divalent linker such as $L^4$ and/or $L^5$) includes a hydrazone bond. In embodiments, the linker (e.g., linker that forms a divalent linker such as $L^4$ and/or $L^5$) includes an ester. In embodiments, the linker (e.g., linker that forms a divalent linker such as $L^4$ and/or $L^5$) includes a sulfonyl. In embodiments, the linker (e.g., linker that forms a divalent linker such as $L^4$ and/or $L^5$) includes a thioether. In embodiments, the linker (e.g., linker that forms a divalent linker such as $L^4$ and/or $L^5$) includes an ether. In embodiments, the linker (e.g., linker that forms a divalent linker such as $L^4$ and/or $L^5$) includes a phosphinate. In embodiments, the linker (e.g., linker that forms a divalent linker such as $L^4$ and/or $L^5$) includes an alkyloxime bond. In embodiments, the linker (e.g., linker that forms a divalent linker such as $L^4$ and/or $L^5$) includes one or more amino acids. In embodiments, the linker (e.g., linker that forms a divalent linker such as $L^4$ and/or $L^5$) consists of amino acids. In embodiments, the linker (e.g., linker that forms a divalent linker such as $L^4$ and/or $L^5$) includes amino acid derivatives. In embodiments, the linker (e.g., linker that forms a divalent linker such as $L^4$ and/or $L^5$) is a linker as described in Bioconjugate Techniques (Second Edition) by Greg T. Hermanson (2008), which is herein incorporated by referenced in its entirety for all purposes. In embodiments, the linker (e.g., linker that forms a divalent linker such as $L^4$ and/or $L^5$) is a linker as described in Flygare J A, Pillow T H, Aristoff P., Antibody-drug conjugates for the treatment of cancer. Chemical Biology and Drug Design. 2013 January; 81(1): 113-21, which is herein incorporated by referenced in its entirety for all purposes. In embodiments, the linker (e.g., linker that forms a divalent linker such as $L^4$ and/or $L^5$) is a linker as described in Drachman J G, Senter P D., Antibody-drug conjugates: the chemistry behind empowering antibodies to fight cancer. Hematology Am Soc Hematol Educ Program. 2013; 2013:306-10, which is herein incorporated by referenced in its entirety for all purposes. In embodiments, $L^4$ and/or $L^5$ are linkers resulting from bioconjugate chemistry as disclosed herein.

In embodiments, $L^4$ is $L^{4A}$-$L^{4B}$-$L^{4C}$ and $L^{4A}$, $L^{4B}$, and $L^{4C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is a bond, —NH—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^4$ is $L^{4A}$-$L^{4B}$-$L^{4C}$. In embodiments, $L^{4A}$ is a bond, —NH—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{4B}$ is a bond, —NH—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{4C}$ is a bond, —NH—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{4A}$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{4B}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{4C}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{4A}$ is substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{4A}$ is substituted or unsubstituted 3 to 8 membered heteroalkylene. In embodiments, $L^{4A}$ is —CH$_2$CH$_2$OCH$_2$—. In embodiments, $L^{4A}$ is unsubstituted 3 to 8 membered heteroalkylene. In embodiments, $L^{4A}$ is unsubstituted 3 to 6 membered heteroalkylene. In embodiments, $L^{4A}$ is unsubstituted 3 to 5 membered heteroalkylene. In embodiments, $L^{4A}$ is a bond.

In embodiments, $L^{4B}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{4B}$ is a substituted or unsubstituted 5 to 10 membered heteroarylene. In embodiments, $L^{4B}$ is a bond. In embodiments, $L^{4B}$ is a substituted or unsubstituted 5 to 6 membered heteroarylene. In embodiments, $L^{4B}$ is an unsubstituted 5 to 6 membered heteroarylene. In embodiments, $L^{4B}$ is unsubstituted divalent triazole. In embodiments, $L^{4B}$ is unsubstituted divalent 1H-1,2,3-triazole. In embodiments, $L^{4B}$ is unsubstituted divalent 2H-1,2,3-triazole. In embodiments, $L^{4B}$ is unsubstituted divalent furan.

In embodiments, $L^{4C}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{4C}$ is a substituted or unsubstituted 2 to 12 membered heteroalkylene. In embodiments, $L^{4C}$ is a substituted or unsubstituted 2 to 32 membered heteroalkylene. In embodiments, $L^{4C}$ is a bond.

In embodiments, $L^{4C}$ is a divalent oligomer of ethylene oxide. In embodiments, $L^{4C}$ is a divalent polyethylene glycol. In embodiments, $L^{4C}$ is a divalent oligomer of ethylene oxide having 2 to 30 linear atoms (carbon and oxygen) between the two termini connecting to the remainder of the compound. In embodiments, $L^{4C}$ is —($CH_2CH_2O$)$_x CH_2CH_2$— and x is an integer from 1 to 16. In embodiments, x is an integer from 2 to 15. In embodiments, x is an integer from 3 to 14. In embodiments, x is an integer from 4 to 12. In embodiments, x is an integer from 5 to 10. In embodiments, x is an integer from 5 to 8. In embodiments, x is an integer from 6 to 7.

In embodiments, $L^5$ is $L^{5A}$-$L^{5B}$-$L^{5C}$ and $L^{5A}$, $L^{5B}$, and $L^{5C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^5$ is a bond, —NH—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^5$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^5$ is $L^{5A}$-$L^{5B}$-$L^{5C}$. In embodiments, $L^{5A}$ is a bond, —NH—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{5B}$ is a bond, —NH—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{5C}$ is a bond, —NH—, —S—, —O—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{5A}$ is substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene. In embodiments, $L^{5B}$ is a bond, substituted or unsubstituted alkylene, substituted or unsubstituted heteroalkylene, substituted or unsubstituted cycloalkylene, substituted or unsubstituted heterocycloalkylene substituted or unsubstituted arylene, or substituted or unsubstituted heteroarylene. In embodiments, $L^{5C}$ is a bond, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

In embodiments, $L^{5A}$ is substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{5A}$ is substituted or unsubstituted 3 to 8 membered heteroalkylene. In embodiments, $L^{5A}$ is —$CH_2CH_2OCH_2$—. In embodiments, $L^{5A}$ is unsubstituted 3 to 8 membered heteroalkylene. In embodiments, $L^{5A}$ is unsubstituted 3 to 6 membered heteroalkylene. In embodiments, $L^{5A}$ is unsubstituted 3 to 5 membered heteroalkylene. In embodiments, $L^{5A}$ is a bond.

In embodiments, $L^{5B}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{5B}$ is a substituted or unsubstituted 5 to 10 membered heteroarylene. In embodiments, $L^{5B}$ is a bond. In embodiments, $L^{5B}$ is a substituted or unsubstituted 5 to 6 membered heteroarylene. In embodiments, $L^{5B}$ is an unsubstituted 5 to 6 membered heteroarylene. In embodiments, $L^{5B}$ is unsubstituted divalent triazole. In embodiments, $L^{5B}$ is unsubstituted divalent 1H-1,2,3-triazole. In embodiments, $L^{5B}$ is unsubstituted divalent 2H-1,2,3-triazole.

In embodiments, $L^{5C}$ is a bond, substituted or unsubstituted $C_1$-$C_{20}$ alkylene, substituted or unsubstituted 2 to 20 membered heteroalkylene, substituted or unsubstituted $C_3$-$C_8$ cycloalkylene, substituted or unsubstituted 3 to 8 membered heterocycloalkylene, substituted or unsubstituted $C_6$-$C_{10}$ arylene, or substituted or unsubstituted 5 to 10 membered heteroarylene. In embodiments, $L^{5C}$ is a substituted or unsubstituted 2 to 12 membered heteroalkylene. In embodiments, $L^{5C}$ is a substituted or unsubstituted 2 to 32 membered heteroalkylene. In embodiments, $L^{5C}$ is a bond.

In embodiments, $L^{5C}$ is a divalent oligomer of ethylene oxide. In embodiments, $L^{5C}$ is a divalent polyethylene glycol. In embodiments, $L^{5C}$ is a divalent oligomer of ethylene oxide having 2 to 30 linear atoms (carbon and oxygen) between the two termini connecting to the remainder of the compound. In embodiments, $L^{5C}$ is —($CH_2CH_2O$)$_x CH_2CH_2$— and x is an integer from 1 to 16.

In embodiments, x is an integer from 2 to 15. In embodiments, x is an integer from 3 to 14. In embodiments, x is an integer from 4 to 12. In embodiments, x is an integer from 5 to 10. In embodiments, x is an integer from 5 to 8. In embodiments, x is an integer from 6 to 7.

Conjugates described herein may be synthesized using bioconjugate or conjugate chemistry. Conjugate chemistry includes coupling two molecules together to form an adduct. Conjugation may be a covalent modification. Currently favored classes of conjugate chemistry reactions available with reactive known reactive groups are those which proceed under relatively mild conditions. These include, but are not limited to nucleophilic substitutions (e.g., reactions of amines and alcohols with aryl halides, active esters), electrophilic substitutions (e.g., enamine reactions) and additions to carbon-carbon and carbon-heteroatom multiple bonds (e.g., Michael reaction, Diels-Alder addition). These and other useful reactions are discussed in, for example, March, ADVANCED ORGANIC CHEMISTRY, 3rd Ed., John Wiley & Sons, New York, 1985; Hermanson, BIOCONJUGATE TECHNIQUES, Academic Press, San Diego, 1996; and Feeney et al., MODIFICATION OF PROTEINS; Advances in Chemistry Series, Vol. 198, American Chemical Society, Washington, D.C., 1982. In embodiments, the bioconjugation reaction is a click chemistry reaction (Angewandte Chemie International Edition 40 (11): 2004-2021). In embodiments, the bioconjugation reaction is a Huisgen cyclization of azides. In embodiments, the bioconjugation reaction is a copper catalyzed Huisgen cyclization of azides.

Useful reactive functional groups used for conjugate chemistries herein include, for example:

(a) carboxyl groups and various derivatives thereof including, but not limited to, N-hydroxysuccinimide esters, N-hydroxybenztriazole esters, acid halides, acyl imidazoles, thioesters, p-nitrophenyl esters, alkyl, alkenyl, alkynyl and aromatic esters;

(b) hydroxyl groups which can be converted to esters, ethers, aldehydes, etc.

(c) haloalkyl groups wherein the halide can be later displaced with a nucleophilic group such as, for example, an amine, a carboxylate action, thiol anion, carbanion, or an alkoxide ion, thereby resulting in the covalent attachment of a new group at the site of the halogen atom;

(d) dienophile groups which are capable of participating in Diels-Alder reactions such as, for example, maleimido groups;

(e) aldehyde or ketone groups such that subsequent derivatization is possible via formation of carbonyl derivatives such as, for example, imines, hydrazones, semicarbazones or oximes, or via such mechanisms as Grignard addition or alkyllithium addition;

(f) sulfonyl halide groups for subsequent reaction with amines, for example, to form sulfonamides;

(g) thiol groups, which can be converted to disulfides, reacted with aryl halides, or bonded to metals such as gold;

(h) amine or sulfhydryl groups, which can be, for example, acylated, alkylated or oxidized;

(i) alkenes, which can undergo, for example, cycloadditions, acylation, Michael addition. etc;

(j) epoxides, which can react with, for example, amines and hydroxyl compounds;

(k) phosphoramidites and other standard functional groups useful in nucleic acid synthesis;

(l) metal silicon oxide bonding; and (m) metal bonding to reactive phosphorus groups (e.g. phosphines) to form, for example, phosphate diester bonds.

(n) azides coupled to alkynes using copper catalyzed cycloaddition click chemistry.

The reactive functional groups can be chosen such that they do not participate in, or interfere with, the chemical stability of the conjugate described herein. Alternatively, a reactive functional group can be protected from participating in the crosslinking reaction by the presence of a protecting group.

In embodiments, $X^1$ is independently —Cl. In embodiments, $X^1$ is independently —Br. In embodiments, $X^1$ is independently —I. In embodiments, $X^1$ is independently —F. In embodiments, $X^2$ is independently —Cl. In embodiments, $X^2$ is independently —Br. In embodiments, $X^2$ is independently —I. In embodiments, $X^2$ is independently —F. In embodiments, $X^3$ is independently —Cl. In embodiments, $X^3$ is independently —Br. In embodiments, $X^3$ is independently —I. In embodiments, $X^3$ is independently —F. In embodiments, $X^4$ is independently —Cl. In embodiments, $X^4$ is independently —Br. In embodiments, $X^4$ is independently —I. In embodiments, $X^4$ is independently —F. In embodiments, $X^5$ is independently —Cl. In embodiments, $X^5$ is independently —Br. In embodiments, $X^5$ is independently —I. In embodiments, $X^5$ is independently —F. In embodiments, $X^6$ is independently —Cl. In embodiments, $X^6$ is independently —Br. In embodiments, $X^6$ is independently —I. In embodiments, $X^6$ is independently —F. In embodiments, $X^A$ is independently —Cl. In embodiments, $X^A$ is independently —Br. In embodiments, $X^A$ is independently —I. In embodiments, $X^A$ is independently —F.

In embodiments, the compound has the formula:

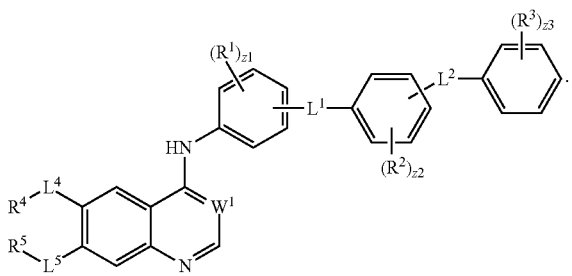

$W^1$, $R^1$, $R^2$, $R^3$, $R^4$, $R^5$, $L^1$, $L^2$, $L^4$, $L^5$, z1, z2, and z3 are as described herein.

In embodiments, the compound has the formula:

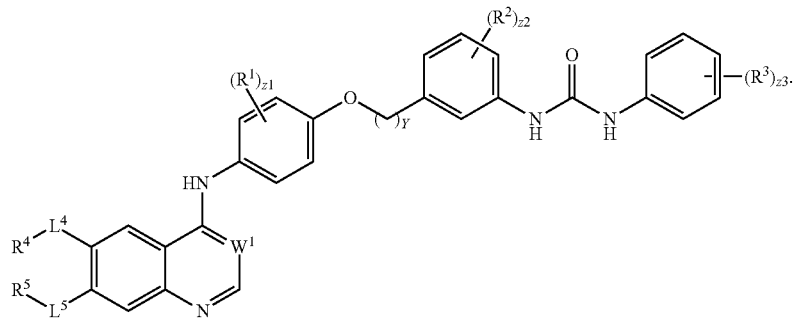

$W^1$, $R^1$, $R^2$, $R^3$, $R^4$, $R^5$, $L^4$, $L^5$, z1, z2, and z3 are as described herein. Y is 0 or 1. In embodiments, Y is 0. In embodiments, Y is 1.

In embodiments, the compound has the formula:

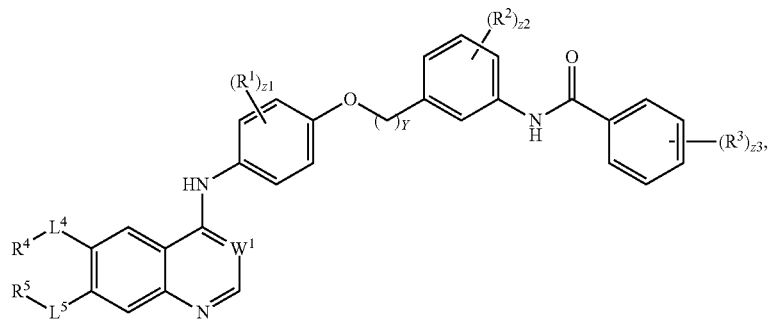

wherein $W^1$, Y, $R^1$, $R^2$, $R^3$, $R^4$, $R^5$, $L^4$, $L^5$, z1, z2, and z3 are as described herein.

In embodiments, $R^1$ is independently halogen, —$CX^1_3$, —$CHX^1_2$, —$CH_2X^1$, —$OCX^1_3$, —$OCH_2X^1$, —$OCHX^1_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{1A}$-substituted or unsubstituted alkyl (e.g., $C_1$-$C_8$, $C_1$-$C_6$, $C_1$-$C_4$, or $C_1$-$C_2$), $R^{1A}$-substituted or unsubstituted heteroalkyl (e.g., 2 to 8 membered, 2 to 6 membered, 4 to 6 membered, or 2 to 3 membered), $R^{1A}$-substituted or unsubstituted cycloalkyl (e.g., $C_3$-$C_8$, $C_3$-$C_6$, $C_4$-$C_6$, or $C_5$-$C_6$), $R^{1A}$-substituted or unsubstituted heterocycloalkyl (e.g., 3 to 6 membered, 4 to 6 membered, 4 to 5 membered, or 5 to 6 membered), $R^{1A}$-substituted or unsubstituted aryl (e.g., $C_6$-$C_{10}$ or phenyl), or $R^{1A}$-substituted or unsubstituted heteroaryl (e.g., 5 to 10 membered, 5 to 9 membered, or 5 to 6 membered). $X^1$ is independently —F, —Cl, —Br, or —I. In embodiments, $R^1$ is independently hydrogen. In embodiments, $R^1$ is independently methyl. In embodiments, $R^1$ is independently ethyl. In embodiments, $R^1$ is independently hydrogen, oxo, halogen, —$CX^1_3$, —$CHX^1_2$, —$CH_2X^1$, —$OCX^1_3$, —$OCH_2X^1$, —$OCHX^1_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, two adjacent $R^1$ substituents may optionally be joined to form an $R^{1A}$-substituted or unsubstituted cycloalkyl (e.g., $C_3$-$C_8$, $C_3$-$C_6$, $C_4$-$C_6$, or $C_5$-$C_6$), $R^{1A}$-substituted or unsubstituted heterocycloalkyl (e.g., 3 to 6 membered, 4 to 6 membered, 4 to 5 membered, or 5 to 6 membered), $R^{1A}$-substituted or unsubstituted aryl (e.g., $C_6$-$C_{10}$ or phenyl), or $R^{1A}$-substituted or unsubstituted heteroaryl (e.g., 5 to 10 membered, 5 to 9 membered, or 5 to 6 membered). In embodiments, two adjacent $R^1$ substituents may optionally be joined to form an unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{1A}$ is independently oxo, halogen, —$CX^{1A}_3$, —$CHX^{1A}_2$, —$CH_2X^{1A}$, —$OCX^{1A}_3$, —$OCH_2X^{1A}$, —$OCHX^{1A}_2$, —CN, —OH, —$NH_2$, —COO H, —$CONH_2$, —$NO_2$, —SH, —$SO_3H$, —$SO_4$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{1B}$-substituted or unsubstituted alkyl (e.g., $C_1$-$C_8$, $C_1$-$C_6$, $C_1$-$C_4$, or $C_1$-$C_2$), $R^{1B}$-substituted or unsubstituted heteroalkyl (e.g., 2 to 8 membered, 2 to 6 membered, 4 to 6 membered, or 2 to 3 membered), $R^{1B}$-substituted or unsubstituted cycloalkyl (e.g., $C_3$-$C_8$, $C_3$-$C_6$, $C_4$-$C_6$, or $C_5$-$C_6$), $R^{1B}$-substituted or unsubstituted heterocycloalkyl (e.g., 3 to 6 membered, 4 to 6 membered, 4 to 5 membered, or 5 to 6 membered), $R^{1B}$-substituted or unsubstituted aryl (e.g., $C_6$-$C_{10}$ or phenyl), or $R^{1B}$-substituted or unsubstituted heteroaryl (e.g., 5 to 10 membered, 5 to 9 membered, or 5 to 6 membered). $X^{1A}$ is independently —F, —Cl, —Br, or —I. In embodiments, $R^{1A}$ is independently oxo, halogen, —$CX^{1A}_3$, —$CHX^{1A}_2$, —$CH_2X^{1A}$, —$OCX^{1A}_3$, —$OCH_2X^{1A}$, —$OCHX^{1A}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{1B}$ is independently oxo, halogen, —$CX^{1B}_3$, —$CHX^{1B}_2$, —$CH_2X^{1B}$, —$OCX^{1B}_3$, —$OCH_2X^{1B}$, —$OCHX^{1B}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{1C}$-substituted or unsubstituted alkyl (e.g., $C_1$-$C_8$, $C_1$-$C_6$, $C_1$-$C_4$, or $C_1$-$C_2$), $R^{1C}$-substituted or unsubstituted heteroalkyl (e.g., 2 to 8 membered, 2 to 6 membered, 4 to 6 membered, or 2 to 3 membered), $R^{1C}$-substituted or unsubstituted cycloalkyl (e.g., $C_3$-$C_8$, $C_3$-$C_6$, $C_4$-$C_6$, or $C_5$-$C_6$), $R^{1C}$-substituted or unsubstituted heterocycloalkyl (e.g., 3 to 6 membered, 4 to 6 membered, 4 to 5 membered, or 5 to 6 membered), $R^{1C}$-substituted or unsubstituted aryl (e.g., $C_6$-$C_{10}$ or phenyl), or $R^{1C}$-substituted or unsubstituted heteroaryl (e.g., 5 to 10 membered, 5 to 9 membered, or 5 to 6 membered). $X^{1B}$ is independently —F, —Cl, —Br, or —I. In embodiments, $R^{1B}$ is independently oxo, halogen, —$CX^{1B}_3$, —$CHX^{1B}_2$, —$CH_2X^{1B}$, —$OCX^{1B}_3$, —$OCH_2X^{1B}$, —$OCHX^{1B}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{1C}$ is independently oxo, halogen, —$CX^{1C}_3$, —$CHX^{1C}_2$, —$CH_2X^{1C}$, —$OCX^{1C}_3$, —$OCH_2X^{1C}$, —$OCHX^{1C}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{1C}$ is independently —F, —Cl, —Br, or —I.

In embodiments, $R^2$ is independently halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{2A}$-substituted or unsubstituted alkyl (e.g., $C_1$-$C_8$, $C_1$-$C_6$, $C_1$-$C_4$, or $C_1$-$C_2$), $R^{2A}$-substituted or unsubstituted heteroalkyl (e.g., 2 to 8 membered, 2 to 6 membered, 4 to 6 membered, or 2 to 3 membered), $R^{2A}$-substituted or unsubstituted cycloalkyl (e.g., $C_3$-$C_8$, $C_3$-$C_6$, $C_4$-$C_6$, or $C_5$-$C_6$), $R^{2A}$-substituted or unsubstituted heterocycloalkyl (e.g., 3 to 6 membered, 4 to 6 membered, 4 to 5 membered, or 5 to 6 membered), $R^{2A}$-substituted or unsubstituted aryl (e.g., $C_6$-$C_{10}$ or phenyl), or $R^{2A}$-substituted or unsubstituted heteroaryl (e.g., 5 to 10 membered, 5 to 9 membered, or 5 to 6 membered). $X^2$ is independently —F, —Cl, —Br, or —I. In embodiments, $R^2$ is independently hydrogen. In embodiments, $R^2$ is independently methyl. In embodiments, $R^2$ is independently ethyl. In embodiments, $R^2$ is independently hydrogen, oxo, halogen, —$CX^2_3$, —$CHX^2_2$, —$CH_2X^2$, —$OCX^2_3$, —$OCH_2X^2$, —$OCHX^2_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, two adjacent $R^2$ substituents may optionally be joined to form an $R^{2A}$-substituted or unsubstituted cycloalkyl (e.g., $C_3$-$C_8$, $C_3$-$C_6$, $C_4$-$C_6$, or $C_5$-$C_6$), $R^{2A}$-substituted or unsubstituted heterocycloalkyl (e.g., 3 to 6 membered, 4 to 6 membered, 4 to 5 membered, or 5 to 6 membered), $R^{2A}$-substituted or unsubstituted aryl (e.g., $C_6$-$C_{10}$ or phenyl), or $R^{2A}$-substituted or unsubstituted heteroaryl (e.g., 5 to 10 membered, 5 to 9 membered, or 5 to 6 membered). In embodiments, two adjacent $R^2$ substituents may optionally be joined to form an unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{2A}$ is independently oxo, halogen, —$CX^{2A}_3$, —$CHX^{2A}_2$, —$CH_2X^{2A}$, —$OCX^{2A}_3$, —$OCH_2X^{2A}$, —$OCHX^{2A}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{2B}$-substituted or unsubstituted alkyl (e.g., $C_1$-$C_8$, $C_1$-$C_6$, $C_1$-$C_4$, or $C_1$-$C_2$), $R^{2B}$-substituted or unsubstituted heteroalkyl (e.g., 2 to 8 membered, 2 to 6 membered, 4 to 6 membered, or 2 to 3 membered), $R^{2B}$-substituted or unsubstituted cycloalkyl (e.g., $C_3$-$C_8$, $C_3$-$C_6$, $C_4$-$C_6$, or $C_5$-$C_6$), $R^{2B}$-substituted or unsubstituted heterocycloalkyl (e.g., 3 to 6 membered, 4 to 6 membered, 4 to 5 membered, or 5 to 6 membered), $R^{2B}$-substituted or unsubstituted aryl (e.g., $C_6$-$C_{10}$ or phenyl), or $R^{2B}$-substituted or unsubstituted heteroaryl (e.g., 5 to 10 membered, 5 to 9 membered, or 5 to 6 membered). $X^{2A}$ is independently —F, —Cl, —Br, or —I. In embodiments, $R^{2A}$ is independently oxo, halogen, —$CX^{2A}_3$, —$CHX^{2A}_2$, —$CH_2X^{2A}$, —$OCX^{2A}_3$, —$OCH_2X^{2A}$, —$OCHX^{2A}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

$R^{2B}$ is independently oxo, halogen, —CX$^{2B}_3$, —CHX$^{2B}_2$, —CH$_2$X$^{2B}$, —OCX$^{2B}_3$, —OCH$_2$X$^{2B}$, —OCHX$^{2B}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{2C}$-substituted or unsubstituted alkyl (e.g., C$_1$-C$_8$, C$_1$-C$_6$, C$_1$-C$_4$, or C$_1$-C$_2$), $R^{2C}$-substituted or unsubstituted heteroalkyl (e.g., 2 to 8 membered, 2 to 6 membered, 4 to 6 membered, or 2 to 3 membered), $R^{2C}$-substituted or unsubstituted cycloalkyl (e.g., C$_3$-C$_8$, C$_3$-C$_6$, C$_4$-C$_6$, or C$_5$-C$_6$), $R^{2C}$-substituted or unsubstituted heterocycloalkyl (e.g., 3 to 6 membered, 4 to 6 membered, 4 to 5 membered, or 5 to 6 membered), $R^{2C}$-substituted or unsubstituted aryl (e.g., C$_6$-C$_{10}$ or phenyl), or $R^{2C}$-substituted or unsubstituted heteroaryl (e.g., 5 to 10 membered, 5 to 9 membered, or 5 to 6 membered). $X^{2B}$ is independently —F, —Cl, —Br, or —I. In embodiments, $R^{2B}$ is independently oxo, halogen, —CX$^{2B}_3$, —CHX$^{2B}_2$, —CH$_2$X$^{2B}$, —OCX$^{2B}_3$, —OCH$_2$X$^{2B}$, —OCHX$^{2B}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

$R^{2C}$ is independently oxo, halogen, —CX$^{2C}_3$, —CHX$^{2C}_2$, —CH$_2$X$^{2C}$, —OCX$^{2C}_3$, —OCH$_2$X$^{2C}$, —OCHX$^{2C}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). $X^{2C}$ is independently —F, —Cl, —Br, or —I.

In embodiments, $R^3$ is independently halogen, —CX$^3_3$, —CHX$^3_2$, —CH$_2$X$^3$, —OCX$^3_3$, —OCH$_2$X$^3$, —OCHX$^3_2$, —CN, —OH, —NH$_2$, —COOH, —CO NH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{3A}$-substituted or unsubstituted alkyl (e.g., C$_1$-C$_8$, C$_1$-C$_6$, C$_1$-C$_4$, or C$_1$-C$_2$), $R^{3A}$-substituted or unsubstituted heteroalkyl (e.g., 2 to 8 membered, 2 to 6 membered, 4 to 6 membered, or 2 to 3 membered), $R^{3A}$-substituted or unsubstituted cycloalkyl (e.g., C$_3$-C$_8$, C$_3$-C$_6$, C$_4$-C$_6$, or C$_5$-C$_6$), $R^{3A}$-substituted or unsubstituted heterocycloalkyl (e.g., 3 to 6 membered, 4 to 6 membered, 4 to 5 membered, or 5 to 6 membered), $R^{3A}$-substituted or unsubstituted aryl (e.g., C$_6$-C$_{10}$ or phenyl), or $R^{3A}$-substituted or unsubstituted heteroaryl (e.g., 5 to 10 membered, 5 to 9 membered, or 5 to 6 membered). $X^3$ is independently —F, —Cl, —Br, or —I. In embodiments, $R^3$ is independently hydrogen. In embodiments, $R^3$ is independently methyl. In embodiments, $R^3$ is independently ethyl. In embodiments, $R^3$ is independently hydrogen, oxo, halogen, —CX$^3_3$, —CHX$^3_2$, —CH$_2$X$^3$, —OCX$^3_3$, —OCH$_2$X$^3$, —OCHX$^3_2$, —CN, —OH, —NH$_2$, —COOH, —CO NH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, two adjacent $R^3$ substituents may optionally be joined to form an $R^{3A}$-substituted or unsubstituted cycloalkyl (e.g., C$_3$-C$_8$, C$_3$-C$_6$, C$_4$-C$_6$, or C$_5$-C$_6$). $R^{3A}$-substituted or unsubstituted heterocycloalkyl (e.g., 3 to 6 membered, 4 to 6 membered, 4 to 5 membered, or 5 to 6 membered), $R^{3A}$-substituted or unsubstituted aryl (e.g., C$_6$-C$_{10}$ or phenyl), or $R^{3A}$-substituted or unsubstituted heteroaryl (e.g., 5 to 10 membered, 5 to 9 membered, or 5 to 6 membered). In embodiments, two adjacent $R^3$ substituents may optionally be joined to form an unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

$R^{3A}$ is independently oxo, halogen, —CX$^{3A}_3$, —CHX$^{3A}_2$, —CH$_2$X$^{3A}$, —OCX$^{3A}_3$, —OCH$_2$X$^{3A}$, —OCHX$^{3A}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{3B}$-substituted or unsubstituted alkyl (e.g., C$_1$-C$_8$, C$_1$-C$_6$, C$_1$-C$_4$, or C$_1$-C$_2$), $R^{3B}$-substituted or unsubstituted heteroalkyl (e.g., 2 to 8 membered, 2 to 6 membered, 4 to 6 membered, or 2 to 3 membered), $R^{3B}$-substituted or unsubstituted cycloalkyl (e.g., C$_3$-C$_8$, C$_3$-C$_6$, C$_4$-C$_6$, or C$_5$-C$_6$), $R^{3B}$-substituted or unsubstituted heterocycloalkyl (e.g., 3 to 6 membered, 4 to 6 membered, 4 to 5 membered, or 5 to 6 membered), $R^{3B}$-substituted or unsubstituted aryl (e.g., C$_6$-C$_{10}$ or phenyl), or $R^{3B}$-substituted or unsubstituted heteroaryl (e.g., 5 to 10 membered, 5 to 9 membered, or 5 to 6 membered). $X^{3A}$ is independently —F, —Cl, —Br, or —I. In embodiments, $R^{3A}$ is independently oxo, halogen, —CX$^{3A}_3$, —CHX$^{3A}_2$, —CH$_2$X$^{3A}$, —OCX$^{3A}_3$, —OCH$_2$X$^{3A}$, —OCHX$^{3A}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{3B}$ is independently oxo, halogen, —$CX^{3B}_3$, —$CHX^{3B}_2$, —$CH_2X^{3B}$, —$OCX^{3B}_3$, —$OCH_2X^{3B}$, —$OCHX^{3B}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{3C}$-substituted or unsubstituted alkyl (e.g., $C_1$-$C_8$, $C_1$-$C_6$, $C_1$-$C_4$, or $C_1$-$C_2$), $R^{3C}$-substituted or unsubstituted heteroalkyl (e.g., 2 to 8 membered, 2 to 6 membered, 4 to 6 membered, or 2 to 3 membered), $R^{3C}$-substituted or unsubstituted cycloalkyl (e.g., $C_3$-$C_8$, $C_3$-$C_6$, $C_4$-$C_6$, or $C_5$-$C_6$), $R^{3C}$-substituted or unsubstituted heterocycloalkyl (e.g., 3 to 6 membered, 4 to 6 membered, 4 to 5 membered, or 5 to 6 membered), $R^{3C}$-substituted or unsubstituted aryl (e.g., $C_6$-$C_{10}$ or phenyl), or $R^{3C}$-substituted or unsubstituted heteroaryl (e.g., 5 to 10 membered, 5 to 9 membered, or 5 to 6 membered). $X^{3B}$ is independently —F, —Cl, —Br, or —I. In embodiments, $R^{3B}$ is independently oxo, halogen, —$CX^{3B}_3$, —$CHX^{3B}_2$, —$CH_2X^{3B}$, —$OCX^{3B}_3$, —$OCH_2X^{3B}$, —$OCHX^{3B}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{3C}$ is independently oxo, halogen, —$CX^{3C}_3$, —$CHX^{3C}_2$, —$CH_2X^{3C}$, —$OCX^{3C}_3$, —$OCH_2X^{3C}$, —$OCHX^{3C}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{3C}$ is independently —F, —Cl, —Br, or —I.

In embodiments, $R^4$ is independently hydrogen, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{4A}$-substituted or unsubstituted alkyl (e.g., $C_1$-$C_8$, $C_1$-$C_6$, $C_1$-$C_4$, or $C_1$-$C_2$), $R^{4A}$-substituted or unsubstituted heteroalkyl (e.g., 2 to 8 membered, 2 to 6 membered, 4 to 6 membered, or 2 to 3 membered), $R^{4A}$-substituted or unsubstituted cycloalkyl (e.g., $C_3$-$C_8$, $C_3$-$C_6$, $C_4$-$C_6$, or $C_5$-$C_6$), $R^{4A}$-substituted or unsubstituted heterocycloalkyl (e.g., 3 to 6 membered, 4 to 6 membered, 4 to 5 membered, or 5 to 6 membered), $R^{4A}$-substituted or unsubstituted aryl (e.g., $C_6$-$C_{10}$ or phenyl), or $R^{4A}$-substituted or unsubstituted heteroaryl (e.g., 5 to 10 membered, 5 to 9 membered, or 5 to 6 membered). $X^4$ is independently —F, —Cl, —Br, or —I. In embodiments, $R^4$ is independently hydrogen. In embodiments, $R^4$ is independently methyl. In embodiments, $R^4$ is independently ethyl. In embodiments, $R^4$ is independently hydrogen, oxo, halogen, —$CX^4_3$, —$CHX^4_2$, —$CH_2X^4$, —$OCX^4_3$, —$OCH_2X^4$, —$OCHX^4_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{4A}$ is independently oxo, halogen, —$CX^{4A}_3$, —$CHX^{4A}_2$, —$CH_2X^{4A}$, —$OCX^{4A}_3$, —$OCH_2X^{4A}$, —$OCHX^{4A}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{4B}$-substituted or unsubstituted alkyl (e.g., $C_1$-$C_8$, $C_1$-$C_6$, $C_1$-$C_4$, or $C_1$-$C_2$), $R^{4B}$-substituted or unsubstituted heteroalkyl (e.g., 2 to 8 membered, 2 to 6 membered, 4 to 6 membered, or 2 to 3 membered), $R^{4B}$-substituted or unsubstituted cycloalkyl (e.g., $C_3$-$C_8$, $C_3$-$C_6$, $C_4$-$C_6$, or $C_5$-$C_6$), $R^{4B}$-substituted or unsubstituted heterocycloalkyl (e.g., 3 to 6 membered, 4 to 6 membered, 4 to 5 membered, or 5 to 6 membered), $R^{4B}$-substituted or unsubstituted aryl (e.g., $C_6$-$C_{10}$ or phenyl), or $R^{4B}$-substituted or unsubstituted heteroaryl (e.g., 5 to 10 membered, 5 to 9 membered, or 5 to 6 membered). $X^{4A}$ is independently —F, —Cl, —Br, or —I. In embodiments, $R^{4A}$ is independently oxo, halogen, —$CX^{4A}_3$, —$CHX^{4A}_2$, —$CH_2X^{4A}$, —$OCX^{4A}_3$, —$OCH_2X^{4A}$, —$OCHX^{4A}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{4B}$ is independently oxo, halogen, —$CX^{4B}_3$, —$CHX^{4B}_2$, —$CH_2X^{4B}$, —$OCX^{4B}_3$, —$OCH_2X^{4B}$, —$OCHX^{4B}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{4C}$-substituted or unsubstituted alkyl (e.g., $C_1$-$C_8$, $C_1$-$C_6$, $C_1$-$C_4$, or $C_1$-$C_2$), $R^{4C}$-substituted or unsubstituted heteroalkyl (e.g., 2 to 8 membered, 2 to 6 membered, 4 to 6 membered, or 2 to 3 membered), $R^{4C}$-substituted or unsubstituted cycloalkyl (e.g., $C_3$-$C_8$, $C_3$-$C_6$, $C_4$-$C_6$, or $C_5$-$C_6$), $R^{4C}$-substituted or unsubstituted heterocycloalkyl (e.g., 3 to 6 membered, 4 to 6 membered, 4 to 5 membered, or 5 to 6 membered), $R^{4C}$-substituted or unsubstituted aryl (e.g., $C_6$-$C_{10}$ or phenyl), or $R^{4C}$-substituted or unsubstituted heteroaryl (e.g., 5 to 10 membered, 5 to 9 membered, or 5 to 6 membered). $X^{4B}$ is independently —F, —Cl, —Br, or —I. In embodiments, $R^{4B}$ is independently oxo, halogen, —$CX^{4B}_3$, —$CHX^{4B}_2$, —$CH_2X^{4B}$, —$OCX^{4B}_3$, —$OCH_2X^{4B}$, —$OCHX^{4B}_2$, —CN, —OH, —$NH_2$, —COO H, —$CONH_2$, —$NO_2$, —SH, —$SO_3H$, —$SO_4H$, —$SO_2NHNH_2$, —$ONH_2$, —NHC=(O)

NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{4C}$ is independently oxo, halogen, —CX$^{4C}_3$, —CHX$^{4C}_2$, —CH$_2$X$^{4C}$, —OCX$^{4C}_3$, —OCH$_2$X$^{4C}$, —OCHX$^{4C}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{4C}$ is independently —F, —Cl, —Br, or —I.

In embodiments, R$^5$ is independently hydrogen, halogen, —CX$^5_3$, —CHX$^5_2$, —CH$_2$X$^5$, —OCX$^5_3$, —OCH$_2$X$^5$, —OCHX$^5_2$, —CN, —OH, —NH$_2$, —COOH, —CO NH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{5A}$-substituted or unsubstituted alkyl (e.g., C$_1$-C$_8$, C$_1$-C$_6$, C$_1$-C$_4$, or C$_1$-C$_2$), R$^{5A}$-substituted or unsubstituted heteroalkyl (e.g., 2 to 8 membered, 2 to 6 membered, 4 to 6 membered, or 2 to 3 membered), R$^{5A}$-substituted or unsubstituted cycloalkyl (e.g., C$_3$-C$_8$, C$_3$-C$_6$, C$_4$-C$_6$, or C$_5$-C$_6$), R$^{5A}$-substituted or unsubstituted heterocycloalkyl (e.g., 3 to 6 membered, 4 to 6 membered, 4 to 5 membered, or 5 to 6 membered), R$^{5A}$-substituted or unsubstituted aryl (e.g., C$_6$-C$_{10}$ or phenyl), or R$^{5A}$-substituted or unsubstituted heteroaryl (e.g., 5 to 10 membered, 5 to 9 membered, or 5 to 6 membered). X$^5$ is independently —F, —Cl, —Br, or —I. In embodiments, R$^5$ is independently hydrogen. In embodiments, R$^5$ is independently methyl. In embodiments, R$^5$ is independently ethyl. In embodiments, R$^5$ is independently hydrogen, oxo, halogen, —CX$^5_3$, —CHX$^5_2$, —CH$_2$X$^5$, —OCX$^5_3$, —OCH$_2$X$^5$, —OCHX$^5_2$, —CN, —OH, —NH$_2$, —COOH, —CO NH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$) unsubstituted heteroalkyl. (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{5A}$ is independently oxo, halogen, —CX$^{5A}_3$, —CHX$^{5A}_2$, —CH$_2$X$^{5A}$, —OCX$^{5A}_3$, —OCH$_2$X$^{5A}$, —OCHX$^{5A}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{5B}$-substituted or unsubstituted alkyl (e.g., C$_1$-C$_8$, C$_1$-C$_6$, C$_1$-C$_4$, or C$_1$-C$_2$), R$^{5B}$-substituted or unsubstituted heteroalkyl (e.g., 2 to 8 membered, 2 to 6 membered, 4 to 6 membered, or 2 to 3 membered), R$^{5B}$-substituted or unsubstituted cycloalkyl (e.g., C$_3$-C$_8$, C$_3$-C$_6$, C$_4$-C$_6$, or C$_5$-C$_6$), R$^{5B}$-substituted or unsubstituted heterocycloalkyl (e.g., 3 to 6 membered, 4 to 6 membered, 4 to 5 membered, or 5 to 6 membered), R$^{5B}$-substituted or unsubstituted aryl (e.g., C$_6$-C$_{10}$ or phenyl), or R$^{5B}$-substituted or unsubstituted heteroaryl (e.g., 5 to 10 membered, 5 to 9 membered, or 5 to 6 membered). X$^{5A}$ is independently —F, —Cl, —Br, or —I. In embodiments, R$^{5A}$ is independently oxo, halogen, —CX$^{5A}_3$, —CHX$^{5A}_2$, —CH$_2$X$^{5A}$, —OCX$^{5A}_3$, —OCH$_2$X$^{5A}$, —OCHX$^{5A}_2$, —CN, —OH, —NH$_2$, —COO H, —CONH$_2$, —NO$_2$, —SH, —SO$_4$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{5B}$ is independently oxo, halogen, —CX$^{5B}_3$, —CHX$^{5B}_2$, —CH$_2$X$^{5B}$, —OCX$^{5B}_3$, —OCH$_2$X$^{5B}$, —OCHX$^{5B}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, R$^{5C}$-substituted or unsubstituted alkyl (e.g., C$_1$-C$_8$, C$_1$-C$_6$, C$_1$-C$_4$, or C$_1$-C$_2$), R$^{5C}$-substituted or unsubstituted heteroalkyl (e.g., 2 to 8 membered, 2 to 6 membered, 4 to 6 membered, or 2 to 3 membered), R$^{5C}$-substituted or unsubstituted cycloalkyl (e.g., C$_3$-C$_8$, C$_3$-C$_6$, C$_4$-C$_6$, or C$_5$-C$_6$), R$^{5C}$-substituted or unsubstituted heterocycloalkyl (e.g., 3 to 6 membered, 4 to 6 membered, 4 to 5 membered, or 5 to 6 membered), R$^{5C}$-substituted or unsubstituted aryl (e.g., C$_6$-C$_{10}$ or phenyl), or R$^{5C}$-substituted or unsubstituted heteroaryl (e.g., 5 to 10 membered, 5 to 9 membered, or 5 to 6 membered). X$^{5B}$ is independently —F, —Cl, —Br, or —I. In embodiments, R$^{5B}$ is independently oxo, halogen, —CX$^{5B}_3$, —CHX$^{5B}_2$, —CH$_2$X$^{5B}$, —OCX$^{5B}_3$, —OCH$_2$X$^{5B}$, —OCHX$^{5B}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{5C}$ is independently oxo, halogen, —CX$^{5C}_3$, —CHX$^{5C}_2$, —CH$_2$X$^{5C}$, —OCX$^{5C}_3$, —OCH$_2$X$^{5C}$, —OCHX$^{5C}_2$, —CN, —OH, —NH$_2$, —COO H, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). $X^{5C}$ is independently —F, —Cl, —Br, or —I.

In embodiments, $R^6$ is independently hydrogen, halogen, —$CX^6_3$, —$CHX^6_2$, —$CH_2X^6$, —$OCX^6_3$, —$OCH_2X^6$, —$OCHX^6_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{6A}$-substituted or unsubstituted alkyl (e.g., $C_1$-$C_8$, $C_1$-$C_6$, $C_1$-$C_4$, or $C_1$-$C_2$), $R^{6A}$-substituted or unsubstituted heteroalkyl (e.g., 2 to 8 membered, 2 to 6 membered, 4 to 6 membered, or 2 to 3 membered), $R^{6A}$-substituted or unsubstituted cycloalkyl (e.g., $C_3$-$C_8$, $C_3$-$C_6$, $C_4$-$C_6$, or $C_5$-$C_6$), $R^{6A}$-substituted or unsubstituted heterocycloalkyl (e.g., 3 to 6 membered, 4 to 6 membered, 4 to 5 membered, or 5 to 6 membered), $R^{6A}$-substituted or unsubstituted aryl (e.g., $C_6$-$C_{10}$ or phenyl), or $R^{6A}$-substituted or unsubstituted heteroaryl (e.g., 5 to 10 membered, 5 to 9 membered, or 5 to 6 membered). $X^6$ is independently —F, —Cl, —Br, or —I. In embodiments, $R^6$ is independently hydrogen. In embodiments, $R^6$ is independently methyl. In embodiments, $R^6$ is independently ethyl. In embodiments, $R^6$ is independently hydrogen, oxo, halogen, —$CX^6_3$, —$CHX^6_2$, —$CH_2X^6$, —$OCX^6_3$, —$OCH_2X^6$, —$OCHX^6_2$, —CN, —OH, —$NH_2$, —COOH, —CO $NH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{6A}$ is independently oxo, halogen, —$CX^{6A}_3$, —$CHX^{6A}_2$, —$CH_2X^{6A}$, —$OCX^{6A}_3$, —$OCH_2X^{6A}$, —$OCHX^{6A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{6B}$-substituted or unsubstituted alkyl (e.g., $C_1$-$C_8$, $C_1$-$C_6$, $C_1$-$C_4$, or $C_1$-$C_2$), $R^{6B}$-substituted or unsubstituted heteroalkyl (e.g., 2 to 8 membered, 2 to 6 membered, 4 to 6 membered, or 2 to 3 membered), $R^{6B}$-substituted or unsubstituted cycloalkyl (e.g., $C_3$-$C_8$, $C_3$-$C_6$, $C_4$-$C_6$, or $C_5$-$C_6$), $R^{6B}$-substituted or unsubstituted heterocycloalkyl (e.g., 3 to 6 membered, 4 to 6 membered, 4 to 5 membered, or 5 to 6 membered), $R^{6B}$-substituted or unsubstituted aryl (e.g., $C_6$-$C_{10}$ or phenyl), or $R^{6B}$-substituted or unsubstituted heteroaryl (e.g., 5 to 10 membered, 5 to 9 membered, or 5 to 6 membered). $X^{6A}$ is independently —F, —Cl, —Br, or —I. In embodiments, $R^{6A}$ is independently oxo, halogen, —$CX^{6A}_3$, —$CHX^{6A}_2$, —$CH_2X^{6A}$, —$OCX^{6A}_3$, —$OCH_2X^{6A}$, —$OCHX^{6A}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{6B}$ is independently oxo, halogen, —$CX^{6B}_3$, —$CHX^{6B}_2$, —$CH_2X^{6B}$, —$OCX^{6B}_3$, —$OCH_2X^{6B}$, —$OCHX^{6B}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{6C}$-substituted or unsubstituted alkyl (e.g., $C_1$-$C_8$, $C_1$-$C_6$, $C_1$-$C_4$, or $C_1$-$C_2$), $R^{6C}$-substituted or unsubstituted heteroalkyl (e.g., 2 to 8 membered, 2 to 6 membered, 4 to 6 membered, or 2 to 3 membered), $R^{6C}$-substituted or unsubstituted cycloalkyl (e.g., $C_3$-$C_8$, $C_3$-$C_6$, $C_4$-$C_6$, or $C_5$-$C_6$), $R^{6C}$-substituted or unsubstituted heterocycloalkyl (e.g., 3 to 6 membered, 4 to 6 membered, 4 to 5 membered, or 5 to 6 membered), $R^{6C}$-substituted or unsubstituted aryl (e.g., $C_6$-$C_{10}$ or phenyl), or $R^{6C}$-substituted or unsubstituted heteroaryl (e.g., 5 to 10 membered, 5 to 9 membered, or 5 to 6 membered). $X^{6B}$ is independently —F, —Cl, —Br, or —I. In embodiments, $R^{6B}$ is independently oxo, halogen, —$CX^{6B}_3$, —$CHX^{6B}_2$, —$CH_2X^{6B}$, —$OCX^{6B}_3$, —$OCH_2X^{6B}$, —$OCHX^{6B}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{6C}$ is independently oxo, halogen, —$CX^{6C}_3$, —$CHX^{6C}_2$, —$CH_2X^{6C}$, —$OCX^{6C}_3$, —$OCH_2X^{6C}$, —$OCHX^{6C}_2$, —CN, —OH, —$NH_2$, —COO H, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{6C}$ is independently —F, —Cl, —Br, or —I.

In embodiments, $R^7$ is independently hydrogen, —$CX^7_3$, —CN, —COOH, —$CONH_2$, —$CHX^7_2$, —$CH_2X^7$, $R^{7A}$-substituted or unsubstituted alkyl (e.g., $C_1$-$C_8$, $C_1$-$C_6$, $C_1$-$C_4$, or $C_1$-$C_2$), $R^{7A}$-substituted or unsubstituted heteroalkyl (e.g., 2 to 8 membered, 2 to 6 membered, 4 to 6 membered, or 2 to 3 membered), $R^{7A}$-substituted or unsubstituted cycloalkyl (e.g., $C_3$-$C_8$, $C_3$-$C_6$, $C_4$-$C_6$, or $C_5$-$C_6$), $R^{7A}$-substituted or unsubstituted heterocycloalkyl (e.g., 3 to 6 membered, 4 to 6 membered, 4 to 5 membered, or 5 to 6 membered), $R^{7A}$-substituted or unsubstituted aryl (e.g., $C_6$-$C_{10}$ or phenyl), or $R^{7A}$-substituted or unsubstituted heteroaryl (e.g., 5 to 10 membered, 5 to 9 membered, or 5 to 6 membered). $X^7$ is independently —F, —Cl, —Br, or —I. In embodiments, $R^7$ is independently hydrogen. In embodiments, $R^7$ is independently methyl. In embodiments, $R^7$ is independently ethyl. In embodiments, $R^7$ is independently hydrogen, $CX^7_3$, —CN, —COOH, —$CONH_2$, —$CHX^7_2$, —$CH_2X^7$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^7$ and $R^8$ substituents bonded to the same nitrogen atom may optionally be joined to form a $R^{7A}$-substituted or unsubstituted heterocycloalkyl or $R^{7A}$-substituted or unsubstituted heteroaryl. In embodiments, $R^7$ and $R^8$ substituents bonded to the same nitrogen atom may optionally be joined to form a $R^{7A}$-substituted or unsubstituted 3 to 6 membered heterocycloalkyl or $R^{7A}$-substituted or unsubstituted 5 to 6 membered heteroaryl. In embodiments, $R^7$ and $R^8$ substituents bonded to the same nitrogen atom may optionally be joined to form an unsubstituted 3 to 6 membered heterocycloalkyl or unsubstituted 5 to 6 membered heteroaryl. In embodiments, $R^7$ and $R^8$ substituents bonded to the same nitrogen atom may optionally be joined to form a $R^{7A}$-substituted or unsubstituted piperazinyl. In embodiments, $R^7$ and $R^8$ substituents bonded to the same nitrogen atom may optionally be joined to form a $R^{7A}$-substituted or unsubstituted piperidinyl. In embodiments, $R^7$ and $R^8$ substituents bonded to the same nitrogen atom may optionally be joined to form a $R^{7A}$-substituted or unsubstituted pyrrolidinyl. In embodiments, $R^7$ and $R^8$ substituents bonded to the same nitrogen atom may optionally be joined to form a $R^{7A}$-substituted or unsubstituted azetidinyl. In embodiments, $R^7$ and $R^8$ substituents bonded to the same nitrogen atom may optionally be joined to form a $R^{7A}$-substituted or unsubstituted morpholinyl. In embodiments, $R^7$ and $R^8$ substituents bonded to the same nitrogen atom may optionally be joined to form a $R^{7A}$-substituted or unsubstituted azeridinyl.

$R^{7A}$ is independently oxo, halogen, —$CX^{7A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{7A}_2$, —$CH_2X^{7A}$, —$OCX^{7A}_3$, —$OCH_2X^{7A}$, —$OCHX^{7A}_2$, $R^{7B}$-substituted or unsubstituted alkyl (e.g., $C_1$-$C_8$, $C_1$-$C_6$, $C_1$-$C_4$, or $C_1$-$C_2$), $R^{7B}$-substituted or unsubstituted heteroalkyl (e.g., 2 to 8 membered, 2 to 6 membered, 4 to 6 membered, or 2 to 3 membered), $R^{7B}$-substituted or unsubstituted cycloalkyl (e.g., $C_3$-$C_8$, $C_3$-$C_6$, $C_4$-$C_6$, or $C_5$-$C_6$), $R^{7B}$-substituted or unsubstituted heterocycloalkyl (e.g., 3 to 6 membered, 4 to 6 membered, 4 to 5 membered, or 5 to 6 membered), $R^{7B}$-substituted or unsubstituted aryl (e.g., $C_6$-$C_{10}$ or phenyl), or $R^{7B}$-substituted or unsubstituted heteroaryl (e.g., 5 to 10 membered, 5 to 9 membered, or 5 to 6 membered). $X^{7A}$ is independently —F, —Cl, —Br, or —I. In embodiments, $R^{7A}$ is independently oxo, halogen, —$CX^{7A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{7A}_2$, —$CH_2X^{7A}$, —$OCX^{7A}_3$, —$OCH_2X^{7A}$, —$OCHX^{7A}_2$, unsubstituted alkyl (e.g., $C_1$-$C_8$, $C_1$-$C_6$, $C_1$-$C_4$, or $C_1$-$C_2$) unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{7B}$ is independently oxo, halogen, —$CX^{7B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{7B}_2$, —$CH_2X^{7B}$, —$OCX^{7B}_3$, —$OCH_2X^{7B}$, —$OCHX^{7B}_2$, $R^{7C}$-substituted or unsubstituted alkyl (e.g., $C_1$-$C_8$, $C_1$-$C_6$, $C_1$-$C_4$, or $C_1$-$C_2$), $R^{7C}$-substituted or unsubstituted heteroalkyl (e.g., 2 to 8 membered, 2 to 6 membered, 4 to 6 membered, or 2 to 3 membered), $R^{7C}$-substituted or unsubstituted cycloalkyl (e.g., $C_3$-$C_8$, $C_3$-$C_6$, $C_4$-$C_6$, or $C_5$-$C_6$), $R^{7C}$-substituted or unsubstituted heterocycloalkyl (e.g., 3 to 6 membered, 4 to 6 membered, 4 to 5 membered, or 5 to 6 membered), $R^{7C}$-substituted or unsubstituted aryl (e.g., $C_6$-$C_{10}$ or phenyl), or $R^{7C}$-substituted or unsubstituted heteroaryl (e.g., 5 to 10 membered, 5 to 9 membered, or 5 to 6 membered). $X^{7B}$ is independently —F, —Cl, —Br, or —I. In embodiments, $R^{7B}$ is independently oxo, halogen, —$CX^{7B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{7B}_2$, —$CH_2X^{7B}$, —$OCX^{7B}_3$, —$OCH_2X^{7B}$, —$OCHX^{7B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{7C}$ is independently oxo, halogen, —$CX^{7C}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{7C}_2$, —$CH_2X^{7C}$, —$OCX^{7C}_3$, —$OCH_2X^{7C}$, —$OCHX^{7C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{7C}$ is independently —F, —Cl, —Br, or —I.

In embodiments, $R^8$ is independently hydrogen, —$CX^8_3$, —CN, —COOH, —$CONH_2$, —$CHX^8_2$, —$CH_2X^8$, $R^{8A}$-substituted or unsubstituted alkyl (e.g., $C_1$-$C_8$, $C_1$-$C_6$, $C_1$-$C_4$, or $C_1$-$C_2$), $R^{8A}$-substituted or unsubstituted heteroalkyl (e.g., 2 to 8 membered, 2 to 6 membered, 4 to 6 membered, or 2 to 3 membered), $R^{8A}$-substituted or unsubstituted cycloalkyl (e.g., $C_3$-$C_8$, $C_3$-$C_6$, $C_4$-$C_6$, or $C_5$-$C_6$), $R^{8A}$-substituted or unsubstituted heterocycloalkyl (e.g., 3 to 6 membered, 4 to 6 membered, 4 to 5 membered, or 5 to 6 membered), $R^{8A}$-substituted or unsubstituted aryl (e.g., $C_6$-$C_{10}$ or phenyl), or $R^{8A}$-substituted or unsubstituted heteroaryl (e.g., 5 to 10 membered, 5 to 9 membered, or 5 to 6 membered). $X^8$ is independently —F, —Cl, —Br, or —I. In embodiments, $R^8$ is independently hydrogen. In embodiments, $R^8$ is independently methyl. In embodiments, $R^8$ is independently ethyl. In embodiments, $R^8$ is independently hydrogen, —$CX^8_3$, —CN, —COOH, —$CONH_2$, —$CHX^8_2$, —$CH_2X^8$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^8$ and $R^7$ substituents bonded to the same nitrogen atom may optionally be joined to form a $R^{8A}$-substituted or unsubstituted heterocycloalkyl or $R^{8A}$- substituted or unsubstituted heteroaryl. In embodiments, $R^8$ and $R^7$ substituents bonded to the same nitrogen atom may optionally be joined to form a $R^{8A}$-substituted or unsubstituted 3 to 6 membered heterocycloalkyl or $R^{8A}$-substituted or unsubstituted 5 to 6 membered heteroaryl. In embodiments, $R^8$ and $R^7$ substituents bonded to the same nitrogen atom may optionally be joined to form an unsubstituted 3 to 6 membered heterocycloalkyl or unsubstituted 5 to 6 membered heteroaryl. In embodiments, $R^8$ and $R^7$ substituents bonded to the same nitrogen atom may optionally be joined to form a $R^{8A}$-substituted or unsubstituted piperazinyl. In embodiments, $R^8$ and $R^7$ substituents bonded to the same nitrogen atom may optionally be joined to form a $R^{8A}$-substituted or unsubstituted piperidinyl. In embodiments, $R^8$ and $R^7$ substituents bonded to the same nitrogen atom may optionally be joined to form a $R^{8A}$-substituted or unsubstituted pyrrolidinyl. In embodiments, $R^8$ and $R^7$ substituents bonded to the same nitrogen atom may optionally be joined to form a $R^{8A}$-substituted or unsubstituted azetidinyl. In embodiments, $R^8$ and $R^7$ substituents bonded to the same nitrogen atom may optionally be joined to form a $R^{8A}$-substituted or unsubstituted morpholinyl. In embodiments, $R^8$ and $R^7$ substituents bonded to the same nitrogen atom may optionally be joined to form a $R^{8A}$-substituted or unsubstituted azeridinyl.

$R^{8A}$ is independently oxo, halogen, —$CX^{8A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{8A}_2$, —$CH_2X^{8A}$, —$OCX^{8A}_3$, —$OCH_2X^{8A}$, —$OCHX^{8A}_2$, $R^{8B}$-substituted or unsubstituted alkyl (e.g., $C_1$-$C_8$, $C_1$-$C_6$, $C_1$-$C_4$, or $C_1$-$C_2$), $R^{8B}$-substituted or unsubstituted heteroalkyl (e.g., 2 to 8 membered, 2 to 6 membered, 4 to 6 membered, or 2 to 3 membered), $R^{8B}$-substituted or unsubstituted cycloalkyl (e.g., $C_3$-$C_8$, $C_3$-$C_6$, $C_4$-$C_6$, or $C_5$-$C_6$), $R^{8B}$-substituted or unsubstituted heterocycloalkyl (e.g., 3 to 6 membered, 4 to 6 membered, 4 to 5 membered, or 5 to 6 membered), $R^{8B}$-substituted or unsubstituted aryl (e.g., $C_6$-$C_{10}$ or phenyl), or $R^{8B}$-substituted or unsubstituted heteroaryl (e.g., 5 to 10 membered, 5 to 9 membered, or 5 to 6 membered). $X^{8A}$ is independently —F, —Cl, —Br, or —I. In embodiments, $R^{8A}$ is independently oxo, halogen, —$CX^{8A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{8A}_2$, —$CH_2X^{8A}$, —$OCX^{8A}_3$, —$OCH_2X^{8A}$, —$OCHX^{8A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{8B}$ is independently oxo, halogen, —$CX^{8B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{8B}_2$, —$CH_2X^{8B}$, —$OCX^{8B}_3$, —$OCH_2X^{8B}$, —$OCHX^{8B}_2$, $R^{8C}$-substituted or unsubstituted alkyl (e.g., $C_1$-$C_8$, $C_1$-$C_6$, $C_1$-$C_4$, or $C_1$-$C_2$), $R^{8C}$-substituted or unsubstituted heteroalkyl (e.g., 2 to 8 membered, 2 to 6 membered, 4 to 6 membered or 2 to 3 membered), $R^{8C}$-substituted or unsubstituted cycloalkyl (e.g., $C_3$-$C_8$, $C_3$-$C_6$, $C_4$-$C_6$, or $C_5$-$C_6$), $R^{8C}$-substituted or unsubstituted heterocycloalkyl (e.g., 3 to 6 membered, 4 to 6 membered, 4 to 5 membered, or 5 to 6 membered), $R^{8C}$-substituted or unsubstituted aryl (e.g., $C_6$-$C_{10}$ or phenyl), or $R^{8C}$-substituted or unsubstituted heteroaryl (e.g., 5 to 10 membered, 5 to 9 membered, or 5 to 6 membered). $X^{8B}$ is independently —F, —Cl, —Br, or —I. In embodiments, $R^{8B}$ is independently oxo, halogen, —$CX^{8B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{8B}_2$, —$CH_2X^{8B}$, —$OCX^{8B}_3$, —$OCH_2X^{8B}$, —$OCHX^{8B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{8C}$ is independently oxo, halogen, —$CX^{8C}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{8C}_2$, —$CH_2X^{8C}$, —$OCX^{8C}_3$, —$OCH_2X^{8C}$, —$OCHX^{8C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{8C}$ is independently —F, —Cl, —Br, or —I.

In embodiments, $R^9$ is independently hydrogen, —$CX^9_3$, —CN, —COOH, —$CONH_2$, —$CHX^9_2$, —$CH_2X^9$, $R^{9A}$-substituted or unsubstituted alkyl (e.g., $C_1$-$C_8$, $C_1$-$C_6$, $C_1$-$C_4$, or $C_1$-$C_2$), $R^{9A}$-substituted or unsubstituted heteroalkyl (e.g., 2 to 8 membered, 2 to 6 membered, 4 to 6 membered, or 2 to 3 membered), $R^{9A}$-substituted or unsubstituted cycloalkyl (e.g., $C_3$-$C_8$, $C_3$-$C_6$, $C_4$-$C_6$, or $C_5$-$C_6$), $R^{9A}$-substituted or unsubstituted heterocycloalkyl (e.g., 3 to 6 membered, 4 to 6 membered, 4 to 5 membered, or 5 to 6 membered), $R^{9A}$-substituted or unsubstituted aryl (e.g., $C_6$-$C_{10}$ or phenyl), or $R^{9A}$-substituted or unsubstituted heteroaryl (e.g., 5 to 10 membered, 5 to 9 membered, or 5 to 6 membered). $X^9$ is independently —F, —Cl, —Br, or —I. In embodiments, $R^9$ is independently hydrogen. In embodiments, $R^9$ is independently methyl. In embodiments, $R^9$ is independently ethyl. In embodiments, $R^9$ is independently hydrogen, —$CX^9_3$, —CN, —COOH, —$CONH_2$, —$CHX^9_2$, —$CH_2X^9$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{9A}$ is independently oxo, halogen, —$CX^{9A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{9A}_2$, —$CH_2X^{9A}$, —$OCX^{9A}_3$, —$OCH_2X^{9A}$, —$OCHX^{9A}_2$, $R^{9B}$-substituted or unsubstituted alkyl (e.g., $C_1$-$C_8$, $C_1$-$C_6$, $C_1$-$C_4$, or $C_1$-$C_2$), $R^{9B}$-substituted or unsubstituted heteroalkyl (e.g., 2 to 8 membered, 2 to 6 membered, 4 to 6 membered, or 2 to 3 membered), $R^{9B}$-substituted or unsubstituted cycloalkyl (e.g., $C_3$-$C_8$, $C_3$-$C_6$, $C_4$-$C_6$, or $C_5$-$C_6$), $R^{9B}$-substituted or unsubstituted heterocycloalkyl (e.g., 3 to 6 membered, 4 to 6 membered, 4 to 5 membered, or 5 to 6 membered), $R^{9B}$-substituted or unsubstituted aryl (e.g., $C_6$-$C_{10}$ or phenyl), or $R^{9B}$-substituted or unsubstituted heteroaryl (e.g., 5 to 10 membered, 5 to 9 membered, or 5 to 6 membered). $X^{9A}$ is independently —F, —Cl, —Br, or —I. In embodiments, $R^{9A}$ is independently oxo, halogen, —$CX^{9A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{9A}_2$, —$CH_2X^{9A}$, —$OCX^{9A}_3$, —$OCH_2X^{9A}$, —$OCHX^{9A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{9B}$ is independently oxo, halogen, —$CX^{9B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{9B}_2$, —$CH_2X^{9B}$, —$OCX^{9B}_3$, —$OCH_2X^{9B}$, —$OCHX^{9B}_2$, $R^{9C}$-substituted or unsubstituted alkyl (e.g., $C_1$-$C_8$, $C_1$-$C_6$, $C_1$-$C_4$, or $C_1$-$C_2$), $R^{9C}$-substituted or unsubstituted heteroalkyl (e.g., 2 to 8 membered, 2 to 6 membered, 4 to 6 membered, or 2 to 3 membered), $R^{9C}$-substituted or unsubstituted cycloalkyl (e.g., $C_3$-$C_8$, $C_3$-$C_6$, $C_4$-$C_6$, or $C_5$-$C_6$), $R^{9C}$-substituted or unsubstituted heterocycloalkyl (e.g., 3 to 6 membered, 4 to 6 membered, 4 to 5 membered, or 5 to 6 membered), $R^{9C}$-substituted or unsubstituted aryl (e.g., $C_6$-$C_{10}$ or phenyl), or $R^{9C}$-substituted or unsubstituted heteroaryl (e.g., 5 to 10 membered, 5 to 9 membered, or 5 to 6 membered). $X^{9B}$ is independently —F, —Cl, —Br, or —I. In embodiments, $R^{9B}$ is independently oxo, halogen, —$CX^{9B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{9B}_2$, —$CH_2X^{9B}$, —$OCX^{9B}_3$, —$OCH_2X^{9B}$, —$OCHX^{9B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{9C}$ is independently oxo, halogen, —$CX^{9C}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{9C}_2$, —$CH_2X^{9C}$, —$OCX^{9C}_3$, —$OCH_2X^{9C}$, —$OCHX^{9C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{9C}$ is independently —F, —Cl, —Br, or —I.

In embodiments, $R^{10}$ is independently hydrogen, —$CX^{10}_3$, —CN, —COOH, —$CONH_2$, —$CHX^{10}_2$, —$CH_2X^{10}$, $R^{10A}$-substituted or unsubstituted alkyl (e.g., $C_1$-$C_8$, $C_1$-$C_6$, $C_1$-$C_4$, or $C_1$-$C_2$), $R^{10A}$-substituted or unsubstituted heteroalkyl (e.g., 2 to 8 membered, 2 to 6 membered, 4 to 6 membered, or 2 to 3 membered), $R^{10A}$-substituted or unsubstituted cycloalkyl (e.g., $C_3$-$C_8$, $C_3$-$C_6$, $C_4$-$C_6$, or $C_5$-$C_6$), $R^{10A}$-substituted or unsubstituted heterocycloalkyl (e.g., 3 to 6 membered, 4 to 6 membered, 4 to 5 membered, or 5 to 6 membered), $R^{10A}$-substituted or unsubstituted aryl (e.g., $C_6$-$C_{10}$ or phenyl), or $R^{10A}$-substituted or unsubstituted heteroaryl (e.g., 5 to 10 membered, 5 to 9 membered, or 5 to 6 membered). $X^{10}$ is independently —F, —Cl, —Br, or —I. In embodiments, $R^{10}$ is independently hydrogen. In embodiments, $R^{10}$ is independently methyl. In embodiments, $R^{10}$ is independently ethyl. In embodiments, $R^{10}$ is independently hydrogen, —$CX^{10}_3$, —CN, —COOH, —$CONH_2$, —$CHX^{10}_2$, —$CH_2X^{10}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{10A}$ is independently oxo, halogen, —$CX^{10A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{10A}_2$, —$CH_2X^{10A}$, —$OCX^{10A}_3$, —$OCH_2X^{10A}$, —$OCHX^{10A}_2$, $R^{10B}$-substituted or unsubstituted alkyl (e.g., $C_1$-$C_8$, $C_1$-$C_6$, $C_1$-$C_4$, or $C_1$-$C_2$), $R^{10B}$-substituted or unsubstituted heteroalkyl (e.g., 2 to 8 membered, 2 to 6 membered, 4 to 6 membered or 2 to 3 membered), $R^{10B}$-substituted or unsubstituted cycloalkyl (e.g., $C_3$-$C_8$, $C_3$-$C_6$, $C_4$-$C_6$, or $C_5$-$C_6$), $R^{10B}$-substituted or unsubstituted heterocycloalkyl (e.g., 3 to 6 membered, 4 to 6 membered, 4 to 5 membered, or 5 to 6 membered), $R^{10B}$-substituted or unsubstituted aryl (e.g., $C_6$-$C_{10}$ or phenyl), or $R^{10B}$-substituted or unsubstituted heteroaryl (e.g., 5 to 10 membered, 5 to 9 membered, or 5 to 6 membered). $X^{10A}$ is independently —F, —Cl, —Br, or —I. In embodiments, $R^{10A}$ is independently oxo, halogen, —$CX^{10A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{10A}_2$, —$CH_2X^{10A}$, —$OCX^{10A}_3$, —$OCH_2X^{10A}$, —$OCHX^{10A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{10B}$ is independently oxo, halogen, —$CX^{10B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{10B}_2$, —$CH_2X^{10B}$, —$OCX^{10B}_3$, —$OCH_2X^{10B}$, —$OCHX^{10B}_2$, $R^{10C}$-substituted or unsubstituted alkyl (e.g., $C_1$-$C_8$, $C_1$-$C_6$, $C_1$-$C_4$, or $C_1$-$C_2$), $R^{10C}$-substituted or unsubstituted heteroalkyl (e.g., 2 to 8 membered, 2 to 6 membered, 4 to 6 membered, or 2 to 3 membered), $R^{10C}$-substituted or unsubstituted cycloalkyl (e.g., $C_3$-$C_8$, $C_3$-$C_6$, $C_4$-$C_6$, or $C_5$-$C_6$), $R^{10C}$-substituted or unsubstituted heterocycloalkyl (e.g., 3 to 6 membered, 4 to 6 membered, 4 to 5 membered, or 5 to 6 membered), $R^{10C}$-substituted or unsubstituted aryl (e.g., $C_6$-$C_{10}$ or phenyl), or $R^{10C}$-substituted or unsubstituted heteroaryl (e.g., 5 to 10 membered, 5 to 9 membered, or 5 to 6 membered). $X^{10B}$ is independently —F, —Cl, —Br, or —I. In embodiments, $R^{10B}$ is independently oxo, halogen, —$CX^{10B}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{10B}{}_2$, —CH$_2$X$^{10B}$, —OCX$_2$X$^{10B}$, —OCX$^{10B}{}_3$, —OCH$_2$X$^{10B}$, —OCHX$^{10B}{}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{10C}$ is independently oxo, halogen, —CX$^{10C}{}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)OH, —NHC(O)OH, —NHOH, —OCX$^{10C}{}_2$, —CH$_2$X$^{10C}$, —OCX$^{10C}{}_3$, —OCH$_2$X$^{10C}$, —OCHX$^{10C}{}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{10C}$ is independently —F, —Cl, —Br, or —I.

In embodiments, R$^{11}$ is independently hydrogen, —CX$^{11}{}_3$, —CN, —COOH, —CONH$_2$, —CHX$^{11}{}_2$, —CH$_2$X$^{11}$, R$^{11A}$-substituted or unsubstituted alkyl (e.g., C$_1$-C$_8$, C$_1$-C$_6$, C$_1$-C$_4$, or C$_1$-C$_2$), R$^{11A}$-substituted or unsubstituted heteroalkyl (e.g., 2 to 8 membered, 2 to 6 membered, 4 to 6 membered, or 2 to 3 membered), R$^{11A}$-substituted or unsubstituted cycloalkyl (e.g., C$_3$-C$_8$, C$_3$-C$_6$, C$_4$-C$_6$, or C$_5$-C$_6$), R$^{11A}$-substituted or unsubstituted heterocycloalkyl (e.g., 3 to 6 membered, 4 to 6 membered, 4 to 5 membered, or 5 to 6 membered), R$^{11A}$-substituted or unsubstituted aryl (e.g., C$_6$-C$_{10}$ or phenyl), or R$^{11A}$-substituted or unsubstituted heteroaryl (e.g., 5 to 10 membered, 5 to 9 membered, or 5 to 6 membered). X$^{11}$ is independently —F, —Cl, —Br, or —I. In embodiments, R$^{11}$ is independently hydrogen. In embodiments, R$^{11}$ is independently methyl. In embodiments, R$^{11}$ is independently ethyl. In embodiments, R$^{11}$ is independently hydrogen, —CX$^{11}{}_3$, —CN, —COOH, —CONH$_2$, —CHX$^{11}{}_2$, —CH$_2$X$^{11}$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^{11}$ and R$^{12}$ substituents bonded to the same nitrogen atom may optionally be joined to form a R$^{11A}$-substituted or unsubstituted heterocycloalkyl or R$^{11A}$-substituted or unsubstituted heteroaryl. In embodiments, R$^{11}$ and R$^{12}$ substituents bonded to the same nitrogen atom may optionally be joined to form a R$^{11A}$-substituted or unsubstituted 3 to 6 membered heterocycloalkyl or R$^{11A}$-substituted or unsubstituted 5 to 6 membered heteroaryl. In embodiments, R$^{11}$ and R$^{12}$ substituents bonded to the same nitrogen atom may optionally be joined to form an unsubstituted 3 to 6 membered heterocycloalkyl or unsubstituted 5 to 6 membered heteroaryl. In embodiments, R$^{11}$ and R$^{12}$ substituents bonded to the same nitrogen atom may optionally be joined to form a R$^{11A}$-substituted or unsubstituted piperazinyl. In embodiments, R$^{11}$ and R$^{12}$ substituents bonded to the same nitrogen atom may optionally be joined to form a R$^{11A}$-substituted or unsubstituted piperidinyl. In embodiments, R$^{11}$ and R$^{12}$ substituents bonded to the same nitrogen atom may optionally be joined to form a R$^{11A}$-substituted or unsubstituted pyrrolidinyl. In embodiments, R$^{11}$ and R$^{12}$ substituents bonded to the same nitrogen atom may optionally be joined to form a R$^{11A}$-substituted or unsubstituted azetidinyl. In embodiments, R$^{11}$ and R$^{12}$ substituents bonded to the same nitrogen atom may optionally be joined to form a R$^{11A}$-substituted or unsubstituted morpholinyl. In embodiments, R$^{11}$ and R$^{12}$ substituents bonded to the same nitrogen atom may optionally be joined to form a R$^{11A}$-substituted or unsubstituted azeridinyl.

R$^{11A}$ is independently oxo, halogen, —CX$^{11A}{}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{11A}{}_2$, —CH$_2$X$^{11A}$, —OCX$^{11A}{}_3$, —OCH$_2$X$^{11A}$, —OCHX$^{11A}{}_2$, R$^{11B}$-substituted or unsubstituted alkyl (e.g., C$_1$-C$_8$, C$_1$-C$_6$, C$_1$-C$_4$, or C$_1$-C$_2$), R$^{11B}$-substituted or unsubstituted heteroalkyl (e.g., 2 to 8 membered, 2 to 6 membered, 4 to 6 membered, or 2 to 3 membered), R$^{11B}$-substituted or unsubstituted cycloalkyl (e.g., C$_3$-C$_8$, C$_3$-C$_6$, C$_4$-C$_6$, or C$_5$-C$_6$), R$^{11B}$-substituted or unsubstituted heterocycloalkyl (e.g., 3 to 6 membered, 4 to 6 membered, 4 to 5 membered or 5 to 6 membered), R$^{11B}$-substituted or unsubstituted aryl (e.g., C$_6$-C$_{10}$ or phenyl), or R$^{11B}$-substituted or unsubstituted heteroaryl (e.g., 5 to 10 membered, 5 to 9 membered, or 5 to 6 membered). X$^{11A}$ is independently —F, —Cl, —Br, or —I. In embodiments, R$^{11A}$ is independently oxo, halogen, —CX$^{11A}{}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{11A}{}_2$, —CH$_2$X$^{11A}$, —OCX$^{11A}{}_3$, —OCH$_2$X$^{11A}$, —OCHX$^{11A}{}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{11B}$ is independently oxo, halogen, —CX$^{11B}{}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{11B}{}_2$, —CH$_2$X$^{11B}$, —OCX$^{11B}{}_3$, —OCH$_2$X$^{11B}$, —OCHX$^{11B}{}_2$, R$^{11C}$-substituted or unsubstituted alkyl (e.g., C$_1$-C$_8$, C$_1$-C$_4$, C$_1$-C$_4$, or C$_1$-C$_2$), R$^{11C}$-substituted or unsubstituted heteroalkyl (e.g., 2 to 8 membered, 2 to 6 membered, 4 to 6 membered, or 2 to 3 membered), R$^{11C}$-substituted or unsubstituted cycloalkyl (e.g., C$_3$-C$_8$, C$_3$-C$_6$, C$_4$-C$_6$, or C$_5$-C$_6$), R$^{11C}$-substituted or unsubstituted heterocycloalkyl (e.g., 3 to 6 membered, 4 to 6 membered, 4 to 5 membered, or 5 to 6 membered), R$^{11C}$-substituted or unsubstituted aryl (e.g., C$_6$-C$_{10}$ or phenyl), or R$^{11C}$-substituted or unsubstituted heteroaryl (e.g., 5 to 10 membered, 5 to 9 membered, or 5 to 6 membered). X$^{11B}$ is independently —F, —Cl, —Br, or —I. In embodiments, R$^{11B}$ is independently oxo, halogen, —CX$^{11B}{}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{11B}{}_2$, —CH$_2$X$^{11B}$, —OCX$^{11B}{}_3$, —OCH$_2$X$^{11B}$, —OCHX$^{11B}{}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl. (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{11C}$ is independently oxo, halogen, —$CX^{11C}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{11C}_2$, —$CH_2X^{11C}$, —$OCX^{11C}_3$, —$OCH_2X^{11C}$, —$OCHX^{11C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{11C}$ is independently —F, —Cl, —Br, or —I.

In embodiments, $R^{12}$ is independently hydrogen, —$CX^{12}_3$, —CN, —COOH, —$CONH_2$, —$CHX^{12}_2$, —$CH_2X^{12}$, $R^{12A}$-substituted or unsubstituted alkyl (e.g., $C_1$-$C_8$, $C_1$-$C_6$, $C_1$-$C_4$, or $C_1$-$C_2$), $R^{12A}$-substituted or unsubstituted heteroalkyl (e.g., 2 to 8 membered, 2 to 6 membered 4 to 6 membered, or 2 to 3 membered), $R^{12A}$-substituted or unsubstituted cycloalkyl (e.g., $C_3$-$C_8$, $C_3$-$C_6$, $C_4$-$C_6$, or $C_5$-$C_6$), $R^{12A}$-substituted or unsubstituted heterocycloalkyl (e.g., 3 to 6 membered, 4 to 6 membered, 4 to 5 membered, or 5 to 6 membered), $R^{12A}$-substituted or unsubstituted aryl (e.g., $C_6$-$C_{10}$ or phenyl), or $R^{12A}$-substituted or unsubstituted heteroaryl (e.g., 5 to 10 membered, 5 to 9 membered, or 5 to 6 membered). $X^{12}$ is independently —F, —Cl, —Br, or —I. In embodiments, $R^{12}$ is independently hydrogen. In embodiments, $R^{12}$ is independently methyl. In embodiments, $R^{12}$ is independently ethyl. In embodiments, $R^{12}$ is independently hydrogen, —$CX^{12}_3$, —CN, —COOH, —$CONH_2$, —$CHX^{12}_2$, —$CH_2X^{12}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{12}$ and $R^{11}$ substituents bonded to the same nitrogen atom may optionally be joined to form a $R^{12A}$-substituted or unsubstituted heterocycloalkyl or $R^{12A}$-substituted or unsubstituted heteroaryl. In embodiments, $R^{12}$ and $R^{11}$ substituents bonded to the same nitrogen atom may optionally be joined to form a $R^{12A}$-substituted or unsubstituted 3 to 6 membered heterocycloalkyl or $R^{12A}$-substituted or unsubstituted 5 to 6 membered heteroaryl. In embodiments, $R^{12}$ and $R^{11}$ substituents bonded to the same nitrogen atom may optionally be joined to form an unsubstituted 3 to 6 membered heterocycloalkyl or unsubstituted 5 to 6 membered heteroaryl. In embodiments, $R^{12}$ and $R^{11}$ substituents bonded to the same nitrogen atom may optionally be joined to form a $R^{12A}$-substituted or unsubstituted piperazinyl. In embodiments, $R^{12}$ and $R^{11}$ substituents bonded to the same nitrogen atom may optionally be joined to form a $R^{12A}$-substituted or unsubstituted piperidinyl. In embodiments, $R^{12}$ and $R^{11}$ substituents bonded to the same nitrogen atom may optionally be joined to form a $R^{12A}$-substituted or unsubstituted pyrrolidinyl. In embodiments, $R^{12}$ and $R^{11}$ substituents bonded to the same nitrogen atom may optionally be joined to form a $R^{12A}$-substituted or unsubstituted azetidinyl. In embodiments, $R^{12}$ and $R^{11}$ substituents bonded to the same nitrogen atom may optionally be joined to form a $R^{12A}$-substituted or unsubstituted morpholinyl. In embodiments, $R^{12}$ and $R^{11}$ substituents bonded to the same nitrogen atom may optionally be joined to form a $R^{12A}$-substituted or unsubstituted azeridinyl.

$R^{12A}$ is independently oxo, halogen, —$CX^{12A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{12A}_2$, —$CH_2X^{12A}$, —$OCX^{12A}_3$, —$OCH_2X^{12A}$, —$OCHX^{12A}_2$, $R^{12B}$-substituted or unsubstituted alkyl (e.g., $C_1$-$C_8$, $C_1$-$C_6$, $C_1$-$C_4$, or $C_1$-$C_2$), $R^{12B}$-substituted or unsubstituted heteroalkyl (e.g., 2 to 8 membered, 2 to 6 membered, 4 to 6 membered, or 2 to 3 membered), $R^{12B}$-substituted or unsubstituted cycloalkyl (e.g., $C_3$-$C_8$, $C_3$-$C_6$, $C_4$-$C_6$, or $C_5$-$C_6$), $R^{12B}$-substituted or unsubstituted heterocycloalkyl (e.g., 3 to 6 membered, 4 to 6 membered, 4 to 5 membered, or 5 to 6 membered), $R^{12B}$-substituted or unsubstituted aryl (e.g., $C_6$-$C_{10}$ or phenyl), or $R^{12B}$-substituted or unsubstituted heteroaryl (e.g., 5 to 10 membered, 5 to 9 membered, or 5 to 6 membered). $X^{12A}$ is independently —F, —Cl, —Br, or —I. In embodiments, $R^{12A}$ is independently oxo, halogen, —$CX^{12A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{12A}_2$, —$CH_2X^{12A}$, —$OCX^{12A}_3$, —$OCH_2X^{12A}$, —$OCHX^{12A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered or 5 to 6 membered).

$R^{12B}$ is independently oxo, halogen, —$CX^{12B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{12B}_2$, —$CH_2X^{12B}$, —$OCX^{12B}_3$, —$OCH_2X^{12B}$, —$OCHX^{12B}_2$, $R^{12C}$-substituted or unsubstituted alkyl (e.g., $C_1$-$C_8$, $C_1$-$C_6$, $C_1$-$C_4$, or $C_1$-$C_2$), $R^{12C}$-substituted or unsubstituted heteroalkyl (e.g., 2 to 8 membered, 2 to 6 membered, 4 to 6 membered, or 2 to 3 membered), $R^{12C}$-substituted or unsubstituted cycloalkyl (e.g., $C_3$-$C_8$, $C_3$-$C_6$, $C_4$-$C_6$, or $C_5$-$C_6$), $R^{12C}$-substituted or unsubstituted heterocycloalkyl (e.g., 3 to 6 membered, 4 to 6 membered, 4 to 5 membered, or 5 to 6 membered), $R^{12C}$-substituted or unsubstituted aryl (e.g., $C_6$-$C_{10}$ or phenyl), or $R^{12C}$-substituted or unsubstituted heteroaryl (e.g., 5 to 10 membered, 5 to 9 membered, or 5 to 6 membered). $X^{12B}$ is independently —F, —Cl, —Br, or —I. In embodiments, $R^{12B}$ is independently oxo, halogen, —$CX^{12B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{12B}_2$, —$CH_2X^{12B}$, —$OCX^{12B}_3$, —$OCH_2X^{12B}$, —$OCHX^{12B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{12C}$ is independently oxo, halogen, —$CX^{12C}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{12C}_2$, —$CH_2X^{12C}$, —$OCX^{12C}_3$, —$OCH_2X^{12C}$, —$OCHX^{12C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{12C}$ is independently —F, —Cl, —Br, or —I.

In embodiments, $R^{13}$ is independently hydrogen, —$CX^{13}_3$, —CN, —COOH, —$CONH_2$, —$CHX^{13}_2$, —$CH_2X^{13}$, $R^{13A}$-substituted or unsubstituted alkyl (e.g., $C_1$-$C_8$, $C_1$-$C_6$, $C_1$-$C_4$, or $C_1$-$C_2$), $R^{13A}$-substituted or unsubstituted heteroalkyl (e.g., 2 to 8 membered, 2 to 6 membered, 4 to 6 membered, or 2 to 3 membered), $R^{13A}$-substituted or unsubstituted cycloalkyl (e.g., $C_3$-$C_8$, $C_3$-$C_6$, $C_4$-$C_6$, or $C_5$-$C_6$), $R^{13A}$-substituted or unsubstituted heterocycloalkyl (e.g., 3 to 6 membered, 4 to 6 membered, 4 to 5 membered, or 5 to 6 membered), $R^{13A}$-substituted or unsubstituted aryl (e.g., $C_6$-$C_{10}$ or phenyl), or $R^{13A}$-substituted or unsubstituted heteroaryl (e.g., 5 to 10 membered, 5 to 9 membered, or 5 to 6 membered). $X^{13}$ is independently —F, —Cl, —Br, or —I. In embodiments, $R^{13}$ is independently hydrogen. In embodiments, $R^{13}$ is independently methyl. In embodiments, $R^{13}$ is independently ethyl. In embodiments, $R^{13}$ is independently hydrogen, —$CX^{13}_3$, —CN, —COOH, —$CONH_2$, —$CHX^{13}_2$, —$CH_2X^{13}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered or 5 to 6 membered).

$R^{13A}$ is independently oxo, halogen, —$CX^{13A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{13A}_2$, —$CH_2X^{13A}$, —$OCX^{13A}_3$, —$OCH_2X^{13A}$, —$OCHX^{13A}_2$, $R^{13B}$-substituted or unsubstituted alkyl (e.g., $C_1$-$C_8$, $C_1$-$C_6$, $C_1$-$C_4$, or $C_1$-$C_2$), $R^{13B}$-substituted or unsubstituted heteroalkyl (e.g., 2 to 8 membered, 2 to 6 membered, 4 to 6 membered, or 2 to 3 membered), $R^{13B}$-substituted or unsubstituted cycloalkyl (e.g., $C_3$-$C_8$, $C_3$-$C_6$, $C_4$-$C_6$, or $C_5$-$C_6$), $R^{13B}$-substituted or unsubstituted heterocycloalkyl (e.g., 3 to 6 membered, 4 to 6 membered, 4 to 5 membered, or 5 to 6 membered), $R^{13B}$-substituted or unsubstituted aryl (e.g., $C_6$-$C_{10}$ or phenyl), or $R^{13B}$-substituted or unsubstituted heteroaryl (e.g., 5 to 10 membered, 5 to 9 membered, or 5 to 6 membered). $X^{13A}$ is independently —F, —Cl, —Br, or —I. In embodiments, $R^{13A}$ is independently oxo, halogen, —$CX^{13A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{13A}_2$, —$CH_2X^{13A}$, —$OCX^{13A}_3$, —$OCH_2X^{13A}$, —$OCHX^{13A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered or 5 to 6 membered).

$R^{13B}$ is independently oxo, halogen, —$CX^{13B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{13B}_2$, —$CH_2X^{13B}$, —$OCX^{13B}_3$, —$OCH_2X^{13B}$, —$OCHX^{13B}_2$, $R^{13C}$-substituted or unsubstituted alkyl (e.g., $C_1$-$C_8$, $C_1$-$C_6$, $C_1$-$C_4$, or $C_1$-$C_2$), $R^{13C}$-substituted or unsubstituted heteroalkyl (e.g., 2 to 8 membered, 2 to 6 membered, 4 to 6 membered, or 2 to 3 membered), $R^{13C}$-substituted or unsubstituted cycloalkyl (e.g., $C_3$-$C_8$, $C_3$-$C_6$, $C_4$-$C_6$, or $C_5$-$C_6$), $R^{13C}$-substituted or unsubstituted heterocycloalkyl (e.g., 3 to 6 membered, 4 to 6 membered, 4 to 5 membered, or 5 to 6 membered), $R^{13C}$-substituted or unsubstituted aryl (e.g., $C_6$-$C_{10}$ or phenyl), or $R^{13C}$-substituted or unsubstituted heteroaryl (e.g., 5 to 10 membered, 5 to 9 membered, or 5 to 6 membered). $X^{13B}$ is independently —F, —Cl, —Br, or —I. In embodiments, $R^{13B}$ is independently oxo, halogen, —$CX^{13B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{13B}_2$, —$CH_2X^{13B}$, —$OCX^{13B}_3$, —$OCH_2X^{13B}$, —$OCHX^{13B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{13C}$ is independently oxo, halogen, —$CX^{13C}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{13C}_2$, —$CH_2X^{13C}$, —$OCX^{13C}_3$, —$OCH_2X^{13C}$, —$OCHX^{13C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{13C}$ is independently —F, —Cl, —Br, or —I.

In embodiments, $R^{14}$ is independently hydrogen, —$CX^{14}_3$, —CN, —COOH, —$CONH_2$, —$CHX^{14}_2$, —$CH_2X^{14}$, $R^{14A}$-substituted or unsubstituted alkyl (e.g., $C_1$-$C_8$, $C_1$-$C_6$, $C_1$-$C_4$, or $C_1$-$C_2$), $R^{14A}$-substituted or unsubstituted heteroalkyl (e.g., 2 to 8 membered, 2 to 6 membered, 4 to 6 membered, or 2 to 3 membered), $R^{14A}$-substituted or unsubstituted cycloalkyl (e.g., $C_3$-$C_8$, $C_3$-$C_6$, $C_4$-$C_6$, or $C_5$-$C_6$). $R^{14A}$-substituted or unsubstituted heterocycloalkyl (e.g., 3 to 6 membered, 4 to 6 membered, 4 to 5 membered, or 5 to 6 membered). $R^{14A}$-substituted or unsubstituted aryl (e.g., $C_6$-$C_{10}$ or phenyl), or $R^{14A}$-substituted or unsubstituted heteroaryl (e.g., 5 to 10 membered, 5 to 9 membered, or 5 to 6 membered). $X^{14}$ is independently —F, —Cl, —Br, or —I. In embodiments, $R^{14}$ is independently hydrogen. In embodiments, $R^{14}$ is independently methyl. In embodiments, $R^{14}$ is independently ethyl. In embodiments, $R^{14}$ is independently hydrogen, —$CX^{14}_3$, —CN, —COOH, —CONH$_2$, —CHX$^{14}_2$, —CH$_2$X$^{14}$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{14A}$ is independently oxo, halogen, —CX$^{14A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{14A}_2$, —CH$_2$X$^{14A}$, —OCX$^{14A}_3$, —OCH$_2$X$^{14A}$, —OCHX$^{14A}_2$, R$^{14B}$-substituted or unsubstituted alkyl (e.g., C$_1$-C$_8$, C$_1$-C$_6$, C$_1$-C$_4$, or C$_1$-C$_2$), R$^{14B}$-substituted or unsubstituted heteroalkyl (e.g., 2 to 8 membered, 2 to 6 membered, 4 to 6 membered, or 2 to 3 membered), R$^{14B}$-substituted or unsubstituted cycloalkyl (e.g., C$_3$-C$_8$, C$_3$-C$_6$, C$_4$-C$_6$, or C$_5$-C$_6$), R$^{14B}$-substituted or unsubstituted heterocycloalkyl (e.g., 3 to 6 membered, 4 to 6 membered, 4 to 5 membered, or 5 to 6 membered), R$^{14B}$-substituted or unsubstituted aryl (e.g., C$_6$-C$_{10}$ or phenyl), or R$^{14B}$-substituted or unsubstituted heteroaryl (e.g., 5 to 10 membered, 5 to 9 membered, or 5 to 6 membered). X$^{14A}$ is independently —F, —Cl, —Br, or —I. In embodiments, R$^{14A}$ is independently oxo, halogen, —CX$^{14A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{14A}_2$, —CH$_2$X$^{14A}$, —OCX$^{14A}_3$, —OCH$_2$X$^{14A}$, —OCHX$^{14A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered or 5 to 6 membered).

R$^{14B}$ is independently oxo, halogen, —CX$^{14B}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{14B}_2$, —CH$_2$X$^{14B}$, —OCX$^{14B}_3$, —OCH$_2$X$^{14B}$, —OCHX$^{14B}_2$, R$^{14C}$-substituted or unsubstituted alkyl (e.g., C$_1$-C$_8$, C$_1$-C$_6$, C$_1$-C$_4$, or C$_1$-C$_2$), R$^{14C}$-substituted or unsubstituted heteroalkyl (e.g., 2 to 8 membered, 2 to 6 membered, 4 to 6 membered, or 2 to 3 membered), R$^{14C}$-substituted or unsubstituted cycloalkyl (e.g., C$_3$-C$_8$, C$_3$-C$_6$, C$_4$-C$_6$, or C$_5$-C$_6$), R$^{14C}$-substituted or unsubstituted heterocycloalkyl (e.g., 3 to 6 membered, 4 to 6 membered, 4 to 5 membered, or 5 to 6 membered), R$^{14C}$-substituted or unsubstituted aryl (e.g., C$_6$-C$_{10}$ or phenyl), or R$^{14C}$-substituted or unsubstituted heteroaryl (e.g., 5 to 10 membered, 5 to 9 membered, or 5 to 6 membered). X$^{14B}$ is independently —F, —Cl, —Br, or —I. In embodiments, R$^{14B}$ is independently oxo, halogen, —CX$^{14B}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{14B}_2$, —CH$_2$X$^{14B}$, —OCX$^{14B}_3$, —OCH$_2$X$^{14B}$, —OCHX$^{14B}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{14C}$ is independently oxo, halogen, —CX$^{14C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{14C}_2$, —CH$_2$X$^{14C}$, —OCX$^{14C}_3$, —OCH$_2$X$^{14C}$, —OCHX$^{14C}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{14C}$ is independently —F, —Cl, —Br, or —I.

In embodiments, R$^{15}$ is independently hydrogen, —CX$^{15}_3$, —CN, —COOH, —CONH$_2$, —CHX$^{15}_2$, —CH$_2$X$^{15}$, R$^{15A}$-substituted or unsubstituted alkyl (e.g., C$_1$-C$_8$, C$_1$-C$_6$, C$_1$-C$_4$, or C$_1$-C$_2$), R$^{15A}$-substituted or unsubstituted heteroalkyl (e.g., 2 to 8 membered, 2 to 6 membered, 4 to 6 membered, or 2 to 3 membered), R$^{15A}$-substituted or unsubstituted cycloalkyl (e.g., C$_3$-C$_8$, C$_3$-C$_6$, C$_4$-C$_6$, or C$_5$-C$_6$). R$^{15A}$-substituted or unsubstituted heterocycloalkyl (e.g., 3 to 6 membered, 4 to 6 membered 4 to 5 membered, or 5 to 6 membered). R$^{15A}$-substituted or unsubstituted aryl (e.g., C$_6$-C$_{10}$ or phenyl), or R$^{15A}$-substituted or unsubstituted heteroaryl (e.g., 5 to 10 membered, 5 to 9 membered, or 5 to 6 membered). X$^{15}$ is independently —F, —Cl, —Br, or —I. In embodiments, R$^{15}$ is independently hydrogen. In embodiments, R$^{15}$ is independently methyl. In embodiments, R$^{15}$ is independently ethyl. In embodiments, R$^{15}$ is independently hydrogen, —CX$^{15}_3$, —CN, —COOH, —CONH$_2$, —CHX$^{15}_2$, —CH$_2$X$^{15}$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

In embodiments, R$^{15}$ and R$^{16}$ substituents bonded to the same nitrogen atom may optionally be joined to form a R$^{15A}$-substituted or unsubstituted heterocycloalkyl or R$^{15A}$-substituted or unsubstituted heteroaryl. In embodiments, R$^{15}$ and R$^{16}$ substituents bonded to the same nitrogen atom may optionally be joined to form a R$^{15A}$-substituted or unsubstituted 3 to 6 membered heterocycloalkyl or R$^{15A}$-substituted or unsubstituted 5 to 6 membered heteroaryl. In embodiments, R$^{15}$ and R$^{16}$ substituents bonded to the same nitrogen atom may optionally be joined to form an unsubstituted 3 to 6 membered heterocycloalkyl or unsubstituted 5 to 6 membered heteroaryl. In embodiments, R$^{15}$ and R$^{16}$ substituents bonded to the same nitrogen atom may optionally be joined to form a R$^{15A}$-substituted or unsubstituted piperazinyl. In embodiments, R$^{15}$ and R$^{16}$ substituents bonded to the same nitrogen atom may optionally be joined to form a R$^{15A}$-substituted or unsubstituted piperidinyl. In embodiments, R$^{15}$ and R$^{16}$ substituents bonded to the same nitrogen atom may optionally be joined to form a R$^{15A}$-substituted or unsubstituted pyrrolidinyl. In embodiments, R$^{15}$ and R$^{16}$ substituents bonded to the same nitrogen atom may optionally be joined to form a R$^{15A}$-substituted or unsubstituted azetidinyl. In embodiments, R$^{15}$ and R$^{16}$ substituents bonded to the same nitrogen atom may optionally be joined to form a $R^{15A}$-substituted or unsubstituted morpholinyl. In embodiments, $R^{15}$ and $R^{16}$ substituents bonded to the same nitrogen atom may optionally be joined to form a $R^{15A}$-substituted or unsubstituted azeridinyl.

$R^{15A}$ is independently oxo, halogen, —$CX^{15A}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{15A}_2$, —$CH_2X^{15A}$, —$OCX^{15A}_3$, —$OCH_2X^{15A}$, —$OCHX^{15A}_2$, $R^{15B}$-substituted or unsubstituted alkyl (e.g., $C_1$-$C_8$, $C_1$-$C_6$, $C_1$-$C_4$, or $C_1$-$C_2$), $R^{15B}$-substituted or unsubstituted heteroalkyl (e.g., 2 to 8 membered, 2 to 6 membered, 4 to 6 membered, or 2 to 3 membered), $R^{15B}$-substituted or unsubstituted cycloalkyl (e.g., $C_3$-$C_8$, $C_3$-$C_6$, $C_4$-$C_6$, or $C_5$-$C_6$), $R^{15B}$-substituted or unsubstituted heterocycloalkyl (e.g., 3 to 6 membered, 4 to 6 membered, 4 to 5 membered, or 5 to 6 membered), $R^{15B}$-substituted or unsubstituted aryl (e.g., $C_6$-$C_{10}$ or phenyl), or $R^{15B}$-substituted or unsubstituted heteroaryl (e.g., 5 to 10 membered, 5 to 9 membered, or 5 to 6 membered). $X^{15A}$ is independently —F, —Cl, —Br, or —I. In embodiments, $R^{15A}$ is independently oxo, halogen, —$CX^{15A}_3$, —CN, —OH, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{15A}_2$, —$CH_2X^{15A}$, —$OCX^{15A}_3$, —$OCH_2X^{15A}$, —$OCHX^{15A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{15B}$ is independently oxo, halogen, —$CX^{15B}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{15B}_2$, —$CH_2X^{15B}$, —$OCX^{15B}_3$, —$OCH_2X^{15B}$, —$OCHX^{15B}_2$, $R^{15C}$-substituted or unsubstituted alkyl (e.g., $C_1$-$C_8$, $C_1$-$C_6$, $C_1$-$C_4$, or $C_1$-$C_2$), $R^{15C}$-substituted or unsubstituted heteroalkyl (e.g., 2 to 8 membered, 2 to 6 membered, 4 to 6 membered, or 2 to 3 membered), $R^{15C}$-substituted or unsubstituted cycloalkyl (e.g., $C_3$-$C_8$, $C_3$-$C_6$, $C_4$-$C_6$, or $C_5$-$C_6$), $R^{15C}$-substituted or unsubstituted heterocycloalkyl (e.g., 3 to 6 membered, 4 to 6 membered, 4 to 5 membered, or 5 to 6 membered), $R^{15C}$-substituted or unsubstituted aryl (e.g., $C_6$-$C_{10}$ or phenyl), or $R^{15C}$-substituted or unsubstituted heteroaryl (e.g., 5 to 10 membered, 5 to 9 membered or 5 to 6 membered). $X^{15B}$ is independently —F, —Cl, —Br, or —I. In embodiments, $R^{15B}$ is independently oxo, halogen, —$CX^{15B}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{15B}_2$, —$CH_2X^{15B}$, —$OCX^{15B}_3$, —$OCH_2X^{15B}$, —$OCHX^{15B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{15C}$ is independently oxo, halogen, —$CX^{15C}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)H, —NHC(O)OH, —NHOH, —$CHX^{15C}_2$, —$CH_2X^{15C}$, —$OCX^{15C}_3$, —$OCH_2X^{15C}$, —$OCHX^{15C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{15C}$ is independently —F, —Cl, —Br, or —I.

In embodiments, $R^{16}$ is independently hydrogen, —$CX^{16}_3$, —CN, —COOH, —$CONH_2$, —$CHX^{16}_2$, —$CH_2X^{16}$, $R^{16A}$-substituted or unsubstituted alkyl (e.g., $C_1$-$C_8$, $C_1$-$C_6$, $C_1$-$C_4$, or $C_1$-$C_2$), $R^{16A}$-substituted or unsubstituted heteroalkyl (e.g., 2 to 8 membered, 2 to 6 membered, 4 to 6 membered, or 2 to 3 membered), $R^{16A}$-substituted or unsubstituted cycloalkyl (e.g., $C_3$-$C_8$, $C_3$-$C_6$, $C_4$-$C_6$, or $C_5$-$C_6$), $R^{16A}$-substituted or unsubstituted heterocycloalkyl (e.g., 3 to 6 membered, 4 to 6 membered, 4 to 5 membered, or 5 to 6 membered), $R^{16A}$-substituted or unsubstituted aryl (e.g., $C_6$-$C_{10}$ or phenyl), or $R^{16A}$-substituted or unsubstituted heteroaryl (e.g., 5 to 10 membered, 5 to 9 membered, or 5 to 6 membered). $X^{16}$ is independently —F, —Cl, —Br, or —I. In embodiments, $R^{16}$ is independently hydrogen. In embodiments, $R^{16}$ is independently methyl. In embodiments, $R^{16}$ is independently ethyl. In embodiments, $R^{16}$ is independently hydrogen, —$CX^{16}_3$, —CN, —COOH, —$CONH_2$, —$CHX^{16}_2$, —$CH_2X^{16}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

In embodiments, $R^{16}$ and $R^{15}$ substituents bonded to the same nitrogen atom may optionally be joined to form a $R^{16A}$-substituted or unsubstituted heterocycloalkyl or $R^{16A}$-substituted or unsubstituted heteroaryl. In embodiments, $R^{16}$ and $R^{15}$ substituents bonded to the same nitrogen atom may optionally be joined to form a $R^{16A}$-substituted or unsubstituted 3 to 6 membered heterocycloalkyl or $R^{16A}$-substituted or unsubstituted 5 to 6 membered heteroaryl. In embodiments, $R^{16}$ and $R^{15}$ substituents bonded to the same nitrogen atom may optionally be joined to form an unsubstituted 3 to 6 membered heterocycloalkyl or unsubstituted 5 to 6 membered heteroaryl. In embodiments, $R^{16}$ and $R^{15}$ substituents bonded to the same nitrogen atom may optionally be joined to form a $R^{16A}$-substituted or unsubstituted piperazinyl. In embodiments, $R^{16}$ and $R^{15}$ substituents bonded to the same nitrogen atom may optionally be joined to form a $R^{16A}$-substituted or unsubstituted piperidinyl. In embodiments, $R^{16}$ and $R^{15}$ substituents bonded to the same nitrogen atom may optionally be joined to form a $R^{16A}$-substituted or unsubstituted pyrrolidinyl. In embodiments, $R^{16}$ and $R^{15}$ substituents bonded to the same nitrogen atom may optionally be joined to form a $R^{16A}$-substituted or unsubstituted azetidinyl. In embodiments, $R^{16}$ and $R^{15}$ substituents bonded to the same nitrogen atom may optionally be joined to form a $R^{16A}$-substituted or unsubstituted morpholinyl. In embodiments, $R^{16}$ and $R^{15}$ substituents bonded to the same nitrogen atom may optionally be joined to form a $R^{16A}$-substituted or unsubstituted azeridinyl.

$R^{16A}$ is independently oxo, halogen, —$CX^{16A}_3$, —CN, —OH, —$NH_2$, —COOH, —$CONH_2$, —SH, —$NHNH_2$, —$ONH_2$, —$NHC(O)NHNH_2$, —$NHC(O)NH_2$, —NHC(O)

H, —NHC(O)OH, —NHOH, —CHX$^{16A}_2$, —CH$_2$X$^{16A}$, —OCX$^{16A}_3$, —OCH$_2$X$^{16A}$, —OCHX$^{16A}_2$, R$^{16B}$-substituted or unsubstituted alkyl (e.g., C$_1$-C$_8$, C$_1$-C$_6$, C$_1$-C$_4$, or C$_1$-C$_2$), R$^{16B}$-substituted or unsubstituted heteroalkyl (e.g., 2 to 8 membered, 2 to 6 membered, 4 to 6 membered, or 2 to 3 membered), R$^{16B}$-substituted or unsubstituted cycloalkyl (e.g., C$_3$-C$_8$, C$_3$-C$_6$, C$_4$-C$_6$, or C$_5$-C$_6$), R$^{16B}$-substituted or unsubstituted heterocycloalkyl (e.g., 3 to 6 membered, 4 to 6 membered, 4 to 5 membered, or 5 to 6 membered), R$^{16B}$-substituted or unsubstituted aryl (e.g., C$_6$-C$_{10}$ or phenyl), or R$^{16B}$-substituted or unsubstituted heteroaryl (e.g., 5 to 10 membered, 5 to 9 membered, or 5 to 6 membered). X$^{16A}$ is independently —F, —Cl, —Br, or —I. In embodiments, R$^{16A}$ is independently oxo, halogen, —CX$^{16A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{16A}_2$, —CH$_2$X$^{16A}$, —OCX$^{16A}_3$, —OCH$_2$X$^{16A}$, —OCHX$^{16A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered or 5 to 6 membered).

R$^{16B}$ is independently oxo, halogen, —CX$^{16B}_3$, —CN, —OH, —NH$_2$, —COOH, —CONH, —SH, —NHNH$_2$, —ONH$_2$, —NHC(O)NHNH$_2$, —NHC(O)NH$_2$, —NHC(O)H, —NHC(O)OH, —NHOH, —CHX$^{16B}_2$, —CH$_2$X$^{16B}$, —OCX$^{16B}_3$, —OCH$_2$X$^{16B}$, —OCHX$^{16B}_2$, R$^{16C}$-substituted or unsubstituted alkyl (e.g., C$_1$-C$_8$, C$_1$-C$_6$, C$_1$-C$_4$, or C$_1$-C$_2$), R$^{16C}$-substituted or unsubstituted heteroalkyl (e.g., 2 to 8 membered, 2 to 6 membered, 4 to 6 membered, or 2 to 3 membered), R$^{16C}$-substituted or unsubstituted cycloalkyl (e.g., C$_3$-C$_8$, C$_3$-C$_6$, C$_4$-C$_6$, or C$_5$-C$_6$), R$^{16C}$-substituted or unsubstituted heterocycloalkyl (e.g., 3 to 6 membered, 4 to 6 membered, 4 to 5 membered, or 5 to 6 membered), R$^{16C}$-substituted or unsubstituted aryl (e.g., C$_6$-C$_{10}$ or phenyl), or R$^{16C}$-substituted or unsubstituted heteroaryl (e.g., 5 to 10 membered, 5 to 9 membered or 5 to 6 membered). X$^{16B}$ is independently —F, —Cl, —Br, or —I. In embodiments, R$^{16B}$ is independently oxo, halogen, —CX$^{16B}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{16B}_2$, —CH$_2$X$^{16B}$, —OCX$^{16B}_3$, —OCH$_2$X$^{16B}$, —OCHX$^{16B}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (ea., 5 to 10 membered, 5 to 9 membered, or 5 to 6 membered).

R$^{16C}$ is independently oxo, halogen, —CX$^{16C}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{16C}_2$, —CH$_2$X$^{16C}$, —OCX$^{16C}_3$, —OCH$_2$X$^{16C}$, —OCHX$^{16C}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered). X$^{16C}$ is independently —F, —Cl, —Br, or —I.

In embodiments, R$^{17}$ is independently hydrogen, —CX$^{17}_3$, —CN, —COOH, —CONH$_2$, —CHX$^{17}_2$, —CH$_2$X$^{17}$, R$^{17A}$-substituted or unsubstituted alkyl (e.g., C$_1$-C$_8$, C$_1$-C$_6$, C$_1$-C$_4$, or C$_1$-C$_2$), R$^{17A}$-substituted or unsubstituted heteroalkyl (e.g., 2 to 8 membered, 2 to 6 membered, 4 to 6 membered, or 2 to 3 membered), R$^{17A}$-substituted or unsubstituted cycloalkyl (e.g., C$_3$-C$_8$, C$_3$-C$_6$, C$_4$-C$_6$, or C$_5$-C$_6$), R$^{17A}$-substituted or unsubstituted heterocycloalkyl (e.g., 3 to 6 membered, 4 to 6 membered, 4 to 5 membered, or 5 to 6 membered), R$^{17A}$-substituted or unsubstituted aryl (e.g., C$_6$-C$_{10}$ or phenyl), or R$^{17A}$-substituted or unsubstituted heteroaryl (e.g., 5 to 10 membered, 5 to 9 membered, or 5 to 6 membered). X$^{17}$ is independently —F, —Cl, —Br, or —I. In embodiments, R$^{17}$ is independently hydrogen. In embodiments, R$^{17}$ is independently methyl. In embodiments, R$^{17}$ is independently ethyl. In embodiments, R$^{17}$ is independently hydrogen, —CX$^{17}_3$, —CN, —COOH, —CONH$_2$, —CHX$^{17}_2$, —CH$_2$X$^{17}$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{17A}$ is independently oxo, halogen, —CX$^{17A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{17A}_2$, —CH$_2$X$^{17A}$, —OCX$^{17A}_3$, —OCH$_2$X$^{17A}$, —OCHX$^{17A}_2$, R$^{17B}$-substituted or unsubstituted alkyl (e.g., C$_1$-C$_8$, C$_1$-C$_6$, C$_1$-C$_4$, or C$_1$-C$_2$), R$^{17B}$-substituted or unsubstituted heteroalkyl (e.g., 2 to 8 membered, 2 to 6 membered, 4 to 6 membered, or 2 to 3 membered), R$^{17B}$-substituted or unsubstituted cycloalkyl (e.g., C$_3$-C$_8$, C$_3$-C$_6$, C$_4$-C$_6$, or C$_5$-C$_6$), R$^{17B}$-substituted or unsubstituted heterocycloalkyl (e.g., 3 to 6 membered, 4 to 6 membered, 4 to 5 membered, or 5 to 6 membered), R$^{17B}$-substituted or unsubstituted aryl (e.g., C$_6$-C$_{10}$ or phenyl), or R$^{17B}$-substituted or unsubstituted heteroaryl (e.g., 5 to 10 membered, 5 to 9 membered, or 5 to 6 membered). X$^{17A}$ is independently —F, —Cl, —Br, or —I. In embodiments, R$^{17A}$ is independently oxo, halogen, —CX$^{17A}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{17A}_2$, —CH$_2$X$^{17A}$, —OCX$^{17A}_3$, —OCH$_2$X$^{17A}$, —OCHX$^{17A}_2$, unsubstituted alkyl (e.g., C$_1$-C$_8$, C$_1$-C$_6$, C$_1$-C$_4$, or C$_1$-C$_2$), unsubstituted heteroalkyl (e.g., 2 to 8 membered, 2 to 6 membered, 4 to 6 membered, or 2 to 3 membered), unsubstituted cycloalkyl (e.g., C$_3$-C$_8$, C$_3$-C$_6$, C$_4$-C$_6$, or C$_5$-C$_6$), unsubstituted heterocycloalkyl (e.g., 3 to 6 membered, 4 to 6 membered, 4 to 5 membered, or 5 to 6 membered), unsubstituted aryl (e.g., C$_6$-C$_{10}$ or phenyl), or unsubstituted heteroaryl (e.g., 5 to 10 membered, 5 to 9 membered, or 5 to 6 membered).

R$^{17B}$ is independently oxo, halogen, —CX$^{17B}_3$, —CN, —OH, —NH$_2$, —COOH, —CONH$_2$, —SH, —NHNH$_2$, —ONH$_2$, —NHC(O)NHNH$_2$, —NHC(O)NH$_2$, —NHC(O)H, —NHC(O)OH, —NHOH, —CHX$^{17B}_2$, —CH$_2$X$^{17B}$, —OCX$^{17B}_3$, —OCH$_2$X$^{17B}$, —OCHX$^{17B}_2$, R$^{17C}$-substituted or unsubstituted alkyl (e.g., C$_1$-C$_8$, C$_1$-C$_6$, C$_1$-C$_4$, or C$_1$-C$_2$), R$^{17C}$-substituted or unsubstituted heteroalkyl (e.g., 2 to 8 membered, 2 to 6 membered, 4 to 6 membered, or 2 to 3 membered), $R^{17C}$-substituted or unsubstituted cycloalkyl (e.g., $C_3$-$C_8$, $C_3$-$C_6$, $C_4$-$C_6$, or $C_5$-$C_6$), $R^{17C}$-substituted or unsubstituted heterocycloalkyl (e.g., 3 to 6 membered, 4 to 6 membered, 4 to 5 membered, or 5 to 6 membered), $R^{17C}$-substituted or unsubstituted aryl (e.g., $C_6$-$C_{10}$ or phenyl), or $R^{17C}$-substituted or unsubstituted heteroaryl (e.g., 5 to 10 membered, 5 to 9 membered, or 5 to 6 membered). $X^{17B}$ is independently —F, —Cl, —Br, or —I. In embodiments, $R^{17B}$ is independently oxo, halogen, —$CX^{17B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{17B}_2$, —$CH_2X^{17B}$, —$OCX^{17B}_3$, —$OCH_2X^{17B}$, —$OCHX^{17B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{17C}$ is independently oxo, halogen, —$CX^{17C}_3$, —CN, —OH, —$NH_2$, —COOH, —$CONH_2$, —SH, —$NHNH_7$, —$ONH_2$, —NHC(O)$NHNH_2$, —NHC(O)$NH_2$, —NHC(O)H, —NHC(O)OH, —NHOH, —$CHX^{17C}_2$, —$CH_2X^{17C}$, —$OCX^{17C}_3$, —$OCH_2X^{17C}$, —$OCHX^{17C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{17C}$ is independently —F, —Cl, —Br, or —I.

In embodiments, $R^{18}$ is independently hydrogen, —$CX^{18}_3$, —CN, —COOH, —$CONH_2$, —$CHX^{18}_2$, —$CH_2X^{18}$, $R^{18A}$-substituted or unsubstituted alkyl (e.g., $C_1$-$C_8$, $C_1$-$C_6$, $C_1$-$C_4$, or $C_1$-$C_2$), $R^{18A}$-substituted or unsubstituted heteroalkyl (e.g., 2 to 8 membered, 2 to 6 membered, 4 to 6 membered, or 2 to 3 membered), $R^{18A}$-substituted or unsubstituted cycloalkyl (e.g., $C_3$-$C_8$, $C_3$-$C_6$, $C_4$-$C_6$, or $C_5$-$C_6$), $R^{18A}$-substituted or unsubstituted heterocycloalkyl (e.g., 3 to 6 membered, 4 to 6 membered, 4 to 5 membered, or 5 to 6 membered). $R^{18A}$-substituted or unsubstituted aryl (e.g., $C_6$-$C_{10}$ or phenyl), or $R^{18A}$-substituted or unsubstituted heteroaryl (e.g., 5 to 10 membered, 5 to 9 membered, or 5 to 6 membered), $X^{18}$ is independently —F, —Cl, —Br, or —I. In embodiments, $R^{18}$ is independently hydrogen. In embodiments, $R^{18}$ is independently methyl. In embodiments, $R^{18}$ is independently ethyl. In embodiments, $R^{18}$ is independently hydrogen, —$CX^{18}_3$, —CN, —COOH, —$CONH_2$, —$CHX^{18}_2$, —$CH_2X^{18}$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{18A}$ is independently oxo, halogen, —$CX^{18A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18A}_2$, —$OCX^{18A}_3$, —$OCH_2X^{18A}$, —$OCHX^{18A}_2$, $R^{18B}$-substituted or unsubstituted alkyl (e.g., $C_1$-$C_8$, $C_1$-$C_6$, $C_1$-$C_4$, or $C_1$-$C_2$), $R^{18B}$-substituted or unsubstituted heteroalkyl (e.g., 2 to 8 membered, 2 to 6 membered, 4 to 6 membered, or 2 to 3 membered), $R^{18B}$-substituted or unsubstituted cycloalkyl (e.g., $C_3$-$C_8$, $C_3$-$C_6$, $C_4$-$C_6$, or $C_5$-$C_6$), $R^{18B}$-substituted or unsubstituted heterocycloalkyl (e.g., 3 to 6 membered, 4 to 6 membered, 4 to 5 membered, or 5 to 6 membered), $R^{18B}$-substituted or unsubstituted aryl (e.g., $C_6$-$C_{10}$ or phenyl), or $R^{18B}$-substituted or unsubstituted heteroaryl (e.g., 5 to 10 membered, 5 to 9 membered, or 5 to 6 membered). $X^{18A}$ is independently —F, —Cl, —Br, or —I. In embodiments, $R^{18A}$ is independently oxo, halogen, —$CX^{18A}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18A}_2$, —$CH_2X^{18A}$, —$OCX^{18A}_3$, —$OCH_2X^{18A}$, —$OCHX^{18A}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{18B}$ is independently oxo, halogen, —$CX^{18B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18B}_2$, —$CH_2X^{18B}$, —$OCX^{18B}_3$, —$OCH_2X^{18B}$, —$OCHX^{18B}_2$, $R^{18C}$-substituted or unsubstituted alkyl (e.g., $C_1$-$C_8$, $C_1$-$C_6$, $C_1$-$C_4$, or $C_1$-$C_2$), $R^{18C}$-substituted or unsubstituted heteroalkyl (e.g., 2 to 8 membered, 2 to 6 membered, 4 to 6 membered, or 2 to 3 membered), $R^{18C}$-substituted or unsubstituted cycloalkyl (e.g., $C_3$-$C_8$, $C_3$-$C_6$, $C_4$-$C_6$, or $C_5$-$C_6$), $R^{18C}$-substituted or unsubstituted heterocycloalkyl (e.g., 3 to 6 membered, 4 to 6 membered, 4 to 5 membered, or 5 to 6 membered), $R^{18C}$-substituted or unsubstituted aryl (e.g., $C_6$-$C_{10}$ or phenyl), or $R^{18C}$-substituted or unsubstituted heteroaryl (e.g., 5 to 10 membered, 5 to 9 membered or 5 to 6 membered). $X^{18B}$ is independently —F, —Cl, —Br, or —I. In embodiments, $R^{18B}$ is independently oxo, halogen, —$CX^{18B}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18B}_2$, —$CH_2X^{18B}$, —$OCX^{18B}_3$, —$OCH_2X^{18B}$, —$OCHX^{18B}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{18C}$ is independently oxo, halogen, —$CX^{18C}_3$, —CN, —OH, —$NH_2$, —COOH, —$CONH_2$, —SH, —$NHNH_2$, —$ONH_2$, —NHC(O)$NHNH_2$, —NHC(O)$NH_2$, —NHC(O)H, —NHC(O)OH, —NHOH, —$CHX^{18C}_2$, —$CH_2X^{18C}$, —$OCX^{18C}_3$, —$OCH_2X^{18C}$, —$OCHX^{18C}_2$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered), $X^{18C}$ is independently —F, —Cl, —Br, or —I.

In embodiments, $L^1$ is independently a bond, —O—, —NH—, —C(O)—, —C(O)NH—, —NHC(O)—, —C(O)O—, —OC(O)—, —NHC(O)NH—, —S—, $R^{23}$-substituted or unsubstituted alkylene (e.g., $C_1$-$C_8$, $C_1$-$C_6$, $C_1$-$C_4$, or $C_1$-$C_2$) or $R^{23}$-substituted or unsubstituted heteroalkylene (e.g., 2 to 8 membered, 2 to 6 membered, 4 to 6 membered, or 2 to 3 membered). In embodiments, $L^1$ is independently a bond, —O—, —NH—, —C(O)—, —C(O)NH—, —NHC(O)—, —C(O)O—, —OC(O)—, —NHC(O)NH—, —S—, unsubstituted alkylene (e.g., $C_1$-$C_8$, $C_1$-$C_6$, $C_1$-$C_4$, or $C_1$-$C_2$) or unsubstituted heteroalkylene e.g., 2 to 8 membered, 2 to 6 membered, 4 to 6 membered, or 2 to 3 membered).

$R^{23}$ is independently oxo, halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{24}$-substituted or unsubstituted alkyl (e, a., $C_1$-$C_8$, $C_1$-$C_6$, $C_1$-$C_4$, or $C_1$-$C_2$), $R^{24}$-substituted or unsubstituted heteroalkyl (e.g., 2 to 8 membered, 2 to 6 membered, 4 to 6 membered, or 2 to 3 membered), $R^{24}$-substituted or unsubstituted cycloalkyl (e.g., $C_3$-$C_8$, $C_3$-$C_6$, $C_4$-$C_6$, or $C_5$-$C_6$), $R^{24}$-substituted or unsubstituted heterocycloalkyl (e.g., 3 to 6 membered, 4 to 6 membered, 4 to 5 membered, or 5 to 6 membered), $R^{24}$-substituted or unsubstituted aryl (e.g., $C_6$-$C_{10}$ or phenyl), or $R^{24}$-substituted or unsubstituted heteroaryl (e.g., 5 to 10 membered, 5 to 9 membered, or 5 to 6 membered). $X^{23}$ is independently —F, —Cl, —Br, or —I. In embodiments, $R^{23}$ is independently oxo, halogen, —CX$^{23}_3$, —CHX$^{23}_2$, —CH$_2$X$^{23}$, —OCX$^{23}_3$, —OCH$_2$X$^{23}$, —OCHX$^{23}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{14}$ is independently oxo, halogen, —CX$^{24}_3$, —CHX$^{24}_2$, —CH$_2$X$^{24}$, —OCX$^{24}_3$, —OCH$_2$X$^{24}$, —OCHX$^{24}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)OH, —NHC(O)—OH, —NHOH, $R^{25}$-substituted or unsubstituted alkyl (e.g., $C_1$-$C_8$, $C_1$-$C_6$, $C_1$-$C_4$, or $C_1$-$C_2$), $R^{25}$-substituted or unsubstituted heteroalkyl (e.g., 2 to 8 membered, 2 to 6 membered, 4 to 6 membered, or 2 to 3 membered), $R^{25}$-substituted or unsubstituted cycloalkyl (e.g., $C_2$-$C_8$, $C_3$-$C_6$, $C_4$-$C_6$, or $C_5$-$C_6$), $R^{25}$-substituted or unsubstituted heterocycloalkyl (e.g., 3 to 6 membered, 4 to 6 membered, 4 to 5 membered, or 5 to 6 membered), $R^{25}$-substituted or unsubstituted aryl (e.g., $C_6$-$C_{10}$ or phenyl), or $R^{25}$-substituted or unsubstituted heteroaryl (e.g., 5 to 10 membered, 5 to 9 membered, or 5 to 6 membered). $X^{24}$ is independently —F, —Cl, —Br, or —I. In embodiments, $R^{24}$ is independently oxo, halogen, —CX$^{24}_3$, —CHX$^{24}_2$, —CH$_2$X$^{24}$, —OCX$^{24}_3$, —OCH$_2$X$^{24}$, —OCHX$^{24}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{25}$ is independently oxo, halogen, —CX$^{25}_3$, —CHX$^{25}_2$, —CH$_2$X$^{25}$, —OCX$^{25}_3$, —OCH$_2$X$^{25}$, —OCH$^{25}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{25}$ is independently —F, —Cl, —Br, or —I.

In embodiments, $L^2$ is independently a bond, —O—, —NH—, —C(O)—, —C(O)NH—, —NHC(O)—, —C(O)O—, —OC(O)—, —NHC(O)NH—, —S—, $R^{26}$-substituted or unsubstituted alkylene (e.g., $C_1$-$C_8$, $C_1$-$C_6$, $C_1$-$C_4$, or $C_1$-$C_2$) or $R^{26}$-substituted or unsubstituted heteroalkylene (e.g., 2 to 8 membered, 2 to 6 membered, 4 to 6 membered, or 2 to 3 membered). In embodiments, $L^2$ is independently a bond, —O—, —NH—, —C(O)—, —C(O)NH—, —NHC(O)—, —C(O)O—, —OC(O)—, —NHC(O)NH—, —S—, unsubstituted alkylene (e.g., $C_1$-$C_8$, $C_1$-$C_6$, $C_1$-$C_4$, or $C_1$-$C_2$) or unsubstituted heteroalkylene (e.g., 2 to 8 membered, 2 to 6 membered, 4 to 6 membered, or 2 to 3 membered).

$R^{26}$ is independently oxo, halogen, —CX$^{26}_3$, —CHX$^{26}_2$, —CH$_2$X$^{26}$, —OCX$^{26}_3$, —OCH$_2$X$^{26}$, —OCHX$^{26}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, $R^{27}$-substituted or unsubstituted alkyl (e.g., $C_1$-$C_8$, $C_1$-$C_6$, $C_1$-$C_4$, or $C_1$-$C_2$), $R^{27}$-substituted or unsubstituted heteroalkyl (e.g., 2 to 8 membered, 2 to 6 membered, 4 to 6 membered, or 2 to 3 membered), $R^{27}$-substituted or unsubstituted cycloalkyl (e.g., $C_3$-$C_8$, $C_3$-$C_6$, $C_4$-$C_6$, or $C_5$-$C_6$), $R^{27}$-substituted or unsubstituted heterocycloalkyl (e.g., 3 to 6 membered, 4 to 5 membered, or 5 to 6 membered), $R^{27}$-substituted or unsubstituted aryl $C_6$-$C_{10}$ or phenyl), or $R^{27}$-substituted or unsubstituted heteroaryl (e.g., 5 to 10 membered, 5 to 9 membered, or 5 to 6 membered). $X^{26}$ is independently —F, —Cl, —Br, or —I. In embodiments, $R^{26}$ is independently oxo, halogen, —CX$^{26}_3$, —CHX$^{26}_2$, —CH$_2$X$^{26}$, —OCX$^{26}_3$, —OCH$_2$X$^{26}$, —OCHX$^{26}_2$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{27}$ is independently oxo, halogen, —$CX^{27}_3$, —$CHX^{27}_2$, —$CH_2X^{27}$, —$OCX^{27}_3$, —$OCH_2X^{27}$, —$OCHX^{27}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{28}$-substituted or unsubstituted alkyl (e.g., $C_1$-$C_8$, $C_1$-$C_6$, $C_1$-$C_4$, or $C_1$-$C_2$), $R^{28}$-substituted or unsubstituted heteroalkyl (e.g., 2 to 8 membered, 2 to 6 membered, 4 to 6 membered, or 2 to 3 membered), $R^{28}$-substituted or unsubstituted cycloalkyl (e.g., $C_3$-$C_8$, $C_3$-$C_6$, $C_4$-$C_6$, or $C_5$-$C_6$), $R^{28}$-substituted or unsubstituted heterocycloalkyl (e.g., 3 to 6 membered, 4 to 6 membered, 4 to 5 membered, or 5 to 6 membered), $R^{28}$-substituted or unsubstituted aryl (e.g., $C_6$-$C_{10}$ or phenyl), or $R^{28}$-substituted or unsubstituted heteroaryl (e.g., 5 to 10 membered, 5 to 9 membered, or 5 to 6 membered). $X^{27}$ is independently —F, —Cl, —Br, or —I. In embodiments, $R^{27}$ is independently oxo, halogen, —$CX^{27}_3$, —$CHX^{27}_2$, —$CH_2X^{27}$, —$OCX^{27}_3$, —$OCH_2X^{27}$, —$OCHX^{27}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{28}$ is independently oxo, halogen, —$CX^{28}_3$, —$CHX^{28}_2$, —$CH_2X^{28}$, —$OCX^{28}_3$, —$OCH_2X^{28}$, —$OCHX^{28}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{28}$ is independently —F, —Cl, —Br, or —I.

In embodiments, $L^{41}$ is independently a bond, —O—, —NH—, —C(O)—, —C(O)NH—, —NHC(O)—, —C(O)O—, —OC(O)—, —NHC(O)NH—, —S—, $R^{29}$-substituted or unsubstituted alkylene (e.g., $C_1$-$C_8$, $C_1$-$C_6$, $C_1$-$C_4$, or $C_1$-$C_2$), $R^{29}$-substituted or unsubstituted heteroalkylene (e.g., 2 to 8 membered, 2 to 6 membered, 4 to 6 membered, or 2 to 3 membered), $R^{29}$-substituted or unsubstituted cycloalkylene (e.g., $C_3$-$C_8$, $C_3$-$C_6$, $C_4$-$C_6$, or $C_5$-$C_6$), $R^{29}$-substituted or unsubstituted heterocycloalkylene(e.g., 3 to 6 membered, 4 to 6 membered 4 to 5 membered, or 5 to 6 membered), $R^{29}$-substituted or unsubstituted arylene (e.g., $C_6$-$C_{10}$ or phenyl), or $R^{29}$-substituted or unsubstituted heteroarylene (e.g., 5 to 10 membered, 5 to 9 membered, or 5 to 6 membered). In embodiments, $L^{44}$ is independently a bond, —O—, —NH—, —C(O)—, —C(O)NH—, —NHC(O)—, —C(O)O—, —OC(O)—, —NHC(O)NH—, —S—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, or 2 to 3 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 6 membered, 4 to 6 membered, 4 to 5 membered, or 5 to 6 membered), unsubstituted arylene (e.g., $C_6$-$C_{10}$ or phenyl), or unsubstituted heteroarylene (e.g., 5 to 10 membered, 5 to 9 membered, or 5 to 6 membered).

$R^{29}$ is independently oxo, halogen, —$CX^{29}_3$, —$CHX^{29}_2$, —$CH_2X^{29}$, —$OCX^{29}_3$, —$OCH_2X^{29}$, —$OCHX^{29}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{30}$-substituted or unsubstituted alkyl (e.g., $C_1$-$C_8$, $C_1$-$C_6$, $C_1$-$C_4$, or $C_1$-$C_2$), $R^{30}$-substituted or unsubstituted heteroalkyl (e.g., 2 to 8 membered, 2 to 6 membered, 4 to 6 membered, or 2 to 3 membered), $R^{30}$-substituted or unsubstituted cycloalkyl (e.g., $C_3$-$C_8$, $C_3$-$C_6$, $C_4$-$C_6$, or $C_5$-$C_6$), $R^{30}$-substituted or unsubstituted heterocycloalkyl (e.g., 3 to 6 membered, 4 to 6 membered, 4 to 5 membered, or 5 to 6 membered), $R^{30}$-substituted or unsubstituted aryl (e.g., $C_6$-$C_{10}$ or phenyl), or $R^{30}$-substituted or unsubstituted heteroaryl (e.g., 5 to 10 membered, 5 to 9 membered, or 5 to 6 membered). $X^{29}$ is independently —F, —Cl, —Br, or —I. In embodiments, $R^{29}$ is independently oxo, halogen, —$CX^{29}_3$, —$CHX^{29}_2$, —$CH_2X^{29}$, —$OCX^{29}_3$, —$OCH_2X^{29}$, —$OCHX^{29}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{30}$ is independently oxo, halogen, —$CX^{30}_3$, —$CHX^{30}_2$, —$CH_2X^{30}$, —$OCX^{30}_3$, —$OCH_2X^{30}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{31}$-substituted or unsubstituted alkyl (e.g., $C_1$-$C_8$, $C_1$-$C_6$, $C_1$-$C_4$, or $C_1$-$C_2$), $R^{31}$-substituted or unsubstituted heteroalkyl (e.g., 2 to 8 membered, 2 to 6 membered, 4 to 6 membered, or 2 to 3 membered), $R^{31}$-substituted or unsubstituted cycloalkyl (e.g., $C_3$-$C_8$, $C_3$-$C_6$, $C_4$-$C_6$, or $C_5$-$C_6$), $R^{31}$-substituted or unsubstituted heterocycloalkyl (e.g., 3 to 6 membered, 4 to 6 membered, 4 to 5 membered, or 5 to 6 membered), $R^{31}$-substituted or unsubstituted aryl (e.g., $C_6$-$C_{10}$ or phenyl), or $R^{31}$-substituted or unsubstituted heteroaryl (e.g., 5 to 10 membered, 5 to 9 membered, or 5 to 6 membered). $X^{30}$ is independently —F, —Cl, —Br, or —I. In embodiments, $R^{30}$ is independently oxo, halogen, —$CX^{30}_3$, —$CHX^{30}_2$, —$CH_2X^{30}$, —$OCX^{30}_3$, —$OCH_2X^{30}$, —$OCHX^{30}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{31}$ is independently oxo, halogen, —$CX^{31}_3$, —$CHX^{31}_2$, —$CH_2X^{31}$, —$OCX^{31}_3$, —$OCH_2X^{31}$, —$OCHX^{31}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{31}$ is independently —F, —Cl, —Br, or —I.

In embodiments, $L^{4B}$ is independently a bond, —O—, —NH—, —C(O)—, —C(O)NH—, —NHC(O)—, —C(O)O—, —OC(O)—, —NHC(O)NH—, —S—, $R^{32}$-substituted or unsubstituted alkylene (e.g., $C_1$-$C_8$, $C_1$-$C_6$, $C_1$-$C_4$, or $C_1$-$C_2$), $R^{32}$-substituted or unsubstituted heteroalkylene (e.g., 2 to 8 membered, 2 to 6 membered, 4 to 6 membered, or 2 to 3 membered), e-substituted or unsubstituted cycloalkylene (e.g., $C_3$-$C_8$, $C_3$-$C_6$, $C_4$-$C_6$, or $C_5$-$C_6$), $R^{32}$-substituted or unsubstituted heterocycloalkylene (e.g., 3 to 6 membered, 4 to 6 membered, 4 to 5 membered, or 5 to 6 membered), $R^{32}$-substituted or unsubstituted arylene (e.g., $C_6$-$C_{10}$ or phenyl), or $R^{32}$-substituted or unsubstituted heteroarylene (e.g., 5 to 10 membered, 5 to 9 membered, or 5 to 6 membered). In embodiments, $L^{4B}$ is independently a bond, —O—, —NH—, —C(O)—, —C(O)NH—, —NHC(O)—, —C(O)O—, —OC(O)—, —NHC(O)NH—, —S—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, or 2 to 3 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 6 membered, 4 to 6 membered, 4 to 5 membered, or 5 to 6 membered), unsubstituted arylene (e.g., $C_6$-$C_{10}$ or phenyl), or unsubstituted heteroarylene (e.g., 5 to 10 membered, 5 to 9 membered, or 5 to 6 membered).

$R^{32}$ is independently oxo, halogen, —$CX^{32}_3$, —$CHX^{32}_2$, —$CH_2X^{32}$, —$OCX^{32}_3$, —$OCH_2X^{32}$, —$OCHX^{32}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{33}$-substituted or unsubstituted alkyl (e.g., $C_1$-$C_8$, $C_1$-$C_6$, $C_1$-$C_4$, or $C_1$-$C_2$), $R^{33}$-substituted or unsubstituted heteroalkyl (e.g., 2 to 8 membered, 2 to 6 membered, 4 to 6 membered, or 2 to 3 membered), $R^{33}$-substituted or unsubstituted cycloalkyl (e.g., $C_3$-$C_8$, $C_3$-$C_6$, $C_4$-$C_6$, or $C_5$-$C_6$), $R^{33}$-substituted or unsubstituted heterocycloalkyl (e.g., 3 to 6 membered, 4 to 6 membered, 4 to 5 membered, or 5 to 6 membered), $R^{33}$-substituted or unsubstituted aryl (e.g., $C_6$-$C_{10}$ or phenyl), or $R^{33}$-substituted or unsubstituted heteroaryl (e.g., 5 to 10 membered, 5 to 9 membered, or 5 to 6 membered). $X^{32}$ is independently —F, —Cl, —Br, or —I. In embodiments, $R^{32}$ is independently oxo, halogen, —$CX^{32}_3$, —$CHX^{32}_2$, —$CH_2X^{32}$, —$OCX^{32}_3$, —$OCH_2X^{32}$, —$OCHX^{32}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{34}$-substituted or unsubstituted alkyl (e.g., $C_1$-$C_8$, $C_1$-$C_6$, $C_1$-$C_4$, or $C_1$-$C_2$), $R^{34}$-substituted or unsubstituted heteroalkyl (e.g., 2 to 8 membered, 2 to 6 membered, 4 to 6 membered, or 2 to 3 membered), $R^{34}$-substituted or unsubstituted cycloalkyl (e.g., $C_3$-$C_8$, $C_3$-$C_6$, $C_4$-$C_6$, or $C_5$-$C_6$), $R^{34}$-substituted or unsubstituted heterocycloalkyl (e.g., 3 to 6 membered, 4 to 6 membered, 4 to 5 membered, or 5 to 6 membered), $R^{34}$-substituted or unsubstituted aryl (e.g., $C_6$-$C_{10}$ or phenyl), or $R^{34}$-substituted or unsubstituted heteroaryl (e.g., 5 to 10 membered, 5 to 9 membered, or 5 to 6 membered). $X^{33}$ is independently —F, —Cl, —Br, or —I. In embodiments, $R^{33}$ is independently oxo, halogen, —$CX^{33}_3$, —$CHX^{33}_2$, —$CH_2X^{33}$, —$OCX^{33}_3$, —$OCH_2X^{33}$, —$OCHX^{33}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{34}$ is independently oxo, halogen, —$CX^{34}_3$, —$CHX^{34}_2$, —$CH_2X^{34}$, —$OCX^{34}_3$, —$OCH_2X^{34}$, —$OCHX^{34}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{34}$ is independently —F, —Cl, —Br, or —I.

In embodiments, $L^{4C}$ is independently a bond, —O—, —NH—, —C(O)—, —C(O)NH—, —NHC(O)—, —C(O)O—, —OC(O)—, —NHC(O)NH—, —S—, $R^{35}$-substituted or unsubstituted alkylene (e.g., $C_1$-$C_8$, $C_1$-$C_6$, $C_1$-$C_4$, or $C_1$-$C_2$), $R^{35}$-substituted or unsubstituted heteroalkylene (e.g., 2 to 8 membered, 2 to 6 membered, 4 to 6 membered, or 2 to 3 membered), $R^{35}$-substituted or unsubstituted cycloalkylene (e.g., $C_3$-$C_8$, $C_3$-$C_6$, $C_4$-$C_6$, or $C_5$-$C_6$), $R^{35}$-substituted or unsubstituted heterocycloalkylene (e.g., 3 to 6 membered, 4 to 6 membered, 4 to 5 membered, or 5 to 6 membered), $R^{35}$-substituted or unsubstituted arylene (e.g., $C_6$-$C_{10}$ or phenyl), or $R^{35}$-substituted or unsubstituted heteroarylene (e.g., 5 to 10 membered, 5 to 9 membered, or 5 to 6 membered). In embodiments, $L^{4C}$ is independently a bond, —O—, —NH—, —C(O)—, —C(O)NH—, —NHC (O)—, —C(O)O—, —OC(O)—, —NHC(O)NH—, —S—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, or 2 to 3 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 6 membered, 4 to 6 membered, 4 to 5 membered, or 5 to 6 membered), unsubstituted arylene (e.g., $C_6$-$C_{10}$ or phenyl), or unsubstituted heteroarylene (e.g., 5 to 10 membered, 5 to 9 membered, or 5 to 6 membered).

$R^{35}$ is independently oxo, halogen, —$CX^{35}_3$, —$CHX^{35}_2$, —$CH_2X^{35}$, —$OCX^{35}_3$, —$OCH_2X^{35}$, —$OCHX^{35}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{36}$-substituted or unsubstituted alkyl (e.g., $C_1$-$C_8$, $C_1$-$C_6$, $C_1$-$C_4$, or $C_1$-$C_2$), $R^{36}$-substituted or unsubstituted heteroalkyl (e.g., 2 to 8 membered, 2 to 6 membered, 4 to 6 membered, or 2 to 3 membered), $R^{36}$-substituted or unsubstituted cycloalkyl (e.g., $C_3$-$C_8$, $C_3$-$C_6$, $C_4$-$C_6$, or $C_5$-$C_6$), $R^{36}$-substituted or unsubstituted heterocycloalkyl (e.g., 3 to 6 membered, 4 to 6 membered, 4 to 5 membered, or 5 to 6 membered), $R^{36}$-substituted or unsubstituted aryl (e.g., $C_6$-$C_{10}$ or phenyl), or $R^{36}$-substituted or unsubstituted heteroaryl (e.g., 5 to 10 membered, 5 to 9 membered, or 5 to 6 membered). $X^{35}$ is independently —F, —Cl, —Br, or —I. In embodiments, $R^{35}$ is independently oxo, halogen, —$CX^{35}_3$, —$CHX^{35}_2$, —$CH_2X^{35}$, —$OCX^{35}_3$, —$OCH_2X^{35}$, —$OCHX^{35}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{36}$ is independently oxo, halogen, —$CX^{36}_3$, —$CHX^{36}_2$, —$CH_2X^{36}$, —$OCX^{36}_3$, —$OCH_2X^{36}$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{37}$-substituted or unsubstituted alkyl (e.g., $C_1$-$C_8$, $C_1$-$C_6$, $C_1$-$C_4$, or $C_1$-$C_2$), $R^{37}$-substituted or unsubstituted heteroalkyl (e.g., 2 to 8 membered, 2 to 6 membered, 4 to 6 membered, or 2 to 3 membered), $R^{37}$-substituted or unsubstituted cycloalkyl (e.g., $C_3$-$C_8$, $C_3$-$C_6$, $C_4$-$C_6$, or $C_5$-$C_6$), $R^{37}$-substituted or unsubstituted heterocycloalkyl (e.g., 3 to 6 membered, 4 to 6 membered, 4 to 5 membered, or 5 to 6 membered), $R^{37}$-substituted or unsubstituted aryl (e.g., $C_6$-$C_{10}$ or phenyl), or $R^{37}$-substituted or unsubstituted heteroaryl (e.g., 5 to 10 membered, 5 to 9 membered, or 5 to 6 membered). $X^{36}$ is independently —F, —Cl, —Br, or —I. In embodiments, $R^{36}$ is independently oxo, halogen, —$CX^{36}_3$, —$CHX^{36}_2$, —$CH_2X^{36}$, —$OCX^{36}_3$, —$OCH_2X^{36}$, —$OCHX^{36}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{37}$ is independently oxo, halogen, —$CX^{37}_3$, —$CHX^{37}_2$, —$CH_2X^{37}$, —$OCX^{37}_3$, —$OCH_2X^{37}$, —$OCHX^{37}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{37}$ is independently —F, —Cl, —Br, or —I.

In embodiments, $L^{54}$ is independently a bond, —O—, —NH—, —C(O)—, —C(O)NH—, —NHC(O)—, —C(O)O—, —OC(O)—, —NHC(O)NH—, —S—, $R^{38}$-substituted or unsubstituted alkylene (e.g., $C_1$-$C_8$, $C_1$-$C_6$, $C_1$-$C_4$, or $C_1$-$C_2$), $R^{38}$-substituted or unsubstituted heteroalkylene (e.g., 2 to 8 membered, 2 to 6 membered, 4 to 6 membered, or 2 to 3 membered), $R^{38}$-substituted or unsubstituted cycloalkylene (e.g., $C_3$-$C_8$, $C_3$-$C_6$, $C_4$-$C_6$, or $C_5$-$C_6$), $R^{38}$-substituted or unsubstituted heterocycloalkylene (e.g., 3 to 6 membered, 4 to 6 membered, 4 to 5 membered, or 5 to 6 membered), $R^{38}$-substituted or unsubstituted arylene (e.g., $C_6$-$C_{10}$ or phenyl), or $R^{38}$-substituted or unsubstituted heteroarylene (e.g., 5 to 10 membered, 5 to 9 membered, or 5 to 6 membered). In embodiments, $L^{54}$ is independently a bond, —O—, —NH—, —C(O)—, —C(O)NH—, —NHC(O)—, —C(O)O—, —OC(O)—, —NHC(O)NH—, —S—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, or 2 to 3 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 6 membered, 4 to 6 membered, 4 to 5 membered, or 5 to 6 membered), unsubstituted arylene (e.g., $C_6$-$C_{10}$ or phenyl), or unsubstituted heteroarylene (e.g., 5 to 10 membered, 5 to 9 membered, or 5 to 6 membered).

$R^{38}$ is independently oxo, halogen, —$CX^{38}_3$, —$CHX^{38}_2$, —$CH_2X^{38}$, —$OCX^{38}_3$, —$OCH_2X^{38}$, —$OCHX^{38}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{39}$-substituted or unsubstituted alkyl (e.g., $C_1$-$C_8$, $C_1$-$C_6$, $C_1$-$C_4$, or $C_1$-$C_2$), $R^{39}$-substituted or unsubstituted heteroalkyl (e.g., 2 to 8 membered, 2 to 6 membered, 4 to 6 membered, or 2 to 3 membered), $R^{39}$-substituted or unsubstituted cycloalkyl (e.g., $C_3$-$C_8$, $C_3$-$C_6$, $C_4$-$C_6$, or $C_5$-$C_6$), $R^{39}$-substituted or unsubstituted heterocycloalkyl (e.g., 3 to 6 membered, 4 to 6 membered, 4 to 5 membered, or 5 to 6 membered), $R^{39}$-substituted or unsubstituted aryl (e.g., $C_6$-$C_{10}$ or phenyl), or $R^{39}$-substituted or unsubstituted heteroaryl (e.g., 5 to 10 membered, 5 to 9 membered, or 5 to 6 membered). $X^{38}$ is independently —F, —Cl, —Br, or —I. In embodiments, $R^{38}$ is independently oxo, halogen, —$CX^{38}_3$, —$CHX^{38}_2$, —$CH_2X^{38}$, —$OCX^{38}_3$, —$OCH_2X^{38}$, —$OCHX^{38}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{39}$ is independently oxo, halogen, —$CX^{39}_3$, —$CHX^{39}_2$, —$CH_2X^{39}$, —$OCX^{39}_3$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{40}$-substituted or unsubstituted alkyl (e.g., $C_1$-$C_8$, $C_1$-$C_6$, $C_1$-$C_4$, or $C_1$-$C_2$), $R^{40}$-substituted or unsubstituted heteroalkyl (e.g., 2 to 8 membered, 2 to 6 membered, 4 to 6 membered, or 2 to 3 membered), $R^{40}$-substituted or unsubstituted cycloalkyl (e.g., $C_3$-$C_8$, $C_3$-$C_6$, $C_4$-$C_6$, or $C_5$-$C_6$), $R^{40}$-substituted or unsubstituted heterocycloalkyl (e.g., 3 to 6 membered, 4 to 6 membered, 4 to 5 membered, or 5 to 6 membered), $R^{40}$-substituted or unsubstituted aryl (e.g., $C_6$-$C_{10}$ or phenyl), or $R^{40}$-substituted or unsubstituted heteroaryl (e.g., 5 to 10 membered, 5 to 9 membered, or 5 to 6 membered). $X^{39}$ is independently —F, —Cl, —Br, or —I. In embodiments, $R^{39}$ is independently oxo, halogen, —$CX^{39}_3$, —$CHX^{39}_2$, —$CH_2X^{39}$, —$OCX^{39}_3$, —$OCH_2X^{39}$, —$OCHX^{39}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{40}$ is independently oxo, halogen, —$CX^{40}_3$, —$CHX^{40}_2$, —$CH_2X^{40}$, —$OCX^{40}_3$, —$OCH_2X^{40}$, —$OCHX^{40}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{40}$ is independently —F, —Cl, —Br, or —I.

In embodiments, $L^{5B}$ is independently a bond, —O—, —NH—, —C(O)—, —C(O)NH—, —NHC(O)—, —C(O)O—, —OC(O)—, —NHC(O)NH—, —S—, $R^{41}$-substituted or unsubstituted alkylene (e.g., $C_1$-$C_8$, $C_1$-$C_6$, $C_1$-$C_4$, or $C_1$-$C_2$), $R^{41}$-substituted or unsubstituted heteroalkylene (e.g., 2 to 8 membered, 2 to 6 membered, 4 to 6 membered, or 2 to 3 membered), $R^{41}$-substituted or unsubstituted cycloalkylene (e.g., $C_3$-$C_8$, $C_3$-$C_6$, $C_4$-$C_6$, or $C_5$-$C_6$), $R^{41}$-substituted or unsubstituted heterocycloalkylene(e.g., 3 to 6 membered, 4 to 6 membered 4 to 5 membered, or 5 to 6 membered), $R^{41}$-substituted or unsubstituted arylene (e.g., $C_6$-$C_{10}$ or phenyl), or $R^{41}$-substituted or unsubstituted heteroarylene (e.g., 5 to 10 membered, 5 to 9 membered, or 5 to 6 membered). In embodiments, $L^{5B}$ is independently a bond, —O—, —NH—, —C(O)—, —C(O)NH—, —NHC(O)—, —C(O)O—, —OC(O)—, —NHC(O)NH—, —S—, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, or 2 to 3 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 6 membered, 4 to 6 membered, 4 to 5 membered, or 5 to 6 membered), unsubstituted arylene (e.g., $C_6$-$C_{10}$ or phenyl), or unsubstituted heteroarylene (e.g., 5 to 10 membered, 5 to 9 membered, or 5 to 6 membered).

$R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{42}$-substituted or unsubstituted alkyl (e.g., $C_1$-$C_8$, $C_1$-$C_6$, $C_1$-$C_4$, or $C_1$-$C_2$), $R^{42}$-substituted or unsubstituted heteroalkyl (e.g., 2 to 8 membered, 2 to 6 membered, 4 to 6 membered, or 2 to 3 membered), $R^{42}$-substituted or unsubstituted cycloalkyl (e.g., $C_3$-$C_8$, $C_3$-$C_6$, $C_4$-$C_6$, or $C_5$-$C_6$), $R^{42}$-substituted or unsubstituted heterocycloalkyl (e.g., 3 to 6 membered, 4 to 6 membered, 4 to 5 membered, or 5 to 6 membered), $R^{42}$-substituted or unsubstituted aryl (e.g., $C_6$-$C_{10}$ or phenyl), or $R^{42}$-substituted or unsubstituted heteroaryl (e.g., 5 to 10 membered, 5 to 9 membered, or 5 to 6 membered). $X^{41}$ is independently —F, —Cl, —Br, or —I. In embodiments, $R^{41}$ is independently oxo, halogen, —$CX^{41}_3$, —$CHX^{41}_2$, —$CH_2X^{41}$, —$OCX^{41}_3$, —$OCH_2X^{41}$, —$OCHX^{41}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{42}$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, $R^{43}$-substituted or unsubstituted alkyl (e.g., $C_1$-$C_8$, $C_1$-$C_6$, $C_1$-$C_4$, or $C_1$-$C_2$), $R^{43}$-substituted or unsubstituted heteroalkyl (e.g., 2 to 8 membered, 2 to 6 membered, 4 to 6 membered, or 2 to 3 membered), $R^{43}$-substituted or unsubstituted cycloalkyl (e.g., $C_3$-$C_8$, $C_3$-$C_6$, $C_4$-$C_6$, or $C_5$-$C_6$), $R^{43}$-substituted or unsubstituted heterocycloalkyl (e.g., 3 to 6 membered, 4 to 6 membered, 4 to 5 membered, or 5 to 6 membered), $R^{43}$-substituted or unsubstituted aryl (e.g., $C_6$-$C_{10}$ or phenyl), or $R^{43}$-substituted or unsubstituted heteroaryl (e.g., 5 to 10 membered, 5 to 9 membered, or 5 to 6 membered). $X^{42}$ is independently —F, —Cl, —Br, or —I. In embodiments, $R^{42}$ is independently oxo, halogen, —$CX^{42}_3$, —$CHX^{42}_2$, —$CH_2X^{42}$, —$OCX^{42}_3$, —$OCH_2X^{42}$, —$OCHX^{42}_2$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{43}$ is independently oxo, halogen, $-CX^{43}_3$, $-CHX^{43}_2$, $-CH_2X^{43}$, $-OCX^{43}_3$, $-OCH_2X^{43}$, $-OCHX^{43}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{43}$ is independently $-F$, $-Cl$, $-Br$, or $-I$.

In embodiments, $L^{5C}$ is independently a bond, $-O-$, $-NH-$, $-C(O)-$, $-C(O)NH-$, $-NHC(O)-$, $-C(O)O-$, $-OC(O)-$, $-NHC(O)NH-$, $-S-$, $R^{44}$-substituted or unsubstituted alkylene (e.g., $C_1$-$C_8$, $C_1$-$C_6$, $C_1$-$C_4$, or $C_1$-$C_2$), $R^{44}$-substituted or unsubstituted heteroalkylene (e.g., 2 to 8 membered, 2 to 6 membered, 4 to 6 membered, or 2 to 3 membered), $R^{44}$-substituted or unsubstituted cycloalkylene (e.g., $C_3$-$C_8$, $C_3$-$C_6$, $C_4$-$C_6$, or $C_5$-$C_6$), $R^{44}$-substituted or unsubstituted heterocycloalkylene (e.g., 3 to 6 membered, 4 to 6 membered, 4 to 5 membered, or 5 to 6 membered), $R^{44}$-substituted or unsubstituted arylene (e.g., $C_6$-$C_{10}$ or phenyl), or $R^{44}$-substituted or unsubstituted heteroarylene (e.g., 5 to 10 membered, 5 to 9 membered, or 5 to 6 membered). In embodiments, $L^{5C}$ is independently a bond, $-O-$, $-NH-$, $-C(O)-$, $-C(O)NH-$, $-NHC(O)-$, $-C(O)O-$, $-OC(O)-$, $-NHC(O)NH-$, $-S-$, unsubstituted alkylene (e.g., $C_1$-$C_8$, $C_1$-$C_6$, $C_1$-$C_4$, or $C_1$-$C_2$), unsubstituted heteroalkylene (e.g., 2 to 8 membered, 2 to 6 membered, 4 to 6 membered, or 2 to 3 membered), unsubstituted cycloalkylene (e.g., $C_3$-$C_8$, $C_3$-$C_6$, $C_4$-$C_6$, or $C_5$-$C_6$), unsubstituted heterocycloalkylene (e.g., 3 to 6 membered, 4 to 6 membered, 4 to 5 membered, or 5 to 6 membered), unsubstituted arylene (e.g., $C_6$-$C_{10}$ or phenyl), or unsubstituted heteroarylene (e.g., 5 to 10 membered, 5 to 9 membered, or 5 to 6 membered).

$R^{44}$ is independently oxo, halogen, $-CX^{44}_3$, $-CHX^{44}_2$, $-CH_2X^{44}$, $-OCX^{44}_3$, $-OCH_2X^{44}$, $-OCHX^{44}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{45}$-substituted or unsubstituted alkyl (e.g., $C_1$-$C_8$, $C_1$-$C_6$, $C_1$-$C_4$, or $C_1$-$C_2$), $R^{45}$-substituted or unsubstituted heteroalkyl (e.g., 2 to 8 membered, 2 to 6 membered, 4 to 6 membered, or 2 to 3 membered), $R^{45}$-substituted or unsubstituted cycloalkyl (e.g., $C_3$-$C_8$, $C_3$-$C_6$, $C_4$-$C_6$, or $C_5$-$C_6$), $R^{45}$-substituted or unsubstituted heterocycloalkyl (e.g., 3 to 6 membered, 4 to 6 membered, 4 to 5 membered, or 5 to 6 membered), $R^{45}$-substituted or unsubstituted aryl (e.g., $C_6$-$C_{10}$ or phenyl), or $R^{45}$-substituted or unsubstituted heteroaryl (e.g., 5 to 10 membered, 5 to 9 membered, or 5 to 6 membered). $X^{44}$ is independently $-F$, $-Cl$, $-Br$, or $-I$. In embodiments, $R^{44}$ is independently oxo, halogen, $-CX^{44}_3$, $-CHX^{44}_2$, $-CH_2X^{44}$, $-OCX^{44}_3$, $-OCH_2X^{44}$, $-OCHX^{44}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{45}$ is independently oxo, halogen, $-CX^{45}_3$, $-CHX^{45}_2$, $-CH_2X^{45}$, $-OCX^{45}_3$, $-OCH_2X^{45}$, $-OCHX^{45}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $R^{46}$-substituted or unsubstituted alkyl (e.g., $C_1$-$C_8$, $C_1$-$C_6$, $C_1$-$C_4$, or $C_1$-$C_2$), $R^{46}$-substituted or unsubstituted heteroalkyl (e.g., 2 to 8 membered, 2 to 6 membered, 4 to 6 membered, or 2 to 3 membered), $R^{46}$-substituted or unsubstituted cycloalkyl (e.g., $C_3$-$C_8$, $C_3$-$C_6$, $C_4$-$C_6$, or $C_5$-$C_6$), $R^{46}$-substituted or unsubstituted heterocycloalkyl (e.g., 3 to 6 membered, 4 to 6 membered, 4 to 5 membered, or 5 to 6 membered), $R^{46}$-substituted or unsubstituted aryl (e.g., $C_6$-$C_{10}$ or phenyl), or $R^{46}$-substituted or unsubstituted heteroaryl (e.g., 5 to 10 membered, 5 to 9 membered, or 5 to 6 membered). $X^{45}$ is independently $-F$, $-Cl$, $-Br$, or $-I$. In embodiments, $R^{45}$ is independently oxo, halogen, $-CX^{45}_3$, $-CHX^{45}_2$, $-CH_2X^{45}$, $-OCX^{45}_3$, $-OCH_2X^{45}$, $-OCHX^{45}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered).

$R^{46}$ is independently oxo, halogen, $-CX^{46}_3$, $-CHX^{46}_2$, $-CH_2X^{46}$, $-OCX^{46}_3$, $-OCH_2X^{46}$, $-OCHX^{46}_2$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, unsubstituted alkyl (e.g., $C_1$-$C_8$, $C_1$-$C_6$, $C_1$-$C_4$, or $C_1$-$C_2$), unsubstituted heteroalkyl (e.g., 2 to 8 membered, 2 to 6 membered, 4 to 6 membered, or 2 to 3 membered), unsubstituted cycloalkyl (e.g., $C_3$-$C_8$, $C_3$-$C_6$, $C_4$-$C_6$, or $C_5$-$C_6$), unsubstituted heterocycloalkyl (e.g., 3 to 6 membered, 4 to 6 membered, 4 to 5 membered, or 5 to 6 membered), unsubstituted aryl (e.g., $C_6$-$C_{10}$ or phenyl), or unsubstituted heteroaryl (e.g., 5 to 10 membered, 5 to 9 membered, or 5 to 6 membered). $X^{46}$ is independently $-F$, $-Cl$, $-Br$, or $-I$.

In embodiments, a compound is:
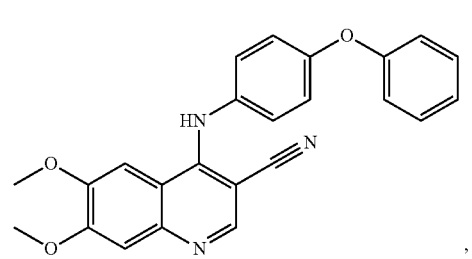
179D
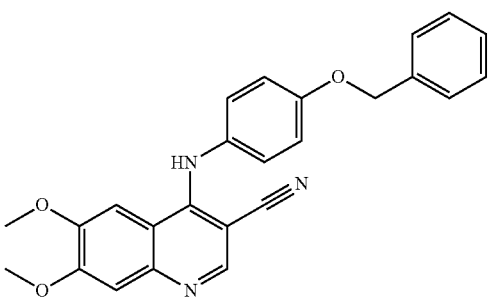
183
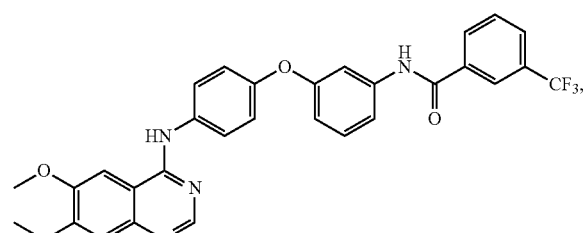
74A
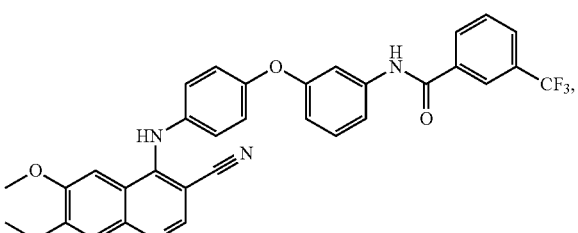
74B
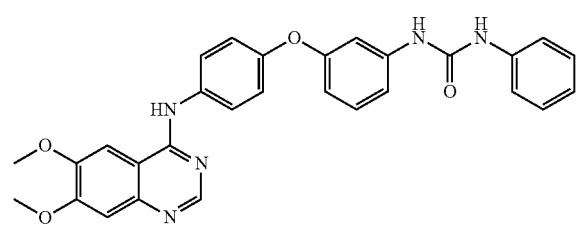
75A
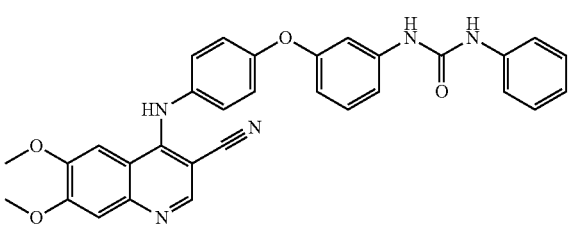
75B
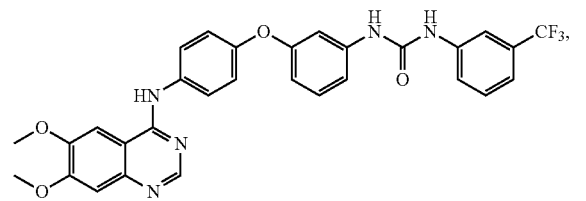
73
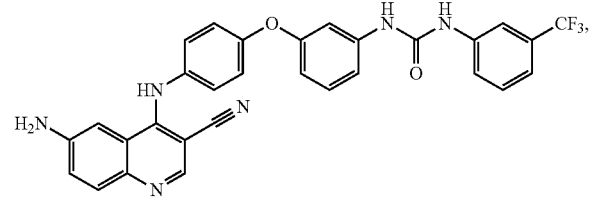
15/191
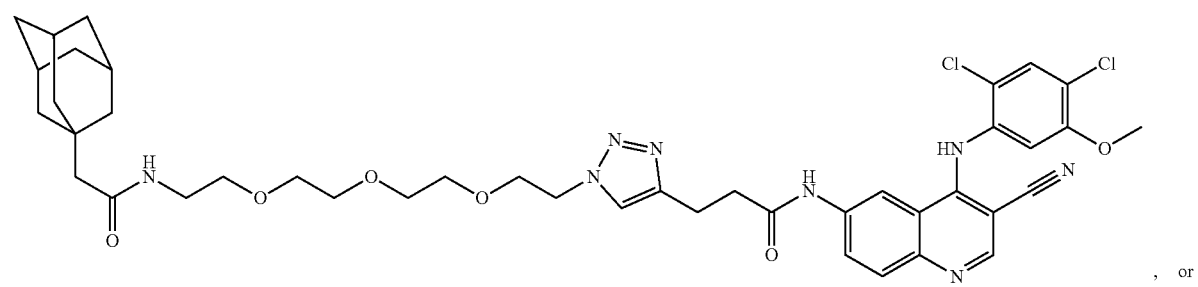
(87)
, or -continued
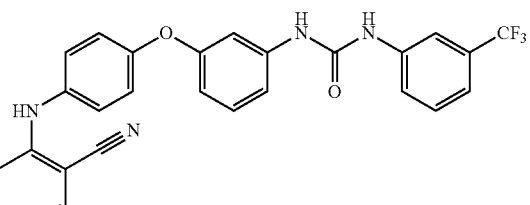
(8003).
In embodiments the compound is
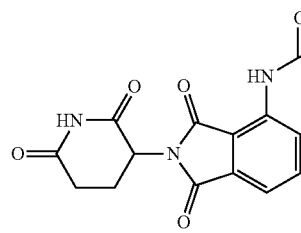
In embodiments, the compound is
(179D)
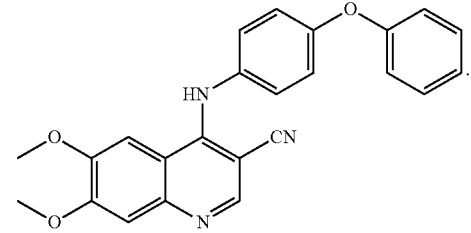
In embodiments, the compound is
(183)
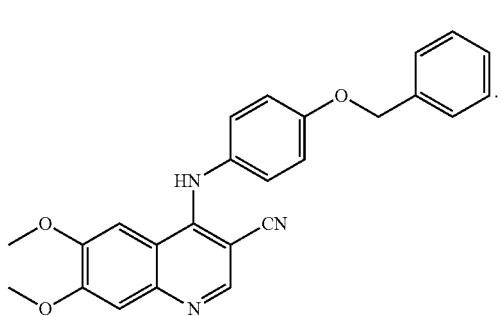
In embodiments, the compound is
(74B)
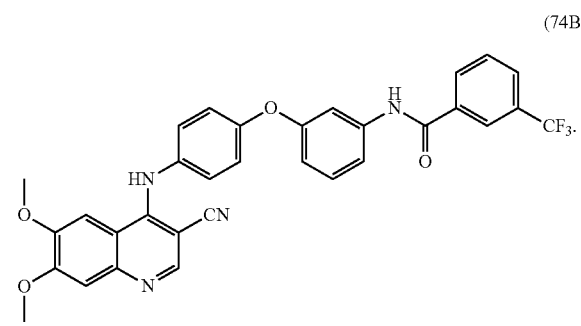 [SMILES: COc1cc2ncnc(Nc3ccc(Oc4cccc(NC(=O)c5cccc(C(F)(F)F)c5)c4)cc3)c2cc1OC]
In embodiments, the compound is
(74A)
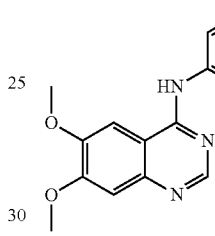
In embodiments, the compound is
(75A)
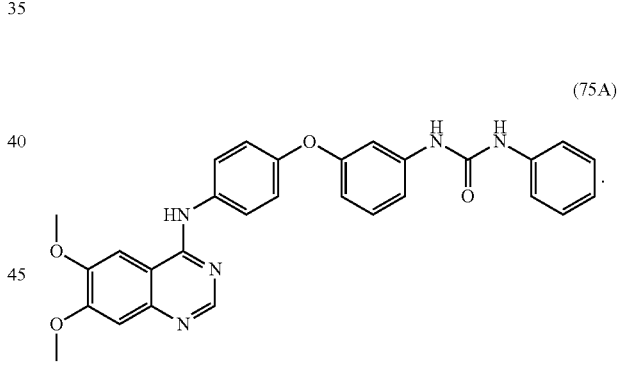
In embodiments, the compound is
(73)
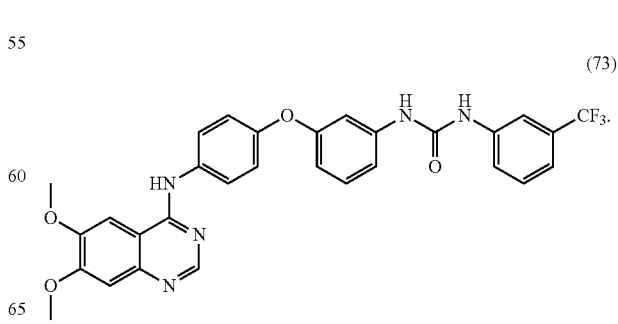

In embodiments, the compound is
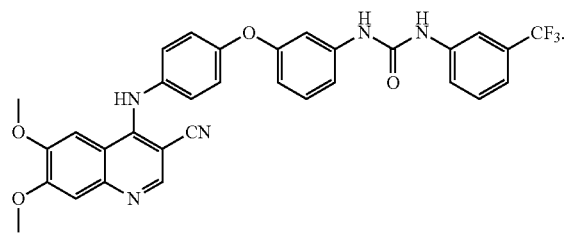
(50A)
In embodiments, the compound is
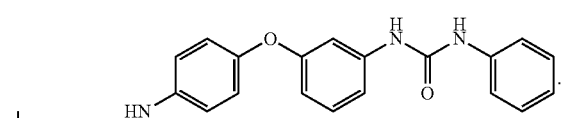
(75B)
In embodiments, the compound is
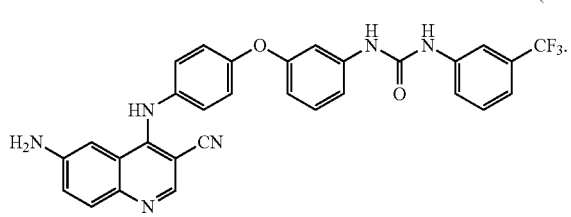
(191)
In embodiments, the compound is
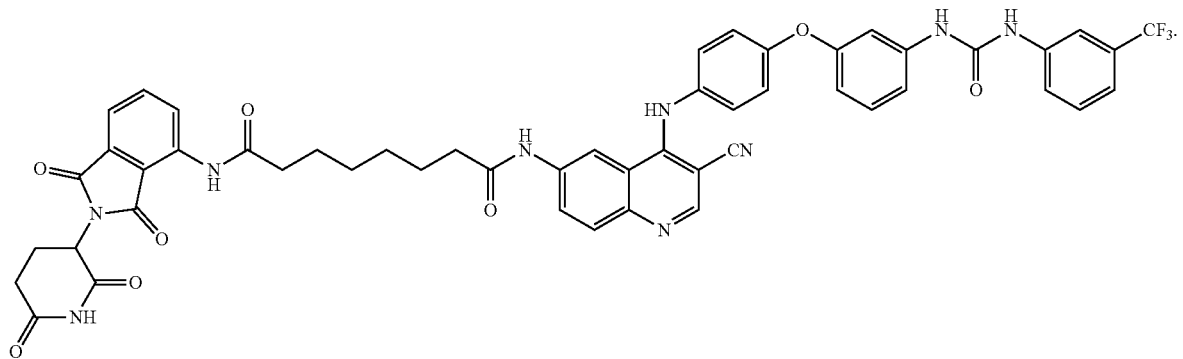
(8003)
In embodiments, the compound is
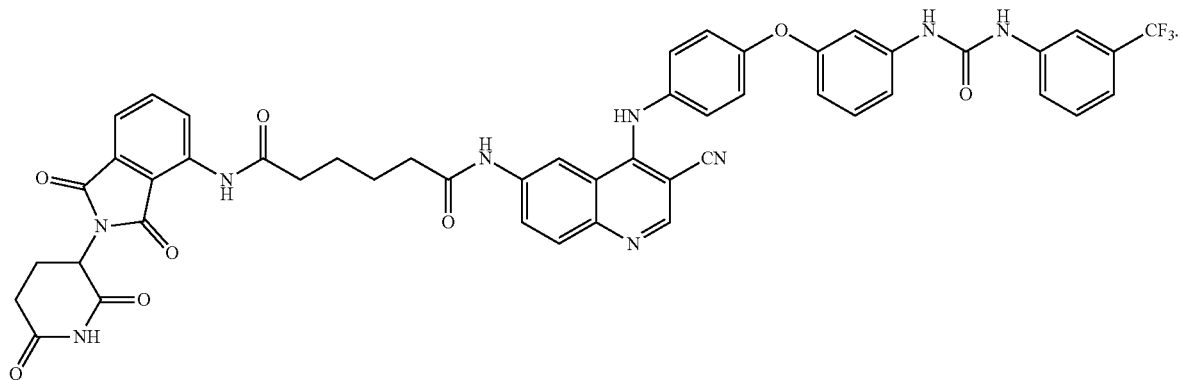
(8003*)

In embodiments, the compound is (87)

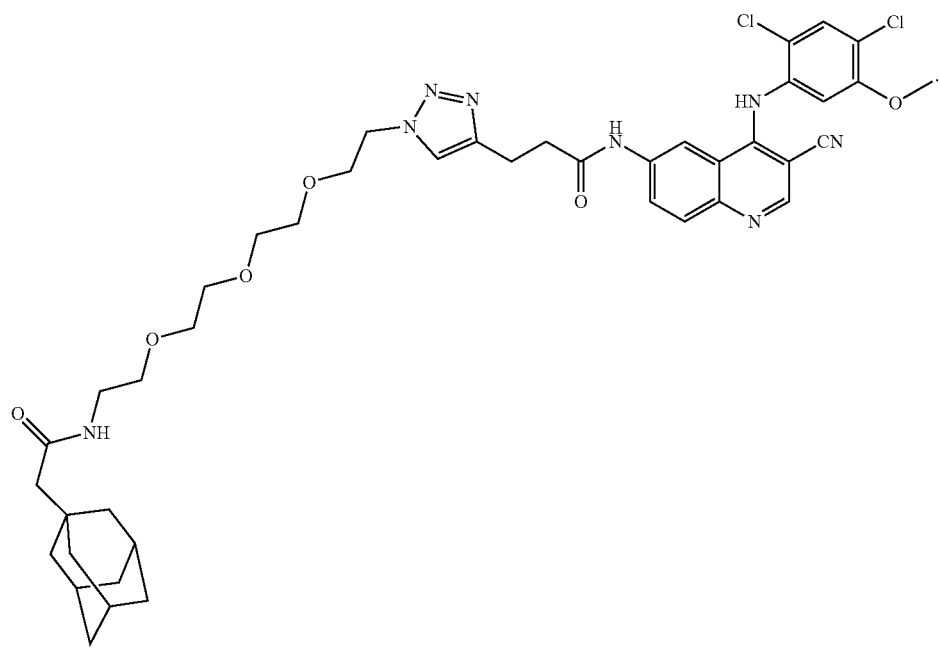

In embodiments, a compound is a compound described herein, including in an aspect, embodiment, table, figure, example, scheme, or claim. In embodiments, the compound is not bosutinib. In embodiments, the compound is not TAK-185. In embodiments, the compound is not CP-724,714. In embodiments, the compound is not lapatinib. In embodiments, the compound is not neratinib.

In embodiments, a compound described herein, including a degradation-increasing moiety (e.g., $R^4$ or $R^5$) increases the degradation of a protein in contact with (e.g., bound to) the compound. In embodiments, the protein contacting the compound is HER protein. In embodiments, the protein contacting the compound is EGFR. In embodiments, the protein contacting the compound is HER2. In embodiments, the protein contacting the compound is HER3. In embodiments, the protein contacting the compound is HER4. In embodiments, a compound described herein, including a degradation-increasing moiety (e.g., $R^4$ or $R^5$) increases the degradation of a complex including a protein in contact with (e.g., bound to) the compound (e.g., EGFR, HER2, HER3, or HER4). In embodiments, the complex includes a second protein selected from EGFR, HER2, HER3, or HER4.

In embodiments, the compound is not

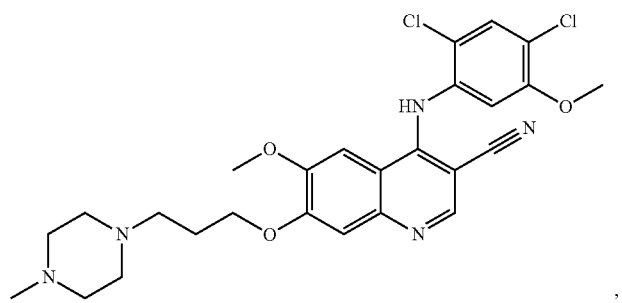

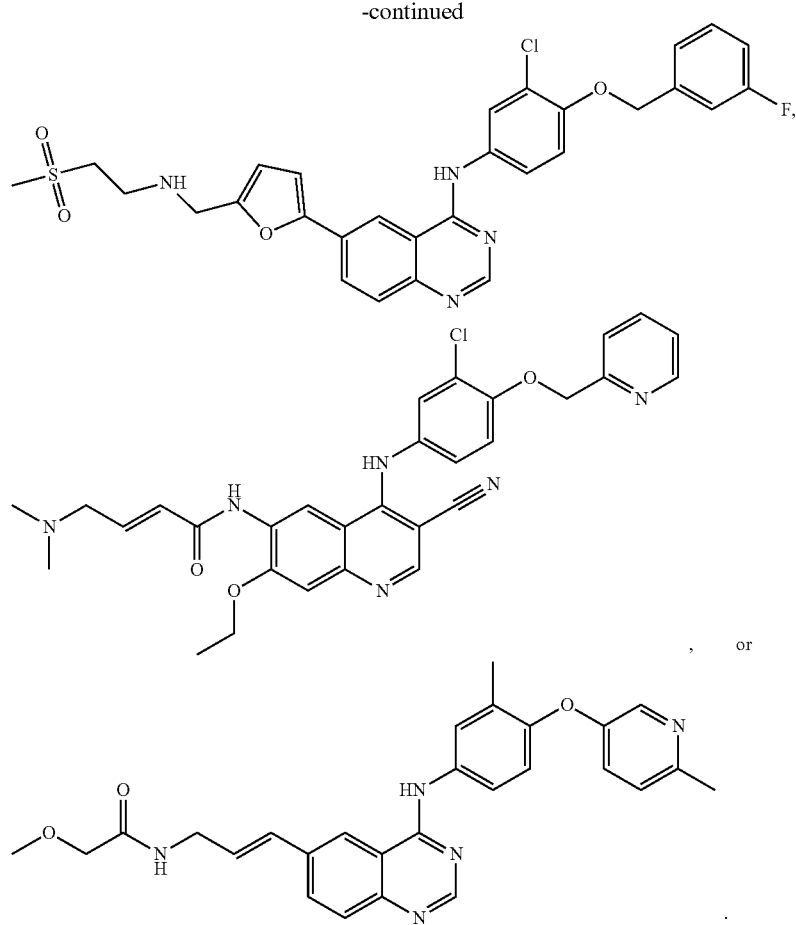
In embodiments, -L⁴-R⁴ is not
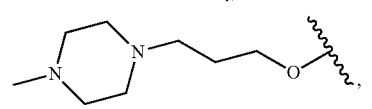,
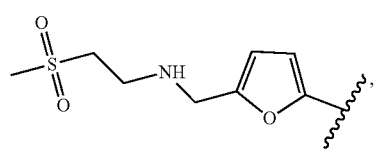
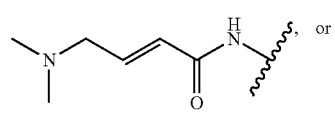, or
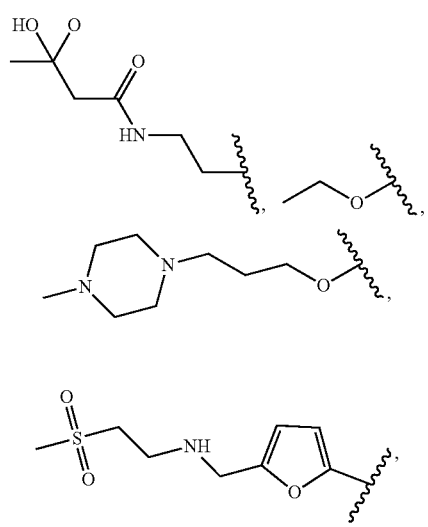
In embodiments, -L⁴-R⁴ is not
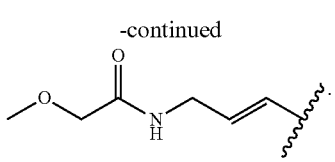.
In embodiments, -L⁴-R⁴ is not
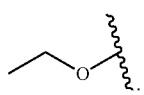.

In embodiments, -L⁴-R⁴ is not

In embodiments, -L⁴-R⁴ is not

In embodiments, -L⁴-R⁴ is not

In embodiments, -L⁴-R⁴ is not

In embodiments, -L⁴-R⁴ is not substituted or unsubstituted 5 to 10 membered heteroalkyl. In embodiments, -L⁴-R⁴ is not substituted or unsubstituted 6 to 10 membered heteroalkyl. In embodiments, -L⁴-R⁴ is not substituted or unsubstituted 7 to 10 membered heteroalkyl. In embodiments, -L⁴-R⁴ is not substituted or unsubstituted 7 to 9 membered heteroalkyl. In embodiments, -L⁴-R⁴ is not substituted or unsubstituted 5 membered heteroaryl. In embodiments, -L⁴-R⁴ is not substituted or unsubstituted 5 to 6 membered heteroaryl. In embodiments, -L⁴-R⁴ is not substituted or unsubstituted 4 to 6 membered heteroaryl. In embodiments, -L⁴-R⁴ is not substituted or unsubstituted heteroaryl. In embodiments, -L⁴-R⁴ is not substituted 5 membered heteroaryl. In embodiments, -L⁴-R⁴ is not substituted 5 to 6 membered heteroaryl. In embodiments, -L⁴-R⁴ is not substituted 4 to 6 membered heteroaryl. In embodiments, -L⁴-R⁴ is not substituted heteroaryl. In embodiments, -L⁴-R⁴ is not unsubstituted 5 membered heteroaryl. In embodiments, -L⁴-R⁴ is not unsubstituted 5 to 6 membered heteroaryl. In embodiments, -L⁴-R⁴ is not unsubstituted heteroaryl. In embodiments, -L⁴-R⁴ is not unsubstituted 4 to 6 membered heteroaryl.

In embodiments, -L⁵-R⁵ is not

In embodiments, -L⁵-R⁵ is not substituted or unsubstituted 5 to 10 membered heteroalkyl. In embodiments, -L⁵-R⁵ is not substituted or unsubstituted 6 to 10 membered heteroalkyl. In embodiments, -L⁵-R⁵ is not substituted or unsubstituted 7 to 10 membered heteroalkyl. In embodiments, -L⁵-R⁵ is not substituted or unsubstituted 7 to 9 membered heteroalkyl. In embodiments, -L⁵-R⁵ is not substituted or unsubstituted 5 membered heteroaryl. In embodiments, -L⁵-R⁵ is not substituted or unsubstituted 5 to 6 membered heteroaryl. In embodiments, -L⁵-R⁵ is not substituted or unsubstituted 4 to 6 membered heteroaryl. In embodiments, -L⁵-R⁵ is not substituted or unsubstituted heteroaryl. In embodiments, -L⁵-R⁵ is not substituted 5 membered heteroaryl. In embodiments, -L⁵-R⁵ is not substituted 5 to 6 membered heteroaryl. In embodiments, -L⁵-R⁵ is not substituted 4 to 6 membered heteroaryl. In embodiments, -L⁵-R⁵ is not substituted heteroaryl. In embodiments, -L⁵-R⁵ is not unsubstituted 5 membered heteroaryl. In embodiments, -L⁵-R⁵ is not unsubstituted 5 to 6 membered heteroaryl. In embodiments, -L⁵-R⁵ is not unsubstituted heteroaryl. In embodiments, -L⁵-R⁵ is not unsubstituted 4 to 6 membered heteroaryl.

In embodiments, -L⁵-R⁵ is not

In embodiments, -L⁵-R⁵ is not

In embodiments, -L$^5$-R$^5$ is not

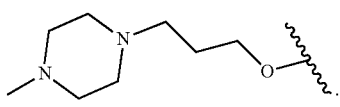 [SMILES: *OCCCN1CCN(C)CC1]

In embodiments, -L$^5$-R$^5$ is not

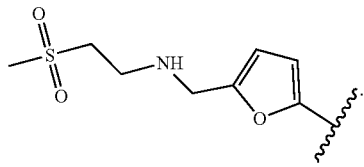 [SMILES: *c1ccc(CNCCS(C)(=O)=O)o1]

In embodiments, -L$^5$-R$^5$ is not

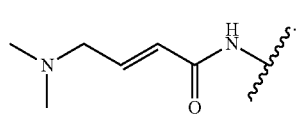 [SMILES: *NC(=O)/C=C/CN(C)C]

In embodiments, -L$^5$-R$^5$ is not

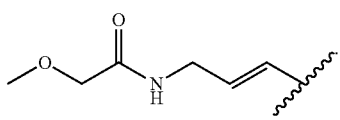 [SMILES: */C=C/CNC(=O)COC]

In embodiments,

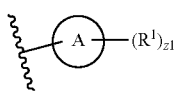

is not

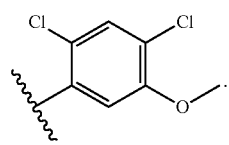 [SMILES: *c1cc(OC)c(Cl)cc1Cl]

in embodiments,

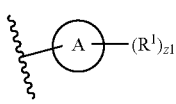

is not

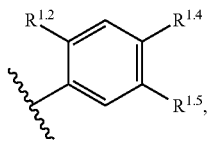

wherein R$^{1.2}$ and R$^{1.4}$ are halogen, and R$^{1.5}$ is unsubstituted methoxy. In embodiments, z1 is 0. In embodiments, Ring A is not aryl when z1 is non-zero. In embodiments, Ring A is not a heteroaryl when z1 is non-zero. In embodiments, Ring A is not a aryl (e.g., C$_6$-C$_{10}$ or phenyl) or 5 to 6 membered heteroaryl when z1 is non-zero. In embodiments, Ring A is not aryl (e.g., C$_6$-C$_{10}$ or phenyl) when z1 is non-zero. In embodiments, Ring A is not 5 to 6 membered heteroaryl when z1 is non-zero.

In embodiments,

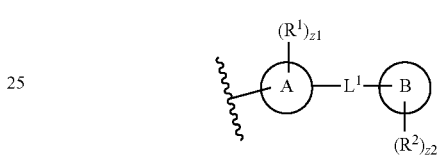

is not

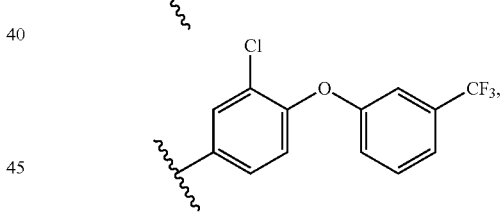

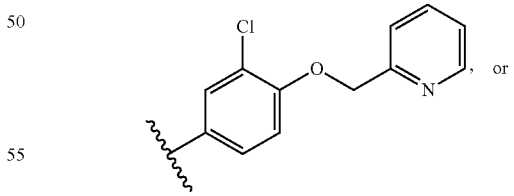

, or

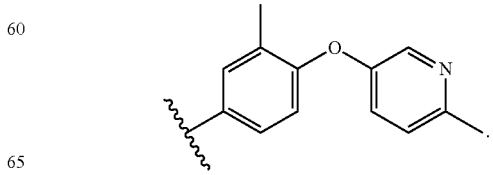

In embodiments,
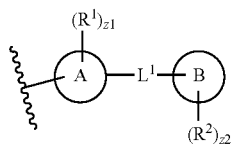
is not
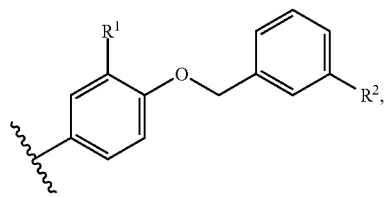
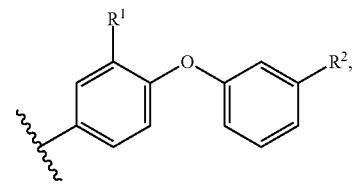
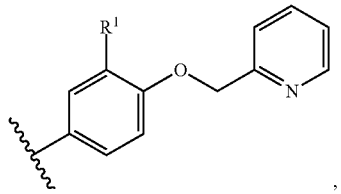
, or
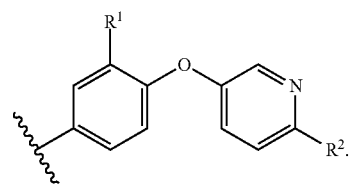
In embodiments,
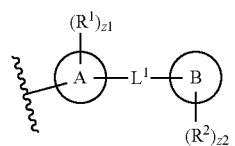
is not
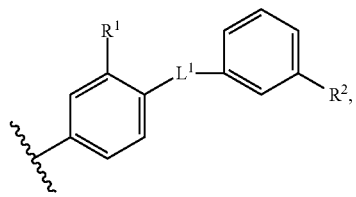
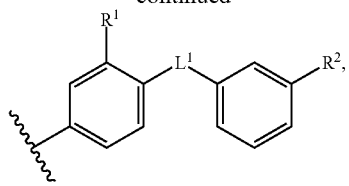
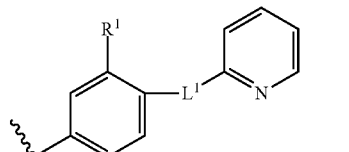
, or
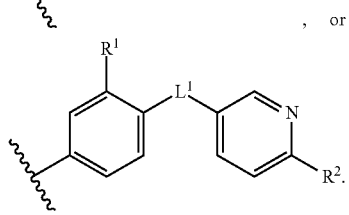
In embodiments,
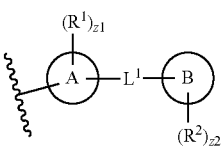
is not
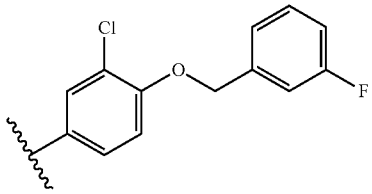 [SMILES: *c1ccc(OCc2cccc(F)c2)c(Cl)c1]
when $W^1$ is N. In embodiments,
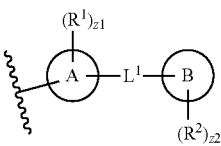
is not
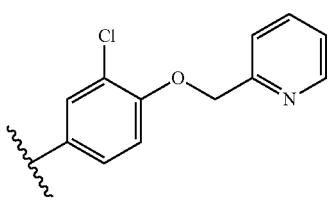 [SMILES: *c1ccc(OCc2ccccn2)c(Cl)c1]

when W¹ is C—R⁶. In embodiments,
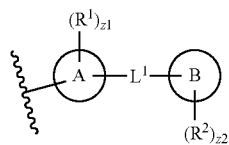
is not
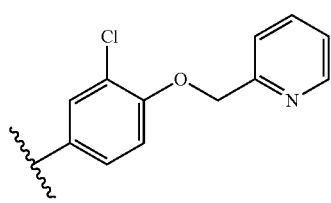 [SMILES: *c1ccc(OCc2ccccn2)c(Cl)c1]
when W¹ is C(CN). In embodiments,
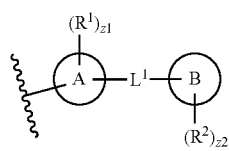
is not
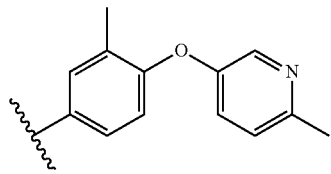 [SMILES: *c1ccc(Oc2ccc(C)nc2)c(C)c1]
when W¹ is N. In embodiments,
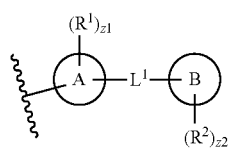
is not
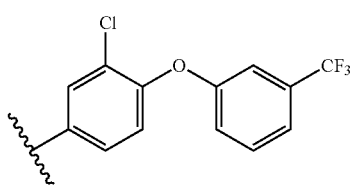 [SMILES: *c1ccc(Oc2cccc(C(F)(F)F)c2)c(Cl)c1]
when W¹ is N.
In embodiments,
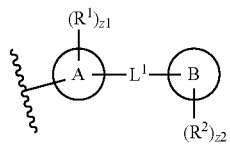
is not
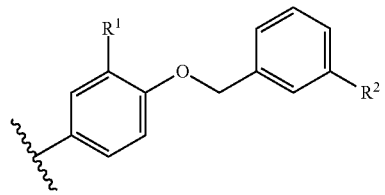
when W¹ is N. In embodiments,
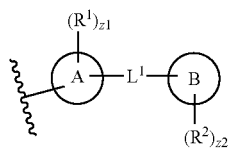
is not
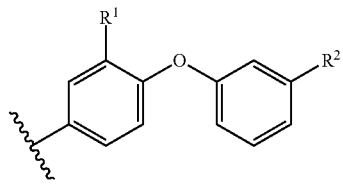
when W¹ is N. In embodiments,
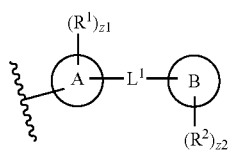
is not
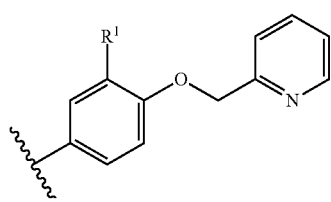
open W¹ is C—R⁶. In embodiments,

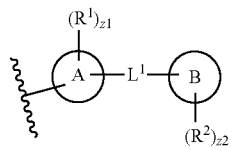
is not
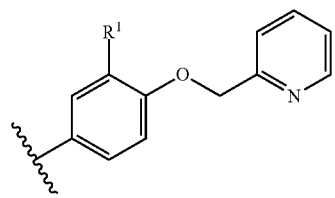
when $W^1$ is C(CN). In embodiments,
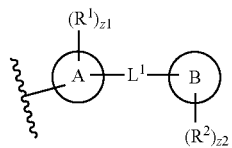
is not
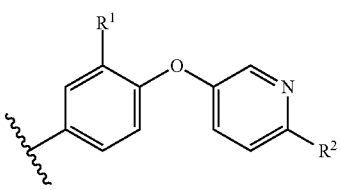
when $W^1$ is N.
In embodiments,
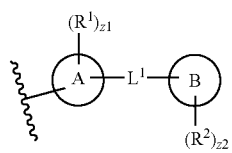
is not
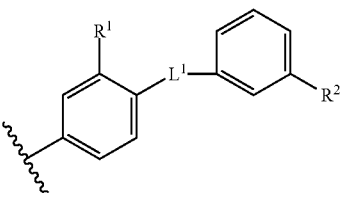
when $W^1$ is N. In embodiments,
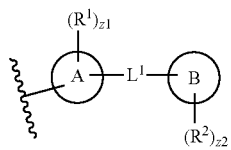
is not
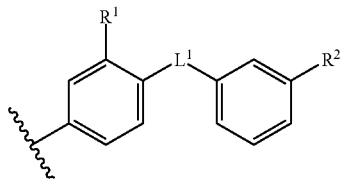
when $W^1$ is N. In embodiments,
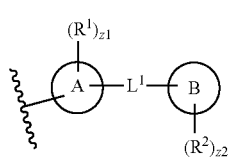
is not
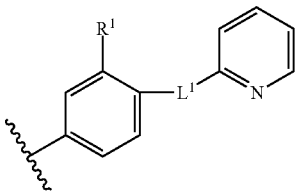
when $W^1$ is C—$R^6$. In embodiments,
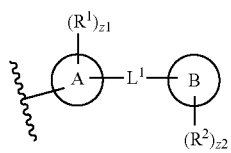
is not
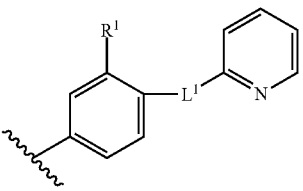
when $W^1$ is C(CN). In embodiments,

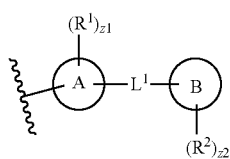

is not

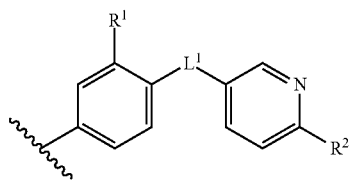

when $W^1$ is N.

In embodiments, Ring B is not

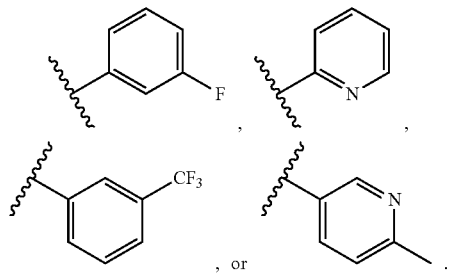

In embodiments, Ring B is not

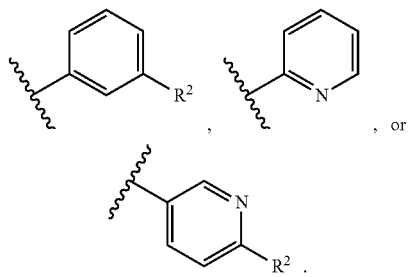

In embodiments, Ring B is not

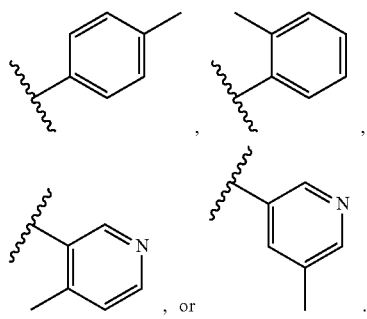

In embodiments, Ring B is not

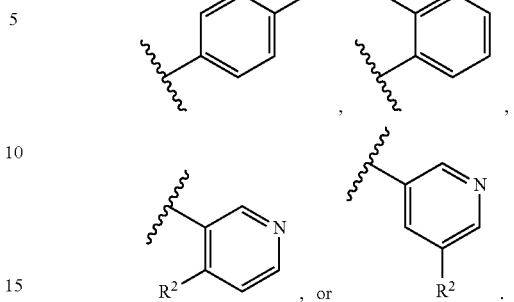

In embodiments, Ring B is not a substituted aryl or substituted heteroaryl. In embodiments, Ring B is not a substituted aryl. In embodiments, Ring B is not a substituted heteroaryl. In embodiments, Ring B is not a substituted or unsubstituted aryl (e.g., $C_6$-$C_{10}$ or phenyl), or substituted or unsubstituted heteroaryl (e.g., 5 to 10 membered, 5 to 9 membered, or 5 to 6 membered). In embodiments, Ring B is not pyridyl when z2 is 1. In embodiments, Ring B is not pyridyl when z2 is 2.

In embodiments, $R^1$ is not —Cl. In embodiments, $R^1$ is not halogen. In embodiments, $R^1$ is not an unsubstituted methyl. In embodiments, $R^1$ is not an unsubstituted $C_1$-$C_2$ alkyl. In embodiments, $R^1$ is not substituted or unsubstituted $C_1$-$C_2$ alkyl. In embodiments, $R^1$ is not a substituted or unsubstituted alkyl (e.g., $C_1$-$C_8$, $C_1$-$C_6$, $C_1$-$C_4$, or $C_1$-$C_2$). In embodiments, $R^1$ is not an unsubstituted alkyl (e.g., $C_1$-$C_8$, $C_1$-$C_6$, $C_1$-$C_4$, or $C_1$-$C_2$).

In embodiments, $R^2$ is not —$CF_3$. In embodiments, $R^2$ is not —F. In embodiments, $R^2$ is not halogen. In embodiments, $R^2$ is not an unsubstituted methyl. In embodiments, $R^2$ is not an unsubstituted $C_1$-$C_2$ alkyl. In embodiments, $R^2$ is not substituted or unsubstituted $C_1$-$C_2$ alkyl. In embodiments, $R^2$ is not a substituted or unsubstituted alkyl (e.g., $C_1$-$C_8$, $C_1$-$C_6$, $C_1$-$C_4$, or $C_1$-$C_2$). In embodiments, $R^2$ is not an unsubstituted alkyl (e.g., $C_1$-$C_8$, $C_1$-$C_6$, $C_1$-$C_4$, or $C_1$-$C_2$).

In embodiments, z1 is not 1. In embodiments, z1 is not 2. In embodiments, z1 is not 3. In embodiments, z1 is not 4. In embodiments, z1 is not 5. In embodiments, z1 is not 6. In embodiments, z1 is not 7. In embodiments, z2 is not 1. In embodiments, z2 is not 2. In embodiments, z2 is not 3. In embodiments, z2 is not 4. In embodiments, z2 is not 5. In embodiments, z2 is not 6. In embodiments, z2 is not 7.

C. Pharmaceutical Compositions

In another aspect is provided a pharmaceutical composition including a pharmaceutically acceptable excipient and a compound, or pharmaceutically acceptable salt thereof, as described herein, including embodiments.

In embodiments, the pharmaceutical compositions include the active ingredient (e.g., compound described herein or pharmaceutically acceptable salt thereof) in a therapeutically effective amount, i.e., in an amount effective to achieve its intended purpose. The actual amount effective for a particular application will depend, inter alia, on the condition being treated. When administered in methods to treat a disease, such compositions will contain an amount of active ingredient effective to achieve the desired result, e.g., inhibiting cell proliferation. In embodiments, the pharmaceutical composition includes an anti-cancer agent. In embodiments, the anti-cancer agent is an EGFR modulator, HER2 modulator, HER4 modulator, c-MET modulator, PI3K modulator, MEK modulator, MAPK modulator, RAF modulator, BRAF modulator, AKT modulator, RAS modulator, KRAS modulator, heregulin modulator, neuregulin modulator, or mTOR modulator. In embodiments, the anti-cancer agent is lapatinib, vemurafenib, or selumetinib.

D. Methods of Treatment

The compounds described herein are useful, inter alia, in methods of treating cancer. Such methods include administering to a subject in need thereof an effective amount of a compound described herein, including embodiments and pharmaceutically acceptable salts thereof. In embodiments, the cancer is lung cancer, non-small cell lung cancer, ovarian cancer, breast cancer, triple negative breast cancer, melanoma, head and neck cancer, colon cancer, gatric cancer, glioma, or glioblastoma.

In an aspect is provided, a method of treating cancer, wherein the method includes administering a compound described herein, or a pharmaceutically acceptable salt thereof, to a subject in need thereof. In embodiments, the cancer is lung cancer, non-small cell lung cancer, ovarian cancer, breast cancer, triple negative breast cancer, melanoma, head and neck cancer, colon cancer, gatric cancer, glioma, or glioblastoma.

In another aspect a compound described herein is provided for use as a medicament.

In another aspect is provided, a method of treating a disease associated with HER3 activity, wherein the method includes administering a compound described herein, or a pharmaceutically acceptable salt thereof, to a subject in need thereof.

In embodiments, the method includes administering a therapeutically effective amount of the compound.

In embodiments, the method includes administering a second agent (e.g., therapeutic agent). In embodiments, the second agent is an anti-cancer agent. In embodiments, the anti-cancer agent is an EGFR modulator, HER2 modulator, HER4 modulator, c-MET modulator, PI3K modulator, MEK modulator, MAPK modulator, RAF modulator, BRAF modulator, AKT modulator, RAS modulator, KRAS modulator, heregulin modulator, neuregulin modulator, or mTOR modulator. In embodiments, the anti-cancer agent is lapatinib, vemurafenib, or selumetinib. In embodiments, the proteins described above are human proteins.

In an aspect is provided a method of treating a disease associated with EGFR activity, HER2 activity, HER4 activity, c-MET activity, PI3K activity, MEK activity, MAPK activity, RAF activity, BRAF activity, AKT activity, RAS activity, KRAS activity, heregulin activity, or neuregulin activity in a patient in need of such treatment, the method including administering a therapeutically effective amount of a compound described herein, or a pharmaceutically acceptable salt thereof. In embodiments, the proteins described above are human proteins. In embodiments, the method includes contacting HER3 with a compound described herein (e.g., including a degradation-increasing moiety, for example as described herein). In embodiments, the method includes contacting HER3 with a compound described herein (e.g., including a degradation-increasing moiety, for example as described herein) and decreasing the level of EGFR activity, HER2 activity, HER4 activity, c-MET activity, PI3K activity, MEK activity, MAPK activity, RAF activity, BRAF activity, AKT activity, RAS activity, KRAS activity, heregulin activity, or neuregulin activity by inhibiting the activity (e.g., binding to a second protein) of HER3 or increasing the degradation of HER3.

E. Methods of Inhibiting HER3

In an aspect is provided a method of inhibiting HER3 activity, the method including contacting HER3 with an effective amount of a compound described herein, or a pharmaceutically acceptable salt thereof.

In embodiments, the HER3 is a human HER3.

F. Further Embodiments

Embodiment P1. A compound having the formula:

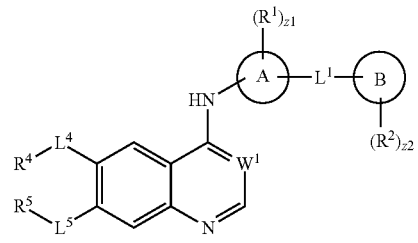

wherein Ring A is aryl or heteroaryl; Ring B is aryl or heteroaryl, $W^1$ is N or $C(R^6)$; $R^1$ is independently a halogen, $-CX^1_3$, $-CHX^1_2$, $-CH_2X^1$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $R^2$ is independently a halogen, $-CX^2_3$, $-CHX^2_2$, $-CH_2X^2$, $-CN$, $-SO_{n2}R^{14}$, $-SO_{v2}NR^{11}R^{12}$, $-NHNH_2$, $-ONR^{11}R^{12}$, $-NHC=(O)NHNR^{11}R^{12}$, $-NHC=(O)NR^{11}R^{12}$, $-N(O)_{m2}$, $-NR^{11}R^{12}$, $-C(O)R^{13}$, $-C(O)-OR^9$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^4$ is independently a hydrogen, halogen, $-CX^4_3$, $-CHX^4_2$, $-CH_2X^4$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently a hydrogen, halogen, $-CX^5_3$, —CHX$^5_2$, —CH$_2$X$^5$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^5_3$, —OCHX$^5_2$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^6$ is independently a hydrogen, halogen, —CX$^6_3$, —CHX$^6_2$, —CH$_2$X$^6$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^6_3$, —OCHX$^6_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$, R$^8$, R$^9$, R$^{10}$, R$^{11}$, R$^{12}$, R$^{13}$, and R$^{14}$ are independently hydrogen, halogen, —CX$^A_3$, —CHX$^A_2$, —CH$_2$X$^A$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^A_3$, —OCHX$^A_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl; L$^1$ is a bond, —O—, —NH—, —C(O)—, —C(O)NH—, —NHC(O)—, —C(O)O—, —OC(O)—, —NHC(O)NH—, —S—, substituted or unsubstituted alkylene or substituted or unsubstituted heteroalkylene; L$^4$ is a bond or a divalent linker; L$^5$ is a bond or a divalent linker; z1 and z2 are independently an integer from 0 to 7; m1, m2, v1, and v2 are independently 1 or 2; n1 and n2 are independently an integer from 0 to 4; X$^1$, X$^2$, X$^4$, X$^5$, X$^6$, and X$^A$ are independently —Cl, —Br, —I, or —F.

Embodiment P2. A compound of embodiment P1 having the formula:

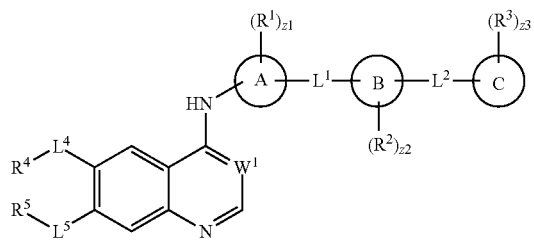

wherein Ring A is phenyl or 5 or 6 membered heteroaryl; Ring B is phenyl or 5 or 6 membered heteroaryl; Ring C is C$_3$-C$_6$ cycloalkyl, 3 to 6 membered heterocycloalkyl, phenyl, or 5 or 6 membered heteroaryl; W$^1$ is N or C(R$^6$). R$^1$ is independently a halogen, —CX$^1_3$, —CHX$^1_2$, —CH$_2$X$^1$, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl; R$^2$ is independently a halogen, —CX$^2_3$, —CHX$^2_2$, —CH$_2$X$^2$, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl; R$^3$ is independently a halogen, —CX$^3_3$, —CHX$^3_2$, —CH$_2$X$^3$, —CN, —SO$_{n3}$R$^{18}$, —SO$_{v3}$NR$^{15}$R$^{16}$, —NHNH$_2$, —ONR$^{15}$R$^{16}$, —NHC=(O)NHNR$^{15}$R$^{16}$, —NHC=(O)NR$^{15}$R$^{16}$, —N(O)$_{m3}$, —NR$^{15}$R$^{16}$, —C(O)R$^{17}$, —C(O)—OR$^{17}$, —C(O)NR$^{15}$R$^{16}$, —OR$^{18}$, —NR$^{15}$SO$_2$R$^{17}$, —NR$^{15}$C=(O)R$^{17}$, —NR$^{15}$C(O)—OR$^{17}$, —NR$^{15}$OR$^{17}$, —OCX$^3_3$, —OCHX$^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^3$ substituents may optionally be joined to form a substituted or unsubstituted cycloalkyl, substituted or unsubstituted heterocycloalkyl, substituted or unsubstituted aryl, or substituted or unsubstituted heteroaryl; R$^6$ is independently a hydrogen, halogen, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl; R$^{15}$, R$^{16}$, R$^{17}$, and R$^{18}$ are independently hydrogen, halogen, —CX$^A_3$, —CHX$^A_2$, —CH$_2$X$^A$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^A_3$, —OCHX$^A_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$ and R$^{16}$ substituents bonded to the same nitrogen atom may optionally be joined to form a substituted or unsubstituted heterocycloalkyl or substituted or unsubstituted heteroaryl; L$^1$ is —O—, substituted or unsubstituted C$_1$-C$_3$ alkylene or substituted or unsubstituted 2 to 3 membered heteroalkylene; L$^2$ is a bond, —O—, —NH—, —C(O)—, —C(O)NH—, —NHC(O)—, —C(O)O—, —OC(O)—, —NHC(O)NH—, —S—, substituted or unsubstituted C$_1$-C$_3$ alkylene or substituted or unsubstituted 2 to 3 membered heteroalkylene; L$^4$ is L$^{4A}$-L$^{4B}$-L$^{4C}$ and L$^{4A}$, L$^{4B}$, and L$^{4C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; L$^5$ is L$^{5A}$-L$^{5B}$-L$^{5C}$ and L$^{5A}$, L$^{5B}$, and L$^{5C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; z1, z2 are independently an integer from 0 to 4; z3 is independently an integer from 0 to 5; m3 and v3 are independently 1 or 2; n3 is independently an integer from 0 to 4; X$^1$, X$^2$, X$^3$, X$^4$, X$^5$, X$^6$, and X$^A$ are independently —Cl, —Br, —I, or —F.

Embodiment P3. The compound of embodiment P2, having the formula:

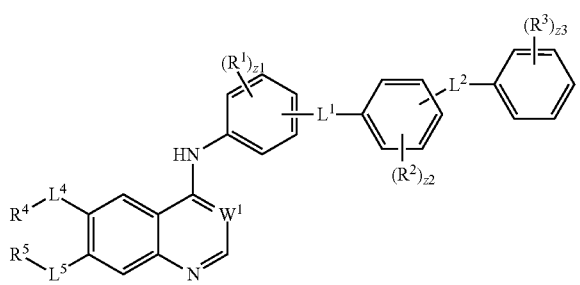

Embodiment P4. The compound of embodiment P3, having the formula:

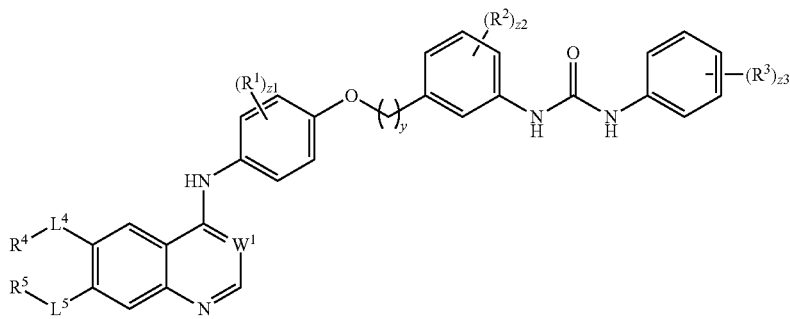

wherein Y is 0 or 1.

Embodiment P5. The compound of embodiment P3, having the formula:

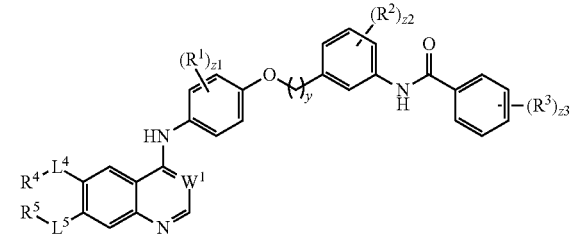

wherein Y is 0 or 1.

Embodiment P6. The compound of one of embodiments P1 to P5, wherein z1 is 0.

Embodiment P7. The compound of one of embodiments P1 to P6, wherein z2 is 0.

Embodiment P8. The compound of one of embodiments P1 to P7, wherein z3 is 1.

Embodiment P9. The compound of embodiment P8, wherein $R^3$ is —$CF_3$.

Embodiment P10. The compound of embodiment P8, wherein $R^3$ is a halogen.

Embodiment P11. The compound of one of embodiments P1 to P10, wherein $W^1$ is N.

Embodiment P12. The compound of one of embodiments P1 to P10, wherein $W^1$ is $C(R^6)$.

Embodiment P13. The compound of embodiment P12, wherein $R^6$ is —CN.

Embodiment P14. The compound of one of embodiments P1 to P13, wherein -$L^4$-$R^4$ is unsubstituted methoxy.

Embodiment P15. The compound of one of embodiments P1 to P14, wherein $R^4$ is a degradation-increasing moiety.

Embodiment P16. The compound of embodiment P15, wherein the degradation-increasing moiety is thalidomide or an analog, derivative, or prodrug thereof; phthalimide or an analog, derivative, or prodrug thereof; adamantyl or an analog, derivative, or prodrug thereof; an IκBα phosphopeptide or an analog, derivative, or prodrug thereof; nutlin or an analog, derivative, or prodrug thereof; HIF-1α pentapeptide or an analog, derivative, or prodrug thereof; or

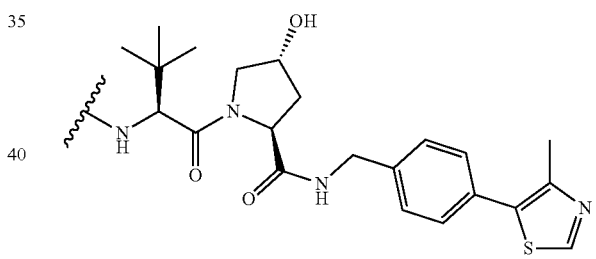

or an analog, derivative, or prodrug thereof.

Embodiment P17. The compound of embodiment P16, wherein the degradation-increasing moiety is thalidomide or an analog, derivative, or prodrug thereof.

Embodiment P18. The compound of one of embodiments P1 to P13, wherein $R^4$ is —$NH_2$.

Embodiment P19. The compound of one of embodiments P1 to P18, wherein -$L^5$-$R^5$ is unsubstituted methoxy.

Embodiment P20. The compound of one of embodiments P1 to P19, wherein $R^5$ is a degradation-increasing moiety.

Embodiment P21. The compound of embodiment P20, wherein the degradation-increasing moiety is thalidomide or an analog, derivative, or prodrug thereof; phthalimide or an analog, derivative, or prodrug thereof; adamantyl or an analog, derivative, or prodrug thereof; an IκBα phosphopeptide or an analog, derivative, or prodrug thereof; nutlin or an analog, derivative, or prodrug thereof; HIF-1α pentapeptide or an analog, derivative, or prodrug thereof; or

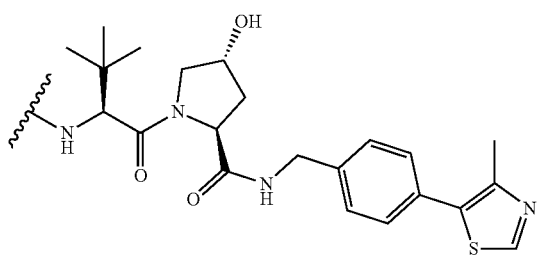 [SMILES: *N[C@H](C(=O)N1C[C@H](O)C[C@H]1C(=O)NCc1ccc(-c2scnc2C)cc1)C(C)(C)C]

or an analog, derivative, or prodrug thereof.

Embodiment P22. The compound of embodiment P20, wherein the degradation-increasing moiety is thalidomide or an analog, derivative, or prodrug thereof.

Embodiment P23. The compound of one of embodiments P1 to P18, wherein $R^5$ is $-NH_2$.

Embodiment P24. A pharmaceutical composition comprising a compound of one of embodiments P1 to P23 or a pharmaceutically acceptable salt thereof, and a pharmaceutically acceptable excipient.

Embodiment P25. The pharmaceutical composition of embodiment P24, further comprising an anti-cancer agent.

Embodiment P26. A method of treating a disease associated with HER3 activity in a patient in need of such treatment, said method comprising administering a therapeutically effective amount of a compound of one of embodiments P1 to P23, or a pharmaceutically acceptable salt thereof.

Embodiment P27. A method of treating a disease associated with EGFR activity, HER2 activity, HER4 activity, c-MET activity, PI3K activity, MEK activity, MAPK activity, RAF activity, BRAF activity, AKT activity, RAS activity, KRAS activity, heregulin activity, or neuregulin activity in a patient in need of such treatment, said method comprising administering a therapeutically effective amount of a compound of one of embodiments P1 to P23, or a pharmaceutically acceptable salt thereof.

Embodiment P28. A method of treating cancer in a patient in need of such treatment, said method comprising administering a therapeutically effective amount of a compound of one of embodiments P1 to P23, or a pharmaceutically acceptable salt thereof.

Embodiment P29. A method of inhibiting HER3 activity, said method comprising contacting HER3 with an effective amount of a compound of one of embodiments P1 to P23, or a pharmaceutically acceptable salt thereof.

G. Additional Embodiments

Embodiment 1. A compound having the formula:

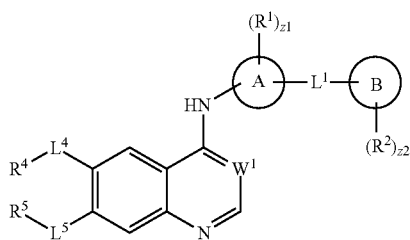

wherein Ring A is aryl or heteroaryl; Ring B is aryl or heteroaryl; $W^1$ is N or $C(R^6)$; $R^1$ is independently a halogen, $-CX^1_2$, $-CHX^1_2$, $-CH_2X^1$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl; $R^2$ is independently a halogen, $-CX^2_3$, $-CHX^2_2$, $-CH_2X^2$, $-CN$, $-SO_{n2}R^{14}$, $-SO_{v2}NR^{11}R^{12}$, $-NHNH_2$, $-ONR^{11}R^{12}$, $-NHC=(O)NHNR^{11}R^{12}$, $-NHC=(O)NR^{11}R^{12}$, $-N(O)_{m2}$, $-NR^{11}R^{12}$, $-C(O)R^{13}$, $-C(O)-OR^9$, $-C(O)NR^{11}R^{12}$, $-OR^{14}$, $-NHC=(O)NHNH^{11}R^{12}$, $-NHC=(O)NR^{11}R^{12}$, $-N(O)_{m2}$, $-NR^{11}R^{12}$, $-C(O)R^{13}$, $-C(O)-OR^9$, $-C(O)NR^{11}R^{12}$, $-OR^{14}$, $-NR^{11}SO_2R^{14}$, $-NR^{11}C=(O)R^{13}$, $-NR^{11}C(O)-OR^{13}$, $-NR^{11}OR^{13}$, $-OCX^2_3$, $-OCHX^2_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl; $R^4$ is independently a hydrogen, halogen, $-CX^4_3$, $-CHX^4_2$, $-CH_2X^4$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^4_3$, $-OCHX^4_2$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^5$ is independently a hydrogen, halogen, $-CX^5_3$, $-CHX^5_2$, $-CH_2X^5$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^5_3$, $-OCHX^5_2$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^6$ is independently a hydrogen, halogen, $-CX^6_3$, $-CHX^6_2$, $-CH_2X^6$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^6_3$, $-OCHX^6_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl, $R^7$, $R^8$, $R^9$, $R^{10}$, $R^{11}$, $R^{12}$, $R^{13}$, and $R^{14}$ are independently hydrogen, halogen, $-CX^A_3$, $-CHX^A_2$, $-CH_2X^A$, $-CN$, $-OH$, $-NH_2$, $-COOH$, $-CONH_2$, $-NO_2$, $-SH$, $-SO_3H$, $-SO_4H$, $-SO_2NH_2$, $-NHNH_2$, $-ONH_2$, $-NHC=(O)NHNH_2$, $-NHC=(O)NH_2$, $-NHSO_2H$, $-NHC=(O)H$, $-NHC(O)-OH$, $-NHOH$, $-OCX^A_3$, $-OCHX^A_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^7$ and $R^8$ substituents bonded to the same nitrogen atom may optionally be joined to form a substituted or unsubstituted heterocycloalkyl or substituted or unsubstituted heteroaryl; $R^{11}$ and $R^{12}$ substituents bonded to the same nitrogen atom may optionally be joined to form a substituted or unsubstituted heterocycloalkyl or substituted or unsubstituted heteroaryl; $L^1$ is a bond, —O—, —NH—, —C(O)—, —C(O)NH—, —NHC(O)—, —C(O)O—, —OC(O)—, —NHC(O)NH—, —S—, substituted or unsubstituted alkylene or substituted or unsubstituted heteroalkylene; $L^4$ is a bond or a divalent linker; $L^5$ is a bond or a divalent linker; z1 and z2 are independently an integer from 0 to 7; m1, m2, v1, and v2 are independently 1 or 2; n1 and n2 are independently an integer from 0 to 4; $X^1$, $X^2$, $X^4$, $X^5$, $X^6$, and $X^A$ are independently —Cl, —Br, —I, or —F.

Embodiment 2. A compound of embodiment 1 having the formula:

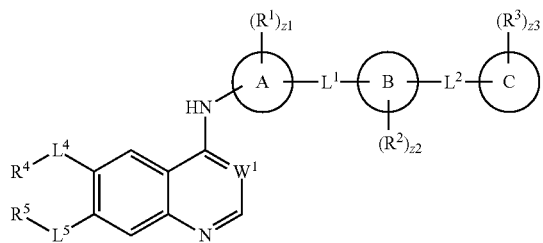

wherein Ring A is phenyl or 5 or 6 membered heteroaryl; Ring B is phenyl or 5 or 6 membered heteroaryl; Ring C is $C_3$-$C_6$ cycloalkyl, 3 to 6 membered heterocycloalkyl, phenyl, or 5 to 6 membered heteroaryl; $W^1$ is N or $C(R^6)$; $R^1$ is independently a halogen, —$CX^1_3$, —$CHX^1_2$, —$CH_2X^1$, —CN, —OH, —$NH_2$, —COOH, —$CONH_2$, —$NO_2$, —SH, substituted or unsubstituted $C_1$-$C_4$ alkyl, or 2 to 4 membered substituted or unsubstituted heteroalkyl; $R^2$ is independently a halogen, —$CX^2_3$, —$CHX^2_2$, —$CH_2X^2$, —CN, —OH, —$NH_2$, —COOH, —$CONH_2$, —$NO_2$, —SH, substituted or unsubstituted $C_1$-$C_4$ alkyl, or 2 to 4 membered substituted or unsubstituted heteroalkyl; $R^3$ is independently a halogen, —$CX^3_3$, —$CHX^3_2$, —$CH_2X^3$, —CN, —$SO_{n3}R^{18}$, —$SO_{v3}NR^{15}R^{16}$, —$NHNH_2$, —$ONR^{15}R^{16}$, —NHC═(O)NHNR$^{15}$R$^{16}$, —NHC═(O)NR$^{15}$R$^{16}$, —N(O)$_{m3}$, —NR$^{15}$R$^{16}$, —C(O)R$^{17}$, —C(O)—OR$^{17}$, —C(O)NR$^{15}$R$^{16}$, —OR$^{18}$, —NR$^{15}$SO$_2$R$^{17}$, —NR$^{15}$C═(O)R$^{17}$, —NR$^{15}$C(O)—OR$^{17}$, —NR$^{15}$OR$^{17}$, —OCX$^3_3$, —OCHX$^3_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^3$ substituents may optionally be joined to form a substituted or unsubstituted cycloalkyl, substituted or unsubstituted heterocycloalkyl, substituted or unsubstituted aryl, or substituted or unsubstituted heteroaryl; $R^6$ is independently a hydrogen, halogen, —CN, —OH, —$NH_2$, —COOH, —$CONH_2$, —$NO_2$, —SH, substituted or unsubstituted $C_1$-$C_4$ alkyl, or 2 to 4 membered substituted or unsubstituted heteroalkyl; $R^{15}$, $R^{16}$, $R^{17}$, and $R^{18}$ are independently hydrogen, halogen, —$CX^A_3$, —$CHX^A_2$, —$CH_2X^A$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC═(O)NHNH$_2$, —NHC═(O)NH$_2$, —NHSO$_2$H, —NHC═(O)H, —NHC(O)—OH, —NHOH, —$OCX^A_3$, —$OCHX^A_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; $R^{15}$ and $R^{16}$ substituents bonded to the same nitrogen atom may optionally be joined to form a substituted or unsubstituted heterocycloalkyl or substituted or unsubstituted heteroaryl; $L^1$ is —O—, substituted or unsubstituted $C_1$-$C_3$ alkylene or substituted or unsubstituted 2 to 3 membered heteroalkylene; $L^2$ is a bond, —O—, —NH—, —C(O)—, —C(O)NH—, —NHC(O)—, —C(O)O—, —OC(O)—, —NHC(O)NH—, —S—, substituted or unsubstituted $C_1$-$C_3$ alkylene or substituted or unsubstituted 2 to 3 membered heteroalkylene; $L^4$ is $L^{4A}$-$L^{4B}$-$L^{4C}$ and $L^{4A}$, $L^{4B}$, and $L^{4C}$ are each independently a bond —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; $L^5$ is $L^{5A}$-$L^{5B}$-$L^{5C}$ and $L^{5A}$, $L^{5B}$, and $L^{5C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; z1, z2 are independently an integer from 0 to 4; z3 is independently an integer from 0 to 5; m3 and v3 are independently 1 or 2; n3 is independently an integer from 0 to 4; $X^1$, $X^2$, $X^3$, $X^4$, $X^5$, $X^6$, and $X^A$ are independently —Cl, —Br, —I, or —F.

Embodiment 3. The compound of embodiment 2, having the formula:

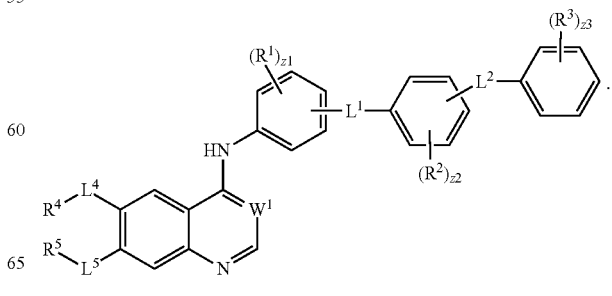

Embodiment 4. The compound of embodiment 3, having the formula:

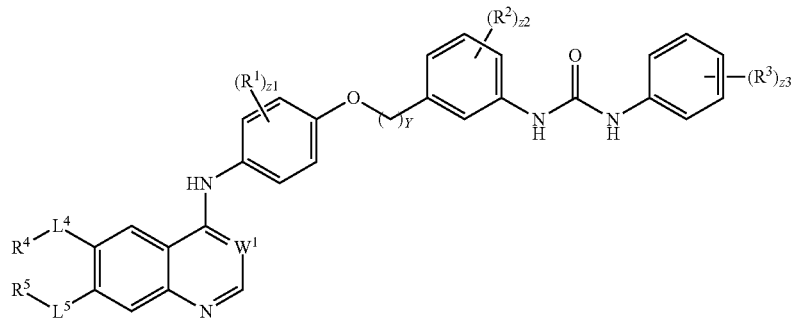

wherein Y is 0 or 1.

Embodiment 5. The compound of embodiment 3, having the formula:

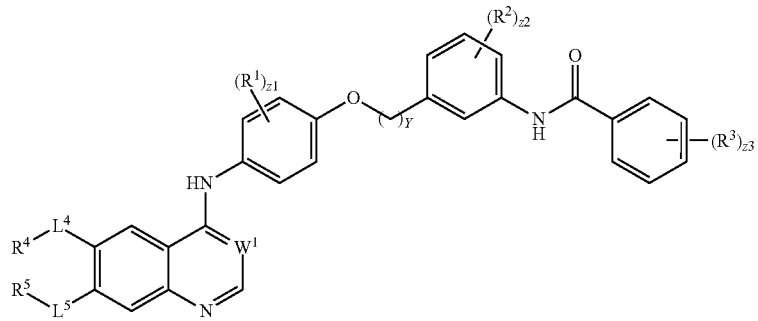

wherein Y is 0 or 1.

Embodiment 6. The compound of one of embodiments 1 to 5, wherein z1 is 0.

Embodiment 7. The compound of one of embodiments 1 to 6, wherein z2 is 0.

Embodiment 8. The compound of one of embodiments 1 to 7, wherein z3 is 1.

Embodiment 9. The compound of embodiment 8, wherein $R^3$ is —$CF_3$.

Embodiment 10. The compound of embodiment 8, wherein $R^3$ is a halogen.

Embodiment 11. The compound of one of embodiments 1 to 10, wherein $W^1$ is N.

Embodiment 12. The compound of one of embodiments 1 to 10, wherein $W^1$ is $C(R^6)$.

Embodiment 13. The compound of embodiment 12, wherein $R^6$ is —CN.

Embodiment 14. The compound of one of embodiments 1 to 13, wherein -$L^4$-$R^4$ is unsubstituted methoxy.

Embodiment 15. The compound of one of embodiments 1 to 14, wherein $R^4$ is a degradation-increasing moiety.

Embodiment 16. The compound of embodiment 15, wherein the degradation-increasing moiety is thalidomide or an analog, derivative, or prodrug thereof; phthalimide or an analog, derivative, or prodrug thereof; adamantyl or an analog, derivative, or prodrug thereof; an IκBα phosphopeptide or an analog, derivative, or prodrug thereof; nutlin or an analog, derivative, or prodrug thereof; HIF-1α pentapeptide or an analog, derivative, or prodrug thereof; or

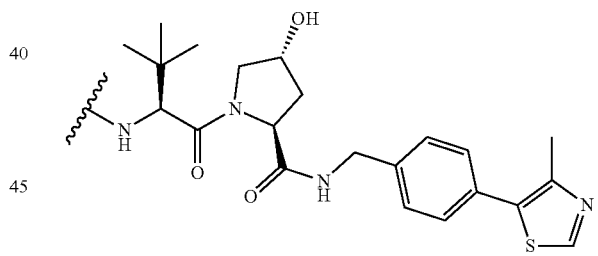

or an analog, derivative, or prodrug thereof.

Embodiment 17. The compound of embodiment 16, wherein the degradation-increasing moiety is thalidomide or an analog, derivative, or prodrug thereof.

Embodiment 18. The compound of one of embodiments 1 to 13, wherein $R^4$ is —$NH_2$.

Embodiment 19. The compound of one of embodiments 1 to 18, wherein -$L^5$-$R^5$ is unsubstituted methoxy.

Embodiment 20. The compound of one of embodiments 1 to 19, wherein $R^5$ is a degradation-increasing moiety.

Embodiment 21. The compound of embodiment 20, wherein the degradation-increasing moiety is thalidomide or an analog, derivative, or prodrug thereof; phthalimide or an analog, derivative, or prodrug thereof; adamantyl or an analog, derivative, or prodrug thereof; an IκBα phosphopeptide or an analog, derivative, or prodrug thereof; nutlin or an analog, derivative, or prodrug thereof; HIF-1α pentapeptide or an analog, derivative, or prodrug thereof; or

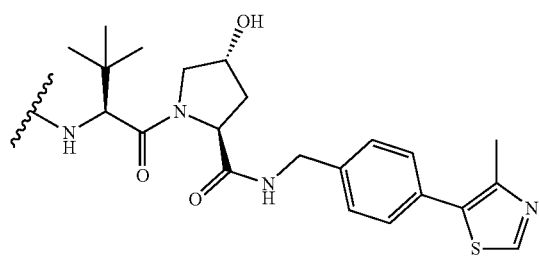 [SMILES: *N[C@H](C(=O)N1C[C@H](O)C[C@H]1C(=O)NCc1ccc(-c2scnc2C)cc1)C(C)(C)C]

or an analog, derivative, or prodrug thereof.

Embodiment 22. The compound of embodiment 20, wherein the degradation-increasing moiety is thalidomide or an analog, derivative, or prodrug thereof.

Embodiment 23. The compound of one of embodiments 1 to 18, wherein $R^5$ is —$NH_2$.

Embodiment 24. A pharmaceutical composition comprising a compound of one of embodiments 1 to 23 or a pharmaceutically acceptable salt thereof, and a pharmaceutically acceptable excipient.

Embodiment 25. The pharmaceutical composition of embodiment 24, further comprising an anti-cancer agent.

Embodiment 26. A method of treating a disease associated with HER3 activity in a patient in need of such treatment, said method comprising administering a therapeutically effective amount of a compound of one of embodiments 1 to 23, or a pharmaceutically acceptable salt thereof.

Embodiment 27. A method of treating a disease associated with EGFR activity, HER2 activity, HER4 activity, c-MET activity, PI3K activity, MEK activity, MAPK activity, RAF activity, BRAF activity, AKT activity, RAS activity, KRAS activity, heregulin activity, or neuregulin activity in a patient in need of such treatment, said method comprising administering a therapeutically effective amount of a compound of one of embodiments 1 to 23, or a pharmaceutically acceptable salt thereof.

Embodiment 28. A method of treating cancer in a patient in need of such treatment, said method comprising administering a therapeutically effective amount of a compound of one of embodiments 1 to 23, or a pharmaceutically acceptable salt thereof.

Embodiment 29. A method of inhibiting HER3 activity, said method comprising contacting HER3 with an effective amount of a compound of one of embodiments 1 to 23, or a pharmaceutically acceptable salt thereof.

Embodiment 30. A compound having the formula:

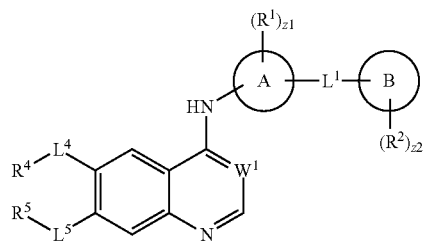

wherein
Ring A is aryl or heteroaryl;
Ring B is aryl or heteroaryl;
$W^1$ is N or $C(R^6)$
$R^1$ is independently a halogen, —$CX^1_3$, —$CHX^1_2$, —$CH_2X^1$, —CN, —$SO_{n1}R^{10}$, —$SO_{v1}NR^7R^8$, —$NHNH_2$, —$ONR^7R^8$, —NHC=(O)$NHNH_2$, —NHC=(O)$NR^7R^8$, —$N(O)_{m1}$, —$NR^7R^8$, —$C(O)R^9$, —C(O)—$OR^9$, —C(O)$NR^7R^8$, —$OR^{10}$, —$NR^7SO_2R^{10}$, —$NR^7C$=(O)$R^9$, —$NR^7C(O)$—$OR^9$, —$NR^7OR^5$, —$OCHX^1_2$, —$OCHX^1_2$, —$OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently a halogen, —$CX^2_3$, —$CHX^2_2$, —$CH_2X^2$, —CN, —$SO_{n2}R^{14}$, —$SO_{v2}NR^{11}R^{12}$, —$NHNH_2$, —$ONR^{11}R^{12}$, —NHC=(O)$NHNR^{11}R^{12}$, —NHC=(O)$NR^{11}R^{12}$, —$N(O)_{m2}$, —$NR^{11}R^{12}$, —$C(O)R^{13}$, —C(O)—$OR^9$, —C(O)$NR^{11}R^{12}$, —$OR^{14}$, —$NR^{11}SO_2R^{14}$, —$NR^{11}C$=(O)$R^{13}$, —$NR^{11}C(O)$—$OR^{13}$, —$NR^{11}OR^{13}$, —$OCX^2_3$, —$OCHX^2_2$, —$OCH_2X^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^2$ substituents may optionally be joined to form a substituted or unsubstituted cycloalkyl, substituted or unsubstituted heterocycloalkyl, substituted or unsubstituted aryl, or substituted or unsubstituted heteroaryl;

$R^4$ is independently a hydrogen, halogen, —$CX^4_3$, —$CHX^4_2$, —$CH_2X^4$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^4_3$, —$OCHX^4_2$, —$OCH_2X^4$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^5$ is independently a hydrogen, halogen, —$CX^5_3$, —$CHX^5_2$, —$CH_2X^5$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^5_3$, —$OCHX^5_2$, —$OCH_2X^5$, degradation-increasing moiety, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

$R^6$ is independently a hydrogen, halogen, —$CX^6_3$, —$CHX^6_2$, —$CH_2X^6$, —CN, —OH, —$NH_2$, —COOH, —$CONH_2$, —$NO_2$, —SH, —$SO_3H$, —$SO_4H$, —$SO_2NH_2$, —$NHNH_2$, —$ONH_2$, —NHC=(O)$NHNH_2$, —NHC=(O)$NH_2$, —$NHSO_2H$, —NHC=(O)H, —NHC(O)—OH, —NHOH, —$OCX^6_3$, —$OCHX^6_2$, —$OCH_2X^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl $R^7$, $R^8$, $R^9$, $R^{10}$, $R^{11}$, $R^{12}$, $R^{13}$, and $R^{14}$ are independently hydrogen, halogen, —$CX^A_3$, —$CHX^A_2$, —$CH_2X^A$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^A_3$, —OCHX$^A_2$, —OCH$_2$X$^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl;

L$^1$ is a bond, —O—, —NH—, —C(O)—, —C(O)NH—, —NHC(O)—, —C(O)O—, —OC(O)—, —NHC(O)NH—, —S—, substituted or unsubstituted alkylene or substituted or unsubstituted heteroalkylene;

L$^4$ is a bond or a divalent linker;

L$^5$ is a bond or a divalent linker;

z1 and z2 are independently an integer from 0 to 7;

m1, m2, v1, and v2 are independently 1 or 2;

n1 and n2 are independently an integer from 0 to 4;

X$^1$, X$^2$, X$^4$, X$^5$, X$^6$, and X$^A$ are independently —Cl, —Br, —I, or —F.

Embodiment 31. The compound of embodiment 30, having the formula:

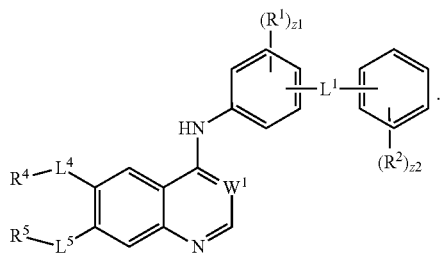

Embodiment 32. A compound of embodiment 30 having the formula:

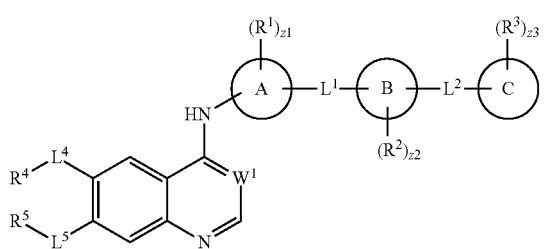

wherein

Ring A is phenyl or 5 or 6 membered heteroaryl;

Ring B is phenyl or 5 or 6 membered heteroaryl;

Ring C is C$_3$-C$_6$ cycloalkyl, 3 to 6 membered heterocycloalkyl, phenyl, or 5 to 6 membered heteroaryl;

W$^1$ is N or C(R$^6$);

R$^1$ is independently a halogen, —CX$^1_3$, —CHX$^1_2$, —CH$_2$X$^1$, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl;

R$^2$ is independently a halogen, —CX$^2_3$, —CHX$^2_2$, —CH$_2$X$^2$, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl;

R$^3$ is independently a halogen, —CX$^3_3$, —CHX$^3_2$, —CH$_2$X$^3$, —CN, —SO$_{n3}$R$^{18}$, —SO$_{v3}$NR$^{15}$R$^{16}$, —NHNH$_2$, —ONR$^{15}$R$^{16}$, —NHC=(O)NHNR$^{15}$R$^{16}$, —NHC=(O)NR$^{15}$R$^{16}$, —N(O)$_{m3}$, —NR$^{15}$R$^{16}$, —C(O)R$^{17}$, —C(O)—OR$^{17}$, —C(O)NR$^{15}$R$^{16}$, —OR$^{18}$, —NR$^{15}$SO$_2$R$^{17}$, —NR$^{15}$C=(O)R$^{17}$, —NR$^{15}$C(O)—OR$^{17}$, —NR$^{15}$OR$^{17}$, —OCX$^3_3$, —OCHX$^3_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^3$ substituents may optionally be joined to form a substituted or unsubstituted cycloalkyl, substituted or unsubstituted heterocycloalkyl, substituted or unsubstituted aryl, or substituted or unsubstituted heteroaryl;

R$^6$ is independently a hydrogen, halogen, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl;

R$^{15}$, R$^{16}$, R$^{17}$, and R$^{18}$ are independently hydrogen, halogen, —CX$^A_3$, —CHX$^A_2$, —CH$_2$X$^A$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^A_3$, —OCHX$^A_2$, —OCH$_2$X$^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^{15}$ and R$^{16}$ substituents bonded to the same nitrogen atom may optionally be joined to form a substituted or unsubstituted heterocycloalkyl or substituted or unsubstituted heteroaryl;

L$^1$ is —O—, substituted or unsubstituted C$_1$-C$_3$ alkylene or substituted or unsubstituted 2 to 3 membered heteroalkylene;

L$^2$ is a bond, —O—, —NH—, —C(O)—, —C(O)NH—, —NHC(O)—, —C(O)O—, —OC(O)—, —NHC(O)NH—, —S—, substituted or unsubstituted C$_1$-C$_3$ alkylene or substituted or unsubstituted 2 to 3 membered heteroalkylene;

L$^4$ is L$^{4A}$-L$^{4B}$-L$^{4C}$ and L$^{4A}$, L$^{4B}$, and L$^{4C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

L$^5$ is L$^{5A}$-L$^{5B}$-L$^{5C}$ and L$^{5A}$, L$^{5B}$, and L$^{5C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene;

z1, z2 are independently an integer from 0 to 4;
z3 is independently an integer from 0 to 5;
m3 and v3 are independently 1 or 2;
n3 is independently an integer from 0 to 4;
$X^1$, $X^2$, $X^3$, $X^4$, $X^5$, $X^6$, and $X^A$ are independently —Cl, —Br, —I, or —F.

Embodiment 33. The compound of embodiment 30 or embodiment 32, having the formula:

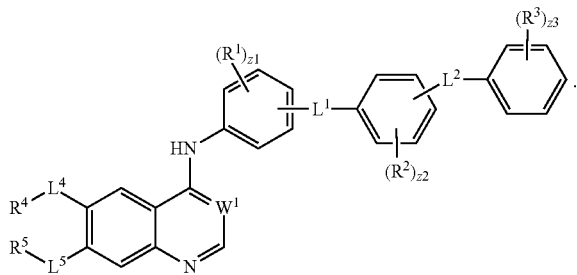

Embodiment 34. The compound of embodiment 32, having the formula:

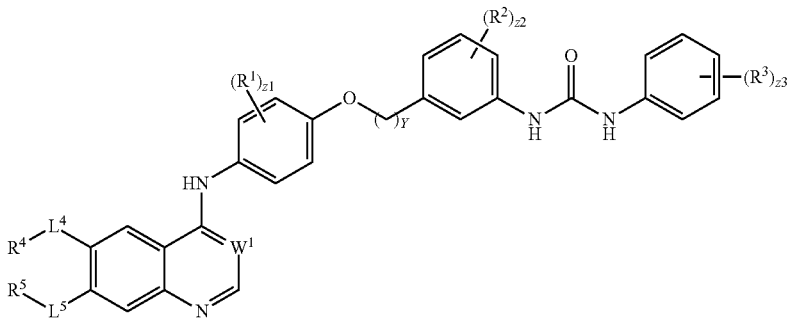

wherein Y is 0 or 1.

Embodiment 35. The compound of embodiment 32, having the formula:

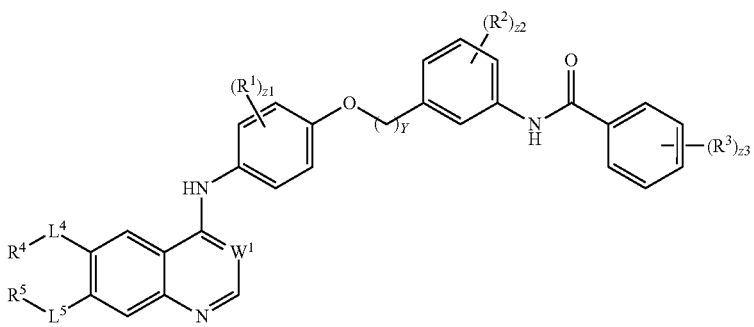

wherein Y is 0 or 1.

Embodiment 36. The compound of one of embodiments 30 to 35, wherein z1 is 0.

Embodiment 37. The compound of one of embodiments 30 to 35, wherein z2 is 0.

Embodiment 38. The compound of one of embodiments 30 to 35, wherein z3 is 1.

Embodiment 39. The compound of one of embodiments 30 to 35, wherein $R^3$ is independently a halogen, $—CX^3{}_3$, $—CHX^3{}_2$, $—CH_2X^3$, $—OCX^3{}_3$, $—OCHX^3{}_2$, $—OCH_2X^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl.

Embodiment 40. The compound of one of embodiments 30 to 35, wherein $R^3$ is independently a halogen, $—CX^3{}_3$, $—CHX^3{}_2$, $—CH_2X^3$, $—OCX^3{}_3$, $—OCHX^3{}_2$, $—OCH_2X^3$.

Embodiment 39. The compound of one of embodiments 30 to 35, wherein $R^3$ is independently a halogen or $—CF_3$.

Embodiment 39. The compound of one of embodiments 30 to 35, wherein $R^3$ is independently —$CF_3$.

Embodiment 40. The compound of one of embodiments 30 to 35, wherein $R^3$ is a halogen.

Embodiment 41. The compound of one of embodiments 30 to 40, wherein $W^1$ is N.

Embodiment 42. The compound of one of embodiments 30 to 40, wherein $W^1$ is $C(R^6)$.

Embodiment 43. The compound of one of embodiments 30 to 42, wherein $R^6$ is —CN.

Embodiment 44. The compound of one of embodiments 30 to 43, wherein -$L^4$-$R^4$ is substituted or unsubstituted 2 to 10 membered heteroalkyl.

Embodiment 45. The compound of one of embodiments 30 to 43, wherein -$L^4$-$R^4$ is substituted or unsubstituted 2 to 6 membered heteroalkyl.

Embodiment 46. The compound of one of embodiments 30 to 43, wherein -$L^4$-$R^4$ is -$L^4$-$R^4$ substituted or unsubstituted 2 membered heteroalkyl.

Embodiment 47. The compound of one of embodiments 30 to 43, wherein -L$^4$-R$^4$ is substituted or unsubstituted methoxy.

Embodiment 48. The compound of one of embodiments 30 to 43, wherein R$^4$ is a degradation-increasing moiety.

Embodiment 49. The compound of one of embodiments 30 to 43, wherein the degradation-increasing moiety is thalidomide or an analog, derivative, or prodrug thereof; phthalimide or an analog, derivative, or prodrug thereof; adamantyl or an analog, derivative, or prodrug thereof; an IκBα phosphopeptide or an analog, derivative, or prodrug thereof; nutlin or an analog, derivative, or prodrug thereof; HIF-1α pentapeptide or an analog, derivative, or prodrug thereof; or

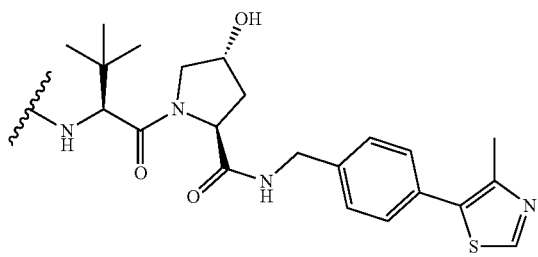 [SMILES: *N[C@H](C(=O)N1C[C@H](O)C[C@H]1C(=O)NCc1ccc(-c2scnc2C)cc1)C(C)(C)C]

or an analog, derivative, or prodrug thereof.

Embodiment 50. The compound of embodiment 48, wherein the degradation-increasing moiety is thalidomide or an analog, derivative, or prodrug thereof.

Embodiment 51. The compound of one of embodiments 30 to 43, wherein R$^4$ is hydrogen, halogen, —CX$^4_3$, —CHX$^4_2$, —CH$_2$X$^4$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^4_3$, —OCHX$^4_2$, or —OCH$_2$X$^4_2$.

Embodiment 52. The compound of one of embodiments 30 to 43, wherein R$^4$ is hydrogen, halogen, —CN, —OH, —NH$_2$, —COOH, —CONH$_2$, —NO$_2$, —NHNH$_2$, —ONH$_2$, —NHC=(O)NHNH$_2$, —NHC=(O)NH$_2$, —NHSO$_2$H, —NHC=(O)H, —NHC(O)—OH, or —NHOH.

Embodiment 53. The compound of one of embodiments 30 to 43, wherein R$^4$ is —O(unsubstituted C$_1$-C$_4$ alkyl) or —NH$_2$.

Embodiment 54. The compound of one of embodiments 30 to 43, wherein R$^4$ is —O(unsubstituted C$_1$-C$_2$ alkyl) or —NH$_2$.

Embodiment 55. The compound of one of embodiments 30 to 43, wherein R$^4$ is unsubstituted methoxy or —NH$_2$.

Embodiment 56. The compound of one of embodiments 30 to 43, wherein R$^4$ is —NH$_2$.

Embodiment 57. The compound of one of embodiments 30 to 56, wherein -L$^5$-R$^5$ is substituted or unsubstituted 2 to 10 membered heteroalkyl.

Embodiment 58. The compound of one of embodiments 30 to 56, wherein -L$^5$-R$^5$ is substituted or unsubstituted 2 to 6 membered heteroalkyl.

Embodiment 59. The compound of one of embodiments 30 to 56, wherein -L$^5$-R$^5$ is -L$^5$-R$^5$ is substituted or unsubstituted 2 membered heteroalkyl.

Embodiment 60. The compound of one of embodiments 30 to 56, wherein -L$^5$-R$^5$ is substituted or unsubstituted methoxy.

Embodiment 61. The compound of one of embodiments 30 to 56, wherein R$^5$ is a degradation-increasing moiety.

Embodiment 62. The compound of one of embodiments 30 to 56, wherein the degradation-increasing moiety is thalidomide or an analog, derivative, or prodrug thereof; phthalimide or an analog, derivative, or prodrug thereof; adamantyl or an analog, derivative, or prodrug thereof; an IκBα phosphopeptide or an analog, derivative, or prodrug thereof; nutlin or an analog, derivative, or prodrug thereof; HIF-1α pentapeptide or an analog, derivative, or prodrug thereof; or

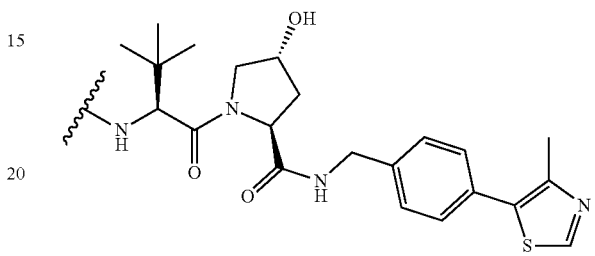

or an analog, derivative, or prodrug thereof.

Embodiment 63. The compound of embodiment 62, wherein the degradation-increasing moiety is thalidomide or an analog, derivative, or prodrug thereof.

Embodiment 64. The compound of one of embodiments 30 to 56, wherein R$^5$ is hydrogen, halogen, —CX$^5_3$, —CHX$^5_2$, —CH$_2$X$^5$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^5_3$, —OCHX$^5_2$, or —OCH$_2$X$^5_2$.

Embodiment 51. The compound of one of embodiments 30 to 56, wherein R$^5$ is hydrogen, halogen, —CN, —OH, —NH$_2$, —COOH, —CONH$_2$, —NO$_2$, —NHNH$_2$, —ONH$_2$, —NHC=(O)NHNH$_2$, —NHC=(O)NH$_2$, —NHSO$_2$H, —NHC=(O)H, —NHC(O)—OH, or —NHOH.

Embodiment 65. The compound of one of embodiments 30 to 56, wherein R$^5$ is —O(unsubstituted C$_1$-C$_4$ alkyl) or —NH$_2$.

Embodiment 66. The compound of one of embodiments 30 to 56, wherein R$^5$ is —O(unsubstituted C$_1$-C$_2$ alkyl) or —NH$_2$.

Embodiment 67. The compound of one of embodiments 30 to 56, wherein R$^5$ is unsubstituted methoxy or —NH$_2$.

Embodiment 68. The compound of one of embodiments 30 to 56, wherein R$^5$ is —NH$_2$.

H. Examples

HER3 Thermofluor Assay. Wt HER3 TKD was purified according to the previously published protocol[1]. Thermofluor reactions were performed in duplicate and set up as follows. 1 μL of an inhibitor or DMSO dilution in 40% DMSO:water was added to 19 μL of the HER3 kinase domain in reaction buffer. The final reaction solution contained 100 mM MOPS, 200 mM NaCl, 5% glycerol, 5 mM MgCl2, 0.1 mM DTT, 5×SYPRO Orange, 2 μM kinase, 2% DMSO and 20 μM inhibitor in the wells of a 96-well, low profile, white, PCR plate (USA scientific). The solution was pipetted up and down to mix, sealed with TempAssure clear PCR flat caps (USA Scientific), centrifuged at 500×g for 30 s, and heated in a Stratagene Mx3005P RT-PCR machine from 25° C. to 95° C. in 0.5° C. increments every 30 s after an initial incubation at 25° C. for 10 min. Fluorescence was measured at the end of each 30 s period with an excitation wavelength of 492 nm and an emission wavelength of 610 nm. To obtain the melting temperature, fluorescent signals were normalized to the maximum fluorescent signal for that well. Values after the well had reached a maximum signal were discarded and the signals were fit to the Boltzmann equation in Graphpad Prism 6. $\Delta T_m$ was calculated as the difference in melting temperature between the compound-treated kinase compared to the DMSO control.

In vitro Kinase Assays. In vitro kinase assays with the HER2 kinase domain (SignalChem) were performed in triplicate as follows. To 9 μL of a 2.5× solution of kinase and substrate in reaction buffer was added 3 μL of a 5×DMSO or inhibitor dilution in 10% DMSO:water. The inhibitor/kinase solution was incubated at room temperature for 10 minutes. The kinase assay was initiated by the addition of 3 μL of a 5× solution of ATP, and ran for 15 minutes. The final reaction conditions were 50 mM Tris (pH7.4), 5 mM $MnCl_2$, 0.01% Tween-20, 2 mM DTT, 100 μM $E_4Y$ substrate (Signal-Chem), 15 nM HER2, 2% DMSO, 50 μM ATP, and 1 μCi $\gamma^{32}P$-ATP. After 15 minutes, 3 μL of each reaction was pipetted onto phosphocellulose sheets (P81, Whatman) and allowed to dry. The sheets were then washed 4×5 min with a solution of 0.5% phosphoric acid, dried, and exposed to a phosphor screen overnight. Src Kinase assays were conducted as previously described[2]. Phosphorimaging was conducted on a Typhoon 9500, image intensities were quantified in ImageQuant 5.2, normalized to the DMSO control and plotted in GraphPad Prism 6.

Immunoblotting. CHLL-1 cells were grown in 6-well plates and treated according to the indicated conditions at which point the media was aspirated, cells were washed with 1 mL of cold PBS, which was then aspirated and the plates were frozen at −80° C. The frozen cells were thawed on the plates in a buffer containing 50 mM Tris pH 7.5, 150 mM NaCl, 1 mM EDTA, and 1% Triton X-100 supplemented with 1× phosphatase (PhoSTOP, Roche) and 1× protease (complete-mini tablets, Roche) inhibitors. Lysates were scraped, transferred to Eppendorf tubes, and cleared by centrifugation at 20,000×g for 20 min at 4° C. The clarified lysates were transferred to chilled, clean tubes, and normalized for protein concentration by Bradford (Bio-Rad). The normalized lysates were diluted with Laemmli loading buffer, and 10 μg of total protein was run on a 4-12% gradient gel (Invitrogen), which was then transferred to 0.45 μM nitrocellulose (Bio-Rad) and analyzed using the indicated primary antibodies according to the manufacturer's recommendations (1:1000 antibody dilution). Primary antibodies were detected using IRDye secondary antibodies (Li-Cor) according to the manufacturer's recommendations and scanned on an Odyssey imager (Li-Cor). Scanned images were cropped and assembled in Adobe Illustrator 6.

Chemical Synthesis

General Methods: Reactions were performed in sealed vials with magnetic stirring. All commercial reagents were used without further purification. Silica gel chromatography was performed on a Combiflash Rf+ using column cartridges pre-packed with 40-60 micron silica (Teledyne Isco). All RP-HPLC purifications were performed with a Waters 2545 binary gradient module equipped with an XBridge prep C18 column using H2O+0.1% formic acid and CH3CN+0.1% formic acid (5-95% gradient) while monitoring at 254 nm. Low resolution mass spectra (LC/ESI-MS) were recorded in positive and negative mode on a Waters TQ detector with an Acquity UPLC equipped with a BUT C18 column.

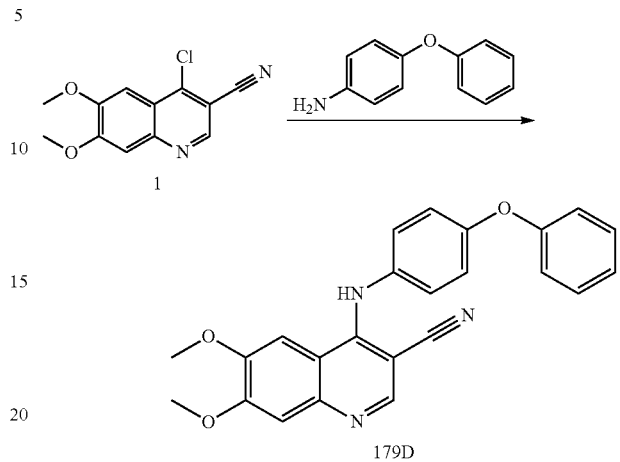

6,7-dimethoxy-4-((4-phenoxyphenyl)amino)quinoline-3-carbonitrile (179D). 1 was synthesized as previously reported[3]. 10 mg of 1 and 7.46 mg of 4-phenoxyaniline was added to a vial with a magnetic stir bar. The vial was capped, purged with argon, and 1 mL of 2-ethoxyethanol was added. The vial was heated at 150° C. for 3 h. The reaction was then cooled and purified by RP-HPLC. Product containing fractions were pooled and dried under reduced pressure to yield 6.4 mg (40%) of 179D as a yellow solid. MS (ES+) m/z 398.3 $(M+H)^+$

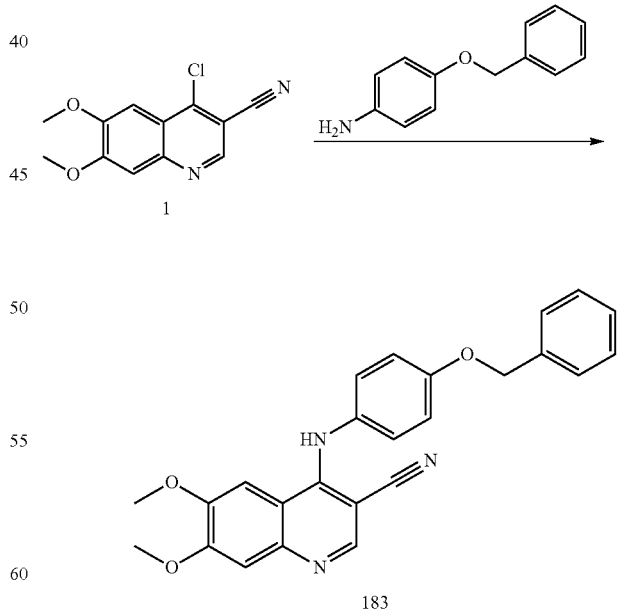

4-((4-(benzyloxy)phenyl)amino-6,7-dimethoxyquinoline-3-carbonitrile (183). 183 was obtained in 61% yield as a yellow solid by a method similar to the one described for compound 179D. MS (ES+) m/z 412.4 $(M+H)^+$

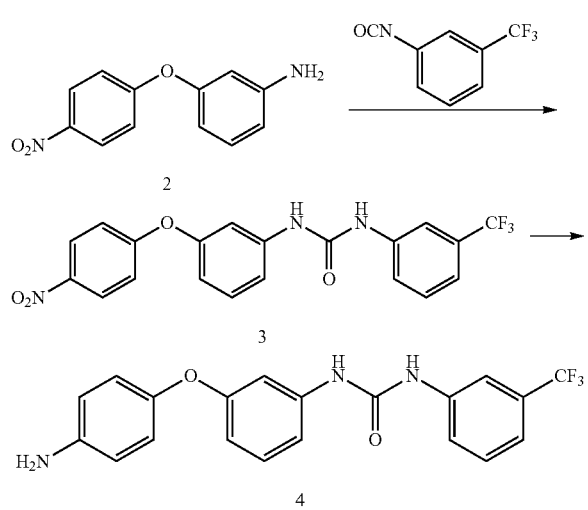

1-(3-(4-aminophenoxy)phenyl)-3-(3-(trifluoromethyl)phenyl)urea (4). 2 was synthesized as previously described[4]. 50 mg of 2 was added to a vial with a stir bar. The vial was capped, purged with argon, and 1 mL of dry dichloromethane was added. The solution was allowed to stir at 0° C. for 15 minutes after which 31 μL of 3-(Trifluoromethyl)phenyl isocyanate was added. The reaction was stirred at 0° C. for 5 min and was then allowed to warm to 25° C. over the course of an hour. The solution was then cooled to −20° C. and filtered to yield 69.3 mg of 3 as a crude solid, which was used in the next step without further purification. 44.8 mg of the crude 3 was added to a vial containing 1 mL of THF and a stirbar. 6.0 mg of 10% palladium on carbon was added, the vial was capped and stirred at 25° C. under a hydrogen atmosphere for 14 h. The reaction was filtered, concentrated in vacuo and purified by silica gel chromatography (eluent, 20% EtOAc/Hex to 100% EtOAc) to give 34.4 mg (63% over 2 steps) of 4 as a white solid. MS (ES+) m/z 388.3 (M+H)$^{+1}$

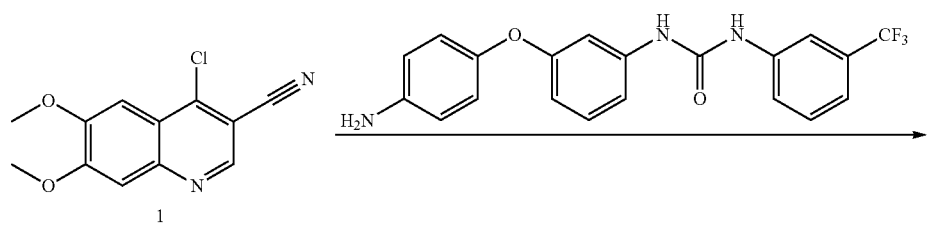

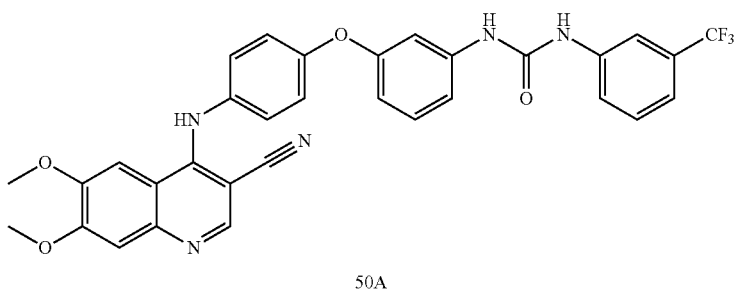

1-(3-(4-((3-cyano-6,7-dimethoxyquinolin-4-yl)amino)phenoxy)phenyl)-3-(3-(trifluoromethyl)phenyl)urea (50A). 50A was obtained in 26% yield as a yellow solid by a method similar to the one described for compound 179D. MS (ES+) m/z 600.3 (M+H)$^+$

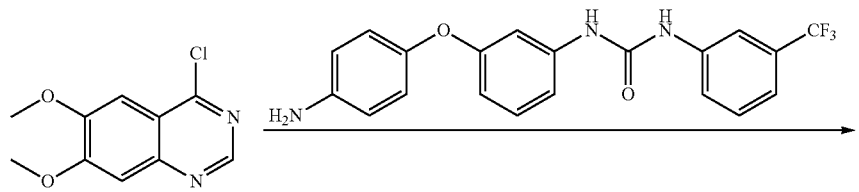

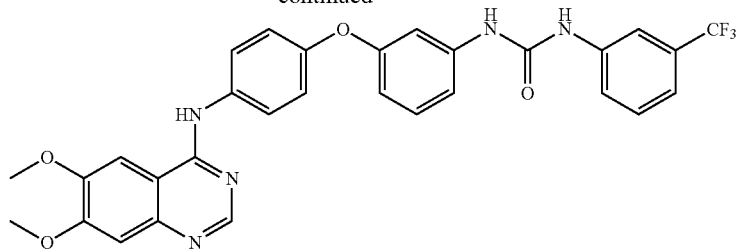

73

1-(3-(4-(((6,7-dimethoxyquinazolin-4-yl)amino)phenoxy) phenyl)-3-(3-(trifluoromethyl)phenyl)urea (73). 5.8 mg (0.025 mmol) of 4-chloro-6,7-dimethoxyquinazoline and 8.5 mg of 4 was added to a vial with a magnetic stir bar. The vial was capped, purged with argon, and 1 mL of isopropanol was added. The vial was heated at 85° C. for 1 h. The reaction was then cooled to −20° C. and the pure product was filtered off to obtain 9.3 mg (63%) of 73 as a yellow solid. MS (ES+) m/z 576.2 (M+H)$^+$

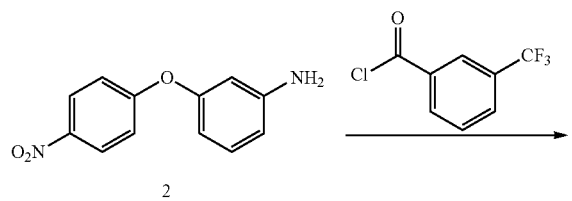

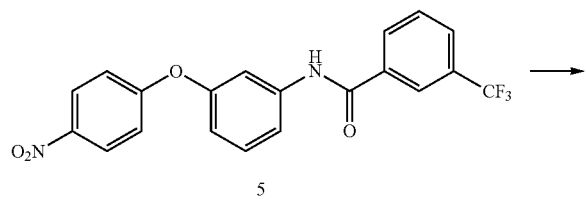

5

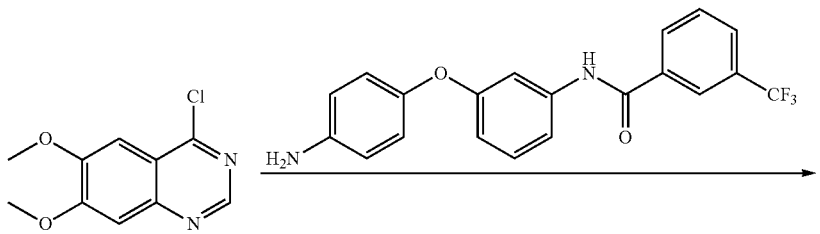

6

N-(3-(4-nitrophenoxy)phenyl)-3-(trifluoromethyl)benzamide (6). 50 mg (0.217 mmol) of 2 was added to a vial with a stir bar. The vial was capped, purged with argon, and 1 mL of dry dichloromethane and 0.5 mL of dry DMF was added. The solution was allowed to stir at 0° C. for 15 minutes after which 34 μL of 3-(trifluoromethyl)benzoyl chloride was added. The reaction was stirred at 0° C. for 5 min and was then allowed to warm to 25° C. over the course of an hour. EtOAc and water were then added to the reaction and the organic layer was separated. The aqueous layer was further extracted with 2 aliquots of EtOAc. The organic layers was pooled, washed once with water, once with brine, and reduced in vacuo. The crude material was purified by column chromatography (eluent HEX to 30% EtOAc/HEX). Product containing fractions were pooled and reduced in vacuo in a vial. 10 mg of 10% palladium on carbon and 1.5 mL of THF was then added to the vial, which was capped and stirred at 25° C. under a hydrogen atmosphere for 12 h. The reaction was filtered, concentrated in vacuo and purified by silica gel chromatography (eluent, 20% EtOAc/Hex to 100% EtOAc) to give 27 mg (31% over 2 steps) of 6. MS (ES+) m/z 373.2 (M+H)$^{+1}$

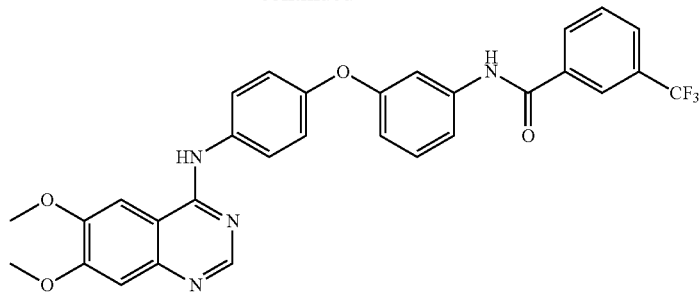

74A 1-(3-(4-((6,7-dimethoxyquinazolin-4-yl)amino)phenoxy)phenyl)-3-(3-(trifluoromethyl)phenyl)urea (74A). 74A was obtained in 85% yield as a yellow solid by a method similar to the one described for compound 73. MS (ES+) m/z 561.2 (M+H)⁺

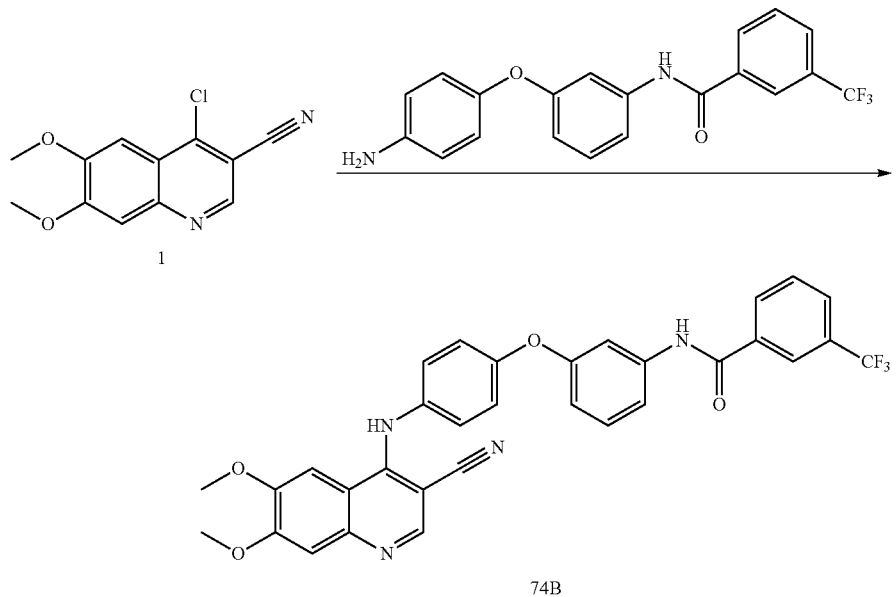 [SMILES: COc1cc2ncc(C#N)c(Cl)c2cc1OC ; Nc1ccc(Oc2cccc(NC(=O)c3cccc(C(F)(F)F)c3)c2)cc1 ; COc1cc2ncc(C#N)c(Nc3ccc(Oc4cccc(NC(=O)c5cccc(C(F)(F)F)c5)c4)cc3)c2cc1OC]

74B

N-(3-(4-((3-cyano-6,7-dimethoxyquinolin-4-yl)amino)phenoxy)phenyl)-3-(trifluoromethyl)benzamide (74B). 74B was obtained in 75% yield by a method similar to the one described for compound 73 using 1 instead of 4-chloro-6,7-dimethoxyquinazoline. MS (ES+) m/z 585.2 (M+H)⁺

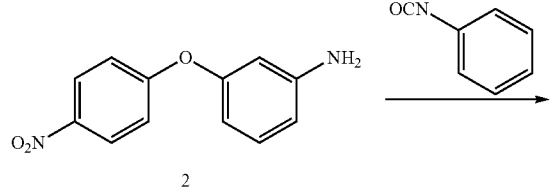

2

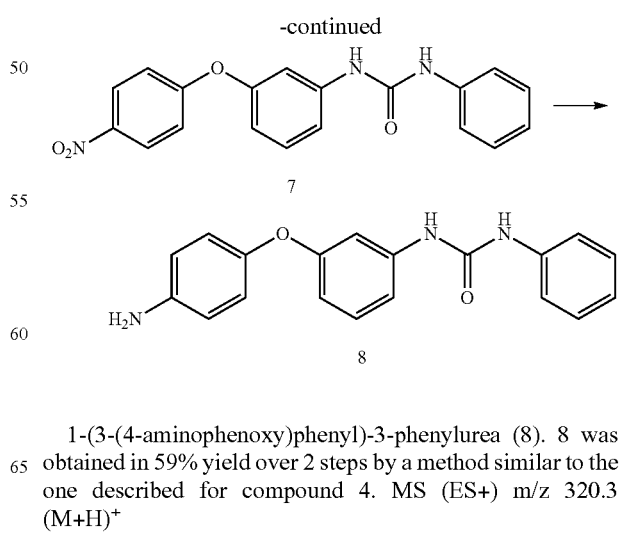

7

8

1-(3-(4-aminophenoxy)phenyl)-3-phenylurea (8). 8 was obtained in 59% yield over 2 steps by a method similar to the one described for compound 4. MS (ES+) m/z 320.3 (M+H)⁺

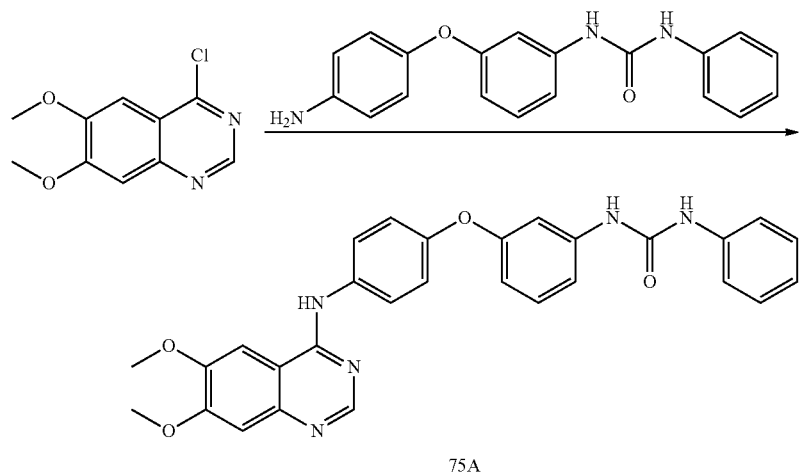
1-(3-(4-((6,7-dimethoxyquinazolin-4-yl)amino)phenoxy)phenyl)-3-phenylurea (75A). 75A was obtained in 83% yield by a method similar to the one described for 73. MS (ES+) m/z 508.2 (M+H)+
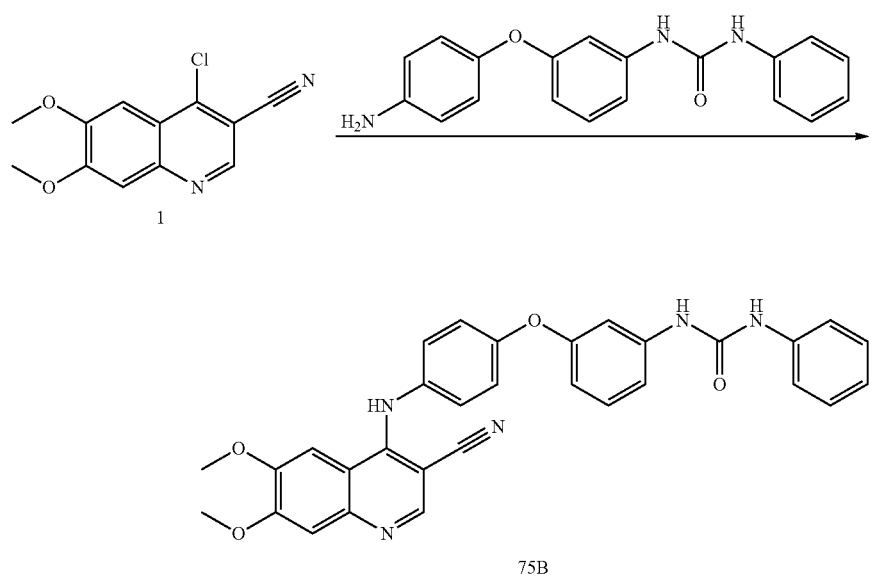
1-(3-(4-((3-cyano-6,7-dimethoxyquinolin-4-yl)amino)phenoxy)phenyl)-3-phenylurea (75B). 75B was obtained in 74% yield by a method similar to the one described for 73 using 1 instead of 4-chloro-6,7-dimethoxyquinazoline. MS (ES+) m/z 532.2 (M+H)+
-continued
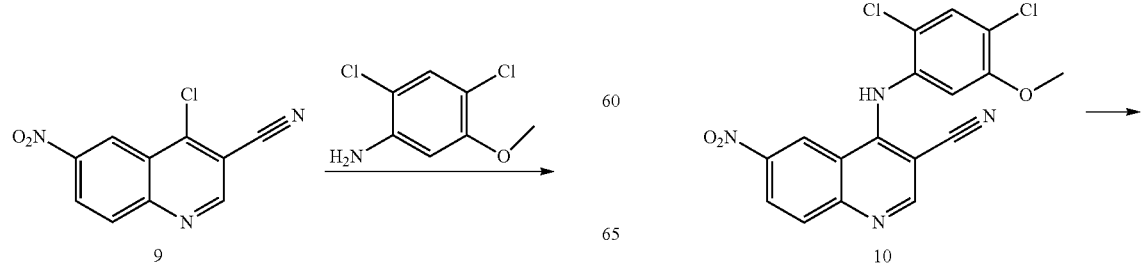

-continued

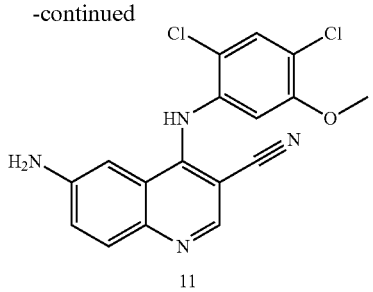

6-amino-4-((2,4-dichloro-5-methoxyphenyl)amino)quinoline-3-carbonitrile (11). 9 was synthesized as previously described[5]. 56.5 mg of 2,4-dichloro-5-methoxyaniline was added to a vial containing 62 mg of 9 and 2.5 mL of 2-ethoxyethanol. The vial was capped and heated to 145° C. for 2 h. The reaction was cooled to rt and reduced in vacuo. 2.9 mL of MeOH, 104 mg of iron powder, and 798 µL of 3M ammonium chloride were added to the crude mixture containing 10, which was refluxed for 1 h at 100° C. The reaction was cooled to room temperature, filtered, and reduced in vacuo. The crude material was purified by column chromatography (eluent 50% EtOAc/HEX to 100% EtOAc). Product containing fractions were pooled and evaporated under reduced pressure yielding 28 mg (29%) of 11 as a yellow solid. MS (ES+) m/z 360.64 (M+H)$^+$

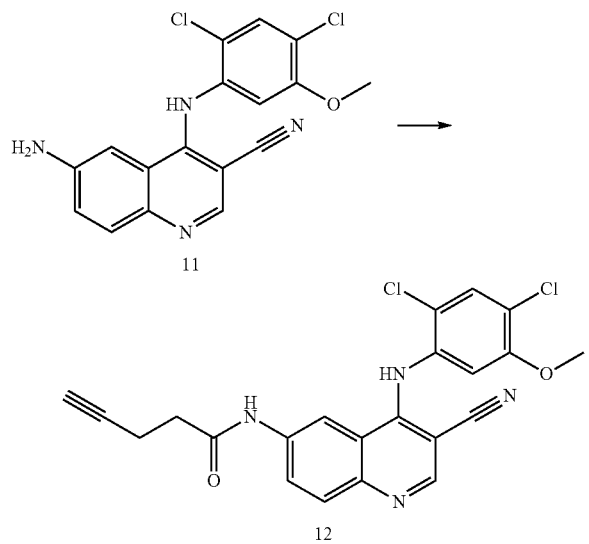

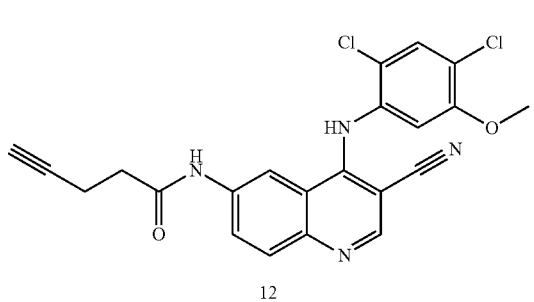

N-(3-cyano-4-((2,4-dichloro-5-methoxyphenyl)amino)quinolin-6-yl)pent-4-ynamide (12). 5.2 mg of 4-Pentynoic acid was stirred in 2 mL of a 1:1 mixture of THF and DMF with 6.93 µL of isobutyl chloroformate at 0° C. under argon. 5.9 µL of N-methyl morpholine was added and the solution was stirred for 15 minutes. 16 mg of 11 was then added and the reaction was allowed to warm to room temperature overnight. The crude reaction was reduced in vacuo and purified by RP-HPLC to yield 8.2 mg (42%) of 12 as a yellow solid. MS (ES+) m/z 440.4 (M+H)$^+$

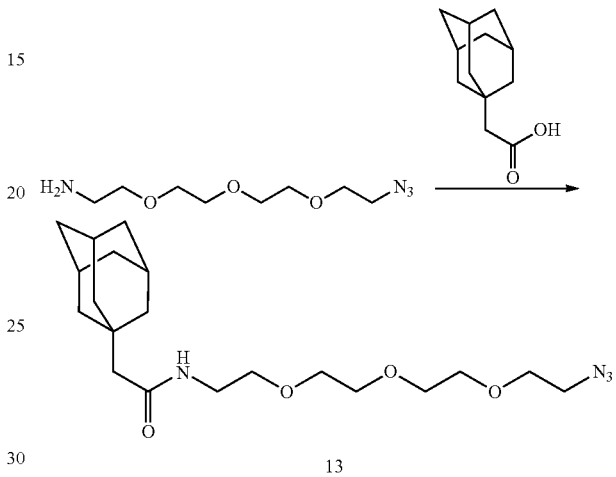

2-((3r,5r,7r)-adamantan-1-yl)-N-(2-(2-(2-(2-azidoethoxy)ethoxy)ethoxy)ethyl)acetamide (13). 88 mg of 1-Adamantaneacetic acid, and 90 µL of 11-Azido-3,6,9-trioxaundecan-1-amine was added to a vial with a stir bar. The vial was capped, purged with argon, and 2.5 mL of dry dichloromethane was added 83 mg of HOBt and 237 µL of DIPEA was added and the solution was stirred at 0° C. for 10 minutes. 104 mg of EDC was added and the reaction was allowed to warm to room temperature overnight. After 12 hours, EtOAc and water were then added to the reaction and the organic layer was separated. The aqueous layer was further extracted with 2 aliquots of EtOAc. The organic layer was pooled, washed once brine, dried with anhydrous MgSO4, which was filtered and reduced in vacuo. The crude material was purified by column chromatography (eluent DCM to 10% MeOH/DCM). Product containing fractions were identified by CAM staining on TLC, pooled, and reduced in vacuo to give 108 mg (60%) of 13 as a clear oil.

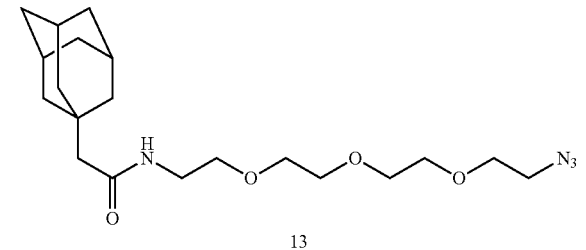

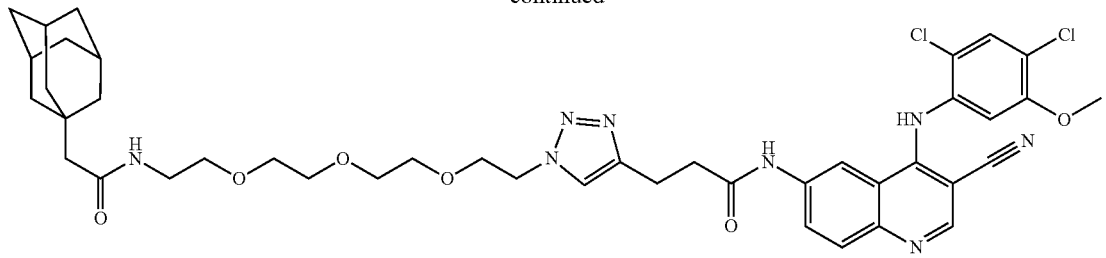

87

3-(1-(1-(((3r,5r,7r)-adamantan-1-yl)-2-oxo-6,9,12-trioxa-3-azatetradecan-14-yl)-1H-1,2,3-triazol-4-yl)-N-(3-cyano-4-((2,4-dichloro-5-methoxyphenyl)amino)quinolin-6-yl)propanamide (87). 10 mg of 12 and 9 mg of 13 were added to a vial containing 1 mL of DMF. 22.7 µL of 1M copper sulfate and 27.3 µL of 1 M Ascorbate were added and the reaction was stirred at room temperature for 1 h after which an additional 5.7 mL of 1M copper sulfate and 6.84 µL of 1M ascorbate was added. After 3 hours EtOAc and water were added to the reaction and the organic layer was separated. The aqueous layer was further extracted with 2 aliquots of EtOAc. The organic layers were pooled, washed once brine, dried with anhydrous MgSO4, filtered, and reduced in vacuo. The crude material was purified by RP-HPLC. Product containing fractions were pooled and reduced in vacuo to give 8.4 mg (44%) of 87 as a yellow oil. MS (ES+) m/z 835.0 (M+H)$^+$

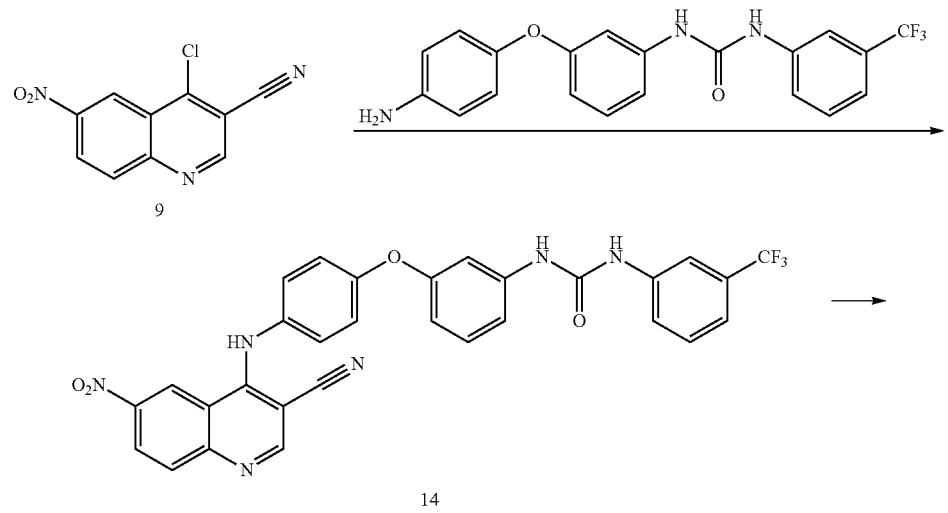

14

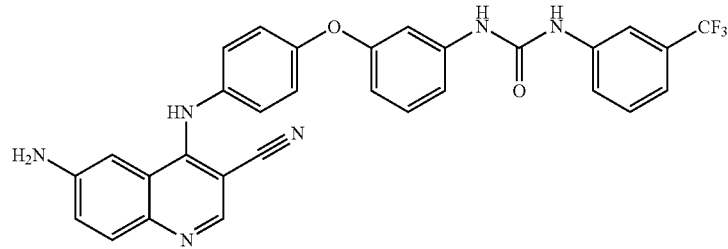

15

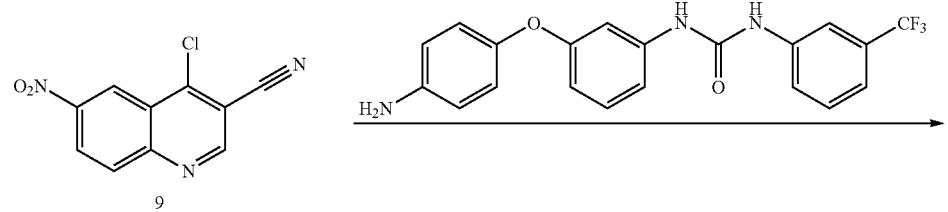

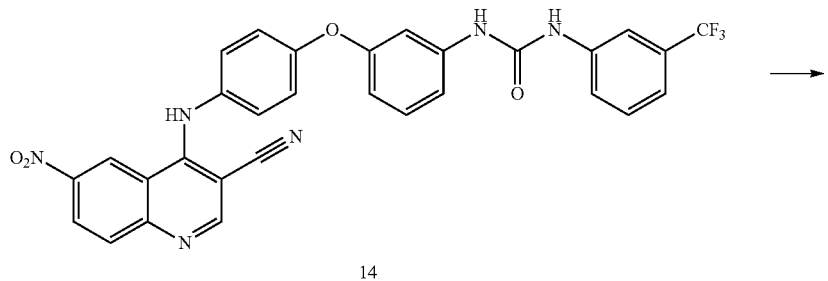

14

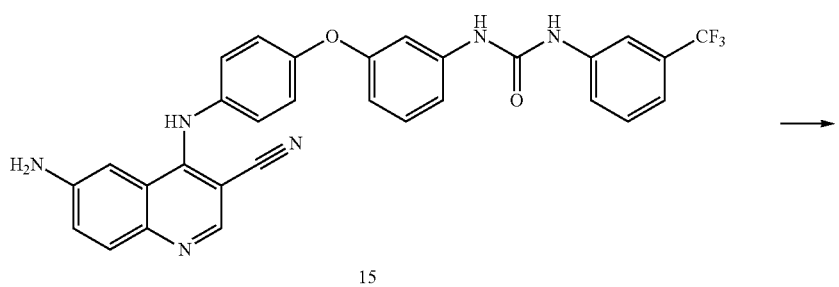

15

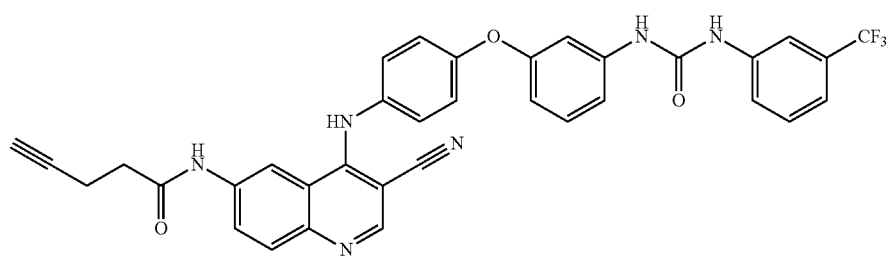

1-(3-(4-((6-amino-3-cyanoquinolin-4-yl)amino)phenoxy)phenyl)-3-(3-(trifluoromethyl)phenyl)urea (15). 15 was obtained in 37% yield from 9 over 2 steps by a method similar to the one described for 11. MS (ES+) m/z 555.6 (M+H)⁺

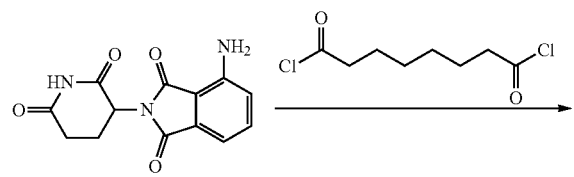

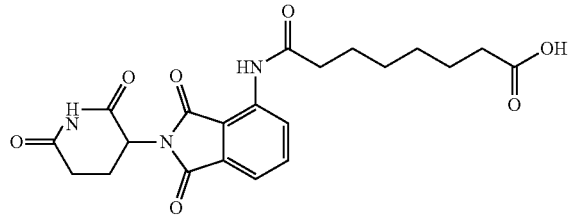

16

8-((2-(2,6-dioxopiperidin-3-yl)-1,3-dioxoisoindolin-4-yl)amino)-8-oxooctanoic acid (16). To a flame dried vial with a stir bar 25 mg of pomalidomide was added. The vial was capped and purged with argon and 1.5 mL of dry THF was added. While stirring at 25° C. 82 μL of Suberoyl chloride was added dropwise. The reaction was heated to 80° C. for 1 hour after which the reaction was cooled to room temperature. Water was added and the reaction was allowed to stir for 15 minutes. The mixture was then extracted with EtOAc three times. The pooled organic layer was dried with MgSO₄, filtered, and evaporated under reduced pressure.

The material was purified b column chromatography (eluent: DCM to 5% MeOH/DCM). Product containing fractions were, pooled, and reduced in vacuo to give 10.7 mg (27%) of 16. MS (ES+) m/z 430.8 (M+H)+

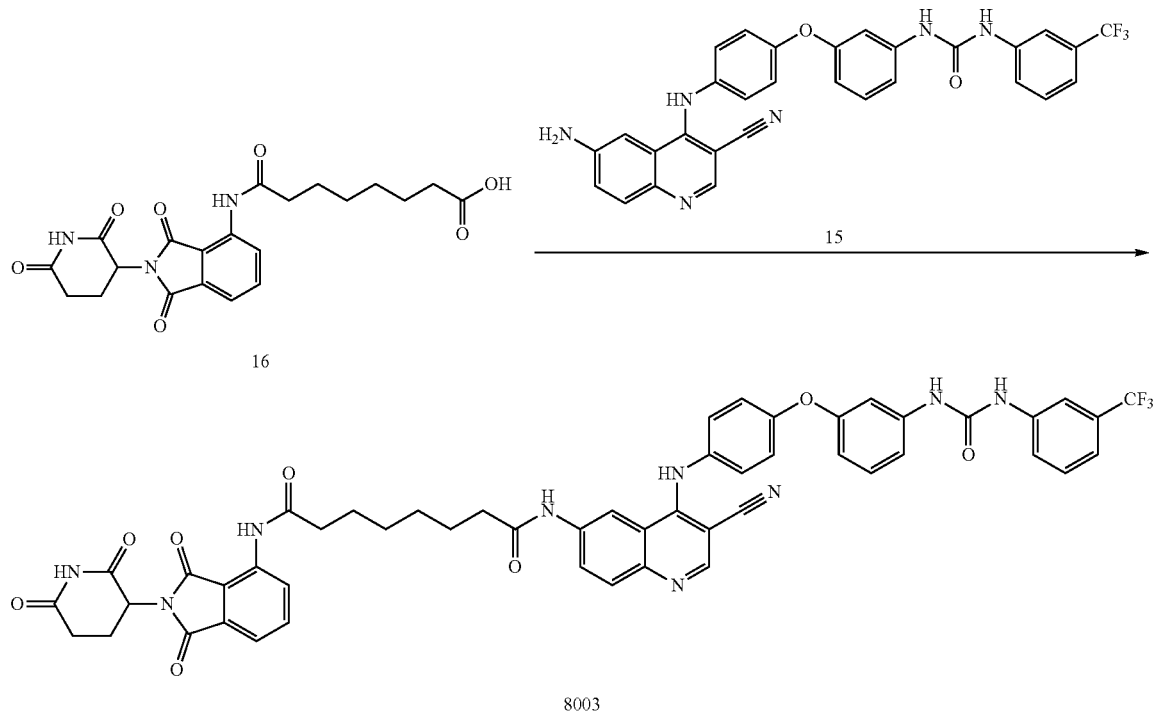

N1-(3-cyano-4-((4-(3-(3-(3-(trifluoromethyl)phenyl) ureido)phenoxy)phenyl)amino)quinolin-6-yl)-N8-(2-(2,6-dioxopiperidin-3-yl)-1,3-dioxoisoindolin-4-yl)octanediamide (8003) 8003 was obtained in 13% yield from 16 and 15 by a method similar to the one described for 12. MS (ES+) m/z 966.8 (M+H).

REFERENCES

1. Shi, F., Telesco, S. E., Liu, Y., Radhakrishnan, R. & Lemmon, M. A. ErbB3/HER3 intracellular domain is competent to bind ATP and catalyze autophosphorylation. Proceedings of the National Academy of Sciences 107, 7692 (2010). 2. Garske, A. L., Peters, U., Cortesi, A. T., Perez, J. L. & Shokat, K. M. Chemical genetic strategy for targeting protein kinases based on covalent complementarity. Proceedings of the National Academy of Sciences 108, 15046-15052 (2011). 3. Wissner, A. et al. 4-Anilino-6,7-dialkoxyquinoline-3-carbonitrile inhibitors of epidermal growth factor receptor kinase and their bioisosteric relationship to the 4-anilino-6,7-dialkoxyquinazoline inhibitors. Journal of Medicinal Chemistry 43, 3244-3256 (2000). 4. Okaniwa. M. et al. Design and synthesis of novel DFG-out RAF/vascular endothelial growth factor receptor 2 (VEGFR2) inhibitors. 1. Exploration of [5,6]-fused bicyclic scaffolds. Journal of Medicinal Chemistry 55, 3452-3478 (2012). 5. Wissner, A. et al. Synthesis and structure-activity relationships of 6,7-disubstituted 4-anilinoquinoline-3-carbonitriles. The design of an orally active, irreversible inhibitor of the tyrosine kinase activity of the epidermal growth factor receptor (EGFR) and the human epidermal growth factor receptor-2 (HER-2). Journal of Medicinal Chemistry 46, 49-63 (2002).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. A compound having the formula:

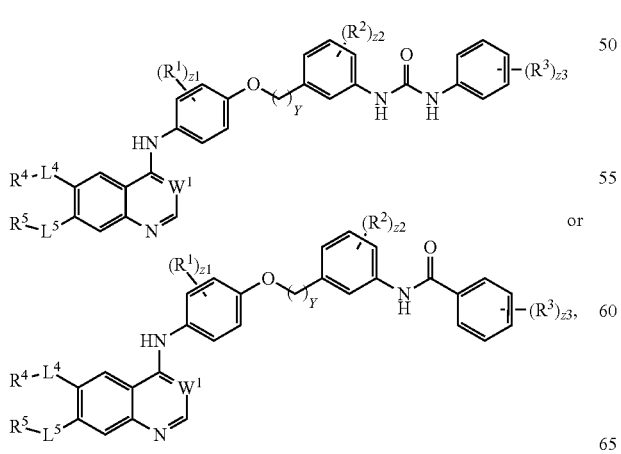

or a pharmaceutically acceptable salt thereof;

wherein

Y is 0 or 1;

$W^1$ is $C(R^6)$;

$R^1$ is independently a halogen, $-CX^1_3$, $-CHX^1_2$, $-CH_2X^1$, $-CN$, $-SO_{n1}R^{10}$, $-SO_{v1}NR^7R^8$, $-NHNH_2$, $-ONR^7R^8$, $-NHC=(O)NHNH_2$, $-NHC=(O)NR^7R^8$, $-N(O)_{m1}$, $-NR^7R^8$, $-C(O)R^9$, $-C(O)-OR^9$, $-C(O)NR^7R^8$, $-OR^{10}$, $-NR^7SO_2R^{10}$, $-NR^7C=(O)R^9$, $-NR^7C(O)-OR^9$, $-NR^7OR^9$, $-OCX^1_3$, $-OCHX^1_2$, $-OCH_2X^1$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent $R^1$ substituents may optionally be joined to form a substituted or unsubstituted cycloalkyl, substituted or unsubstituted heterocycloalkyl, substituted or unsubstituted aryl, or substituted or unsubstituted heteroaryl;

$R^2$ is independently a halogen, $-CX^2_3$, $-CHX^2_2$, $-CH_2X^2$, $-CN$, $-SO_{n2}R^{14}$, $-SO_{v2}NR^{11}R^{12}$, —NHNH$_2$, —ONR$^{11}$R$^{12}$, —NHC=(O)NHNR$^{11}$R$^{12}$, —NHC=(O)NR$^{11}$R$^{12}$, —N(O)$_{m2}$, —NR$^{11}$R$^{12}$, —C(O)R$^{13}$, —C(O)—OR$^9$, —C(O)NR$^{11}$R$^{12}$, —OR$^{14}$, —NR$^{11}$SO$_2$R$^{14}$, —NR$^{11}$C=(O)R$^{13}$, —NR$^{11}$C(O)—OR$^{13}$, —NR$^{11}$OR$^{13}$, —OCX$^2{}_3$, —OCHX$^2{}_2$, —OCH$_2$X$^2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^2$ substituents may optionally be joined to form a substituted or unsubstituted cycloalkyl, substituted or unsubstituted heterocycloalkyl, substituted or unsubstituted aryl, or substituted or unsubstituted heteroaryl;

R$^3$ is independently a halogen, —CX$^3{}_3$, —CHX$^3{}_2$, —CH$_2$X$^3$, —CN, —SO$_{n3}$R$^{18}$, —SO$_{v3}$NR$^{15}$R$^{16}$, —NHNH$_2$, —ONR$^{15}$R$^{16}$, —NHC=(O)NHNR$^{15}$R$^{16}$, —NHC=(O)NR$^{15}$R$^{16}$, —N(O)$_{m3}$, —NR$^{15}$R$^{16}$, —C(O)R$^{17}$, —C(O)—OR$^{17}$, —C(O)NR$^{15}$R$^{16}$, —OR$^{18}$, —NR$^{15}$SO$_2$R$^{17}$, —NR$^{15}$C=(O)R$^{17}$, —NR$^{15}$C(O)—OR$^{17}$, —NR$^{15}$OR$^{17}$, —OCX$^3{}_3$, —OCHX$^3{}_2$, —OCH$_2$X$^3$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; two adjacent R$^3$ substituents may optionally be joined to form a substituted or unsubstituted cycloalkyl, substituted or unsubstituted heterocycloalkyl, substituted or unsubstituted aryl, or substituted or unsubstituted heteroaryl;

R$^4$ is a hydrogen, halogen, —CX$^4{}_3$, —CHX$^4{}_2$, —CH$_2$X$^4$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O)NH$_2$, —NHSO$_2$H, —NHC=(O)H, —NHC(O)—OH, —NHOH, —OCX$^4{}_3$, —OCHX$^4{}_2$, —OCH$_2$X$^4{}_2$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^5$ is a hydrogen, halogen, —CX$^5{}_3$, —CHX$^5{}_2$, —CH$_2$X$^5$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCX$^5{}_3$, —OCHX$^5{}_2$, —OCH$_2$X$^5$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^6$ is halogen, —CX$^6{}_3$, —CHX$^6{}_2$, —CH$_2$X$^6$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O)NHNH$_2$, —NHC=(O) NH$_2$, —NHSO$_2$H, —NHC=(O)H, —NHC(O)—OH, —NHOH, —OCX$^6{}_3$, —OCHX$^6{}_2$, —OCH$_2$X$^6$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl;

R$^7$, R$^8$, R$^9$, R$^{10}$, R$^{11}$, R$^{12}$, R$^{13}$, R$^{14}$, R$^{15}$, R$^{16}$, R$^{17}$, and R$^{18}$ are independently hydrogen, halogen, —CX$^A{}_3$, —CHX$^A{}_2$, —CH$_2$X$^A$, —CN, —OH, —NH$_2$, —COOH, —CONH$_2$, —NO$_2$, —SH, —SO$_3$H, —SO$_4$H, —SO$_2$NH$_2$, —NHNH$_2$, —ONH$_2$, —NHC=(O) NHNH$_2$, —NHC=(O) NH$_2$, —NHSO$_2$H, —NHC=(O)H, —NHC(O)—OH, —NHOH, —OCX$^A{}_3$, —OCHX$^A{}_2$, —OCH$_2$X$^A$, substituted or unsubstituted alkyl, substituted or unsubstituted heteroalkyl, substituted or unsubstituted cycloalkyl, substituted or unsubstituted heterocycloalkyl, substituted or unsubstituted aryl, or substituted or unsubstituted heteroaryl; R$^7$ and R$^8$ substituents bonded to the same nitrogen atom may optionally be joined to form a substituted or unsubstituted heterocycloalkyl or substituted or unsubstituted heteroaryl; R$^{11}$ and R$^{12}$ substituents bonded to the same nitrogen atom may optionally be joined to form a substituted or unsubstituted heterocycloalkyl or substituted or unsubstituted heteroaryl; R$^{15}$ and R$^{16}$ substituents bonded to the same nitrogen atom may optionally be joined to form a substituted or unsubstituted heterocycloalkyl or substituted or unsubstituted heteroaryl;

L$^4$ is a bond or a divalent linker;
L$^5$ is a bond or a divalent linker;
z1 and z2 are independently an integer from 0 to 4;
z3 is an integer from 0 to 5;
m1, m2, m3, v1, v2, and v3 are independently 1 or 2;
n1, n2, and n3 are independently an integer from 0 to 4; and
X$^1$, X$^2$, X$^3$, X$^4$, X$^5$, X$^6$, and X$^A$ are independently —Cl, —Br, —I, or —F.

2. The compound of claim 1, wherein

R$^1$ is independently a halogen, —CX$^1{}_3$, —CHX$^1{}_2$, —CH$_2$X$^1$, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl;

R$^2$ is independently a halogen, —CX$^2{}_3$, —CHX$^2{}_2$, —CH$_2$X$^2$, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl;

R$^6$ is halogen, —CN, —OH, —NH$_2$, —COOH, —CONH$_2$, —NO$_2$, —SH, substituted or unsubstituted C$_1$-C$_4$ alkyl, or 2 to 4 membered substituted or unsubstituted heteroalkyl;

L$^4$ is L$^{4A}$-L$^{4B}$-L$^{4C}$ and L$^{4A}$, L$^{4B}$, and L$^{4C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene; and L$^5$ is L$^{5A}$-L$^{5B}$-L$^{5C}$ and L$^{5A}$, L$^{5B}$, and L$^{5C}$ are each independently a bond, —O—, —NH—, —C(O)—, —C(O)NH—, —NHC(O)—, —C(O)O—, —OC(O)—, —NHC(O)NH—, —S—, substituted or unsubstituted alkylene, substituted or unsubstituted heteroalkylene, substituted or unsubstituted cycloalkylene, substituted or unsubstituted heterocycloalkylene, substituted or unsubstituted arylene, or substituted or unsubstituted heteroarylene.

3. The compound of claim 1, wherein z1 and z2 are 0.

4. The compound of claim 1, wherein R$^3$ is independently —CF$_3$ or halogen.

5. The compound of claim 1, wherein R$^6$ is —CN.

6. The compound of claim 1, wherein -L$^4$-R$^4$ is unsubstituted methoxy.

7. The compound of claim 1, wherein $R^4$ is —$NH_2$.

8. The compound of claim 1, wherein -$L^5$-$R^5$ is unsubstituted methoxy.

9. The compound of claim 1, wherein $R^5$ is —$NH_2$.

10. A pharmaceutical composition comprising a compound of claim 1, or a pharmaceutically acceptable salt thereof, and a pharmaceutically acceptable excipient.

11. The pharmaceutical composition of claim 10, further comprising an anti-cancer agent.

12. The compound of claim 1, wherein z3 is 1.

13. The compound of claim 1, having the formula

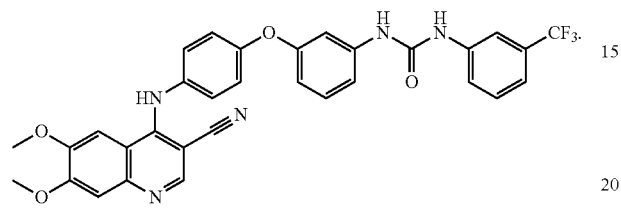

* * * * *